(12) United States Patent
Martin et al.

(10) Patent No.: US 10,457,918 B2
(45) Date of Patent: Oct. 29, 2019

(54) TYROSINE HYDROXYLASE VARIANTS AND METHODS OF USE THEREOF

(71) Applicants: The Regents of the University of California, Oakland, CA (US); Valorbec S.E.C., Montreal (CA)

(72) Inventors: Vincent J. J. Martin, Montreal (CA); Lauren Narcross, Montreal (CA); John E. Dueber, San Francisco, CA (US); William C. DeLoache, Oakland, CA (US); Zachary N. Russ, Berkeley, CA (US); P. James Scrivens, St. Constant (CA)

(73) Assignees: THE REGENTS OF THE UNIVERSITY OF CALIFORNIA, Oakland, CA (US); VALORBEC S.E.C., Montreal (CA)

(*) Notice: Subject to any disclaimer, the term of this patent is extended or adjusted under 35 U.S.C. 154(b) by 0 days.

(21) Appl. No.: 15/507,711

(22) PCT Filed: Sep. 24, 2015

(86) PCT No.: PCT/US2015/052040
§ 371 (c)(1),
(2) Date: Feb. 28, 2017

(87) PCT Pub. No.: WO2016/049364
PCT Pub. Date: Mar. 31, 2016

(65) Prior Publication Data
US 2017/0306301 A1    Oct. 26, 2017

Related U.S. Application Data

(60) Provisional application No. 62/094,877, filed on Dec. 19, 2014, provisional application No. 62/056,238, filed on Sep. 26, 2014.

(51) Int. Cl.
| C12P 13/04 | (2006.01) |
| C12P 17/10 | (2006.01) |
| C12P 17/12 | (2006.01) |
| C12P 17/16 | (2006.01) |
| C12P 7/22 | (2006.01) |
| C12N 9/02 | (2006.01) |
| C12Q 1/26 | (2006.01) |
| C12P 7/24 | (2006.01) |
| C12P 13/00 | (2006.01) |
| C12P 13/22 | (2006.01) |

(52) U.S. Cl.
CPC .............. *C12N 9/0071* (2013.01); *C12P 7/24* (2013.01); *C12P 13/001* (2013.01); *C12P 13/225* (2013.01); *C12P 17/10* (2013.01); *C12Q 1/26* (2013.01); *C12Y 114/16002* (2013.01)

(58) Field of Classification Search
None
See application file for complete search history.

(56) References Cited

U.S. PATENT DOCUMENTS

| 5,300,436 A | 4/1994 | Goldstein et al. |
| 2008/0176754 A1 | 7/2008 | Smolke et al. |

FOREIGN PATENT DOCUMENTS

| WO | WO 2017/122189 | 7/2017 |

OTHER PUBLICATIONS

GenBank Database Accession No. HQ656023, Jun. 2012, 2 pages (Year: 2012).*
UniProt Database Accession No. Q83WS2, Jul. 2013, 3 pages (Year: 2013).*
UniProt Database Accession No. B6E2Z2, May 2013, 1 page (Year: 2013).*
Christinet, et al; "Characterization and functional identification of a novel plant 4,5-extradiol dioxygenase involved in betalain pigment biosynthesis in Portulaca grandiflora"; Plant Physiology; vol. 134, No. 1, pp. 265-274 (Jan. 2004).
Fossati, et al.; "Reconstitution of a 10-gene pathway for synthesis of the plant alkaloid dihydrosanguinarine in *Saccharomyces cerevisiae*"; Nature Communications; vol. 5, No. 3283, 11 pages (Feb. 11, 2014).
Hagel, et al.; "Benzylisoquinoline Alkaloid Metabolism: A Century of Discovery and a Brave New World"; Plant and Cell Physiology; vol. 54, No. 5, pp. 647-672 (2013).
Harris, et al.; "Betalain production is possible in anthocyanin producing plant species given the presence of DOPA-dioxygenase and L-DOPA"; BMC Plant Biology; vol. 12, No. 34, pp. 1-12 (Mar. 12, 2012).
Hatlestad, et al.; "The beet R locus encodes a new cytochrome P450 required for red betalain production"; Nature Genetics; vol. 44, No. 7, 6 pages (Jul. 2012).
Hawkins; "Metabolic Engineering of *Saccharomyces cerevisiae* for the Production of Benzylisoquinoline Alkaloids"; Thesis by Kristy Hawkins; 168 pages (2009).

(Continued)

*Primary Examiner* — David Steadman
(74) *Attorney, Agent, or Firm* — Paula A. Borden; Bozicevic, Field & Francis LLP

(57) ABSTRACT

The present disclosure provides a variant tyrosine hydroxylase that provides for increased production of L-DOPA in a host cell that expresses the tyrosine hydroxylase. The present disclosure provides nucleic acids encoding the variant tyrosine hydroxylase, and host cells genetically modified with the nucleic acids. The present disclosure provides methods of making L-DOPA in a host cell. The present disclosure provides methods of making a benzylisoquinoline alkaloid (BIA), or a BIA precursor. The present disclosure provides methods of detecting L-DOPA level in a cell. The present disclosure provides methods of identifying tyrosine hydroxylase variants that provide for increased L-DOPA production; and methods of identifying gene products that provide for increased tyrosine production.

8 Claims, 39 Drawing Sheets
Specification includes a Sequence Listing.

(56) References Cited

OTHER PUBLICATIONS

Hawkins, et al.; "Production of benzylisoquinoline alkaloids in *Saccharomyces cerevisiae*"; Nature Chemical Biology; vol. 4, No. 9, pp. 564-573 (Sep. 2008).
Minami, et al.; "Microbial production of plant benzylisoquinoline alkaloids"; Proceedings of the National Academy of Sciences of the United States of America; vol. 105, No. 21, pp. 7393-7398 (May 27, 2008).
Mishra, et al.; "Wound Induced Tanscriptional Regulation of Benzylisoquinoline Pathway and Characterization of Wound Inducible PsWRKY Transcription Factor from Papaver somniferum"; PloS One; vol. 8, No. 1, 15 pages (Jan. 2013).
Nakagawa, et al.; "A bacterial platform for fermentative production of plant alkaloids"; Nature Communications; vol. 2, No. 326, 8 pages (May 24, 2011).
Nakagawa, et al.; "Bench-top fermentative production of plant benzylisoquinoline alkaloids using a bacterial platform"; Bioengineered Bugs; vol. 3, No. 1, pp. 49-53 (Jan. 1, 2012).
Nakatsuka, et al.; "Genetic engineering of yellow betalain pigments beyond the species barrier"; Scientific Reports; vol. 3, No. 1970, pp. 1-7 (Jun. 12, 2013).
Royo, et al.; "Effects of Mutations in Tyrosine Hydroxylase Associated With Progressive Dystonia on the Activity and Stability of the Protein"; Proteins; vol. 58, No. 1, pp. 14-21 (Jan. 1, 2005).
Sasaki, et al.; "Detection of DOPA 4,5-Dioxygenase (DOD) Activity Using Recombinant Protein Prepared from *Escherichia coli* Cells Harboring cDNA Encoding DOD from Mirabilis jalapa"; Plant and Cell Physiology; vol. 50, No. 5, pp. 1012-1016 (2009).
Thodey, et al.; "A microbial biomanufacturing platform for natural and semisynthetic opioids"; Nature Chemical Biology; vol. 10, No. 10, 10 pages (Aug. 24, 2014).
Thodey, et al.; "Supplementary Information: A microbial biomanufacturing platform for natural and semisynthetic opioids"; Nature Chemical Biology; vol. 10, No. 10, 10 pages (Aug. 24, 2014).
Deloache, et al.; "An enzyme-coupled biosensor enables (S)-reticuline production in yeast from glucose"; Nature Chemical Biology; vol. 11, pp. 465-471 (Jul. 2015).
Grewal, et al.; "Bioproduction of a betalain color palette in *Saccharomyces cerevisiae*"; Metabolic Engineering; vol. 45, pp. 180-188 (2018).
Sunnadeniya, et al.; "Tyrosine Hydroxylation in Betalain Pigment Biosynthesis is Performed by Cytochrome P450 Enzymes in Beets (*Beta vulgaris*)"; PLoS One; 16 pages (Feb. 18, 2016).

* cited by examiner

| | Mutations | | | | |
|---|---|---|---|---|---|
| Mutant #1 | *87A>C* | L141I | | | |
| Mutant #2 | *123T>A* | F309L | E465D | | |
| Mutant #3 | D2E | *150G>A* | *327C>T* | Y380H | |
| Mutant #4 | *9T>C* | W13L | *1236T>C* | *1281T>C* | |
| Mutant #5 | *180T>A* | F127L | *576G>A* | S232T | *714G>A* |
| Mutant #6 | *684C>T* | F309L | | | |

```
              13
CYP76AD2  MDNATLAMILTIWFISINFIKMFFYHQNTKLSLPPGPKPLPIIGNILEVGKKPHRSFANL   60
CYP76AD4  MDNATLAMLLAIWFISFHFIKMLFTNQSTKL-LPPGPKPLPIIGNILEVGKKPHRSFANL   59
CYP76AD1  MDHATLAMILAIWFISFHFIKLLFSQQTTKL-LPPGPKPLPIIGNILEVGKKPHRSFANL   59
CYP76AD3  MDFLTLVMILSIIFFFYNLLKMKFTTHSDAQ-LPPGPKPMPIFGNIFELGEKPHRSFANL   59
          **  *****   *  ** *   *   **    *   *:* :***::*.  *:******

CYP76AD2  AKIHGPLISLRLGSVTTIVVSSAEVAKEMFLKKDQPLSNRVPNSVTAGDHHKLTMSWLP  120
CYP76AD4  AKIHGPLISLRLGSVTTIVVSSAEVAKEMFLKKDQPLSNRTVPNSVTAGDHHKLTMSWLP  119
CYP76AD1  AKIHGPLISLRLGSVTTIVVSSADVAKEMFLKKDHPLSNRTIPNSVTAGDHHKLTMSWLP  119
CYP76AD3  AKTHGPLMSLRLGSVTTIVVSSAEVAKEMFLKNDQSLADRSVPNSVTAGDHHKLTMSWLP  119
          ** ****:***************:********:*: *::*  *****************

CYP76AD2  VSPKWRNFRKITAVHLLSPLRLDACQSLRHAKVQQLYQYVQECALKGQSVDIGKAAFTTS  180
CYP76AD4  VSPKWRNFRKITAVHLLSPLRLDACQSLRHAKVQQLFQYVQECAQKGQAVDIGKAAFTTS  179
CYP76AD1  VSPKWRNFRKITAVHLLSPQRLDACQTFRHAKVQQLYEYVQECAQKGQAVDIGKAAFTTS  179
CYP76AD3  VSPKWKNFRKITAVHLLSPQRLDACHALRHAKVKQLYEYVQECALKGEAVDIGKAAFTTS  179
          *****:************* ****   *****.**::******:**::**********

CYP76AD2  LNLLSKLFFSKELACHKSHESQELKQLIWNIMEDIGKPNYADYFPILGCIDPLGIRRRLA  240
CYP76AD4  LNLLSKLFFSKELASHKSRESQEFKQLIWNIMEDIGKPNYADYFPILGCVDPSGIRRRLA  239
CYP76AD1  LNLLSKLFFSVELAHHKSHTSQEFKELIWNIMEDIGKPNYADYFPILGCVDPSGIRRRLA  239
CYP76AD3  LNLLSNLFFSVELANHTSNTSQEFKQLIWDIMEDIGKPNYADYFPLLKYVDPSGIRRRLA  239
          *****.****.*** *.*: ***.*:***:***************:*  .**.******

CYP76AD2  ANFDKLISVFQTIISERLENDIN--SNATTNDVLDVLLQLYKQELSMGEINHLLVDIFD  298
CYP76AD4  SNFDKLIEVFQCIIRQRLRENP---STPPTNDVLDVLLELYKQNELSMGEINHLLVDIFD  296
CYP76AD1  CSFDKLIAVFQGIICERLAPDSSTTTTTTDDVLDVLLQLFKQNELTMGEINHLLVDIFD  299
CYP76AD3  ANFDKLIDVFQSFISKRLSSAYS--SATSLDDVLLKLLKEKELNMGEINHLLVDIFD  297
           .:****  ***  *..:*    .      ::****  * *:::**.***********
```

FIG. 6A

```
              309
CYP76AD2    AGTDTTSSTFEWVMAELIRNPKMMEKAQQEIHEVLGKD-RQIQESDIIKLPYLQALIKET  357
CYP76AD4    AGTDTTSSTFEWVMAELIRNPEMMAKAQDEIEQVLGKD-RQIQESDIIKLPYLQAIIKET  355
CYP76AD1    AGTDTTSSTFEWMTELIRNPEMMEKAQEEIKQVLGKD-KQIQESDIINLPYLQAIIKET   358
CYP76AD3    AGTDTTSNTFEWAMAELMRNPIMMKRAQNEIALVLGKDNATIQESDIANMPYLQAIIKET  357
            ******.****: ***:***:**::**:**  :***     *****:  ***:*:****

CYP76AD2    LRLHPPTVFLLPRKADMDVELYGYVVPKDAQILVNLWAIGRDSQVWEKPNVFLPERFLGS  417
CYP76AD4    LRLHPPTVFLLPRKADTDVELYGYIVPKDAQILVNLWAIGRDSQAWENPKVFSPDRFLGC  415
CYP76AD1    LRLHPPTVFLLPRKADTDVELYGYIVPKDAQILVNLWAIGRDPNAWQNADIFSPERFIGC  418
CYP76AD3    LRLHPPTVFLLPRKAITNVKLYGYIVPKNAQILVNLWAIGRDPKVWKNPNEFLPDRFLNS  417
            ***************   *:.****:***:************ .:*:.  .*  :**..

CYP76AD2    DVDVKGRDFGLLPFGAGKRICPGMNLAIRMLTLMLATLLQFFNWKLEDGMNPQDLDMDEK  477
CYP76AD4    EIDVKGRDFGLLPFGAGKRICPGMNLAIRMLTLMLATLLQFFNWKLQDGMSLEDLDMEEK  475
CYP76AD1    EIDVKGRDFGLLPFGAGRRICPGMNLAIRMLTLMLATLLQFFNWKLEGDISPKDLDMDEK  478
CYP76AD3    DIDVKGRDFGLLPFGAGRRICPGMNLAYRMLTLMLATLLQSFDWKLPHRNSPLDLDMDEK  477
            ::***************:********* *************.*:***       ***:*

CYP76AD2    FGIALQKNKPLEIIPSLRH  496  (SEQ ID NO:2)
CYP76AD4    FGIALQKTKPLRIIPVSRY  494  (SEQ ID NO:4)
CYP76AD1    FGIALQKTKPLKLIPIPRY  497  (SEQ ID NO:1)
CYP76AD3    FGIALQKTKPLEIIPLIKY  496  (SEQ ID NO:3)
            *******:***.:**  ::

SEQ ID NO:1 - Beta vulgaris
SEQ ID NO:2 - Amaranthus cruentus
SEQ ID NO:3 - Mirabilis jalapa
SEQ ID NO:4 - Celosia cristata
```

FIG. 6B

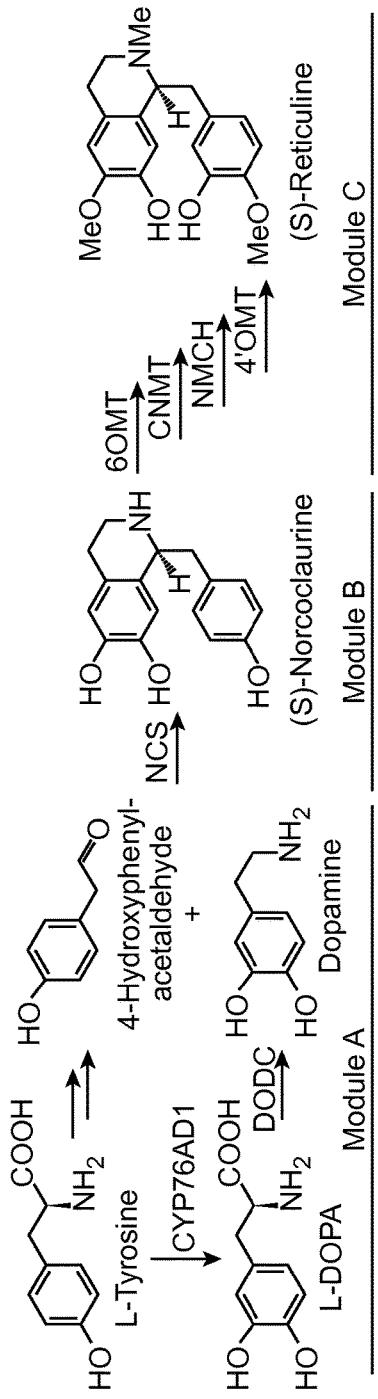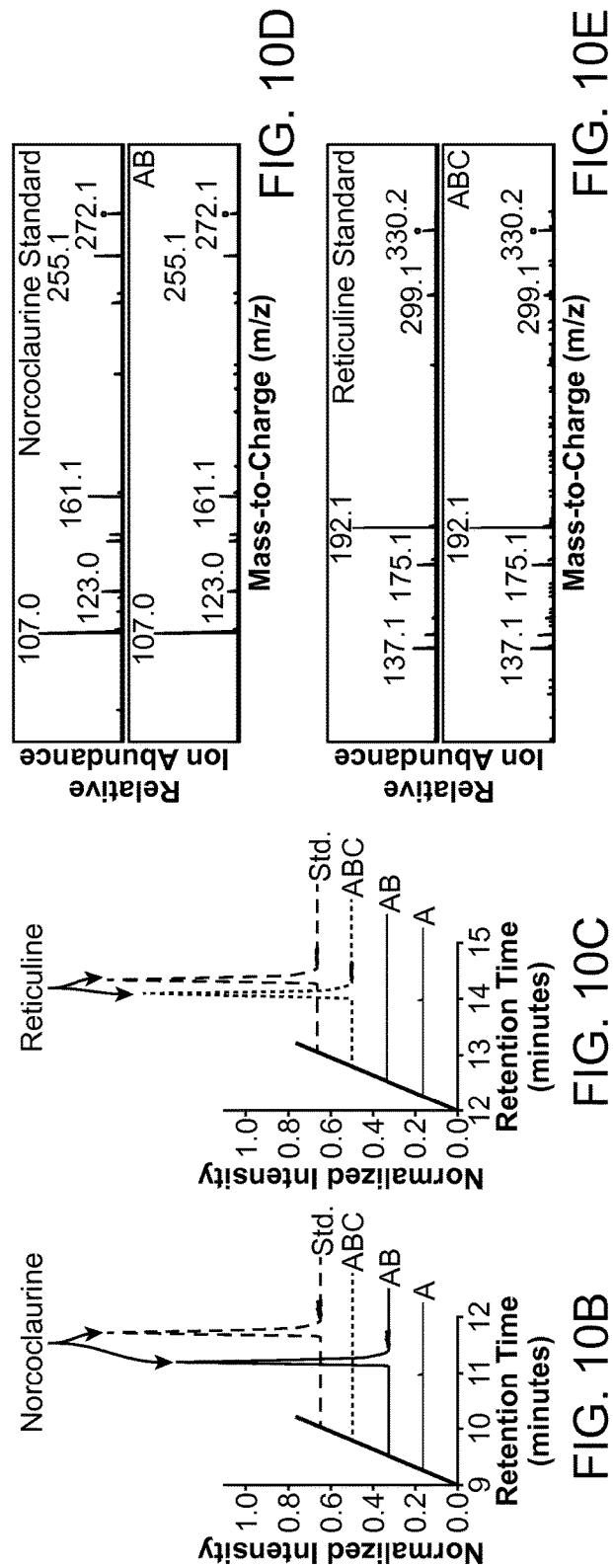
FIG. 10A
FIG. 10B
FIG. 10C
FIG. 10D
FIG. 10E

```
                    13
CYP76AD1_W13L    MDHATLAMILAILFISFHFIKLLFSQQTTKL-LPPGPKPLPIGNILEVGKKPHRSFANL  59
CYP76AD1_W13L    AKIHGPLISLRLGSVTTIVVSSADVAKEMFLKKDHPLSNRTIPNSVTAGDHHKLTMSWLP 119
CYP76AD1_W13L    VSPKWRNFRKITAVHLLSPQRLDACQTFRHAKVQQLYEYVQECAQKGQAVDIGKAAFTTS 179
CYP76AD1_W13L    LNLLSKLFFSVELAHHKSHTSQEFKELIWNIMEDIGKPNYADYFPILGCVDPSGIRRRLA 239
CYP76AD1_W13L    CSFDKLIAVFQGIICERLAPDSSTTTTTTDDVLDVLLQLFKQNELTMGEINHLLVDIFD  299
                                                     309
CYP76AD1_W13L    AGTDTTSSTFEWVMTELIRNPEMMEKAQEEIKQVLGKD-KQIQESDIINLPYLQAIIKET 358
CYP76AD1_W13L    LRLHPPTVFLLPRKADTDVELYGIVPKDAQILVNLWAIGRDPNAWQNADIFSPERFIGC  418
CYP76AD1_W13L    EIDVKGRDFGLLPFGAGRRICPGMNLAIRMLTLMLATLLQFFNWKLEGDISPKDLDMDEK 478
CYP76AD1_W13L    FGIALQKTKPLKLIPIPRY 497  (SEQ ID NO:5)
```

FIG. 13A

```
CYP76AD1 F309L    13
CYP76AD1 F309L    MDHATLAMILAIWFISFHFIKLLFSQQTTKL-LPPGPKPLPIIGNILEVGKKPHRSFANL  59
CYP76AD1 F309L    AKIHGPLISLRLGSVTTIVVSSADVAKEMFLKKDHPLSNRTIPNSVTAGDHHKLTMSWLP 119
CYP76AD1 F309L    VSPKWRNFRKITAVHLLSPQRLDACQTFRHAKVQQLYEYVQECAQKGQAVDIGKAAFTTS 179
CYP76AD1 F309L    LNLLSKLFFSVELAHHKSHTSQEFKELIWNIMEDIGKPNYADYFPILGCVDPSGIRRRLA 239
CYP76AD1 F309L    CSFDKLIAVFQGIICERLAPDSSTTTTTTDDVLDVLLQLFKQNELTMGEINHLLVDIFD 299
                   309
CYP76AD1 F309L    AGTDTTSSTLEWVMTELIRNPEMMEKAQEEIKQVLGKD-KQIQESDIINLPYLQAIIKET 358
CYP76AD1 F309L    LRLHPPTVFLLPRKADTDVELYGYIVPKDAQILVNLWAIGRDPNAWQNADIFSPERFIGC 418
CYP76AD1 F309L    EIDVKGRDFGLLPFGAGRRICPGMNLAIRMLTLMLATLLQFFNWKLEGDISPKDLDMDEK 478
CYP76AD1 F309L    FGIALQKTKPLKLIPIPRY 497 (SEQ ID NO:6)
```

FIG. 13B

```
CYP76AD1 W13L/F309L    MDHATLAMILAILFISFHFIKLLFSQQTTKL-LPPGPKLPIIGNILEVGKKPHRSFANL  59
                                   13
CYP76AD1 W13L/F309L    AKIHGPLISLRLGSVTTIVVSSADVAKEMFLKKDHPLSNRTIPNSVTAGDHHKLTMSWLP 119
CYP76AD1 W13L/F309L    VSPKWRNFRKITAVHLLSPQRLDACQTFRHAKVQQLYEYVQECAQKGQAVDIGKAAFTTS 179
CYP76AD1 W13L/F309L    LNLLSKLFFSVELAHHKSHTSQEFKELIWNIMEDIGKPNYADYFPILGCVDPSGIRRRLA 239
CYP76AD1 W13L/F309L    CSFDKLIAVFQGIICERLAPDSSTTTTTTDDVLDVLQLFKQNELTMGEINHLLVDIFD   299
CYP76AD1 W13L/F309L    AGTDTTSSTLEWVMTELIRNPEMMEKAQEEIKQVLGKD-KQIQESDIINLPYLQAIIKET 358
                                309
CYP76AD1 W13L/F309L    LRLHPPTVFLLPRKADTDVELYGYIVPKDAQILVNLWAIGRDPNAWQNADIFSPERFIGC 418
CYP76AD1 W13L/F309L    EIDVKGRDFGLLPFGAGRRICPGMNLAIRMLTIMLATLLQFFNWKLEGDISPKDLDMDEK 478
CYP76AD1 W13L/F309L    FGIALQKTKPLKLIPIPRY 497 (SEQ ID NO:7)
```

FIG. 13C

DOPA decarboxylase
Genbank AF314150
*Thalictrum flavum*

```
  1 mgslhvedld niskctvenp ldpeefrrqg hmmidflady yrdiekypvr sqvepgylrk
 61 eipdsapynp esietiledv hkqiipgith wqspnyfayf pssgsvagfl gemlstgfnv
121 vgfnwmsspa atelesivmd wlgkmlklpk sflfsgnggg vlqgttceai lctltaardr
181 mlnkigreni cklvvygsdq thcalqkaaq iagihpnnfr avpttkandy glsasalrst
241 iledieaglv plflcatvgt tsstavdpig plckvasdys iwvhvdaaya gsacicpefr
301 hfidgvenad sfslnahkwf fttldccclw vkepsalika lstnpeylrn kateshqvvd
361 ykdwqialsr rframklwlv lrsygvanlr nflrshvkma knfegfiald krfeivvprt
421 famvcfrllp prspliiktn gyqngngvyh kdesraneln rrllesinas gsaymthsmv
481 ggvymirfav gaslteerhv ilawkvvqeh adavlatf (SEQ ID NO:11)
```

FIG. 14A

Genbank AAA62346
*Papaver somniferum*
DOPA decarboxylase

```
  1 mgslpannfe smslcsqnpl dpdefrrqgh miidfladyy knvekypvrt qvdpgylkkr
 61 lpesapynpe sietiledvt ndiipglthw qspnyfayfp ssgsiagflg emlstgfnvv
121 gfnwmsspaa telesivmnw lgqmltlpks flfssdgssg gggvlqgttc eailctltaa
181 rdkmlnkigr eninklvvya sdqtlsalqk aaqiaginpk nflaiatska tnfglspnsl
241 qstiladies glvplflcat vgttsstavd pigplcavak lhgiwvhida ayagsacicp
301 efrhfidgve dadsfslnah kwfftldcc clwvkdsdsl vkalstspey lknkatdskq
361 vidykdwqia lsrrfrsmkl wlvlrsygia nlrtflrshv kmakhfqgli gmdnrfeivv
421 prtfamvcfr lkpaaifrkk iveddhieaq tnevnaklle svnasgkiym thavvggvym
481 irfavgatlt eerhvtgawk vvqehtdail galgedvc (SEQ ID NO:12)
```

FIG. 14B

WP_010953480.1
*Pseudomonas putida*
DOPA decarboxylase

MTPEQFRQYGHQLIDLIADYRQTVGERPVMAQVEPGYLKAALPATAPQQGEPFAAILDDVNNLVMPGLSHWQHPDFYGYFPSNGTLSS
VLGDFLSTGLGVLGLSWQSSPALSELEETTLDWLRQLLGLSGQWSGVIQDTASTSTLVALISARERATDYALVRGGLQAEPKPLIVYSA
HAHSSVDKAALLAGFGRDNIRLIPTDERYALRPEALQAAIEQDLAAGNQPCAVVATTGTTTTALDPLRPVGEIAQANGLWLHVDSAMA
GSAMILPECRWMWDGIELADSVVVNAHKWLGVAFDCSIYYVRDPQHLIRVMSTNPSYLQSAVDGEVKNLRDWGIPLGRRFRALKLWF
MLRSEGVDALQARLRRDLDNAQWLAGQVEAAAEWEVLAPVQLQTLCIRHRPAGLEGEALDAHTKGWAERLNASGAAYVTPATLDGR
WMVRVSIGALPTERGDVQRLWARLQDVIKG
(SEQ ID NO:13)

FIG. 14C

GenBank BAA31471
*Micrococcus luteus*
Tyramine oxidase (MAO)

```
  1 msnphvvivg agfaglvaar elqmagvdve iveardrvgg rawteermgr plelgatwvh
 61 wmqphvwsei trydqsiyps pfcddaywit ggrvehgtea dldaalarpm akifedsref
121 fpypyeplhv ldessgstpe lrerfraadq gsvldclkgg dftqeerdlc daywsaayig
181 dphqgsplma kqwaalsdhr lslvdeqtlr fklthgmrgl yeniaadlrc pirlntpvta
241 vdhrsdgatv tlgtgekisc dsvivtvpvg alptieftpg lpsgmrtvid qrwnstgcki
301 wvkvkghhsi lgyaptphka avfrseffmd ddtticvgfg shhdavdltd prdaqaivdq
361 wrpdlevvdc tghdwvadrw sgqawatlrs gqftngwhhf rstdsrlrfa gadwargwrg
421 vvvdgaietg lstardvlrd ira    (SEQ ID NO:14)
```

FIG. 15A

GenBank CAE02362
*Oryza sativa*
Tyramine oxidase

```
  1  mlchvgvasg  gggdeytqtq  iciqrlkarh  aatvlaalrs  afgggaefsl  rhggrrrrw
 61  esaarwsasg  eksggsafil  trdeairtyr  ergetisgve  iiartqrshp  ldplsaaeia
121  vavttvkaaa  stpevrdgmr  fvevallepe  knvvaladay  ffppfqpsll  pgnrnapiip
181  tklppsrakl  vvynrqtnet  siwivefsev  hadsdtrggy  erggklvsse  vvpdvqpamd
241  amefveceat  vkshppfiea  mrkrgiddmd  lvtvdpwcag  yysdadapsr  riakplvfcr
301  tesdnpieng  yarpvegvhi  ivdmqnntvi  efedrklvpl  ppsdhlrnyt  sgetrggvdr
361  tdvkplvinq  pqgpsfhvng  ylvewqkwnf  rigftpkegl  vlhsvayvdg  nrgrrpiahr
421  lsfvemvvpy  gdpnephyrk  nafdagedgl  gknanslkkg  cdclgvikyf  dahftnftgg
481  vetienavcl  heedhgilwk  hrdwrtglae  vrrsrrltvs  fictianyey  gfywhfyqdg
541  kieaevkltg  ilsvgalmpg  eqrkygttia  pslyapvhqh  ffvtrmdmav  dckpneaynq
601  vvevnvntec  agpnnmhnna  fyaeekllks  elqamrdchp  ssarywivrn  trtvnrtgqp
661  tgyklipgsn  clplalpeak  flrragflkh  nlwvtsyknd  emypggefpn  qnprinegla
721  twvkqdrsle  etnivlwyvf  gvthvprled  wpvmpvehig  fmlkpdgffd  cspaidvplg
781  sevhtkngwi  ny (SEQ ID NO:15)
```

FIG. 15B

NP_000231.1
*Homo sapiens* monoamine oxidase A (MAO-A)

MENQEKASIAGHMFDVVVIGGGISGLSAAKLLTEYGVSVLVLEARDRVGGRTYTIRNEHVDYDVDVGGAYVGPTQNRILRLSKELGIETY
KVNVSERLVQYVKGKTYPFRGAFPPVWNPIAYLDYNNLWRTIDNMGKEIPTDAPWEAQHADKWDKMTMKELIDKICWTKTARRFAYL
FVNINVTSEPHEVSALWFLWYVKQCGGTTRIFSVTNGGQERKFVGGSGQVSERIMDLLGDQVKLNHPVTHVDQSSDNIIETLNHEHYEC
KYVINAIPPTLTAKIHFRPELPAERNQLIQRLPMGAVIKCMMYYKEAFWKKKDYCGCMIIEDEDAPISITLDDTKPDGSLPAIMGFILARKA
DRLAKLHKEIRKKKICELYAKVLGSQEALHPVHYEEKNWCEEQYSGGCYTAYFPPGIMTQYGRVIRQPVGRIFFAGTETATKWSGYMEG
AVEAGERAAREVLNGLGKVTEKDIWVQEPESKDVPAVEITHTFWERNLPSVSGLLKIIGFSTSVTALGFVLYKYKLLPRS (SEQ ID NO:16)

FIG. 15C

*Papaver somniferum*
GenBank AAX56303.1
S-norcoclaurine synthase 1

```
  1 msklittepl ksmaevisny amkqgsvser nipkkqsllr keityetevq tsadsiwnvy
 61 sspdiprllr dvllpgvfek ldviagnggv gtvldiafpl gavprrykek fvkinhekrl
121 kevvmieggy ldmgctfymd rihifektpn scviessiiy evkeeyagkm aklitteple
181 smaevisgyv lkkrlqvfgf eikpklrfnl llcliiclvi aggmfvagvp l (SEQ ID NO:17)
```

FIG. 16A

*Thalictrum flavum*
GenBank AAR22502
S-norcoclaurine synthase 1

```
  1 mmkmevvfvf lmllgtincq kliltgrpfl hhqgiinqvs tvtkvihhel evaasaddiw
 61 tvyswpglak hlpdllpgaf ekleiigdgg vgtildmtfv pgefpheyke kfilvdnehr
121 lkkvqmiegg yldlgvtyym dtihvvptgk dscviksste yhvkpefvki veplittgpl
181 aamadaiskl vlehksksns deieaaiitv (SEQ ID NO:18)
```

FIG. 16B

6OMT
GenBank BAB08004
*Coptis japonica*

```
  1 mevkkdnlss qaklwnfiyg faeslvlkca vqldlaniih nsgtsmtlse lssrlpsqpv
 61 nedalyrvmr ylvhmklftk asidgelryg lappakylvk gwdkcmvgsi laitdkdfma
121 pwhylkdgls gesgtafeka lgtniwgyma ehpeknqlfn eamandsrli msalvkecgn
181 ifngittlvd vgggtgtavr nianafphik ctvydlphvi adspgysevh cvagdmfkfi
241 pkadaimmkc ilhdwddkec ieilkrckea vpvkggkvii vdivlnvqse hpytkmrltl
301 dldmmlntgg kerteeewkk lihdagykgh kitqitavqs vieaypy (SEQ ID NO:19)
```

FIG. 17A

6OMT
GenBank Q6WUC1
*Papaver somniferum*

```
  1 metvskidqq nqakiwkqiy gfaeslvlkc avqleiaetl hnnvkpmsls elasklpvaq
 61 pvnedrlfri mrylvhmelf kidattqkys lappakyllr gweksmvdsi lcindkdfla
121 pwhhlgdglt gncdafekal gksiwvymsv npeknqlfna amacdtrlvt salanecksi
181 fsdgistlvd vgggtgtavk aiskafpdik ctiydlphvi adspeipnit kisgdmfksi
241 psadaifmkc iqilkrckea lpkggkviiv dvvidmdsth pyakirltld
301 ldmmlntggk ertkeewktl fdaagfashk vtqisavqsv ieaypy (SEQ ID NO:20)
```

FIG. 17B

CNMT
GenBank AAU20766
*Thalictrum flavum*

```
  1 mavegkqvap kkaiivellk kleleglvpdd eikkliriql grrlqwgcks tyeeqiaqlv
 61 nlthslrqmk iatevetldd qmyevpidfl kimngsnlkg sccyfkndst tldeaeiaml
121 elyceraqik dghsvldlgc gqqaltlyva qkyknsrvta vtnsvsqkef ieeesrkrnl
181 snvevlladi tthkmpdtyd rilvvelfeh mknyelllrk ikewmakdgl lfvehichkt
241 fayhyepide ddwfteyvfp agtmiipsas fflyfqddvs vvnhwtlsgk hfsrtneewl
301 krldanveli kpmfvtitgq crqeamklin ywrgfclsgm emfgynngee wmashvlfkk
361 k (SEQ ID NO:21)
```

FIG. 18A

GenBank AAP45316
CNMT
*Papaver somniferum*

```
  1 mqlkakeell rnmelglipd qeirqlirve lekrlqwgyk etheeqlsql ldlvhslkgm
 61 kmatemenld lklyeapmef lkiqhgsnmk qsagyytdes ttldeaeiam ldlymeraqi
121 kdgqsvldlg cglgavalfg ankfkkcqft gvtssveqkd yiegkckelk ltnvkvllad
181 ittyeteerf drifavelie hmknyqlllk kisewmkddg llfvehvchk tlayhyepvd
241 aedwytnyif pagtltlssa smllyfqddv svvnqwtlsg khysrsheew lknmdknive
301 fkeimrsitk tekeaiklln fwrifcmcga elfgykngee wmlthllfkk k (SEQ ID NO:22)
```

FIG. 18B

CYP80B1 ((S)-N-methylcoclaurine 3'-hydroxylase)
GenBank AAF61400
*Papaver somniferum*

```
  1 slvavvittf lylifrdssp kglpppgkpw pivgnllqlg ekphsqfaql aetygdlfsl
 61 klgsetvvva stplaaseil kthdrvlsgr yvfqsfrvke hvensivwse cnetwkklrk
121 vcrtdlftqk miesqaevre skamemveyl kknvgnevki aevvfgtlvn ifgnlifsqn
181 ifklgdessg svemkehlwr mlelgnstnp adyfpflgkf dlfgqskdva dclqgiysvw
241 gamlkeskia kqhnnskknd fveilldsgl ddqqinallm eifgagtets astiewalse
301 ltknpqvtan mrlellsvvg krpvkesdip nmpylqafvk etlrlhpatp lllprralet
361 ckvlnytipk ecqimvnawg igrdpkrwtd plkfsperfl nssidfkgnd felipfgagr
421 ricpgvplat qfislivssl vqnfdwglpk gmdpsqlime ekfgltlqke pplyivpktr
481 d (SEQ ID NO:23)
```

FIG. 19

ARO4 K229L

```
  1 msespmfaan gmpkvnqgae edvrilgydp laspallqvq ipatptslet akrgrreaid
 61 iitgkddrvl vivgpcsihd leaaqeyalr lkklsdelkg dlsiimrayl ekprttvgwk
121 glindpdvnn tfninkglqs arqlfvnltn iglpigseml dtispqylad lvsfgaigar
181 ttesqlhrel asglsfpvgf kngtdgtlnv avdacqaaah shhfmgvtlh gvaaitttkg
241 nehcfvilrg gkkgtnydak svaeakaqlp agsnglmidy shgnsnkdfr nqpkvndvvc
301 eqiangenai tgvmiesnin egnqgipaeg kaglkygvsi tdacigwett edvlrklaaa
361 vrqrrevnkk  (SEQ ID NO:24)
```

FIG. 20

> Papaver somniferum NCS
MRKVIKYDMEVAVSADSVWAVYSSPDIPRLLRDVLLPGVFEKLDVIEGNGGVGTVLDIVFPPGAVPRSYKEKFVNIDREKRL
KEVIMEGGYLDMGCTFYLDRIHVEKTKSSCVIESSIVYDVKEECADAMSKLITTEPLKSMAEVISNYVIQKELFSARNILSK
QSVVKKEIRYDLEVPISVDSIWSVYSCPDIPRLL (SEQ ID NO:25)

FIG. 21A

> Thalictrum flavum NCS
MQKLILTGRPFLHHQGIINQVSTVTKVIHHELEVAASADDIWTVYSWPGLAKHLPDLLPGAFEKLEIIGDGGVGTILDMTFVP
GEFPHEYKEKFILVDNEHRLKKVQMIEGGYLDLGVTYYMDTIHVVPTGKDSCVIKSSTEYHVKPEFVKIVEPLITTGPLAAMA
DAISKLVLEHKSKSNSDEIEAAIITV (SEQ ID NO:26)

FIG. 21B

GenBank CAA61562
*Agaricus bisporus* tyrosinase (AbPPO2)

```
  1 gtraaqdlrq pywdwgfelm ppdeviknee vnitnydgkk isvknpilry hfhpidpsfk
 61 pygdfatwrt tvrnpdrnrr edipglikkm rleegqirek tynmlkfnda werfsnhgis
121 ddqhansles vhddihvmvg ygkieghmdh pffaafdpif wlhhtnvdrl lslwkainpd
181 vwvtsgrnrd gtmgiapnaq insetplepf yqsgdkvwts asladtarlg ysypdfdklv
241 ggtkelirda iddlideryg skpssgarnt afdlladfkg itkehkedlk mydwtihvaf
301 kkfelkesfs llfyfasdgg dydqenalld qltpsvgllp klartakitr t (SEQ ID NO:8)
```

FIG. 22

DOPA 4,5-dioxygenase
*Mirabilis jalapa*
GenBank AB435372.1 and BAG80686.1

MKGTYYINHGDPLMYLKKHIKLRQFLEGWMQENVVIEKPKSILIISAHWDTNVPTVNFVEHCDTIHDFDDYPDPLYQIQYRAPGAPNLAKKVEELLKES
GMECEIDTKRGLDHAAWFPLMFMYPEANIPICELSVQPSKDGIHHYNVGKALSPLLQQGVLIGSGGTVHPSDDTPHCPNGVAPWAIEFDNWLEDALL
SGRYEDVNNFKKLAPNWEISHPGQEHLYPLHVALGAAGKNPKTQLIHRSWAANGVFGYSTYNFTPTTQKTD (SEQ ID NO:9)

FIG. 23A

DOPA 4,5-dioxygenase
*Amanita muscaria*

MVPSFVVYSSWVNGRQRYITRQAFASILFYIIRDTTLSFPSHTTMSTKPETDLQTVLDSEI
KEWHFHIYFHQNNAAEHQAALELRDAVLRLRQDGAFVAVPLFRVNMDPMGPHPVGSYEIW
VPSETFASVFSYLCMNRGRLSILVHPLTREELRDHEIRNAWIGPSFPLNLANLPIKSDEI
PLQYPSLKLGYSSTAHKMSLEERRKLGDDIEAVLRGEKEAARAPHRDA (SEQ ID NO:10)

FIG. 23B

```
Bv1u_022460_qtnn    MEYFTTLILLLSIIILTILLSTKL---------FTKSNLPPGPKPWPIIGNILELGKLPHQ  52
Bv1u_022470_qtfp    MEYYT-LSLIFVPIIFTTLFFLQT---------LSKSKLPPGPKPWPIIGSLHKLGDRPHR  51
Bv1u_022400_apow    ---------------------------------------SIHKLGDKPHH         177
Bv1_001290_xkhk     MDYTTLL-ILCSIFFAFFHIYKLISPSSKLTSNDSRLPEGPKPIPILGNLSHLGDSPHL    59
Bv1_001300_sidm     MDYTTLFFILLPIFFALLYLYVFKRNPTFTTNNNARLPEGPKPIPILGNLPHLGDKPHH   60
Bv9_228610_yqeq     MDNATLAV--ILSILFVFYHIFKS----FFTNSSSRRLPEGPKPVPIFGNIFDLGEKPHR  54
Bv9_228860_ickx     ----------------------------------------MPIFGNIFDLGEKPHR    16
CYP76AD1            MDHATLAM--ILAIWFISFHEIKL------LFSQQTTKLLPFGPKPLPIGNILEVGKKPHR  54
                                                                 *:  .::*. :*.:

Bv1u_022460_qtnn    AVDKLSKTYGPILSLKLGSITTIVISSPEIVKEMFLEHDLALSSRPSPDASRVGNHNKFS   112
Bv1u_022470_qtfp    AVAELSKIYGPIMSLKLGTITTIVISSPEIVKELFLKHDLAVSSRTVPNAARAVDHDKFS   111
Bv1u_022400_apow    VVARLSKIYGPIMSLKLGSITTIVISSPEIAKEMFLEHDLALSSRPMQTKS----LKKFS   233
Bv1_001290_xkhk     SLANLAKTYGPLMSLKFGSITTIVVSSSIVAKEMFQKHDLTLSSRHASAAVRANGHDKCS   119
Bv1_001300_sidm     SLANLAKTYGPLMSLKFGSITTIVVSSSIVAKEMFQKHDLTLSSRHVSAAVRANGHDKFS   120
Bv9_228610_yqeq     SFANLSKIHGPLISLKLGSVTTIVVSSASVAEEMFLKNDQALANRTIPDSVRAGDHDKLS   114
Bv9_228860_ickx     SFANLAKIHGPLVSLQLGSVTTVVVSSADVAKEMFLKNDQALANRTIPDSVRAGDHDKLS   76
CYP76AD1            SFANLAKIHGPLISLRLGSVTTIVVSSADVAKEMFLKKDHPLSNRTIPNSVTAGDHHKLT   114
                     :**:::*:**:**:*:**:**:*:***..****:* ::*  *:   . *    ::
```

FIG. 25A

| | | |
|---|---|---|
| Bv1u_022460_qtnn | IVWLPVSPKWRDLRKIATIQLFTTQRLDSSQELRQIKVNELVDYVRQCCEKGLPVDVGKA | 172 |
| Bv1u_022470_qlfp | MVWLPVCPKWRDLRKIATIQLFTTQRLDTSQFLRQKKVKELVEYARQCCEKGVALDIGKA | 171 |
| Bv1u_022400_apow | MVWLPVCPKWRHLRKIATLQLFTTQRLDISQVIRHTKVKELMEYAQQCCENNLPVDIGKA | 293 |
| Bv1_001290_xkhk | IAWLPVCAKWRSLRKISAIHLFSSQKLDSSQALRQEKVSKLIDYVKECCNVGEEIDVGGV | 179 |
| Bv1_001300_sidm | MAWLPVGPKWRALRKITIHLFSSQRLDSSQALRREKVSKLIDYVKECCNVGEAIDVGGV | 180 |
| Bv9_228610_yqeq | MSWLPVSQKWRNMRKISAVQLLSNQKLDASQPLRQTKVKQLLSYVQDCSKKMQPVDIGRA | 174 |
| Bv9_228860_ickx | MSWLPVSAKWRNLRKISAVQLLSTQRLDASQAHRQSKVQCLLEYVHDCSKKGQPVDIGRA | 136 |
| CYP76AD1 | MSWLPVSPKWRNFRKITAVHLLSPQRLDACQTFRHAKVQQLYEYVQECAQKGQAVDIGKA | 174 |
| | :: **** *. * *: .*.:.:::.:: . :.**. .:::..: | |

| | | |
|---|---|---|
| Bv1u_022460_qtnn | GFTTTLNMLSNTFFSMDLASHASSNSQEFKDLVWSLLEEGAKPNVSDFFPIVRELDLQGV | 232 |
| Bv1u_022470_qtfp | GFTTTLNLLSNTFFSMDLASYDSLDSQEFKDLVWHLLEEGARPNVSDFFPLVKHFDLQGV | 231 |
| Bv1u_022400_apow | AFTTSLNLLSNTIFSMDLASHVSSNSQEEKDIVWNIMES--RPNVLDYIPLVRKLDLQGV | 351 |
| Bv1_001290_xkhk | AFTTSLNLLSNTFFSEDLASYNSSDSGEFKELVWKIMEEIGKPNLVDCFPMLRELSVFSV | 239 |
| Bv1_001300_sidm | AFTTSLNLLSNTFFSFDLASYNSSDSGEFKELVWKIMEEIGKPNLADCFPMLRFLSVFSV | 240 |
| Bv9_228610_yqeq | AFTTSLNLLSNTFFSIELASHESSASQEFKQLMWNIMEEIGRPNYADFFPILGYIDPFGI | 234 |
| Bv9_228860_ickx | AFTTSLNLLSNTFFSVELASHESSASQEFKQLMWNIMEEIGRPNYADFFPILGYLDPFGI | 196 |
| CYP76AD1 | AFTTSLNLLSKLFFSVELAHHKSHTSQEEKELIWNIMEDIGKPNYADYFPILGCVDPSGI | 234 |
| | .**:*.: **: *:..: *:*:::* : **.: .* | |

FIG. 25B

```
Bv1u_022460_qtnn    SKNRRVHMKKLMGIFEEIIDGRLTKLKDVK------DDVLSTLLKLVKDEE--LNLDDVK  284
Bv1u_022470_qtfp    LKTTTSYLKKLIGIFEEIIDKRLKDPTDVK------DDVLSTLLKLVEDDE--LSLDDVK  283
Bv1u_022400_apow    LKRKRSYFKKIMGVFEEIIDVRLKDPTDVK------DDV_GTLLKLVKDEE--LSLHDVK  403
Bv1_001290_xkhk     KGKLLGYDNKLNEVFENIIQKRLQNYCGDSS----SGGDVLDTLLRLMKENELDLDLGDIK  296
Bv1_001300_sidm     NYKVMVYGNRLNDVFEDIIQNRLISSSADK-----IGGDVLDTLLRLMKENESELSLDDIK  296
Bv9_228610_yqeq     RRRLAGYFDKLIDVFQDIIREROKLRSSNSSGAKQTNDILDTLLKLHEDNE--LSMPEIN  292
Bv9_228860_ickx     RRRLAGYFDQLIAVFQDIIGEROKIRSANLSGGKQTNDILDTLLNLYDEKE--LSMGEIN  254
CYP76AD1            RRRLACSFDKLIAVFQGIICERLAPDSSTTT-TTTTDDVLDVLLQLFKQNE--LTMGEIN  291
                      :  ::   :  :*   .. ::  *         *.:  .:**.. ..    *   :

Bv1u_022460_qtnn    HMLMDLFLAGTDTTSITLEWAMTELLRNPEKMEKVQIELDKVLGKD-SSLQESMISKLPY  343
Bv1u_022470_qtfp    HLLADLFIAGTDTTSNTLEWAMAELLRNPEKMEKAQAEINKVLGKD-SSMQENDISKLPY  342
Bv1u_022400_apow    HMLFDLFLAGTDTTSSTLEWAMTELLRNPKVMEKAQIEIDQVLGKD-GSMQELDIAKLPY  462
Bv1_001290_xkhk     HLLIMDFFTAGTDTTSSTLEWAMTELLRNPEKMAKAQVELEQVLGKN-KVVGEFDISKLPY  355
Bv1_001300_sidm     HLLIMDFFTAGTDTTSSTLEWAMTELLRNPEKLAKAQAELEQVVGKN-KVVKEADISKLPY  355
Bv9_228610_yqeq     HLLVDIFDAGTDTTASTLEWAMAELVKNPEMMTKVQIEIEQALGKDCLDIQESDISKLPY  352
Bv9_228860_ickx     HLLVDIFDAGTDTTASTLEWAMAELVKNPYMMVKVQDEIEKAIGKGCSMVQESDISKLPY  314
CYP76AD1            HLLVDIFDAGTDTTSSTLEEWVMTELLRNPEMMEKAQEEIKQVLGKD-KQIQESDIINLPY  350
                    *:* ::* :***** *** .*:*::.** :::    .  .: .:::
```

FIG. 25C

```
Bv1u_022460_qtnn   IQAIVKETLRLHPPTPFLIPHKAEKDVLLCNYLVPKNSIIWVNLWSIARSPSVWPNPESF  403
Bv1u_022470_qtfp   VQAIVKETFRLRLHPVTPFLVPHKAEKDILLGNYLVPKNSTIWVNVWSIGRNPSVWSKPELF 402
Bv1u_022400_apow   IQALVKEILRLHPPAPFLIPHMAIEDVQLCGYLVPKNSTIWVNVWSIGRDPSVWTKSKMF   522
Bv1_001290_xkhk    LQAIVKETLRLRMHPPTVFLLPRKANNDVELYGYVFVNVAISRDPNHWENPNSF         415
Bv1_001300_sidm    LQAIIKETLRLRMHPPTVFLLPRKANNDVKLYGYIVPKNAQIFVNLLAISRDPTHWKNPDLF 415
Bv9_228610_yqeq    LQGIIKETLRLHPPTVFLLPRKADNDVELYGYVVPKNAQVLVNLWAIGRDPKVWKNPEVF  412
Bv9_228860_ickx    LQAIIKETLRLHPPTVFLLPRKADADVELYGYIVPKNAQVLVNLWAIGRDPKVWKNPEVF  374
CY

```
Bv1u_022460_qtnn      SPKDIDMKEKFGLTLQKAQPLQAIPIPR- 488  (SEQ ID NO:27)
Bv1u_022470_qtfp      SPEDIDMEEKFGITLQKVEPLQAIPISR- 488  (SEQ ID NO:28)
Bv1u_022400_apow      ATCTIDVEEKFGITLQKAEPLQAIPLPR- 610  (SEQ ID NO:29)
Bv1_001290_xkhk       SPQDLDMTDKFGITIQKAIPLRALPIPK- 501  (SEQ ID NO:30)
Bv1_001300_sidm       -DEDLDMNDKFGITIQKAKPLHVIPISKL 499  (SEQ ID NO:31)
Bv9_228610_yqeq       NPKDLDMDEKFGITLQKVKPLQVIPVPRN 499  (SEQ ID NO:32)
Bv9_228860_ickx       HPKDLDMDEKFGITLQKVKPLQVIPVPRK 461  (SEQ ID NO:33)
CYP76AD1              SPKDLDMDEKFGIALQKTKPLKLIPIPRY 497  (SEQ ID NO:1)
                       *: :****::::**. ***;   *: ::
```

FIG. 25E

| | 1 | 2 | 3 | 4 | 5 | 6 | 7 | 8 |
|---|---|---|---|---|---|---|---|---|
| 1. Bv1u_022460_qtnn | | 74.2% | 66.8% | 56.6% | 55.8% | 54.2% | 55.9% | 53.4% |
| 2. Bv1u_022470_qtfp | 74.2% | | 67.6% | 55.1% | 55.6% | 54.7% | 56.1% | 51.5% |
| 3. Bv1u_022400_apow | 66.8% | 67.6% | | 50.9% | 50.6% | 52.0% | 53.7% | 51.2% |
| 4. Bv1_001290_xkhk | 56.6% | 55.1% | 50.9% | | 80.0% | 58.3% | 60.3% | 56.3% |
| 5. Bv1_001300_sidm | 55.8% | 55.6% | 50.6% | 80.0% | | 56.9% | 59.8% | 55.9% |
| 6. Bv9_228610_yqeq | 54.2% | 54.7% | 52.0% | 58.3% | 56.9% | | 87.9% | 71.3% |
| 7. Bv9_228860_ickx | 55.9% | 56.1% | 53.7% | 60.3% | 59.8% | 87.9% | | 71.6% |
| 8. CYP76AD1 | 53.4% | 51.5% | 51.2% | 56.3% | 55.9% | 71.3% | 71.6% | |

FIG. 25F

| Strain # | Strain Name | Strain Parent | Plasmid Name | Description | Yeast Marker | Used in Figure |
|---|---|---|---|---|---|---|
| 1 | yWCD098 | BY4741 | pWCD1134 | Empty Vector | URA3 | 1b |
| 2 | yWCD538 | BY4741 | pWCD1870 | pTDH3-DOD-tADH1 | URA3 | 1b |
| 3 | yWCD683 | BY4741 | pWCD2104 | pCCW12-DOD-tADH1 | URA3 | 2a, 2b, 3b |
| 4 | yWCD684 | BY4741 | pWCD2105 | pTDH3-CYP76AD1-tTDH1-pCCW12-DOD-tADH1 | URA3 | 2a, 2b, 3b, 3c, S6, S7 |
| 5 | yWCD732 | BY4741 | pWCD2236 | pTDH3-AbPPO2-tTDH1-pCCW12-DOD-tADH1 | URA3 | 2a, 2b |
| 6 | yWCD688 | BY4741 | pWCD2109 | pTDH3-CYP76AD1_F309L-tTDH1-pCCW12-DOD-tADH1 | URA3 | 2b, 3b, 3c, S6, S7 |
| 7 | yWCD735 | BY4741 | pWCD2239 | pTDH3-CYP76AD1_W13L-tTDH1-pCCW12-DOD-tADH1 | URA3 | 2b |
| 8 | yWCD736 | BY4741 | pWCD2240 | pTDH3-CYP76AD1_W13L_F309L-tTDH1-pCCW12-DOD-tADH1 | URA3 | 2b |
| 9 | yWCD694 | BY4741 | pWCD2134 | pCCW12-DODC-tADH1 | URA3 | 2b, S4 |
| 10 | yWCD739 | BY4741 | pWCD2243 | pTDH3-AbPPO2-tTDH1-pCCW12-DODC-tADH1 | URA3 | 2b, S4 |
| 11 | yWCD695 | BY4741 | pWCD2135 | pTDH3-CYP76AD1-tTDH1-pCCW12-DODC-tADH1 | URA3 | 2b, 2c, S4 |
| 12 | yWCD699 | BY4741 | pWCD2139 | pTDH3-CYP76AD1_F309L-tTDH1-pCCW12-DODC-tADH1 | URA3 | 2b |
| 13 | yWCD742 | BY4741 | pWCD2246 | pTDH3-CYP76AD1_W13L-tTDH1-pCCW12-DODC-tADH1 | URA3 | 2b |
| 14 | yWCD743 | BY4741 | pWCD2247 | pTDH3-CYP76AD1_W13L_F309L-tTDH1-pCCW12-DODC-tADH1 | URA3 | 2b, 2c, S4 |
| 15 | yWCD748 | BY4741 | pWCD2267 | pTDH3-CYP76AD1-tTDH1-pCCW12-DODC-tADH1-pPGK1-ARO4_FBR-tPGK1 | URA3 | 2c, S4 |
| 16 | yWCD745 | BY4741 | pWCD2249 | pTDH3-CYP76AD1_W13L_F309L-tTDH1-pCCW12-DODC-tADH1-pPGK1-ARO4_FBR-tPGK1 | URA3 | 2c, S4 |
| 17 | yWCD685 | BY4741 | pWCD2106 | pTDH3-CYP76AD2-tTDH1-pCCW12-DOD-tADH1 | URA3 | 3b, 3c, S6, S7 |
| 18 | yWCD686 | BY4741 | pWCD2107 | pTDH3-CYP76AD3-tTDH1-pCCW12-DOD-tADH1 | URA3 | 3b, 3c, S6, S7 |
| 19 | yWCD687 | BY4741 | pWCD2108 | pTDH3-CYP76AD4-tTDH1-pCCW12-DOD-tADH1 | URA3 | 3b, 3c, S6, S7 |
| 20 | yWCD689 | BY4741 | pWCD2110 | pTDH3-CYP76AD2_F308L-tTDH1-pCCW12-DOD-tADH1 | URA3 | 3b, 3c, S6, S7 |

FIG. 26A

| | | | | | | |
|---|---|---|---|---|---|---|
| 21 | yWCD690 | BY4741 | pWCD2111 | pTDH3-CYP76AD3_F307L-tTDH1-pCCW12-DOD-tADH1 | URA3 | 3b, 3c, S6, S7 |
| 22 | yWCD691 | BY4741 | pWCD2112 | pTDH3-CYP76AD4_F306L-tTDH1-pCCW12-DOD-tADH1 | URA3 | 3b, 3c, S6, S7 |
| 23 | yWCD303 | BY4741 | pWCD1610 | pRPL18B-mKate2-DOD-tADH1 | URA3 | S2 |
| 24 | yWCD619 | yWCD538 | pWCD2040 | pTDH3-CYP76AD1-mKate2-tADH1 | URA3, LEU2 | S3 |
| 25 | yWCD620 | yWCD538 | pWCD1950 | pTDH3-CYP76AD1_mut1-mKate2-tADH1 | URA3, LEU2 | S3 |
| 26 | yWCD621 | yWCD538 | pWCD1951 | pTDH3-CYP76AD1_mut2-mKate2-tADH1 | URA3, LEU2 | S3 |
| 27 | yWCD622 | yWCD538 | pWCD1952 | pTDH3-CYP76AD1_mut3-mKate2-tADH1 | URA3, LEU2 | S3 |
| 28 | yWCD623 | yWCD538 | pWCD1953 | pTDH3-CYP76AD1_mut4-mKate2-tADH1 | URA3, LEU2 | S3 |
| 29 | yWCD624 | yWCD538 | pWCD1954 | pTDH3-CYP76AD1_mut5-mKate2-tADH1 | URA3, LEU2 | S3 |
| 30 | yWCD625 | yWCD538 | pWCD1955 | pTDH3-CYP76AD1_mut6-mKate2-tADH1 | URA3, LEU2 | S3 |
| 31 | yWCD747 | BY4741 | pWCD2266 | pTDH3-AbPPO2-tTDH1-pCCW12-DODC-tADH1-pPGK1-ARO4_FBR-tPGK1 | URA3 | S4 |
| Strain # | Strain Name | Strain Parent | Plasmid Name | Description | Yeast Marker | Used in Figure |
| 32 (A) | yWCD714 | BY4741 | pWCD2211 | pTDH3-CYP76AD1_W13L_F309L-tTDH1-pCCW12-DODC-tADH1-pPGK1-ARO4_FBR-tPGK1 | URA3 | 4b, 4c |
| 33 (AB) | yWCD758 | yWCD714 | pWCD2338 | pTDH3-PsNCS-3-tENO2 | URA3, LEU2 | 4b, 4c, 4d, S9, S10 |
| 34 (ABC) | yWCD782 | yWCD758 | pWCD2353 | pTDH3-Ps_6OMT-tADH1-pCCW12-Ps_CNMT-tPGK1-pPGK1-Ps_4'OMT2-tENO2-pTEF1-Ec_CYP80B1-tTDH1 | URA3, LEU2, HIS3 | 4b, 4c, 4e, S10 |

FIG. 26B

| Plasmid # | Plasmid Name | Description | Yeast Marker | Yeast Origin | Purpose |
|---|---|---|---|---|---|
| 1 | pZNR0926 | CYP76AD1 | N/A | N/A | Error-prone PCR template |
| 2 | pZNR0943 | pRPL18B-(dropout)-mKate2-tADH1 | LEU2 | CEN6/ARS4 | CYP76AD1 error-prone PCR library vector |
| 3 | pZNR0964 | pRPL18B-CYP76AD1-mKate2-tADH1 | LEU2 | CEN6/ARS4 | CYP76AD1 library wildtype control |

FIG. 27

| Oligo # | Oligo Name | Description | Sequence |
|---|---|---|---|
| 1 | CN40 | Error-prone PCR – forward | TTGGTAGTCGGTCTCCTATG (SEQ ID NO:35) |
| 2 | DC48 | Error-prone PCR - reverse | TTTTTATTGGTCTGGTCTCAGGAT (SEQ ID NO:36) |
| 3 | S16 | Forward sequencing off of pZNR0943 | CAAAACTACCTGTTTCACCAAAGG (SEQ ID NO:37) |
| 4 | AA05 | Reverse sequence off of pZNR0943 | ACTTGAAGTGGTGGTTGTTC (SEQ ID NO:38) |
| 5 | CW77 | CYP76AD1 shuffling 1F | GCATGGTCTCATATGGATCATGCAACATTAGC (SEQ ID NO:39) |
| 6 | CW78 | CYP76AD1 shuffling 1R | ATGCGGTCTCAACAGCAGTTATCTTTCTGA (SEQ ID NO:40) |
| 7 | CW79 | CYP76AD1 shuffling 2F | GCATGGTCTCACTGTTCATTTATTGTCTCCACA (SEQ ID NO:41) |
| 8 | CW80 | CYP76AD1 shuffling 2R | ATGCGGTCTCAAGTTGTAGTAGTTGTAGTTGAT (SEQ ID NO:42) |
| 9 | CW81 | CYP76AD1 shuffling 3F | GCATGGTCTCAAACTACAGATGATGTCTTGGA (SEQ ID NO:43) |
| 10 | CX01 | CYP76AD1 shuffling 3R | ATGCGGTCTCAGGCAACAAGAAAACTGTAGG (SEQ ID NO:44) |
| 11 | CX02 | CYP76AD1 shuffling 4F | GCATGGTCTCATGCCTAGAAAAGCCGAC (SEQ ID NO:45) |
| 12 | CX03 | CYP76AD1 shuffling 4R | ATGCGGTCTCAGGATCCGTATCTTGGAATTG (SEQ ID NO:46) |
| 13 | CW76 | CYP76AD1 shuffling 1F – alt1 | GCATCGTCTCATCGGTCTCCTATGGAACATGCAACATTAGCTATGAT (SEQ ID NO:47) |
| 14 | CW61 | CYP76AD1 shuffling 1F – alt2 | GCATCGTCTCATCGGTCTCCTATGGATCACGCAACATTAGCTATG (SEQ ID NO:48) |

FIG. 28

>sp|O64899|C80B1_ESCCA (S)-N-methylcoclaurine 3'-hydroxylase isozyme 1 (Fragment) OS=Eschscholzia californica GN=CYP80B1 PE=2 SV=1

GTSTVALIAVIISSILYLLFGGSGHKNLPPGPKPWPIVGNLLQLGEKPHAQFAELAQTYG
DIFTLKMGTETVVVASTSSAASEILKTHDRILSARYVFQSFRVKGHVENSIVWSDCTETW
KNLRKVCRTELFTQKMIESQAHVREKKCEEMVEYLMKKQGEEVKIVEVIFGTLVNIFGNL
IFSQNIFELGDPNSGSSEFKEYLWRMLELGNSTNPADYFPMLGKFDLFGQRKEVAECLKG
IYAIWGAMLQERKLAKKVDGYKSKNDFVDVCLDSGLNDYQINALLMELFGAGTETSASTI
EWAMTELTKNPKITAKIRSEIQTVVGERSVKESDFPNLPYLEATVKETLRLHPPTPLLLP
RRALETCTILNYTIPKDCQIMVNAWGIGRDPKTWTDPLTFSPERFLNSSVDFRGNDFSLI
PFGAGRRICPGLPIANQFIALLVATFVQNLDWCLPNGMSVDHLIVEEKFGLTLQKEPPLF
IVPKSRV  (SEQ ID NO:49)

FIG. 29

TYROSINE HYDROXYLASE VARIANTS AND METHODS OF USE THEREOF

CROSS-REFERENCE

This application is a national stage application under 35 U.S.C. § 371 of PCT/US2015/052040, filed Sep. 24, 2015, which claims the benefit of U.S. Provisional Patent Application No. 62/056,238, filed Sep. 26, 2014, and U.S. Provisional Patent Application No. 62/094,877, filed Dec. 19, 2014, which applications are incorporated herein by reference in their entirety.

STATEMENT REGARDING FEDERALLY SPONSORED RESEARCH

This invention was made with government support under Grant No. DE-SC0008084 awarded by the U.S. Department of Energy. The government has certain rights in the invention.

INTRODUCTION

L-3,4-dihydroxyphenylalanine (L-DOPA) is an intermediate metabolite in the biosynthetic pathway for the production of many compounds, including the benzylisoquinoline alkaloids (BIA). BIA compounds include, e.g., morphine, codeine, and thebaine. Engineering efforts to produce these compounds in useful quantities in yeast by microbial fermentation have been hindered by inefficiencies in the enzymatic step that converts tyrosine to L-DOPA.

There is a need in the art for methods of producing L-DOPA and BIA compounds in host cells.

SUMMARY

The present disclosure provides a variant tyrosine hydroxylase that provides for increased production of L-DOPA in a host cell that expresses the tyrosine hydroxylase. The present disclosure provides nucleic acids encoding the variant tyrosine hydroxylase, and host cells genetically modified with the nucleic acids. The present disclosure provides methods of making L-DOPA in a host cell. The present disclosure provides methods of making a benzylisoquinoline alkaloid (BIA), or a BIA precursor. The present disclosure provides methods of detecting L-DOPA level in a cell. The present disclosure provides methods of identifying tyrosine hydroxylase variants that provide for increased L-DOPA production; and methods of identifying gene products that provide for increased tyrosine production.

(a) The present disclosure provides a variant tyrosine hydroxylase comprising an amino acid sequence having at least 75%, at least 80%, at least 85%, at least 90%, at least 95%, at least 96%, at least 97%, at least 98%, or at least 99%, amino acid sequence identity to the amino acid sequence set forth in SEQ ID NO:1, and comprising: a) an amino acid substitution for the tryptophan at amino acid 13 of SEQ ID NO:1, or a corresponding amino acid in another tyrosine hydroxylase; and/or b) an amino acid substitution for the phenylalanine at amino acid 309 of SEQ ID NO:1, or a corresponding amino acid in another tyrosine hydroxylase. In some cases, the variant tyrosine hydroxylase exhibits enzymatic activity that is at least 25% higher than the enzymatic activity of the tyrosine hydroxylase of SEQ ID NO:8. In some cases, the variant tyrosine hydroxylase exhibits enzymatic activity that is at least 50% higher than the enzymatic activity of the tyrosine hydroxylase of SEQ ID NO:8. In some cases, the variant tyrosine hydroxylase exhibits enzymatic activity that is at least 10-fold higher than the enzymatic activity of the tyrosine hydroxylase of SEQ ID NO:8. In some cases, the variant tyrosine hydroxylase exhibits enzymatic activity that is at least 50-fold higher than the enzymatic activity of the tyrosine hydroxylase of SEQ ID NO:8. In some cases, the variant tyrosine hydroxylase exhibits enzymatic activity that is at least 25% higher than the enzymatic activity of the tyrosine hydroxylase of SEQ ID NO:1. In some cases, the variant tyrosine hydroxylase exhibits enzymatic activity that is at least 50% higher than the enzymatic activity of the tyrosine hydroxylase of SEQ ID NO:1. In some cases, the variant tyrosine hydroxylase exhibits enzymatic activity that is at least 2-fold higher than the enzymatic activity of the tyrosine hydroxylase of SEQ ID NO:1. In some cases, the variant tyrosine hydroxylase exhibits enzymatic activity that is at least 5-fold higher than the enzymatic activity of the tyrosine hydroxylase of SEQ ID NO:1. In some cases, the variant tyrosine hydroxylase exhibits enzymatic activity that is at least 10-fold higher than the enzymatic activity of the tyrosine hydroxylase of SEQ ID NO:1.

(b) In any of the embodiments described in the paragraph labeled (a) above, or as described elsewhere herein, in some cases, the amino acid substitution for the tryptophan at amino acid 13 of SEQ ID NO:1, or a corresponding amino acid in another tyrosine hydroxylase, is a W13L substitution. In any of the embodiments described in the paragraph labeled (a) above, or as described elsewhere herein, in some cases, the amino acid substitution for the phenylalanine at amino acid 309 of SEQ ID NO:1, or a corresponding amino acid in another tyrosine hydroxylase, is a F309L substitution. In any of the embodiments described in the paragraph labeled (a), above, or as described elsewhere herein, in some cases, the variant tyrosine hydroxylase comprises a W13L and an F309L substitution.

(c) The present disclosure provides a nucleic acid comprising a nucleotide sequence encoding a variant tyrosine hydroxylase of the present disclosure. The present disclosure provides a nucleic acid comprising a nucleotide sequence encoding a polypeptide as described in the paragraphs labeled (a) and (b) above, or as described elsewhere herein. In some cases, the nucleotide sequence is operably linked to a promoter that is functional in a eukaryotic cell. In some cases, the nucleotide sequence is operably linked to a promoter that is functional in a yeast cell. In some cases, the nucleotide sequence is operably linked to a promoter that is functional in a prokaryotic cell. In some cases, the promoter is a constitutive promoter. In some cases, the promoter is an inducible promoter. In some cases, the promoter is a constitutive promoter that is functional in a eukaryotic cell, e.g., a yeast cell. In some cases, the promoter is a constitutive promoter that is functional in a prokaryotic cell. In some cases, the promoter is an inducible promoter that is functional in a eukaryotic cell, e.g., a yeast cell. In some cases, the promoter is an inducible promoter that is functional in a prokaryotic cell.

(d) The present disclosure provides a recombinant expression vector comprising a nucleic acid as described in the paragraph labeled (c) above, or as described elsewhere herein. In some cases, the recombinant expression vector is a virus-based vector. In some cases, the recombinant expression vector provides for expression of the encoded variant tyrosine hydroxylase in a yeast cell. In some cases, the recombinant vector is a yeast artificial chromosome-based vector. In some cases, the recombinant expression vector comprises a high copy number origin of replication. In some cases, the recombinant expression vector is a high copy number vector. In some cases, the recombinant expression vector is a medium copy number vector. In some cases, the recombinant expression vector is a low copy number vector.

The present disclosure provides a genetically modified host cell comprising a nucleic acid as described in the paragraph labeled (c) above, or as described elsewhere herein. The present disclosure provides a genetically modified host cell comprising a recombinant expression vector as described in the paragraph labeled (d) above, or as described elsewhere herein. In some cases, the genetically modified host cell is a prokaryotic cell and is in vitro. In some cases, the genetically modified host cell is a prokaryotic cell and is present in a culture medium in vitro. In some cases, the host cell is a eukaryotic cell; in some cases, the eukaryotic cell is a single-celled organism and is present in a culture medium. In some cases, the host cell is a yeast cell.

(e) The present disclosure provides a method of producing L-3,4-dihydroxyphenylalanine (L-DOPA), the method comprising culturing a host cell genetically modified to express a heterologous tyrosine hydroxylase, wherein the heterologous tyrosine hydroxylase comprises an amino acid sequence having at least 75%, at least 80%, at least 85%, at least 90%, at least 95%, at least 96%, at least 97%, at least 98%, at least 99%, or 100%, amino acid sequence identity to SEQ ID NO:1, wherein the variant tyrosine hydroxylase is produced in the cell, and catalyzes the conversion of tyrosine to L-DOPA. In some cases, the heterologous tyrosine hydroxylase comprises: a) an amino acid substitution for the tryptophan at amino acid 13 of SEQ ID NO:1, or a corresponding amino acid in another tyrosine hydroxylase; and/or b) an amino acid substitution for the phenylalanine at amino acid 309 of SEQ ID NO:1, or a corresponding amino acid in another tyrosine hydroxylase. In some cases, the L-DOPA is produced in an amount of at least 5 µg per milliliter of culture. In some cases, the L-DOPA is produced in an amount of at least 10 mg/L, at least 25 mg/L, at least 50 mg/L, or more than 50 mg/L, culture medium.

The present disclosure provides a method of producing a benzylisoquinoline alkaloid (BIA) or a BIA precursor, the method comprising modifying L-DOPA produced by a method as described in the paragraph labeled (e) above, or as described elsewhere herein. In some cases, the modifying step involves enzymatic modification. In some cases, the modifying step involves chemical modification. In some cases, a genetically modified host cell as described herein is used to produce the BIA or BIA precursor; and the genetically modified host cell is cultured in culture medium with no dopamine. In some cases, a genetically modified host cell as described herein is used to produce the BIA or BIA precursor; and the genetically modified host cell is cultured in culture medium comprising less than 5 mM, less than 1 mM, or less than 0.1 mM dopamine. In some cases, the method comprises purifying the BIA or BIA precursor. In some cases, the BIA or BIA precursor is reticuline. In some cases, the BIA or BIA precursor is thebaine. In some cases, the BIA or BIA precursor is norcocauclorine. In some cases, the BIA or BIA precursor is norlaudanosoline.

The present disclosure provides a method of detecting a level of L-DOPA in a host cell, the method comprising detecting, in a host cell genetically modified to produce a heterologous L-3,4-dihydroxyphenylalanine (L-DOPA) 4,5-dioxygenase (DOD), betalamic acid or a colored or fluorescent product of betalamic acid, produced by action of the heterologous DOD on L-DOPA produced in the cell, wherein the level of L-DOPA produced in the cell is directly proportional to the level of betalamic acid or a colored or fluorescent product of betalamic acid produced in the cell. In some cases, a level of betalamic acid is detected. In some cases, the colored product of betalamic acid is betaxanthin. In some cases, the colored product of betalamic acid is betanidin. In some cases, the fluorescent product of betalamic acid is betaxanthin. In some cases, the method comprises genetically modifying the cell with a nucleic acid comprising a nucleotide sequence encoding a variant benzylisoquinoline alkaloid (BIA) biosynthetic pathway enzyme other than tyrosine hydroxylase, wherein a level of betalamic acid or a colored or fluorescent product of betalamic acid that is lower than the level of the betalamic acid or the colored or fluorescent product of betalamic acid in a control cell not comprising the nucleotide sequence encoding the variant BIA pathway enzyme indicates that the variant BIA pathway enzyme increases flux through the BIA biosynthetic pathway. In some cases, the method comprises modifying the cell with a nucleic acid comprising a nucleotide sequence encoding a variant benzylisoquinoline alkaloid (BIA) biosynthetic pathway enzyme other than tyrosine hydroxylase, wherein a level of betalamic acid or a colored or fluorescent product of betalamic acid that is higher than the level of the betalamic acid or the colored or fluorescent product of betalamic acid in a control cell not comprising the nucleotide sequence encoding the variant BIA pathway enzyme indicates that the variant BIA pathway enzyme decreases flux through the BIA biosynthetic pathway. In some cases, the method comprises mutating the host cell, wherein a level of betalamic acid or a colored or fluorescent product of betalamic acid that is lower than the level of the betalamic acid or the colored or fluorescent product of betalamic acid in a control cell not comprising the mutation indicates that the mutation decreases L-DOPA levels in the cell. In some cases, the method comprises mutating the host cell, wherein a level of betalamic acid or a colored or fluorescent product of betalamic acid that is higher than the level of the betalamic acid or the colored or fluorescent product of betalamic acid in a control cell not comprising the mutation indicates that the mutation increases L-DOPA levels in the cell.

The present disclosure provides a method of identifying a variant tyrosine hydroxylase that exhibits at least 10% greater enzymatic activity than the enzymatic activity of the tyrosine hydroxylase of SEQ ID NO:1, the method comprising: detecting, in a host cell genetically modified with a test tyrosine hydroxylase and a heterologous L-3,4-dihydroxyphenylalanine (L-DOPA) 4,5-dioxygenase (DOD), betalamic acid or a colored or fluorescent product of betalamic acid produced by action of the heterologous 4,5-dioxygenase on L-DOPA produced by action of the test tyrosine hydroxylase, wherein a level of betalamic acid or a colored or fluorescent product of betalamic acid produced that is higher than the level of betalamic acid or a colored or fluorescent product of betalamic acid produced in a control host cell genetically modified with the tyrosine hydroxylase of SEQ ID NO:1 indicates that the test tyrosine hydroxylase is a variant tyrosine hydroxylase that exhibits at least 10% greater enzymatic activity than the enzymatic activity of the tyrosine hydroxylase of SEQ ID NO:1. In some cases, a level of betalamic acid is detected. In some cases, a level of betanidin is detected. In some cases, a level of betaxanthin is detected. In some cases, the betaxanthin is detected colorimetrically. In some cases, the detecting step comprises detecting betaxanthin fluorescence. In some cases, the host cell is a eukaryotic cell. In some cases, the eukaryotic cell is a yeast cell. In some cases, the method comprises isolating a genetically modified host cell that comprises a variant tyrosine hydroxylase identified as exhibiting at least 10% greater enzymatic activity than the enzymatic activity of the tyrosine hydroxylase of SEQ ID NO:1. In some cases, the cell is isolated using fluorescence activated cell sorting. In some cases, the DOPA 4,5-dioxygenase comprises an amino acid sequence having at least 75%, at least 80%, at least 85%, at least 90%, at least 95%, at least 96%, at least 97%, at least 98%, at least 99%, or 100%, amino acid sequence identity to the amino acid sequence set forth in SEQ ID NO:9.

The present disclosure provides a method of identifying a gene product that increases tyrosine production in a cell, the method comprising: detecting, in a host cell genetically modified with: i) a test modified gene; ii) a heterologous tyrosine hydroxylase; and iii) a heterologous L-3,4-dihydroxyphenylalanine (L-DOPA) 4,5-dioxygenase (DOD), betaxanthin produced by action of the heterologous 4,5-dioxygenase on L-DOPA produced by action of the tyrosine hydroxylase on tyrosine produced by action of the gene product, wherein a level of betaxanthin produced that is higher than the level of betaxanthin produced in a control host cell genetically modified with the heterologous tyrosine hydroxylase and the heterologous L-DOPA-4,5-dioxygenase indicates that the test gene product is a gene product that increases tyrosine production in the cell. In some cases, the test modified gene comprises a modification that renders the test gene non-functional. In some cases, the modification is a deletion of all or a portion of the test gene. In some cases, the test modified gene comprises a modification that increases the level and/or activity of a product of the test gene. In some cases, the modification comprises one or more nucleotide substitutions relative to a parent unmodified gene. In some cases, the heterologous tyrosine hydroxylase comprises an amino acid sequence having at least 80%, at least 85%, at least 90%, at least 95%, at least 96%, at least 97%, at least 98%, at least 99%, or 100%, amino acid sequence identity to SEQ ID NO:1 or SEQ ID NO:8.

BRIEF DESCRIPTION OF THE DRAWINGS

FIG. 6A-6B provide an alignment of amino acid sequences of tyrosine hydroxylases from *Beta vulgaris*, *Amaranthus cruentus*, *Mirabilis jalapa*, and *Celosia cristata*.

FIG. 10A-10E depict production of (S)-reticuline from glucose.

FIG. 13A-13C provide amino acid sequences of exemplary variant tyrosine hydroxylases.

FIG. 14A-14C provide amino acid sequences of exemplary DOPA decarboxylases.

FIG. 15A-15C provide amino acid sequences of exemplary tyramine oxidases.

FIG. 16A-16B provide amino acid sequences of exemplary (S)-norcoclaurine synthases.

FIG. 17A-17B provide amino acid sequences of exemplary 6OMT polypeptides.

FIG. 18A-18B provide amino acid sequences of exemplary CNMT polypeptides.

FIG. 19 provides amino acid sequences of an exemplary (S)—N-methylcoclaurine-3'-hydroxylase.

FIG. 20 provides an amino acid sequence of a K229L variant of 3-deoxy-D-arabino-heptulosonate-7-phosphate (DAHP) synthase.

FIG. 21A-21B provide amino acid sequences of exemplary norcoclaurine synthases.

FIG. 22 provides an amino acid sequence of AbPPO2 tyrosinase.

FIG. 23A-23B provide amino acid sequences of DOPA 4,5-dioxygenase.

FIG. 25A-25F provide a comparison of CYP76AD1 with seven paralogs from *B. vulgaris*. A multiple sequence alignment of CYP76AD1 with seven paralogs from *B. vulgaris* is provided in FIG. 25A-25E; the percent amino acid sequence identity between the enzymes is provided in FIG. 25F.

FIG. 26A-26B provides Table 1.

FIG. 27 provides Table 2.

FIG. 28 provides Table 3.

FIG. 29 provides an amino acid sequence of an exemplary NMCH (CYP70B1) polypeptide.

DEFINITIONS

Figure 1A:
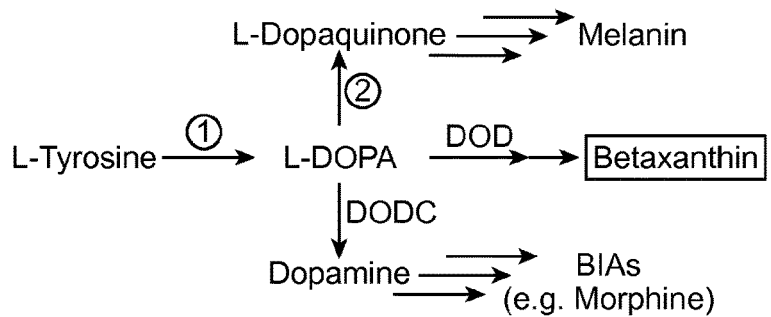
FIG. 1A-1C depict development of an enzyme-coupled L-DOPA biosensor.

The terms "nucleic acid," used herein, refer to a polymeric form of nucleotides of any length, either ribonucleotides or deoxynucleotides. Thus, this term includes, but is not limited to, single-, double-, or multi-stranded DNA or RNA, genomic DNA, cDNA, DNA-RNA hybrids, or a polymer comprising purine and pyrimidine bases or other natural, chemically or biochemically modified, non-natural, or derivatized nucleotide bases.

The terms "peptide," "polypeptide," and "protein" are used interchangeably herein, and refer to a polymeric form of amino acids of any length, which can include coded and non-coded amino acids, chemically or biochemically modified or derivatized amino acids, and polypeptides having modified peptide backbones.

As used herein, the term "heterologous" refers to what is not normally found in nature. The term "heterologous nucleotide sequence" refers to a nucleotide sequence not normally found in a given cell in nature. As such, a heterologous nucleotide sequence may be: (a) foreign to its host cell (i.e., is "exogenous" to the cell); (b) naturally found in the host cell (i.e., "endogenous") but present at an unnatural quantity in the cell (i.e., greater or lesser quantity than naturally found in the host cell); or (c) be naturally found in the host cell but positioned outside of its natural locus. The term "heterologous enzyme" refers to an enzyme that is not normally found in a given cell in nature. The term encompasses an enzyme that is: (a) exogenous to a given cell (i.e., encoded by a nucleotide sequence that is not naturally present in the host cell or not naturally present in a given context in the host cell); and (b) naturally found in the host cell (e.g., the enzyme is encoded by a nucleotide sequence that is endogenous to the cell) but that is produced in an unnatural amount (e.g., greater or lesser than that naturally found) in the host cell.

"Operably linked" refers to an arrangement of elements wherein the components so described are configured so as to perform their usual function. Thus, control sequences operably linked to a coding sequence are capable of effecting the expression of the coding sequence. The control sequences need not be contiguous with the coding sequence, so long as they function to direct the expression thereof. Thus, for example, intervening untranslated yet transcribed sequences can be present between a promoter sequence and the coding sequence and the promoter sequence can still be considered "operably linked" to the coding sequence.

A "host cell," as used herein, denotes an in vivo or in vitro eukaryotic cell, a prokaryotic cell, or a cell from a multicellular organism (e.g., a cell line) cultured as a unicellular entity, which eukaryotic or prokaryotic cells can be, or have been, used as recipients for a nucleic acid (e.g., an expression vector that comprises a nucleotide sequence encoding one or more biosynthetic pathway gene products such as BIA pathway gene products), and include the progeny of the original cell which has been genetically modified by the nucleic acid. It is understood that the progeny of a single cell may not necessarily be completely identical in morphology or in genomic or total DNA complement as the original parent, due to natural, accidental, or deliberate mutation.

A "genetically modified host cell" (also referred to as a "recombinant host cell") is a host cell into which has been introduced a heterologous nucleic acid, e.g., an expression vector. For example, a prokaryotic host cell is a genetically modified prokaryotic host cell (e.g., a bacterium), by virtue of introduction into a suitable prokaryotic host cell of a heterologous nucleic acid, e.g., an exogenous nucleic acid that is foreign to (not normally found in nature in) the prokaryotic host cell, or a recombinant nucleic acid that is not normally found in the prokaryotic host cell; and a eukaryotic host cell is a genetically modified eukaryotic host cell, by virtue of introduction into a suitable eukaryotic host cell of a heterologous nucleic acid, e.g., an exogenous nucleic acid that is foreign to the eukaryotic host cell, or a recombinant nucleic acid that is not normally found in the eukaryotic host cell.

As used herein, a "cell-free system" refers to a cell lysate, cell extract or other preparation in which substantially all of the cells in the preparation have been disrupted or otherwise processed so that all or selected cellular components, e.g., organelles, proteins, nucleic acids, the cell membrane itself (or fragments or components thereof), or the like, are released from the cell or resuspended into an appropriate medium and/or purified from the cellular milieu. Cell-free systems can include reaction mixtures prepared from purified or isolated proteins and suitable reagents and buffers.

The term "conservative amino acid substitution" refers to the interchangeability in proteins of amino acid residues having similar side chains. For example, a group of amino acids having aliphatic side chains consists of glycine, alanine, valine, leucine, and isoleucine; a group of amino acids having aliphatic-hydroxyl side chains consists of serine and threonine; a group of amino acids having amide containing side chains consisting of asparagine and glutamine; a group of amino acids having aromatic side chains consists of phenylalanine, tyrosine, and tryptophan; a group of amino acids having basic side chains consists of lysine, arginine, and histidine; a group of amino acids having acidic side chains consists of glutamate and aspartate; and a group of amino acids having sulfur containing side chains consists of cysteine and methionine. Exemplary conservative amino acid substitution groups are: valine-leucine-isoleucine, phenylalanine-tyrosine, lysine-arginine, alanine-valine, and asparagine-glutamine.

A polynucleotide or polypeptide has a certain percent "sequence identity" to another polynucleotide or polypeptide, meaning that, when aligned, that percentage of bases or amino acids are the same, and in the same relative position, when comparing the two sequences. Sequence identity can be determined in a number of different manners. To determine sequence identity, sequences can be aligned using various methods and computer programs (e.g., BLAST, T-COFFEE, MUSCLE, MAFFT, etc.), available over the world wide web at sites including ncbi.nlm.nili.gov/BLAST, ebi.ac.uldTools/msa/tcoffee/, ebi.ac.uk/Tools/msa/muscle/, mafft.cbrc.jp/alignment/software/. See, e.g., Altschul et al. (1990), J. Mol. Bioi. 215:403-10.

Before the present invention is further described, it is to be understood that this invention is not limited to particular embodiments described, as such may, of course, vary. It is also to be understood that the terminology used herein is for the purpose of describing particular embodiments only, and is not intended to be limiting, since the scope of the present invention will be limited only by the appended claims.

Where a range of values is provided, it is understood that each intervening value, to the tenth of the unit of the lower limit unless the context clearly dictates otherwise, between the upper and lower limit of that range and any other stated or intervening value in that stated range, is encompassed within the invention. The upper and lower limits of these smaller ranges may independently be included in the smaller ranges, and are also encompassed within the invention, subject to any specifically excluded limit in the stated range. Where the stated range includes one or both of the limits, ranges excluding either or both of those included limits are also included in the invention.

Unless defined otherwise, all technical and scientific terms used herein have the same meaning as commonly understood by one of ordinary skill in the art to which this invention belongs. Although any methods and materials similar or equivalent to those described herein can also be used in the practice or testing of the present invention, the preferred methods and materials are now described. All publications mentioned herein are incorporated herein by reference to disclose and describe the methods and/or materials in connection with which the publications are cited.

It must be noted that as used herein and in the appended claims, the singular forms "a," "an," and "the" include plural referents unless the context clearly dictates otherwise. Thus, for example, reference to "a tyrosine hydroxylase" includes a plurality of such tyrosine hydroxylases and reference to "the expression vector" includes reference to one or more expression vectors and equivalents thereof known to those skilled in the art, and so forth. It is further noted that the claims may be drafted to exclude any optional element. As such, this statement is intended to serve as antecedent basis for use of such exclusive terminology as "solely," "only" and the like in connection with the recitation of claim elements, or use of a "negative" limitation.

It is appreciated that certain features of the invention, which are, for clarity, described in the context of separate embodiments, may also be provided in combination in a single embodiment. Conversely, various features of the invention, which are, for brevity, described in the context of a single embodiment, may also be provided separately or in any suitable sub-combination. All combinations of the embodiments pertaining to the invention are specifically embraced by the present invention and are disclosed herein just as if each and every combination was individually and explicitly disclosed. In addition, all sub-combinations of the various embodiments and elements thereof are also specifically embraced by the present invention and are disclosed herein just as if each and every such sub-combination was individually and explicitly disclosed herein.

The publications discussed herein are provided solely for their disclosure prior to the filing date of the present application. Nothing herein is to be construed as an admission that the present invention is not entitled to antedate such publication by virtue of prior invention. Further, the dates of publication provided may be different from the actual publication dates which may need to be independently confirmed.

DETAILED DESCRIPTION

The present disclosure provides a variant tyrosine hydroxylase that provides for increased production of L-DOPA in a host cell that expresses the tyrosine hydroxylase. The present disclosure provides nucleic acids encoding the variant tyrosine hydroxylase, and host cells genetically modified with the nucleic acids. The present disclosure provides methods of making L-DOPA in a host cell. The present disclosure provides methods of making a BIA compound or a BIA precursor. The present disclosure provides methods of detecting L-DOPA level in a cell. The present disclosure provides methods of identifying tyrosine hydroxylase variants that provide for increased L-DOPA production; and methods of identifying gene products that provide for increased tyrosine production.

Variant Tyrosine Hydroxylase

The present disclosure provides a variant tyrosine hydroxylase comprising an amino acid sequence having at least 75% amino acid sequence identity to the amino acid sequence set forth in SEQ ID NO:1, and comprising: a) an amino acid substitution for the tryptophan at amino acid 13 of SEQ ID NO:1, or a corresponding amino acid in another tyrosine hydroxylase; and/or b) an amino acid substitution for the phenylalanine at amino acid 309 of SEQ ID NO:1, or a corresponding amino acid in another tyrosine hydroxylase. SEQ ID NOs:1, 2, 3, and 4 are specifically excluded.

A variant tyrosine hydroxylase of the present disclosure comprises an amino acid sequence having at least 75%, at least 80%, at least 85%, at least 90%, at least 95%, at least 96%, at least 97%, at least 98%, or at least 99%, amino acid sequence identity to the amino acid sequence set forth in SEQ ID NO:1 (and depicted in FIG. 6A-6B), and comprises an amino acid substitution of the tryptophan at amino acid 13 (W13) of SEQ ID NO:1, or a corresponding amino acid in another tyrosine hydroxylase; and/or b) an amino acid substitution for the phenylalanine at amino acid 309 (F309) of SEQ ID NO:1, or a corresponding amino acid in another tyrosine hydroxylase.

As depicted in FIG. 6A-6B, W13 of SEQ ID NO:1 corresponds to W13 in SEQ ID NOs:2 and 4. As depicted in FIG. 6A-6B, F309 of SEQ ID NO:1 corresponds to F308 of SEQ ID NO:2; F309 of SEQ ID NO:1 corresponds to F308 in SEQ ID NO:3; and F309 of SEQ ID NO:1 corresponds to F306 in SEQ ID NO:4. Those skilled in the art would understand that, given an alignment as depicted in FIG. 6A-6B, a residue corresponding to W13 of SEQ ID NO:1, or a residue corresponding to F309 of SEQ ID NO:1, could be readily identified.

In some cases, a variant tyrosine hydroxylase of the present disclosure differs in amino acid sequence from one of SEQ ID NOs:1, 2, 3, or 4 by no more than 1 amino acid (aa), no more than 2 aa, no more than 3 aa, no more than 4 aa, no more than 5 aa, no more than 10 aa, no more than 15 aa, no more than 20 aa, no more than 25 aa, no more than 30 aa, no more than 40 aa, no more than 45 aa, or no more than 50 aa. In some cases, a variant tyrosine hydroxylase of the present disclosure differs in amino acid sequence from SEQ ID NO:1 by no more than 1 amino acid (aa), no more than 2 aa, no more than 3 aa, no more than 4 aa, no more than 5 aa, no more than 10 aa, no more than 15 aa, no more than 20 aa, no more than 25 aa, no more than 30 aa, no more than 40 aa, no more than 45 aa, or no more than 50 aa.

In some cases, a variant tyrosine hydroxylase of the present disclosure comprises an amino acid sequence having at least 75%, at least 80%, at least 85%, at least 90%, at least 95%, at least 98%, or at least 99%, amino acid sequence identity to the amino acid sequence set forth in SEQ ID NO:1 (and depicted in FIG. 6A-6B), and comprises an amino acid substitution of W13, or a corresponding amino acid in another tyrosine hydroxylase; and does not comprise an amino acid substitution of F309 of SEQ ID NO:1, or a corresponding amino acid in another tyrosine hydroxylase. In some cases, the amino acid substitution of W13 is a W13L substitution. In some cases, the amino acid substitution of W13 is a W13V substitution. In some cases, the amino acid substitution of W13 is a W13I substitution.

In some cases, a variant tyrosine hydroxylase of the present disclosure comprises an amino acid sequence having at least 75%, at least 80%, at least 85%, at least 90%, at least 95%, at least 98%, or at least 99%, amino acid sequence identity to the amino acid sequence set forth in SEQ ID NO:1 (and depicted in FIG. 6A-6B), and comprises an amino acid substitution F309 of SEQ ID NO:1, or a corresponding amino acid in another tyrosine hydroxylase; and does not comprise an amino acid substitution of W13, or a corresponding amino acid in another tyrosine hydroxylase. In some cases, the amino acid substitution at F309 is an F309L substitution. In some cases, the amino acid substitution of F309 is a F309I substitution. In some cases, the amino acid substitution of F309 is a F309V substitution. In some cases, the amino acid substitution of F309 is a F309S substitution.

In some cases, a variant tyrosine hydroxylase of the present disclosure has at least 75%, at least 80%, at least 85%, at least 90%, at least 95%, at least 98%, or at least 99%, amino acid sequence identity to the amino acid sequence set forth in SEQ ID NO:1 (and depicted in FIG. 6A-6B), and comprises an amino acid substitution of W13, or a corresponding amino acid in another tyrosine hydroxylase; and comprises an amino acid substitution F309 of SEQ ID NO:1, or a corresponding amino acid in another tyrosine hydroxylase. In some cases, the amino acid substitution of W13 is a W13L substitution. In some cases, the amino acid substitution of W13 is a W13V substitution. In some cases, the amino acid substitution of W13 is a W13I substitution.

In some cases, the amino acid substitution at F309 is an F309L substitution. In some cases, the amino acid substitution of F309 is a F309V substitution. In some cases, the amino acid substitution of F309 is a F309I substitution. In some cases, the amino acid substitution of F309 is a F309S substitution. For example, in some cases, the variant tyrosine hydroxylase comprises a W13L substitution and an F309L substitution.

In some cases, a variant tyrosine hydroxylase of the present disclosure comprises an amino acid sequence having at least 75%, at least 80%, at least 85%, at least 90%, at least 95%, at least 98%, or at least 99%, amino acid sequence identity to the amino acid sequence set forth in SEQ ID NO:2 or 3 (and depicted in FIG. 6A-6B), and comprises an amino acid substitution of W13, or a corresponding amino acid in another tyrosine hydroxylase; and does not comprise an amino acid substitution of F308 of SEQ ID NO:2 or 3, or a corresponding amino acid in another tyrosine hydroxylase. In some cases, the amino acid substitution of W13 is a W13L substitution. In some cases, the amino acid substitution of W13 is a W13V substitution. In some cases, the amino acid substitution of W13 is a W13I substitution.

In some cases, a variant tyrosine hydroxylase of the present disclosure comprises an amino acid sequence having at least 75%, at least 80%, at least 85%, at least 90%, at least 95%, at least 98%, or at least 99%, amino acid sequence identity to the amino acid sequence set forth in SEQ ID NO:2 or 3 (and depicted in FIG. 6A-6B), and comprises an amino acid substitution F308 of SEQ ID NO:2 or 3, or a corresponding amino acid in another tyrosine hydroxylase; and does not comprise an amino acid substitution of W13, or a corresponding amino acid in another tyrosine hydroxylase. In some cases, the amino acid substitution at F308 is an F308L substitution. In some cases, the amino acid substitution of F308 is a F308I substitution. In some cases, the amino acid substitution of F308 is a F308V substitution. In some cases, the amino acid substitution of F308 is a 308S substitution.

In some cases, a variant tyrosine hydroxylase of the present disclosure has at least 75%, at least 80%, at least 85%, at least 90%, at least 95%, at least 98%, or at least 99%, amino acid sequence identity to the amino acid sequence set forth in SEQ ID NO:2 or 3 (and depicted in FIG. 6A-6B), and comprises an amino acid substitution of W13, or a corresponding amino acid in another tyrosine hydroxylase; and comprises an amino acid substitution F308 of SEQ ID NO:2 or 3, or a corresponding amino acid in another tyrosine hydroxylase. In some cases, the amino acid substitution of W13 is a W13L substitution. In some cases, the amino acid substitution of W13 is a W13V substitution. In some cases, the amino acid substitution of W13 is a W13I substitution. In some cases, the amino acid substitution at F308 is an F308L substitution. In some cases, the amino acid substitution of F308 is a F308V substitution. In some cases, the amino acid substitution of F308 is a F308I substitution. In some cases, the amino acid substitution of F308 is a 308S substitution. For example, in some cases, the variant tyrosine hydroxylase comprises a W13L substitution and an F308L substitution.

In some cases, a variant tyrosine hydroxylase of the present disclosure comprises an amino acid sequence having at least 75%, at least 80%, at least 85%, at least 90%, at least 95%, at least 98%, or at least 99%, amino acid sequence identity to the amino acid sequence set forth in SEQ ID NO:4 (and depicted in FIG. 6A-6B), and comprises an amino acid substitution of W13, or a corresponding amino acid in another tyrosine hydroxylase; and does not comprise an amino acid substitution of F306 of SEQ ID NO:4, or a corresponding amino acid in another tyrosine hydroxylase. In some cases, the amino acid substitution of W13 is a W13L substitution. In some cases, the amino acid substitution of W13 is a W13V substitution. In some cases, the amino acid substitution of W13 is a W13I substitution.

In some cases, a variant tyrosine hydroxylase of the present disclosure comprises an amino acid sequence having at least 75%, at least 80%, at least 85%, at least 90%, at least 95%, at least 98%, or at least 99%, amino acid sequence identity to the amino acid sequence set forth in SEQ ID NO:4 (and depicted in FIG. 6A-6B), and comprises an amino acid substitution F306 of SEQ ID NO:4, or a corresponding amino acid in another tyrosine hydroxylase; and does not comprise an amino acid substitution of W13, or a corresponding amino acid in another tyrosine hydroxylase. In some cases, the amino acid substitution at F306 is an F308L substitution. In some cases, the amino acid substitution of F306 is a F306I substitution. In some cases, the amino acid substitution of F306 is a F306V substitution. In some cases, the amino acid substitution of F306 is a F306S substitution.

In some cases, a variant tyrosine hydroxylase of the present disclosure has at least 75%, at least 80%, at least 85%, at least 90%, at least 95%, at least 98%, or at least 99%, amino acid sequence identity to the amino acid sequence set forth in SEQ ID NO:4 (and depicted in FIG. 6A-6B), and comprises an amino acid substitution of W13, or a corresponding amino acid in another tyrosine hydroxylase; and comprises an amino acid substitution F306 of SEQ ID NO:4, or a corresponding amino acid in another tyrosine hydroxylase. In some cases, the amino acid substitution of W13 is a W13L substitution. In some cases, the amino acid substitution of W13 is a W13V substitution. In some cases, the amino acid substitution of W13 is a W13I substitution. In some cases, the amino acid substitution at F306 is an F306L substitution. In some cases, the amino acid substitution of F306 is a F306V substitution. In some cases, the amino acid substitution of F306 is a F306I substitution. In some cases, the amino acid substitution of F306 is a F306S substitution. For example, in some cases, the variant tyrosine hydroxylase comprises a W13L substitution and an F306L substitution.

In some cases, a variant tyrosine hydroxylase of the present disclosure has at least 75%, at least 80%, at least 85%, at least 90%, at least 95%, at least 98%, or at least 99%, amino acid sequence identity to the amino acid sequence set forth in SEQ ID NO:5 (and depicted in FIG. 13A), where the variant tyrosine hydroxylase comprises an L at amino acid 13 of SEQ ID NO:5, and an F at amino acid 309 of SEQ ID NO:5. In some cases, a variant tyrosine hydroxylase of the present disclosure has at least 75%, at least 80%, at least 85%, at least 90%, at least 95%, at least 98%, or at least 99%, amino acid sequence identity to the amino acid sequence set forth in SEQ ID NO:5 (and depicted in FIG. 13A), where the variant tyrosine hydroxylase comprises an I (isoleucine) at amino acid 13 of SEQ ID NO:5, and an F at amino acid 309 of SEQ ID NO:5.

In some cases, a variant tyrosine hydroxylase of the present disclosure has at least 75%, at least 80%, at least 85%, at least 90%, at least 95%, at least 98%, or at least 99%, amino acid sequence identity to the amino acid sequence set forth in SEQ ID NO:6 (and depicted in FIG. 13B), where the variant tyrosine hydroxylase comprises a W at amino acid 13 of SEQ ID NO:6, and an L at amino acid 309 of SEQ ID NO:6. In some cases, a variant tyrosine hydroxylase of the present disclosure has at least 75%, at least 80%, at least 85%, at least 90%, at least 95%, at least 98%, or at least 99%, amino acid sequence identity to the amino acid sequence set forth in SEQ ID NO:6 (and depicted in FIG. 13B), where the variant tyrosine hydroxylase comprises a W at amino acid 13 of SEQ ID NO:6, and an I (isoleucine) at amino acid 309 of SEQ ID NO:6.

In some cases, a variant tyrosine hydroxylase of the present disclosure has at least 75%, at least 80%, at least 85%, at least 90%, at least 95%, at least 98%, or at least 99%, amino acid sequence identity to the amino acid sequence set forth in SEQ ID NO:7 (and depicted in FIG. 13C), where the variant tyrosine hydroxylase comprises an L at amino acid 13 of SEQ ID NO:7, and an L at amino acid 309 of SEQ ID NO:7. In some cases, a variant tyrosine hydroxylase of the present disclosure has at least 75%, at least 80%, at least 85%, at least 90%, at least 95%, at least 98%, or at least 99%, amino acid sequence identity to the amino acid sequence set forth in SEQ ID NO:7 (and depicted in FIG. 13C), where the variant tyrosine hydroxylase comprises an I (isoleucine) at amino acid 13 of SEQ ID NO:7, and an I (isoleucine) at amino acid 309 of SEQ ID NO:7.

In some cases, a variant tyrosine hydroxylase of the present disclosure exhibits higher enzymatic activity than a tyrosine hydroxylase of SEQ ID NO:8 (AbPPO2). For example, a variant tyrosine hydroxylase of the present disclosure exhibits at least 10%, at least 15%, at least 20%, at least 25%, at least 30%, at least 35%, at least 40%, at least 45%, at least 50%, at least 75%, at least 100% (or 2-fold), at least 2.5-fold, at least 5-fold, at least 7.5-fold, at least 10-fold, from 10-fold to 15-fold, from 15-fold to 20-fold, from 20-fold to 25-fold, or from 25-fold to 50-fold, or greater than 50-fold, higher enzymatic activity than a tyrosine hydroxylase of SEQ ID NO:8. Enzymatic activity of a tyrosine hydroxylase refers to catalytic conversion of tyrosine to L-3,4-dihydroxyphenylalanine (L-DOPA).

In some cases, a variant tyrosine hydroxylase of the present disclosure exhibits higher enzymatic activity than a tyrosine hydroxylase of SEQ ID NO:1 (CYP76AD1). For example, a variant tyrosine hydroxylase of the present disclosure exhibits at least 10%, at least 15%, at least 20%, at least 25%, at least 30%, at least 35%, at least 40%, at least 45%, at least 50%, at least 75%, at least 100% (or 2-fold), at least 2.5-fold, at least 5-fold, at least 7.5-fold, at least 10-fold, from 10-fold to 15-fold, from 15-fold to 20-fold, from 20-fold to 25-fold, or from 25-fold to 50-fold, or greater than 50-fold, higher enzymatic activity than a tyrosine hydroxylase of SEQ ID NO:1. Enzymatic activity of a tyrosine hydroxylase refers to catalytic conversion of tyrosine to L-DOPA.

Whether the tyrosine hydroxylase activity of a variant tyrosine hydroxylase is higher than the tyrosine hydroxylase activity of a tyrosine hydroxylase of SEQ ID NO:1 or SEQ ID NO:8 can be determined using any known assay for production of L-DOPA. In some cases, the tyrosine hydroxylase activity of a variant tyrosine hydroxylase is determined using an assay, as described herein, that uses DOPA 4,5-dioxygenase (DOD) to convert L-DOPA (produced by the action of a test variant tyrosine hydroxylase on tyrosine) to betaxanthin; and detecting the amount of betaxanthin produced. The amount of betaxanthin produced in this assay is directly proportional to the tyrosine hydroxylase activity of the tyrosine hydroxylase. The amount of betaxanthin can be determined using a colorimetric assay or a fluorescent assay.

In some cases, a variant tyrosine hydroxylase of the present disclosure exhibits reduced DOPA oxidase activity, compared to DOPA oxidase activity of a tyrosine hydroxylase of SEQ ID NO:1 or SEQ ID NO:8. For example, in some cases, a variant tyrosine hydroxylase of the present disclosure exhibits 50% or less, 40% or less, 30% or less, 25% or less, 10% or less, 5% or less, or 1% or less, of the DOPA oxidase activity exhibited by a tyrosine hydroxylase of SEQ ID NO:1 or SEQ ID NO:8. In some cases, a variant tyrosine hydroxylase of the present disclosure does not exhibit detectable DOPA oxidase activity.

Figure 2:
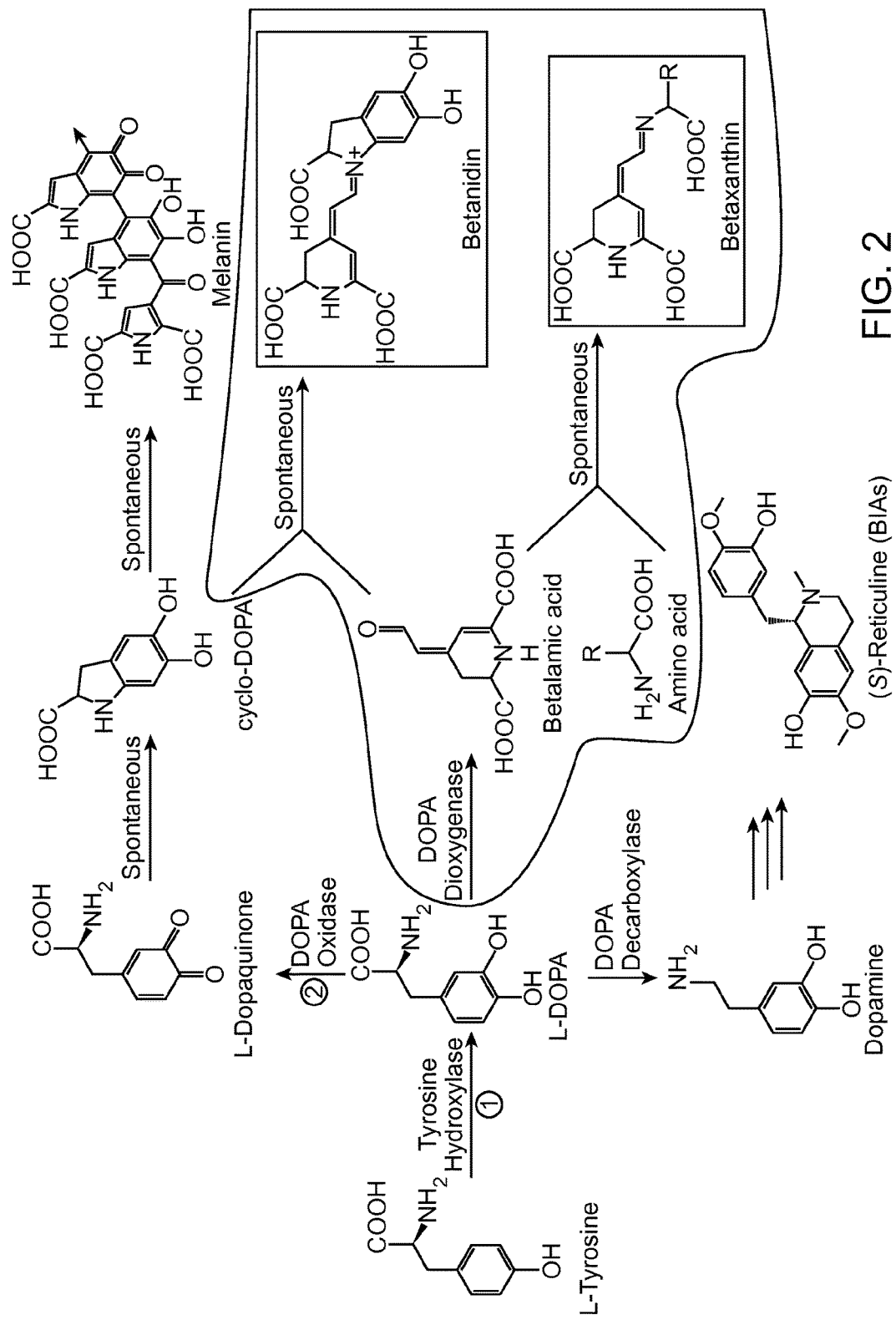
FIG. 2 is a schematic diagram showing conversion of L-tyrosine to L-DOPA by action of tyrosine hydroxylase, and conversion of L-DOPA to dopamine by action of DOPA decarboxylase. L-DOPA concentration can be measured using DOPA 4,5-dioxygenase (DOD), which converts L-DOPA to betaxanthin, a highly fluorescent and yellow-colored plant pigment.

Whether the DOPA oxidase enzymatic activity of a variant tyrosine hydroxylase of the present disclosure is lower than the DOPA oxidase enzymatic activity of a tyrosine hydroxylase of SEQ ID NO:1 or SEQ ID NO:8 can be determined using any known assay for production of dopaquinone. In some cases, the DOPA oxidase enzymatic activity of a variant tyrosine hydroxylase is determined using an assay, as described herein, and as depicted in FIG. 2; where the assay involves detecting the amount of betanidin produced. The amount of betanidin produced in this assay is directly proportional to the DOPA oxidase activity of the tyrosine hydroxylase. The amount of betanidin can be determined using a colorimetric assay.

In some cases, a variant tyrosine hydroxylase of the present disclosure exhibits a ratio of tyrosine hydroxylase activity to DOPA oxidase activity that is at least 5:1, at least 10:1, at least 50:1, at least 100:1, at least 200:1, at least 250:1, at least 500:1, or greater than 500:1. The ratio tyrosine hydroxylase activity to DOPA oxidase activity can be determined in an assay as described herein, where the ratio of betaxanthin (indicative of tyrosine hydroxylase activity) to betanidin (indicative of DOPA oxidase activity) is detected.

Nucleic Acids

The present disclosure provides a nucleic acid (including an isolated nucleic acid, or a recombinant nucleic acid) that comprises a nucleotide sequence that encodes a variant tyrosine hydroxylase of the present disclosure. In some cases, a subject nucleic acid is isolated. In some cases, a nucleic acid of the present disclosure is present in a host cell in vitro.

A nucleic acid comprising a nucleotide sequence encoding a variant tyrosine hydroxylase of the present disclosure will in some embodiments be included in a recombinant expression vector. A nucleic acid comprising a nucleotide sequence encoding a variant tyrosine hydroxylase of the present disclosure will in some embodiments be RNA, e.g., in vitro synthesized RNA.

In some cases, a subject nucleic acid provides for production of a variant tyrosine hydroxylase of the present disclosure in a eukaryotic cell. In some cases, a subject nucleic acid provides for production of a variant tyrosine hydroxylase of the present disclosure in a prokaryotic cell. In other cases, a subject nucleic acid provides for amplification of the variant tyrosine hydroxylase-encoding nucleic acid.

A nucleotide sequence encoding a variant tyrosine hydroxylase of the present disclosure can be operably linked to a transcriptional control element, e.g., a promoter, an enhancer, a transcription terminator, etc. Depending on the host/vector system utilized, any of a number of suitable transcription and translation control elements, including constitutive and inducible promoters, transcription enhancer elements, transcription terminators, etc. may be used in the expression vector (see, e.g., Bitter et al. (1987) Methods in Enzymology, 153:516-544). Suitable promoter and enhancer elements are known in the art.

In some cases, e.g., for expression in a yeast cell, a suitable promoter is a constitutive promoter such as an ADH1 promoter, a PGK1 promoter, an ENO promoter, a PYK1 promoter and the like; or a regulatable promoter such as a GAL1 promoter, a GAL10 promoter, an ADH2 promoter, a PHO5 promoter, a CUP1 promoter, a GALT promoter, a MET25 promoter, a MET3 promoter, a CYC1 promoter, a HIS3 promoter, an ADH1 promoter, a PGK promoter, a GAPDH promoter, an ADC1 promoter, a TRP1 promoter, a URA3 promoter, a LEU2 promoter, an ENO promoter, a TP1 promoter, and AOX1 (e.g., for use in *Pichia*). Selection of the appropriate vector and promoter is well within the level of ordinary skill in the art.

For expression in a bacterial cell, suitable promoters include, but are not limited to, pLac, T3, T7, gpt, lambda P and trc. Suitable promoters for use in prokaryotic host cells include, but are not limited to, a bacteriophage T7 RNA polymerase promoter; a trp promoter; a lac operon promoter; a hybrid promoter, e.g., a lac/tac hybrid promoter, a tac/trc hybrid promoter, a trp/lac promoter, a T7/lac promoter; a trc promoter; a tac promoter, and the like; an araBAD promoter; in vivo regulated promoters, such as an ssaG promoter or a related promoter (see, e.g., U.S. Patent Publication No. 20040131637), a pagC promoter (Pulkkinen and Miller, *J. Bacteriol.*, 1991: 173(1): 86-93; Alpuche-Aranda et al., *Proc. Natl. Acad. Sci. USA,* 1992; 89(21): 10079-83), a nirB promoter (Harborne et al. (1992) *Mol. Micro.* 6:2805-2813), and the like (see, e.g., Dunstan et al. (1999) *Infect. Immun.* 67:5133-5141; McKelvie et al. (2004) *Vaccine* 22:3243-3255; and Chatfield et al. (1992) *Biotechnol.* 10:888-892); a sigma70 promoter, e.g., a consensus sigma70 promoter (see, e.g., GenBank Accession Nos. AX798980, AX798961, and AX798183); a stationary phase promoter, e.g., a dps promoter, an spy promoter, and the like; a promoter derived from the pathogenicity island SPI-2 (see, e.g., WO96/17951); an actA promoter (see, e.g., Shetron-Rama et al. (2002) *Infect. Immun.* 70:1087-1096); an rpsM promoter (see, e.g., Valdivia and Falkow (1996). *Mol. Microbiol.* 22:367); a tet promoter (see, e.g., Hillen, W. and Wissmann, A. (1989) In Saenger, W. and Heinemann, U. (eds), *Topics in Molecular and Structural Biology, Protein-Nucleic Acid Interaction.* Macmillan, London, UK, Vol. 10, pp. 143-162); an SP6 promoter (see, e.g., Melton et al. (1984) *Nucl. Acids Res.* 12:7035); and the like. Suitable strong promoters for use in prokaryotes such as *Escherichia coli* include, but are not limited to Trc, Tac, T5, T7, and $P_{Lambda}$. Non-limiting examples of operators for use in bacterial host cells include a lactose promoter operator (Lad repressor protein changes conformation when contacted with lactose, thereby preventing the Lad repressor protein from binding to the operator), a tryptophan promoter operator (when complexed with tryptophan, TrpR repressor protein has a conformation that binds the operator; in the absence of tryptophan, the TrpR repressor protein has a conformation that does not bind to the operator), and a tac promoter operator (see, for example, deBoer et al. (1983) *Proc. Natl. Acad. Sci. USA.* 80:21-25).

In some cases, a nucleotide sequence encoding a variant tyrosine hydroxylase of the present disclosure is operably linked to an inducible promoter. Inducible promoters are well known in the art. Suitable inducible promoters include, but are not limited to, the pL of bacteriophage λ; Plac; Ptrp; Ptac (Ptrp-lac hybrid promoter); an isopropyl-beta-D-thiogalactopyranoside (IPTG)-inducible promoter, e.g., a lacZ promoter; a tetracycline-inducible promoter; an arabinose inducible promoter, e.g., PBAD (see, e.g., Guzman et al. (1995) *J. Bacteriol.* 177:4121-4130); a xylose-inducible promoter, e.g., Pxyl (see, e.g., Kim et al. (1996) *Gene* 181:71-76); a GAL1 promoter; a tryptophan promoter; a lac promoter; an alcohol-inducible promoter, e.g., a methanol-inducible promoter, an ethanol-inducible promoter; a raffinose-inducible promoter; a heat-inducible promoter, e.g., heat inducible lambda PL promoter, a promoter controlled by a heat-sensitive repressor (e.g., CI857-repressed lambda-based expression vectors; see, e.g., Hoffmann et al. (1999) *FEMS Microbiol Lett.* 177(2):327-34); and the like.

In some cases, a nucleotide sequence encoding a variant tyrosine hydroxylase of the present disclosure is operably linked to a constitutive promoter. In yeast, a number of vectors containing constitutive or inducible promoters may be used. For a review see, Current Protocols in Molecular Biology, Vol. 2, 1988, Ed. Ausubel, et al., Greene Publish. Assoc. & Wiley Interscience, Ch. 13; Grant, et al., 1987, Expression and Secretion Vectors for Yeast, in Methods in Enzymology, Eds. Wu & Grossman, 31987, Acad. Press, N.Y., Vol. 153, pp. 516-544; Glover, 1986, DNA Cloning, Vol. II, IRL Press, Wash., D.C., Ch. 3; Bitter, 1987, Heterologous Gene Expression in Yeast, Methods in Enzymology, Eds. Berger & Kimmel, Acad. Press, N.Y., Vol. 152, pp. 673-684; and The Molecular Biology of the Yeast *Saccharomyces,* 1982, Eds. Strathern et al., Cold Spring Harbor Press, Vols. I and II. A constitutive yeast promoter such as ADH or LEU2 or an inducible promoter such as GAL may be used (Cloning in Yeast, Ch. 3, R. Rothstein in: DNA Cloning Vol. 11, A Practical Approach, Ed. DM Glover, 1986, IRL Press, Wash., D.C.). Alternatively, vectors may be used which promote integration of foreign DNA sequences into the yeast chromosome.

A nucleotide sequence encoding a variant tyrosine hydroxylase of the present disclosure can be present in an expression vector and/or a cloning vector. Suitable expression vectors include, e.g., plasmids, viral vectors, and the like.

Large numbers of suitable vectors and promoters are known to those of skill in the art; many are commercially available for generating a subject recombinant constructs. The following vectors are provided by way of example. Bacterial: pBs, phagescript, PsiX174, pBluescript SK, pBs KS, pNH8a, pNH16a, pNH18a, pNH46a (Stratagene, La Jolla, Calif., USA); pTrc99A, pKK223-3, pKK233-3, pDR540, and pRIT5 (Pharmacia, Uppsala, Sweden). Eukaryotic: pWLneo, pSV2cat, pOG44, PXR1, pSG (Stratagene) pSVK3, pBPV, pMSG and pSVL (Pharmacia).

Expression vectors generally have convenient restriction sites located near the promoter sequence to provide for the insertion of nucleic acid sequences encoding heterologous proteins. A selectable marker operative in the expression host may be present. Suitable expression vectors include, but are not limited to, baculovirus vectors, bacteriophage vectors, plasmids, phagemids, cosmids, fosmids, bacterial artificial chromosomes, viral vectors (e.g. viral vectors based on vaccinia virus, poliovirus, adenovirus, adeno-associated virus, SV40, herpes simplex virus, and the like), P1-based artificial chromosomes, yeast plasmids, yeast artificial chromosomes, and any other vectors specific for specific hosts of interest (such as yeast). Thus, for example, a nucleic acid encoding a gene product(s) is included in any one of a variety of expression vectors for expressing the gene product(s). Such vectors include chromosomal, nonchromosomal and synthetic DNA sequences.

Expression vectors suitable for use in yeast host cells include, but are not limited to, yeast integrating plasmids; yeast replicating plasmids; yeast centromere plasmids; and yeast episomal plasmids. In some cases, the expression vector includes a yeast-specific origin of replication (ORI). In some cases, the expression vector includes an Autonomously Replicating Sequence (ARS). In some cases, the expression vector includes at least a portion of a 2 micron circle.

In some cases, a nucleotide sequence encoding a variant tyrosine hydroxylase of the present disclosure is present in a low copy number expression vector (e.g., a low copy number plasmid). In some cases, a nucleotide sequence encoding a variant tyrosine hydroxylase of the present disclosure is present in a medium copy number expression vector (e.g., a medium copy number plasmid). In some cases, a nucleotide sequence encoding a variant tyrosine hydroxylase of the present disclosure is present in a high copy number expression vector (e.g., a high copy number plasmid).

An expression vector can include a selectable marker. For example, the selectable marker can be an antibiotic resistance marker. Illustrative examples of antibiotic resistance markers include, but are not limited to, the BLA, NAT1, PAT, AUR1-C, PDR4, SMR1, CAT, mouse dhfr, HPH, DSDA, kanamycin resistance ($KAN^R$), and SH BLE gene products. The BLA gene product from *Escherichia coli* confers resistance to beta-lactam antibiotics (e.g., narrow-spectrum cephalosporins, cephamycins, and carbapenems (ertapenem), cefamandole, and cefoperazone) and to the anti-gram-negative-bacterium penicillins except temocillin; the NAT1 gene product from *S. noursei* confers resistance to nourseothricin; the PAT gene product from *S. viridochromogenes* Tu94 confers resistance to bialophos; the AUR1-C gene product from *Saccharomyces cerevisiae* confers resistance to Auerobasidin A (AbA); the PDR4 gene product confers resistance to cerulenin; the SMR1 gene product confers resistance to sulfometuron methyl; the CAT gene product from Tn9 transposon confers resistance to chloramphenicol; the mouse dhfr gene product confers resistance to methotrexate; the HPH gene product of *Klebsiella pneumonia* confers resistance to Hygromycin B; the DSDA gene product of *E. coli* allows cells to grow on plates with D-serine as the sole nitrogen source; the kanamycin resistance ($KAN^R$) gene of the Tn903 transposon confers resistance to G418; and the SH BLE gene product from *Streptoalloteichus hindustanus* confers resistance to Zeocin (bleomycin). In some embodiments, the antibiotic resistance marker is deleted after the genetically modified host cell disclosed herein is isolated.

In some embodiments, the selectable marker rescues an auxotrophy (e.g., a nutritional auxotrophy) in the genetically modified microorganism. In such embodiments, a parent microorganism comprises a functional disruption in one or more gene products that function in an amino acid or nucleotide biosynthetic pathway and that when non-functional renders a parent cell incapable of growing in media without supplementation with one or more nutrients. Such gene products include, but are not limited to, the HIS3, LEU2, LYS1, LYS2, MET15, TRP1, ADE2, and URA3 gene products in yeast. The auxotrophic phenotype can then be rescued by transforming the parent cell with an expression vector or chromosomal integration construct encoding a functional copy of the disrupted gene product, and the genetically modified host cell generated can be selected for based on the loss of the auxotrophic phenotype of the parent cell. Utilization of the URA3, TRP1, and LYS2 genes as selectable markers has a marked advantage because both positive and negative selections are possible. Positive selection is carried out by auxotrophic complementation of the URA3, TRP1, and LYS2 mutations, whereas negative selection is based on specific inhibitors, i.e., 5-fluoro-orotic acid (FOA), 5-fluoroanthranilic acid, and aminoadipic acid (aAA), respectively, that prevent growth of the prototrophic strains but allows growth of the URA3, TRP1, and LYS2 mutants, respectively. In other embodiments, the selectable marker rescues other non-lethal deficiencies or phenotypes that can be identified by a known selection method.

In some cases, a nucleic acid of the present disclosure comprises a nucleotide sequence encoding a variant tyrosine hydroxylase of the present disclosure, where the nucleotide sequence is codon optimized for expression in a yeast cell.

In some cases, a nucleic acid of the present disclosure comprises a nucleotide sequence encoding a variant tyrosine hydroxylase of the present disclosure, where the nucleic acid includes an element that promotes integration of the nucleic acid into a host cell's genome.

Host Cells

The present disclosure provides genetically modified host cells that are genetically modified with a subject nucleic acid comprising a nucleotide sequence encoding a variant tyrosine hydroxylase of the present disclosure. A genetically modified host cell of the present disclosure can be used to generate L-DOPA. A genetically modified host cell of the present disclosure can be used to generate dopamine. A genetically modified host cell of the present disclosure can be used to generate a benzylisoquinoline alkaloid (BIA) compound or a BIA precursor other than L-DOPA.

BIA compounds and BIA precursors include, but are not limited to, berberine, canadine, cheilanthifoline, codeine, codeinone, cularine, dauricine, dopamine, 2-hydroxycoclaurine, 2-hydroxy-N-methylcoclaurine, magnoflorine (aporphine), morphine, morphinone, norcoclaurine, norlaudanosoline, (S)-norreticuline, noscarpine, oripavine, papaverine, (S)-dihydropapaverine, (S)-tetrahydropapaverine, protopine, reticuline (e.g., (S)-reticuline; (R)-reticuline), salutaridine, salutaridinol, salutaridinol-7-O-acetate, sanguinarine, dihydrosanguinarine, (S)-scoulerine, scoulerine, stylopine, cis-N-methylstylopine, tetrahydrocolumbamine, thebaine, etc. BIA precursors include any intermediate in a biosynthetic pathway to generate a BIA compound, e.g., an intermediate in a biosynthetic pathway to generate papaverine, morphine, codeine, sanguinarine, noscapine, berberine, thebaine, scoulerine, etc.

A genetically modified host cell of the present disclosure can be a unicellular organism, or can be a cell grown in culture as a single cell or a population of single cells. In some cases, a genetically modified host cell of the present disclosure is a eukaryotic cell. In some cases, a genetically modified host cell of the present disclosure is a prokaryotic cell. In some cases, a genetically modified host cell of the present disclosure is in vitro; e.g., in some cases, a genetically modified host cell of the present disclosure is an isolated cell present in vitro.

Suitable eukaryotic host cells include, but are not limited to, yeast cells, insect cells, plant cells, fungal cells, and algal cells. Suitable eukaryotic host cells include, but are not limited to, *Pichia pastoris, Pichia finlandica, Pichia trehalophila, Pichia koclamae, Pichia membranaefaciens, Pichia opuntiae, Pichia thermotolerans, Pichia salictaria, Pichia guercuum, Pichia ptjperi, Pichia stiptis, Pichia methanolica, Pichia* sp., *Saccharomyces cerevisiae, Saccharomyces* sp., *Hansenula polymorpha, Kluyveromyces* sp., *Kluyveromyces lactis, Candida albicans, Aspergillus nidulans, Aspergillus niger, Aspergillus oryzae, Trichoderma reesei, Chrysosporium lucknowense, Fusarium* sp., *Fusarium gramineum, Fusarium venenatum, Neurospora crassa, Chlamydomonas reinhardtii*, and the like. In some cases, the host cell is a eukaryotic cell other than a plant cell.

In some cases, subject genetically modified host cell is a yeast cell. In some instances, the yeast cell is *Saccharomyces cerevisiae*.

Suitable prokaryotic cells include any of a variety of laboratory bacterial strains. Suitable prokaryotic hosts include, but are not limited to, any of a variety of gram-positive, gram-negative, or gram-variable bacteria. Examples include, but are not limited to, cells belonging to the genera: *Agrobacterium, Alicyclobacillus, Anabaena, Anacystis, Arthrobacter, Azobacter, Bacillus, Brevibacterium, Chromatium, Clostridium, Corynebacterium, Enterobacter, Erwinia, Escherichia, Lactobacillus, Lactococcus, Mesorhizobium, Methylobacterium, Microbacterium, Phormidium, Pseudomonas, Rhodobacter, Rhodopseudomonas, Rhodospirillum, Rhodococcus, Salmonella, Scenedesmun, Serratia, Shigella, Staphylococcus, Strepromyces, Synnecoccus*, and *Zymomonas*. Examples of prokaryotic strains include, but are not limited to: *Bacillus subtilis, Bacillus amyloliquefacines, Brevibacterium ammoniagenes, Brevibacterium immariophilum, Clostridium beigerinckii, Enterobacter sakazakii, Escherichia coli, Lactococcus lactis, Mesorhizobium loti, Pseudomonas aeruginosa, Pseudomonas mevalonii, Pseudomonas pudica, Rhodobacter capsulatus, Rhodobacter sphaeroides, Rhodospirillum rubrum, Salmonella enterica, Salmonella typhi, Salmonella typhimurium, Shigella dysenteriae, Shigella flexneri, Shigella sonnei*, and *Staphylococcus aureus*. In some cases, the host cell is an *Escherichia coli* cell.

In some instances, genetically modified cells of the present disclosure are non-plant cells. In some cases, the cells are insect cells, mammalian cells, bacterial cells or yeast cells. Representative examples of appropriate hosts include, but are not limited to, bacterial cells, such as *Bacillus subtilis, Escherichia coli, Streptomyces*, and *Salmonella* typhimuium cells; and insect cells such as *Drosophila* S2 and *Spodoptera* Sf9 cells. In some cases, the cells are yeast cells or *E. coli* cells. As a non-limiting example, the yeast cells can be of the species *Saccharomyces cerevisiae* (*S. cerevisiae*). In some cases, yeast cells are used as the host cell, e.g., to allow proteins to fold properly into the endoplasmic reticulum membrane so that activity is maintained. Examples of yeast strains that can be used, but are not limited to, S288C, W303, D273-10B, X2180, A364A, Sigma 1278B, AB972, SK1 and FL100. In some cases, the yeast strain is any of S288C (MATα; SUC2 mal mel gal2 CUP1 flo1 flo8-1 hap1), BY4741 (MATa; his3Δ1; leu2Δ0; met15Δ0; ura3Δ0), BY4742 (MATα; his3Δ1; leu2Δ0; lys2Δ0; ura3Δ0), BY4743 (MATa/MATα; his3Δ1/his3Δ1; leu2Δ0/leu2Δ0; met15Δ0/MET15; LYS2/lys2Δ0; ura3Δ0/ura3Δ0), and WAT11 or W(R), derivatives of the W303-B strain (MATa; ade2-1; his3-11, -15; leu2-3,-112; ura3-1; canR; cyr+) which express the *Arabidopsis thaliana* NADPH-P450 reductase ATR1 and the yeast NADPH-P450 reductase CPR1, respectively. As another example, the yeast strain is W303α. (MATα; his3-11,15 trp1-1 leu2-3 ura3-1 ade2-1). Additional suitable yeast strains are found at EUROSCARF.

A genetically modified host cell of the present disclosure comprises a nucleic acid comprising a nucleotide sequence encoding a variant tyrosine hydroxylase of the present disclosure. In some cases, a genetically modified host cell of the present disclosure comprises a nucleic acid comprising a nucleotide sequence encoding a variant tyrosine hydroxylase of the present disclosure, where the nucleic acid is present in the host cell episomally. In some cases, a genetically modified host cell of the present disclosure comprises a nucleic acid comprising a nucleotide sequence encoding a variant tyrosine hydroxylase of the present disclosure, where the nucleic acid is integrated into the host cell genome. In some cases, the genetically modified host cell is a *Saccharomyces cerevisiae* host cell.

In some cases, the host cell comprises a nucleic acid encoding a 3-deoxy-D-arabino-heptulosonate-7-phosphate (DAHP) synthase variant that is insensitive to tyrosine repression. For example, in some cases, the host cell is genetically modified to include an ARO4 (K229L) allele. In some cases, the host cell is genetically modified to include a DAHP synthase that comprises an amino acid sequence having at least 75%, at least 80%, at least 85%, at least 90%, at least 95%, at least 98%, or 100%, amino acid sequence identity to the DAHP synthase amino acid sequence depicted in FIG. 20, where the DAHP synthase comprises a K229L substitution (comprises a leucine at amino acid 229).

In some cases, a genetically modified host cell of the present disclosure comprises a recombinant expression vector of the present disclosure, where the recombinant expression vector comprises a nucleotide sequence encoding a variant tyrosine hydroxylase of the present disclosure. In some cases, the recombinant expression vector is present in the cell episomally, e.g., the recombinant expression vector replicates autonomously and is not integrated into the genome of the host cell. In some cases, the genetically modified host cell is a yeast cell. In some cases, the genetically modified host cell is a *Saccharomyces cerevisiae* host cell.

In some cases, a genetically modified host cell of the present disclosure is a single-celled organism, and is present in vitro, e.g., the cell is a cultured in vitro cell. In some instances, the cell is a yeast cell. In some cases, the cell is a prokaryotic cell.

In some cases, a genetically modified host cell of the present disclosure is genetically modified with a nucleic acid comprising a nucleotide sequence encoding a variant tyrosine hydroxylase of the present disclosure; and includes one or more additional genetic modifications.

For example, the present disclosure provides a genetically modified host cell, where the host cell is genetically modified with one or more nucleic acids comprising nucleotide sequences encoding: i) a variant tyrosine hydroxylase of the present disclosure; and ii) a heterologous DOPA decarboxylase (DODC). In some cases, the cell is a prokaryotic cell. In some cases, the cell is a eukaryotic cell. In some cases, the cell is a yeast cell. In some cases, the cell is a yeast cell; and the cell is genetically modified with one or more nucleic acids comprising nucleotide sequences encoding a variant tyrosine hydroxylase of the present disclosure and the heterologous DODC. In some cases, the cell is a yeast cell; and the cell is genetically modified with one or more nucleic acids comprising nucleotide sequences encoding a variant tyrosine hydroxylase of the present disclosure and the heterologous DODC, where the nucleotide sequences encoding the heterologous tyrosine hydroxylase and the heterologous DODC are codon optimized for expression in yeast.

A suitable DODC can comprise an amino acid sequence having at least 75%, at least 80%, at least 85%, at least 90%, at least 95%, at least 98%, at least 99%, or 100%, amino acid sequence identity to a stretch of from 350 to 400 aa, or from 400 aa to 518, contiguous amino acids of the amino acid sequence set forth in FIG. 14A or FIG. 14B. A suitable DODC can comprise an amino acid sequence having at least 75%, at least 80%, at least 85%, at least 90%, at least 95%, at least 98%, at least 99%, or 100%, amino acid sequence identity to a stretch of from 350 to 400 aa, or from 400 aa to 470, contiguous amino acids of the amino acid sequence set forth in FIG. 14C.

As another example the present disclosure provides a genetically modified host cell, where the host cell is genetically modified with one or more nucleic acids comprising nucleotide sequences encoding: i) a variant tyrosine hydroxylase of the present disclosure; ii) a heterologous DODC; and iii) a heterologous monamine oxidase (MAO) or a heterologous tyramine oxidase. In some cases, the cell is a prokaryotic cell. In some cases, the cell is a eukaryotic cell. In some cases, the cell is a yeast cell. In some cases, the cell is a yeast cell; and the cell is genetically modified with one or more nucleic acids comprising nucleotide sequences encoding a variant tyrosine hydroxylase of the present disclosure, the heterologous DODC, and the heterologous MAO or tyramine oxidase. In some cases, the cell is a yeast cell; and the cell is genetically modified with one or more nucleic acids comprising nucleotide sequences encoding a variant tyrosine hydroxylase of the present disclosure the heterologous DODC, and the heterologous MAO or tyramine oxidase, where the nucleotide sequences encoding the heterologous tyrosine hydroxylase the heterologous DODC, and the heterologous MAO or tyramine oxidase are codon optimized for expression in yeast.

A suitable MAO (or tyramine oxidase) can comprise an amino acid sequence having at least 75%, at least 80%, at least 85%, at least 90%, at least 95%, at least 98%, at least 99%, or 100%, amino acid sequence identity to a stretch of from 350 to 400, or from 400-443, contiguous amino acids of the amino acid sequence set forth in FIG. 15A. A suitable MAO (or tyramine oxidase) can comprise an amino acid sequence having at least 75%, at least 80%, at least 85%, at least 90%, at least 95%, at least 98%, at least 99%, or 100%, amino acid sequence identity to a stretch of from 650 to 700, from 700 to 750, or from 750 to 792 contiguous amino acids of the amino acid sequence set forth in FIG. 15B. A suitable MAO (or tyramine oxidase) can comprise an amino acid sequence having at least 75%, at least 80%, at least 85%, at least 90%, at least 95%, at least 98%, at least 99%, or 100%, amino acid sequence identity to a stretch of from 450 to 500, or from 500 to 527, contiguous amino acids of the amino acid sequence set forth in FIG. 15C.

As another example, the present disclosure provides a genetically modified host cell, where the host cell is genetically modified with one or more nucleic acids comprising nucleotide sequences encoding: i) a variant tyrosine hydroxylase of the present disclosure; ii) a heterologous DODC; iii) a heterologous MAO or a heterologous tyramine oxidase; and iv) a heterologous norcoclaurine synthase (NCS). In some cases, the cell is a prokaryotic cell. In some cases, the cell is a eukaryotic cell. In some cases, the cell is a yeast cell. In some cases, the cell is a yeast cell; and the cell is genetically modified with one or more nucleic acids comprising nucleotide sequences encoding a variant tyrosine hydroxylase of the present disclosure, the heterologous DODC, the heterologous MAO or tyramine oxidase, and the heterologous NCS. In some cases, the cell is a yeast cell; and the cell is genetically modified with one or more nucleic acids comprising nucleotide sequences encoding a variant tyrosine hydroxylase of the present disclosure the heterologous DODC, the heterologous MAO or tyramine oxidase, and the heterologous NCS, where the nucleotide sequences encoding the heterologous tyrosine hydroxylase the heterologous DODC, the heterologous MAO or tyramine oxidase, and the heterologous NCS are codon optimized for expression in yeast.

As another example, the present disclosure provides a genetically modified host cell, where the host cell is genetically modified with one or more nucleic acids comprising nucleotide sequences encoding: i) a variant tyrosine hydroxylase of the present disclosure; ii) a heterologous DODC; and iii) a heterologous norcoclaurine synthase (NCS). In some cases, the cell is a prokaryotic cell. In some cases, the cell is a eukaryotic cell. In some cases, the cell is a yeast cell. In some cases, the cell is a yeast cell; and the cell is genetically modified with one or more nucleic acids comprising nucleotide sequences encoding a variant tyrosine hydroxylase of the present disclosure, the heterologous DODC, and the heterologous NCS. In some cases, the cell is a yeast cell; and the cell is genetically modified with one or more nucleic acids comprising nucleotide sequences encoding a variant tyrosine hydroxylase of the present disclosure the heterologous DODC, and the heterologous NCS, where the nucleotide sequences encoding the heterologous tyrosine hydroxylase the heterologous DODC, and the heterologous NCS are codon optimized for expression in yeast.

A suitable NCS can comprise an amino acid sequence having at least 75%, at least 80%, at least 85%, at least 90%, at least 95%, at least 98%, at least 99%, or 100%, amino acid sequence identity to a stretch of from 150 to 200, or from 200 to 231, contiguous amino acids of the amino acid sequence set forth in FIG. 16A. A suitable NCS can comprise an amino acid sequence having at least 75%, at least 80%, at least 85%, at least 90%, at least 95%, at least 98%, at least 99%, or 100%, amino acid sequence identity to a stretch of from 150 to 200, or from 200 to 210, contiguous amino acids of the amino acid sequence set forth in FIG. 16B.

A suitable NCS can comprise an amino acid sequence having at least 75%, at least 80%, at least 85%, at least 90%, at least 95%, at least 98%, at least 99%, or 100%, amino acid sequence identity to a stretch of from 150 to 200 contiguous amino acids of the amino acid sequence set forth in FIG. 21A. A suitable NCS can comprise an amino acid sequence having at least 75%, at least 80%, at least 85%, at least 90%, at least 95%, at least 98%, at least 99%, or 100%, amino acid sequence identity to a stretch of from 150 to 192, contiguous amino acids of the amino acid sequence set forth in FIG. 21B.

As another example, the present disclosure provides a genetically modified host cell, where the host cell is genetically modified with one or more nucleic acids comprising nucleotide sequences encoding: i) a variant tyrosine hydroxylase of the present disclosure; ii) a heterologous DODC; iii) a heterologous MAO or a heterologous tyramine oxidase; iv) a heterologous NCS; and v) a heterologous norcoclaurine 6-O-methyltransferase (6OMT). In some cases, the cell is a prokaryotic cell. In some cases, the cell is a eukaryotic cell. In some cases, the cell is a yeast cell. In some cases, the cell is a yeast cell; and the cell is genetically modified with one or more nucleic acids comprising nucleotide sequences encoding a variant tyrosine hydroxylase of the present disclosure, the heterologous DODC, the heterologous MAO or tyramine oxidase, the heterologous NCS, and the heterologous 6OMT. In some cases, the cell is a yeast cell; and the cell is genetically modified with one or more nucleic acids comprising nucleotide sequences encoding a variant tyrosine hydroxylase of the present disclosure the heterologous DODC, the heterologous MAO or tyramine oxidase, the heterologous NCS, and the heterologous 6OMT, where the nucleotide sequences encoding the heterologous tyrosine hydroxylase the heterologous DODC, the heterologous MAO or tyramine oxidase, the heterologous NCS, and the heterologous 6OMT are codon optimized for expression in yeast.

As another example, the present disclosure provides a genetically modified host cell, where the host cell is genetically modified with one or more nucleic acids comprising nucleotide sequences encoding: i) a variant tyrosine hydroxylase of the present disclosure; ii) a heterologous DODC; iii) a heterologous NCS; and iv) a heterologous norcoclaurine 6-O-methyltransferase (6OMT). In some cases, the cell is a prokaryotic cell. In some cases, the cell is a eukaryotic cell. In some cases, the cell is a yeast cell. In some cases, the cell is a yeast cell; and the cell is genetically modified with one or more nucleic acids comprising nucleotide sequences encoding a variant tyrosine hydroxylase of the present disclosure, the heterologous DODC, the heterologous NCS, and the heterologous 6OMT. In some cases, the cell is a yeast cell; and the cell is genetically modified with one or more nucleic acids comprising nucleotide sequences encoding a variant tyrosine hydroxylase of the present disclosure the heterologous DODC, the heterologous NCS, and the heterologous 6OMT, where the nucleotide sequences encoding the heterologous tyrosine hydroxylase the heterologous DODC, the heterologous NCS, and the heterologous 6OMT are codon optimized for expression in yeast.

A suitable 6OMT can comprise an amino acid sequence having at least 75%, at least 80%, at least 85%, at least 90%, at least 95%, at least 98%, at least 99%, or 100%, amino acid sequence identity to a stretch of from 250 to 300, or from 300 to 346 or 347, contiguous amino acids of the amino acid sequence set forth in FIG. 17A or FIG. 17B.

As another example, the present disclosure provides a genetically modified host cell, where the host cell is genetically modified with one or more nucleic acids comprising nucleotide sequences encoding: i) a variant tyrosine hydroxylase of the present disclosure; ii) a heterologous DODC; iii) a heterologous MAO or a heterologous tyramine oxidase; iv) a heterologous NCS; v) a heterologous norcoclaurine 6-O-methyltransferase (6OMT); and vi) a heterologous coclaurine-N-methyltransferase (CNMT). In some cases, the cell is a prokaryotic cell. In some cases, the cell is a eukaryotic cell. In some cases, the cell is a yeast cell. In some cases, the cell is a yeast cell; and the cell is genetically modified with one or more nucleic acids comprising nucleotide sequences encoding a variant tyrosine hydroxylase of the present disclosure, the heterologous DODC, the heterologous MAO or tyramine oxidase, the heterologous NCS, the heterologous 6OMT, and the heterologous CNMT. In some cases, the cell is a yeast cell; and the cell is genetically modified with one or more nucleic acids comprising nucleotide sequences encoding a variant tyrosine hydroxylase of the present disclosure the heterologous DODC, the heterologous MAO or tyramine oxidase, the heterologous NCS, the heterologous 6OMT, and the heterologous CNMT, where the nucleotide sequences encoding the heterologous tyrosine hydroxylase the heterologous DODC, the heterologous MAO or tyramine oxidase, the heterologous NCS, the heterologous 6OMT, and the heterologous CNMT are codon optimized for expression in yeast.

As another example, the present disclosure provides a genetically modified host cell, where the host cell is genetically modified with one or more nucleic acids comprising nucleotide sequences encoding: i) a variant tyrosine hydroxylase of the present disclosure; ii) a heterologous DODC; iii) a heterologous NCS; v) a heterologous norcoclaurine 6-O-methyltransferase (6OMT); and iv) a heterologous coclaurine-N-methyltransferase (CNMT). In some cases, the cell is a prokaryotic cell. In some cases, the cell is a eukaryotic cell. In some cases, the cell is a yeast cell. In some cases, the cell is a yeast cell; and the cell is genetically modified with one or more nucleic acids comprising nucleotide sequences encoding a variant tyrosine hydroxylase of the present disclosure, the heterologous DODC, the heterologous NCS, the heterologous 6OMT, and the heterologous CNMT. In some cases, the cell is a yeast cell; and the cell is genetically modified with one or more nucleic acids comprising nucleotide sequences encoding a variant tyrosine hydroxylase of the present disclosure the heterologous DODC, the heterologous NCS, the heterologous 6OMT, and the heterologous CNMT, where the nucleotide sequences encoding the heterologous tyrosine hydroxylase the heterologous DODC, the heterologous NCS, the heterologous 6OMT, and the heterologous CNMT are codon optimized for expression in yeast.

A suitable CNMT can comprise an amino acid sequence having at least 75%, at least 80%, at least 85%, at least 90%, at least 95%, at least 98%, at least 99%, or 100%, amino acid sequence identity to a stretch of from 250 to 300, or from 300 to 351 or 361, contiguous amino acids of the amino acid sequence set forth in FIG. 18A or FIG. 18B.

As another example, the present disclosure provides a genetically modified host cell, where the host cell is genetically modified with one or more nucleic acids comprising nucleotide sequences encoding: i) a variant tyrosine hydroxylase of the present disclosure; ii) a heterologous DODC; iii) a heterologous MAO or a heterologous tyramine oxidase; iv) a heterologous NCS; v) a heterologous norcoclaurine 6-O-methyltransferase (6OMT); vi) a heterologous CNMT; and vii) a heterologous CYP80B1 ((S)—N-methylcoclaurine 3'-hydroxylase). In some cases, the cell is a prokaryotic cell. In some cases, the cell is a eukaryotic cell. In some cases, the cell is a yeast cell. In some cases, the cell is a yeast cell; and the cell is genetically modified with one or more nucleic acids comprising nucleotide sequences encoding a variant tyrosine hydroxylase of the present disclosure, the heterologous DODC, the heterologous MAO or tyramine oxidase, the heterologous NCS, the heterologous 6OMT, the heterologous CNMT, and the heterologous CYP80B1. In some cases, the cell is a yeast cell; and the cell is genetically modified with one or more nucleic acids comprising nucleotide sequences encoding a variant tyrosine hydroxylase of the present disclosure the heterologous DODC, the heterologous MAO or tyramine oxidase, the heterologous NCS, the heterologous 6OMT, the heterologous CNMT, and the heterologous CYP80B1, where the nucleotide sequences encoding the heterologous tyrosine hydroxylase the heterologous DODC, the heterologous MAO or tyramine oxidase, the heterologous NCS, the heterologous 6OMT, the heterologous CNMT, and the heterologous CYP80B1 are codon optimized for expression in yeast.

As another example, the present disclosure provides a genetically modified host cell, where the host cell is genetically modified with one or more nucleic acids comprising nucleotide sequences encoding: i) a variant tyrosine hydroxylase of the present disclosure; ii) a heterologous DODC; iii) a heterologous NCS; iv) a heterologous norcoclaurine 6-O-methyltransferase (6OMT); v) a heterologous CNMT; and vi) a heterologous CYP80B1 ((S)—N-methylcoclaurine 3'-hydroxylase). In some cases, the cell is a prokaryotic cell. In some cases, the cell is a eukaryotic cell. In some cases, the cell is a yeast cell. In some cases, the cell is a yeast cell; and the cell is genetically modified with one or more nucleic acids comprising nucleotide sequences encoding a variant tyrosine hydroxylase of the present disclosure, the heterologous DODC, the heterologous NCS, the heterologous 6OMT, the heterologous CNMT, and the heterologous CYP80B1. In some cases, the cell is a yeast cell; and the cell is genetically modified with one or more nucleic acids comprising nucleotide sequences encoding a variant tyrosine hydroxylase of the present disclosure the heterologous DODC, the heterologous NCS, the heterologous 6OMT, the heterologous CNMT, and the heterologous CYP80B1, where the nucleotide sequences encoding the heterologous tyrosine hydroxylase the heterologous DODC, the heterologous NCS, the heterologous 6OMT, the heterologous CNMT, and the heterologous CYP80B1 are codon optimized for expression in yeast.

A suitable CYP80B1 ((S)—N-methylcoclaurine 3'-hydroxylase) can comprise an amino acid sequence having at least 75%, at least 80%, at least 85%, at least 90%, at least 95%, at least 98%, at least 99%, or 100%, amino acid sequence identity to a stretch of from 350 to 400, from 400 to 450, or from 450 to 481, contiguous amino acids of the amino acid sequence set forth in FIG. 19.

A suitable CYP80B1 can comprise an amino acid sequence having at least 75%, at least 80%, at least 85%, at least 90%, at least 95%, at least 98%, at least 99%, or 100%, amino acid sequence identity to a stretch of from 350 to 400, from 400 to 450, or from 450 to 487, contiguous amino acids of the amino acid sequence set forth in FIG. 29.

As another example, the present disclosure provides a genetically modified host cell, where the host cell is genetically modified with one or more nucleic acids comprising nucleotide sequences encoding: i) a variant tyrosine hydroxylase of the present disclosure; ii) a heterologous DODC; iii) a heterologous MAO or a heterologous tyramine oxidase; iv) a heterologous NCS; v) a heterologous norcoclaurine 6-O-methyltransferase (6OMT); vi) a heterologous CNMT; vii) a heterologous CYP80B1 ((S)—N-methylcoclaurine 3'-hydroxylase); and viii) a heterologous 3'-hydroxy-N-methylcoclaurine-4'-O-methyltransferase (4'OMT). In some cases, the cell is a prokaryotic cell. In some cases, the cell is a eukaryotic cell. In some cases, the cell is a yeast cell. In some cases, the cell is a yeast cell; and the cell is genetically modified with one or more nucleic acids comprising nucleotide sequences encoding a variant tyrosine hydroxylase of the present disclosure, the heterologous DODC, the heterologous MAO or tyramine oxidase, the heterologous NCS, the heterologous 6OMT, the heterologous CNMT, the heterologous CYP80B1, and the heterologous 4'OMT. In some cases, the cell is a yeast cell; and the cell is genetically modified with one or more nucleic acids comprising nucleotide sequences encoding a variant tyrosine hydroxylase of the present disclosure the heterologous DODC, the heterologous MAO or tyramine oxidase, the heterologous NCS, the heterologous 6OMT, the heterologous CNMT, the heterologous CYP80B1, and the heterologous 4'OMT, where the nucleotide sequences encoding the heterologous tyrosine hydroxylase the heterologous DODC, the heterologous MAO or tyramine oxidase, the heterologous NCS, the heterologous 6OMT, the heterologous CNMT, the heterologous CYP80B1, and the heterologous 4'OMT are codon optimized for expression in yeast.

As another example, the present disclosure provides a genetically modified host cell, where the host cell is genetically modified with one or more nucleic acids comprising nucleotide sequences encoding: i) a variant tyrosine hydroxylase of the present disclosure; ii) a heterologous DODC; iii) a heterologous NCS; v) a heterologous norcoclaurine 6-O-methyltransferase (6OMT); iv) a heterologous CNMT; vi) a heterologous CYP80B1 ((S)—N-methylcoclaurine 3'-hydroxylase); and vii) a heterologous 3'-hydroxy-N-methylcoclaurine-4'-O-methyltransferase (4'OMT). In some cases, the cell is a prokaryotic cell. In some cases, the cell is a eukaryotic cell. In some cases, the cell is a yeast cell. In some cases, the cell is a yeast cell; and the cell is genetically modified with one or more nucleic acids comprising nucleotide sequences encoding a variant tyrosine hydroxylase of the present disclosure, the heterologous DODC, the heterologous NCS, the heterologous 6OMT, the heterologous CNMT, the heterologous CYP80B1, and the heterologous 4'OMT. In some cases, the cell is a yeast cell; and the cell is genetically modified with one or more nucleic acids comprising nucleotide sequences encoding a variant tyrosine hydroxylase of the present disclosure the heterologous DODC, the heterologous NCS, the heterologous 6OMT, the heterologous CNMT, the heterologous CYP80B1, and the heterologous 4'OMT, where the nucleotide sequences encoding the heterologous tyrosine hydroxylase the heterologous DODC, the heterologous NCS, the heterologous 6OMT, the heterologous CNMT, the heterologous CYP80B1, and the heterologous 4'OMT are codon optimized for expression in yeast.

Methods of Making L-DOPA

The present disclosure provides methods of making L-DOPA in a host cell. The methods generally involve culturing a host cell genetically modified to express a heterologous tyrosine hydroxylase, where the heterologous tyrosine hydroxylase comprises an amino acid sequence having at least 75% amino acid sequence identity to SEQ ID NO:1, where the heterologous tyrosine hydroxylase is produced in the cell, and catalyzes the conversion of tyrosine to L-DOPA. In some cases, the heterologous tyrosine hydroxylase comprises an amino acid sequence having at least 75%, at least 80%, at least 85%, at least 90%, at least 95%, at least 96%, at least 97%, at least 98%, or at least 99%, amino acid sequence identity to the amino acid sequence set forth in SEQ ID NO:1.

The present disclosure provides methods of making L-DOPA in a host cell. In some cases, the methods generally involve culturing a host cell genetically modified to express a heterologous tyrosine hydroxylase, where the heterologous tyrosine hydroxylase comprises an amino acid sequence having at least 75% amino acid sequence identity to any one of the amino acid sequences depicted in FIG. 25A-25F, where the heterologous tyrosine hydroxylase is produced in the cell, and catalyzes the conversion of tyrosine to L-DOPA. In some cases, the heterologous tyrosine hydroxylase comprises an amino acid sequence having at least 75% amino acid, at least 80%, at least 85%, at least 90%, at least 95%, at least 96%, at least 97%, at least 98%, or at least 99%, sequence identity to any one of the amino acid sequences depicted in FIG. 25A-25F.

The present disclosure provides methods of making L-DOPA in a host cell. In some cases, the methods generally involve culturing a host cell genetically modified to express a heterologous tyrosine hydroxylase, where the heterologous tyrosine hydroxylase comprises an amino acid sequence having at least 75% amino acid sequence identity to any one of the amino acid sequences depicted in FIG. 13A-13C, where the heterologous tyrosine hydroxylase is produced in the cell, and catalyzes the conversion of tyrosine to L-DOPA. In some cases, the heterologous tyrosine hydroxylase comprises an amino acid sequence having at least 75% amino acid, at least 80%, at least 85%, at least 90%, at least 95%, at least 96%, at least 97%, at least 98%, or at least 99%, sequence identity to any one of the amino acid sequences depicted in FIG. 13A-13C.

In some cases, a method of the present disclosure for producing L-DOPA provides for the production of L-DOPA in an amount of from about 5 mg/L to about 500 mg/L culture medium, e.g., from about 5 mg/L to about 10 mg/L, from about 10 mg/L to about 20 mg/L, from about 20 mg/L to about 30 mg/L, from about 30 mg/L to about 40 mg/L, from about 40 mg/L to about 50 mg/L, from about 50 mg/L to about 75 mg/L, from about 75 mg/L to about 100 mg/L, from about 100 mg/L to about 150 mg/L, from about 150 mg/L to about 200 mg/L, from about 200 mg/L to about 250 mg/L, from about 250 mg/L to about 300 mg/L, from about 300 mg/L to about 350 mg/L, from about 350 mg/L to about 400 mg/L, from about 400 mg/L to about 450 mg/L, or from about 450 mg/L to about 500 mg/L culture medium. In some cases, a method of the present disclosure for producing L-DOPA provides for the production of L-DOPA in an amount of greater than 500 mg/L culture medium. In some cases, a method of the present disclosure for producing L-DOPA provides for the production of L-DOPA in an amount of at least 5 mg/L, at least 10 mg/L, at least 20 mg/L, at least 25 mg/L, at least 30 mg/L, at least 40 mg/L, at least 50 mg/L, at least 75 mg/L, at least 100 mg/L, at least 150 mg/L, at least 200 mg/L, at least 250 mg/L, at least 300 mg/L, at least 350 mg/L, at least 400 mg/L, at least 450 mg/L, or at least 500 mg/L. In some cases, the cells are grown in culture medium comprising from 2% glucose to 20% glucose. For example, in some cases, the cells are grown in culture medium comprising 2% glucose. In some cases, the cells are grown in culture medium comprising from 2% to 5% glucose, from 5% to 10% glucose, from 10% to 15% glucose, or from 15% to 20% glucose. In some cases, the cells are cultured in culture medium for 24 hours to 7 days; e.g., the cells are cultured from 24 hours to 36 hours, from 36 hours to 48 hours, from 48 hours to 3 days, from 3 days to 4 days, from 4 days to 5 days, from 5 days to 6 days, or from 6 days to 7 days. In some cases, the cells are cultured for longer than 7 days.

In some cases, the heterologous tyrosine hydroxylase comprises an amino acid sequence having at least 75%, at least 80%, at least 85%, at least 90%, at least 95%, at least 96%, at least 97%, at least 98%, or at least 99%, amino acid sequence identity to the amino acid sequence set forth in SEQ ID NO:1.

In some cases, the heterologous tyrosine hydroxylase comprises an amino acid sequence having at least 75% amino acid, at least 80%, at least 85%, at least 90%, at least 95%, at least 96%, at least 97%, at least 98%, or at least 99%, sequence identity to any one of the amino acid sequences depicted in FIG. 25A-25F. In some cases, the heterologous tyrosine hydroxylase comprises a substitution of F309 relative to CYP76AD1, as depicted in FIG. 25A-25F. In some cases, the substitution of F309 relative to CYP76AD1 is an F309L substitution. In some cases, the substitution of F309 relative to CYP76AD1 is an F309I substitution.

In some cases, the heterologous tyrosine hydroxylase comprises an amino acid sequence having at least 75%, at least 80%, at least 85%, at least 90%, at least 95%, at least 96%, at least 97%, at least 98%, or at least 99%, amino acid sequence identity to the amino acid sequence set forth in SEQ ID NO:1 (and depicted in FIG. 6A-6B), and comprises an amino acid substitution of the tryptophan at amino acid 13 (W13) of SEQ ID NO:1, or a corresponding amino acid in another tyrosine hydroxylase; and/or b) an amino acid substitution for the phenylalanine at amino acid 309 (F309) of SEQ ID NO:1, or a corresponding amino acid in another tyrosine hydroxylase.

As depicted in FIG. 6A-6B, W13 of SEQ ID NO:1 corresponds to W13 in SEQ ID NOs:2 and 4. As depicted in FIG. 6A-6B, F309 of SEQ ID NO:1 corresponds to F308 in SEQ ID NO:3 and to F306 in SEQ ID NO:4. Those skilled in the art would understand that, given an alignment as depicted in FIG. 6A-6B, a residue corresponding to W13 of SEQ ID NO:1, or a residue corresponding to F309 of SEQ ID NO:1, could be readily identified.

In some cases, the heterologous tyrosine hydroxylase comprises an amino acid sequence that differs in amino acid sequence from one of SEQ ID NOs:1, 2, 3, or 4 by no more than 1 amino acid (aa), no more than 2 aa, no more than 3 aa, no more than 4 aa, no more than 5 aa, no more than 10 aa, no more than 15 aa, no more than 20 aa, no more than 25 aa, no more than 30 aa, no more than 40 aa, no more than 45 aa, or no more than 50 aa. In some cases, the heterologous tyrosine hydroxylase comprises an amino acid sequence that differs in amino acid sequence from SEQ ID NO:1 by no more than 1 amino acid (aa), no more than 2 aa, no more than 3 aa, no more than 4 aa, no more than 5 aa, no more than 10 aa, no more than 15 aa, no more than 20 aa, no more than 25 aa, no more than 30 aa, no more than 40 aa, no more than 45 aa, or no more than 50 aa.

In some cases, the heterologous tyrosine hydroxylase comprises an amino acid sequence that at least 75%, at least 80%, at least 85%, at least 90%, at least 95%, at least 98%, or at least 99%, amino acid sequence identity to the amino acid sequence set forth in SEQ ID NO:1 (and depicted in FIG. 6A-6B), and comprises an amino acid substitution of W13, or a corresponding amino acid in another tyrosine hydroxylase; and does not comprise an amino acid substitution of F309 of SEQ ID NO:1, or a corresponding amino acid in another tyrosine hydroxylase. In some cases, the amino acid substitution of W13 is a W13L substitution. In some cases, the amino acid substitution of W13 is a W13V substitution. In some cases, the amino acid substitution of W13 is a W13I substitution.

In some cases, the heterologous tyrosine hydroxylase comprises an amino acid sequence having at least 75%, at least 80%, at least 85%, at least 90%, at least 95%, at least 98%, or at least 99%, amino acid sequence identity to the amino acid sequence set forth in SEQ ID NO:1 (and depicted in FIG. 6A-6B), and comprises an amino acid substitution F309 of SEQ ID NO:1, or a corresponding amino acid in another tyrosine hydroxylase; and does not comprise an amino acid substitution of W13, or a corresponding amino acid in another tyrosine hydroxylase. In some cases, the amino acid substitution at F309 is an F309L substitution. In some cases, the amino acid substitution of F309 is a F309V substitution. In some cases, the amino acid substitution of F309 is a F309I substitution. In some cases, the amino acid substitution of F309 is a F309S substitution.

In some cases, the heterologous tyrosine hydroxylase comprises an amino acid sequence having at least 75%, at least 80%, at least 85%, at least 90%, at least 95%, at least 98%, or at least 99%, amino acid sequence identity to the amino acid sequence set forth in SEQ ID NO:1 (and depicted in FIG. 6A-6B), and comprises an amino acid substitution of W13, or a corresponding amino acid in another tyrosine hydroxylase; and comprises an amino acid substitution F309 of SEQ ID NO:1, or a corresponding amino acid in another tyrosine hydroxylase. In some cases, the amino acid substitution of W13 is a W13L substitution. In some cases, the amino acid substitution of W13 is a W13V substitution. In some cases, the amino acid substitution of W13 is a W13I substitution. In some cases, the amino acid substitution at F309 is an F309L substitution. In some cases, the amino acid substitution of F309 is a F309V substitution. In some cases, the amino acid substitution of F309 is a F309I substitution. In some cases, the amino acid substitution of F309 is a F309S substitution. For example, in some cases, the variant tyrosine hydroxylase comprises a W13L substitution and an F309L substitution.

In some cases, the heterologous tyrosine hydroxylase exhibits higher enzymatic activity than a tyrosine hydroxylase of SEQ ID NO:8 (and depicted in FIG. 22) (AbPPO2). For example, in some cases the heterologous tyrosine hydroxylase exhibits at least 10%, at least 15%, at least 20%, at least 25%, at least 30%, at least 35%, at least 40%, at least 45%, at least 50%, at least 75%, at least 100% (or 2-fold), at least 2.5-fold, at least 5-fold, at least 7.5-fold, at least 10-fold, at least 25-fold, at least 50-fold, at least 100-fold, from 10-fold to 15-fold, from 15-fold to 20-fold, from 20-fold to 25-fold, or from 25-fold to 50-fold, from 50-fold to 100-fold, or greater than 100-fold, higher enzymatic activity than a tyrosine hydroxylase of SEQ ID NO:8. Enzymatic activity of a tyrosine hydroxylase refers to catalytic conversion of tyrosine to L-3,4-dihydroxyphenylalanine (L-DOPA).

In some cases, the heterologous tyrosine hydroxylase exhibits higher enzymatic activity than a tyrosine hydroxylase of SEQ ID NO:1 (CYP76AD1). For example, in some cases the heterologous tyrosine hydroxylase exhibits at least 10%, at least 15%, at least 20%, at least 25%, at least 30%, at least 35%, at least 40%, at least 45%, at least 50%, at least 75%, at least 100% (or 2-fold), at least 2.5-fold, at least 5-fold, at least 7.5-fold, at least 10-fold, from 10-fold to 15-fold, or greater than 15-fold, higher enzymatic activity than a tyrosine hydroxylase of SEQ ID NO:1. Enzymatic activity of a tyrosine hydroxylase refers to catalytic conversion of tyrosine to L-DOPA.

Methods of Making a Benzylisoquinoline Compound

The present disclosure provides a method of producing a benzylisoquinoline alkaloid (BIA) compound or a BIA precursor compound, the method comprising modifying L-DOPA produced by a method of present disclosure for producing L-DOPA. Thus, for example, the present disclosure provides a method of making a BIA compound or a BIA precursor compound, the method comprising producing L-DOPA, as described above; and enzymatically modifying L-DOPA, or a downstream intermediate, to generate a BIA compound or a BIA precursor compound.

As described in detail above, in some cases, a method of the present disclosure for producing L-DOPA generally involves culturing a host cell genetically modified to express a heterologous tyrosine hydroxylase, where the heterologous tyrosine hydroxylase comprises an amino acid sequence having at least 75%, at least 80%, at least 85%, at least 90%, at least 95%, at least 96%, at least 97%, at least 98%, or at least 99%, amino acid sequence identity to SEQ ID NO:1, where the heterologous tyrosine hydroxylase is produced in the cell, and catalyzes the conversion of tyrosine to L-DOPA. Thus, a method of the present disclosure for producing a BIA compound or a BIA precursor compound comprises: a) culturing a host cell genetically modified to express a heterologous tyrosine hydroxylase, where the heterologous tyrosine hydroxylase comprises an amino acid sequence having at least 75%, at least 80%, at least 85%, at least 90%, at least 95%, at least 96%, at least 97%, at least 98%, or at least 99%, amino acid sequence identity to SEQ ID NO:1, where the heterologous tyrosine hydroxylase is produced in the cell, and catalyzes the conversion of tyrosine to L-DOPA; and b) modifying the L-DOPA produced in the host cell. The L-DOPA produced in the host cell can be modified enzymatically in the host cell, to generate a BIA compound or a BIA precursor compound. The BIA compound or a BIA precursor compound can be further enzymatically modified in the host cell. In some cases, the L-DOPA is modified enzymatically in the host cell, to generate a BIA compound or a BIA precursor compound; and the BIA compound or a BIA precursor compound so generated is further enzymatically modified in the host cell. In some cases, the L-DOPA is modified enzymatically in the host cell, to generate a BIA compound or a BIA precursor compound; and the BIA compound or a BIA precursor compound so generated is isolated or purified from the host cell. In some cases, the L-DOPA is modified enzymatically in the host cell, to generate a BIA compound or a BIA precursor compound; and the BIA compound or BIA precursor compound so generated is isolated or purified from the host cell; and the isolated or purified BIA compound or BIA precursor compound is chemically modified.

As described in detail above, in some cases, a method of the present disclosure for producing L-DOPA generally involves culturing a host cell genetically modified to express a heterologous tyrosine hydroxylase, where the heterologous tyrosine hydroxylase having at least 75% amino acid, at least 80%, at least 85%, at least 90%, at least 95%, at least 96%, at least 97%, at least 98%, or at least 99%, sequence identity to any one of the amino acid sequences depicted in FIG. 25A-25F, where the heterologous tyrosine hydroxylase is produced in the cell, and catalyzes the conversion of tyrosine to L-DOPA. Thus, a method of the present disclosure for producing a BIA compound or a BIA precursor compound comprises: a) culturing a host cell genetically modified to express a heterologous tyrosine hydroxylase, where the heterologous tyrosine hydroxylase comprises an amino acid sequence having at least 75% amino acid, at least 80%, at least 85%, at least 90%, at least 95%, at least 96%, at least 97%, at least 98%, or at least 99%, sequence identity to any one of the amino acid sequences depicted in FIG. 25A-25F, where the heterologous tyrosine hydroxylase is produced in the cell, and catalyzes the conversion of tyrosine to L-DOPA; and b) modifying the L-DOPA produced in the host cell. The L-DOPA produced in the host cell can be modified enzymatically in the host cell, to generate a BIA compound or a BIA precursor compound. The BIA compound or a BIA precursor compound can be further enzymatically modified in the host cell. In some cases, the L-DOPA is modified enzymatically in the host cell, to generate a BIA compound or a BIA precursor compound; and the BIA compound or a BIA precursor compound so generated is further enzymatically modified in the host cell. In some cases, the L-DOPA is modified enzymatically in the host cell, to generate a BIA compound or a BIA precursor compound; and the BIA compound or a BIA precursor compound so generated is isolated or purified from the host cell. In some cases, the L-DOPA is modified enzymatically in the host cell, to generate a BIA compound or a BIA precursor compound; and the BIA compound or BIA precursor compound so generated is isolated or purified from the host cell; and the isolated or purified BIA compound or BIA precursor compound is chemically modified. In some cases, the heterologous tyrosine hydroxylase comprises an amino acid sequence having at least 75% amino acid, at least 80%, at least 85%, at least 90%, at least 95%, at least 96%, at least 97%, at least 98%, or at least 99%, sequence identity to any one of the amino acid sequences depicted in FIG. 25A-25F, where the heterologous tyrosine hydroxylase comprises a substitution of F309 relative to CYP76AD1, as depicted in FIG. 25A-25F. In some cases, the substitution of F309 relative to CYP76AD1 is an F309L substitution. In some cases, the substitution of F309 relative to CYP76AD1 is an F309I substitution.

In some cases, a method of the present disclosure for producing a BIA compound or a BIA precursor compound provides for the production of the BIA compound or BIA precursor compound in an amount of from about 5 mg/L to about 500 mg/L culture medium, e.g., from about 5 mg/L to about 10 mg/L, from about 10 mg/L to about 20 mg/L, from about 20 mg/L to about 30 mg/L, from about 30 mg/L to about 40 mg/L, from about 40 mg/L to about 50 mg/L, from about 50 mg/L to about 75 mg/L, from about 75 mg/L to about 100 mg/L, from about 100 mg/L to about 150 mg/L, from about 150 mg/L to about 200 mg/L, from about 200 mg/L to about 250 mg/L, from about 250 mg/L to about 300 mg/L, from about 300 mg/L to about 350 mg/L, from about 350 mg/L to about 400 mg/L, from about 400 mg/L to about 450 mg/L, or from about 450 mg/L to about 500 mg/L culture medium. In some cases, a method of the present disclosure for producing a BIA compound or a BIA precursor compound provides for the production of the BIA compound or BIA precursor compound in an amount of greater than 500 mg/L culture medium. In some cases, a method of the present disclosure for producing a BIA compound or a BIA precursor compound provides for the production of the BIA compound or the BIA precursor compound in an amount of at least 5 mg/L, at least 10 mg/L, at least 20 mg/L, at least 25 mg/L, at least 30 mg/L, at least 40 mg/L, at least 50 mg/L, at least 75 mg/L, at least 100 mg/L, at least 150 mg/L, at least 200 mg/L, at least 250 mg/L, at least 300 mg/L, at least 350 mg/L, at least 400 mg/L, at least 450 mg/L, or at least 500 mg/L. In some cases, the cells are grown in culture medium comprising from 2% glucose to 20% glucose. For example, in some cases, the cells are grown in culture medium comprising 2% glucose. In some cases, the cells are grown in culture medium comprising from 2% to 5% glucose, from 5% to 10% glucose, from 10% to 15% glucose, or from 15% to 20% glucose. In some cases, the cells are cultured in culture medium for 24 hours to 7 days; e.g., the cells are cultured from 24 hours to 36 hours, from 36 hours to 48 hours, from 48 hours to 3 days, from 3 days to 4 days, from 4 days to 5 days, from 5 days to 6 days, or from 6 days to 7 days. In some cases, the cells are cultured for longer than 7 days.

In some cases, the BIA compound or BIA precursor compound is 3,4-dihydroxyphenylacetic acid (3,4-DHPAA). In some cases, the BIA compound or BIA precursor compound is (S)-norlaudanosoline (NLDS). In some cases, the BIA compound or BIA precursor compound is (S)-3'-hydroxycoclaurine. In some cases, the BIA compound or BIA precursor compound is (S)-3'-hydroxy-N-methylcoclaurine. In some cases, the BIA compound or BIA precursor compound is (S)-reticuline.

In some cases, the BIA compound or BIA precursor compound is 4-hydroxyphenylacetic acid (4HPA). In some cases, the BIA compound or BIA precursor compound is (S)-norcoclaurine. In some cases, the BIA compound or BIA precursor compound is (S)-coclaurine. In some cases, the BIA compound or BIA precursor compound is (S)—N-methylcoclaurine. In some cases, the BIA compound or BIA precursor compound is (S)-3'-hydroxy-N-methylcoclaurine. In some cases, the BIA compound or BIA precursor compound is (S)-reticuline.

In some cases, the BIA compound or BIA precursor compound is noscarpine. In some cases, the BIA compound or BIA precursor compound is papaverine. In some cases, the BIA compound or BIA precursor compound is scouler-ine. In some cases, the BIA compound or BIA precursor compound is sanguinarine. In some cases, the BIA compound or BIA precursor compound is berberine. In some cases, the BIA compound or BIA precursor compound is protopine.

Enzymes for generating various BIA compounds and BIA precursor compounds from (S)-reticuline are known in the art. See, e.g., Hagel and Facchini (2013) *Plant Cell Physiol.* 54:647. Enzymes for generating various BIA compounds and BIA precursor compounds from (R)-reticuline are known in the art. See, e.g., Hagel and Facchini (2013) *Plant Cell Physiol.* 54:647. Enzymes for generating berberine from (S)-reticuline are known in the art. Enzymes for generating papaverine from (S)-reticuline are known in the art. See, e.g., Hagel and Facchini (2013) *Plant Cell Physiol.* 54:647.

In some cases, the BIA compound or BIA precursor compound is thebaine. In some cases, the BIA compound or BIA precursor compound is palmatine. In some cases, the BIA compound or BIA precursor compound is berberine. In some cases, the BIA compound or BIA precursor compound is codeine. In some cases, the BIA compound or BIA precursor compound is morphine. Methods for converting thebaine to morphine are known in the art. See, e.g., Thodey et al. (2014) *Nat. Chem. Biol.* 10:837.

In some cases, one or more enzymes in a BIA biosynthetic pathway include an endoplasmic reticulum (ER) routing tag. Suitable ER routing tags include, but are not limited to, a 28-amino acid transmembrane domain of integral membrane protein calnexin (e.g., an ER routing tag comprising the amino acid sequence ILEQPLKFVLTAAVVLLTTSVCCV-VFT; SEQ ID NO:50); and the like.

In some cases, a method of the present disclosure for producing a BIA compound or BIA precursor compound comprises enzymatically modifying L-DOPA produced in a genetically modified host cell by a method of present disclosure for producing L-DOPA. In some cases, a method of the present disclosure for producing a BIA compound or BIA precursor compound comprises enzymatically modifying L-DOPA produced in a genetically modified host cell by a method of present disclosure for producing L-DOPA, thereby producing dopamine; and enzymatically modifying a product of L-DOPA, e.g., enzymatically modifying dopamine. In some cases, a method of the present disclosure for producing a BIA compound or BIA precursor compound comprises enzymatically modifying L-DOPA produced in a genetically modified host cell by a method of present disclosure for producing L-DOPA, thereby producing dopamine and 3,4-dihydroxyphenylacetic acid (3,4-DHPAA); and enzymatically modifying (condensing) the dopamine and the 3,4-DHPAA to produce (S)-norlaudanosoline (NLDS). In some cases, a method of the present disclosure for producing a BIA compound or BIA precursor compound comprises enzymatically modifying L-DOPA produced in a genetically modified host cell by a method of present disclosure for producing L-DOPA, thereby producing dopamine and 3,4-DHPAA; enzymatically modifying the dopamine and 3,4-DHPAA to produce NLDS; and enzymatically modifying the NLDS to produce (S)-3'-hydroxycoclaurine. In some cases, a method of the present disclosure for producing a BIA compound or BIA precursor compound comprises enzymatically modifying L-DOPA produced in a genetically modified host cell by a method of present disclosure for producing L-DOPA, thereby producing dopamine and 3,4-DHPAA; enzymatically modifying the dopamine and 3,4-DHPAA to produce NLDS; enzymatically modifying the NLDS to produce (S)-3'-hydroxycoclaurine; and enzymatically modifying the (S)-3'-hydroxycoclaurine to produce (S)-3'-hydroxy-N-methylcoclaurine. In some cases, a method of the present disclosure for producing a BIA compound or BIA precursor compound comprises enzymatically modifying L-DOPA produced in a genetically modified host cell by a method of present disclosure for producing L-DOPA, thereby producing dopamine and 3,4-DHPAA; enzymatically modifying the dopamine and 3,4-DHPAA to produce NLDS; enzymatically modifying the NLDS to produce (S)-3'-hydroxycoclaurine; enzymatically modifying the (S)-3'-hydroxycoclaurine to produce (S)-3'-hydroxy-N-methylcoclaurine; and enzymatically modifying the (S)-3'-hydroxy-N-methylcoclaurine to produce reticuline. In some cases, the reticuline is purified from the host cell in which it is produced. In some cases, the purified reticuline is chemically modified in a cell-free reaction in vitro to produce a BIA compound or a BIA precursor compound. In other cases, the host cell is genetically modified to express one or more additional enzymes that modify reticuline and enzymatic products of reticuline.

In some cases, a method of the present disclosure of producing a BIA compound or a BIA precursor compound comprises culturing a genetically modified host cell in a culture medium that does not include dopamine (e.g., culturing a genetically modified prokaryotic host cell in vitro in a culture medium that does not include dopamine; or culturing a genetically modified eukaryotic host cell (e.g., where the eukaryotic host cell is a unicellular organism, such as a yeast cell) in a culture medium that does not include dopamine).

In some cases, a method of the present disclosure of producing a BIA compound or a BIA precursor compound comprises culturing a genetically modified host cell in a culture medium that does not include dopamine (e.g., culturing a genetically modified prokaryotic host cell in vitro in a culture medium that does not include dopamine; or culturing a genetically modified eukaryotic host cell (e.g., where the eukaryotic host cell is a unicellular organism, such as a yeast cell) in a culture medium that does not include dopamine), where the carbon source for the BIA compound or BIA precursor compound comprises a monosaccharide, a disaccharide, or a polysaccharide. In some cases, a method of the present disclosure of producing a BIA compound or a BIA precursor compound comprises culturing a genetically modified host cell in a culture medium that does not include dopamine (e.g., culturing a genetically modified prokaryotic host cell in vitro in a culture medium that does not include dopamine; or culturing a genetically modified eukaryotic host cell (e.g., where the eukaryotic host cell is a unicellular organism, such as a yeast cell) in a culture medium that does not include dopamine), where the carbon source for the BIA compound or BIA precursor compound comprises glucose.

In some cases, a method of the present disclosure of producing a BIA compound or a BIA precursor compound comprises culturing a genetically modified host cell in vitro in a culture medium comprising dopamine (e.g., culturing a genetically modified prokaryotic host cell in vitro in a culture medium that includes dopamine; or culturing a genetically modified eukaryotic host cell (e.g., where the eukaryotic host cell is a unicellular organism, such as a yeast cell) in a culture medium that includes dopamine). In some cases, the concentration of dopamine in the culture medium ranges from about 0.1 mM to about 5 mM, e.g., from about 0.1 mM to about 0.5 mM, from about 0.5 mM to about 1 mM, from about 1 mM to about 2 mM, from about 2 mM to about 3 mM, from about 3 mM to about 4 mM, or from about 4 mM to about 5 mM. In some cases, the concentration of dopamine in the culture medium ranges from about 0.1 mM to about 1 mM, e.g., from about 0.1 mM to about 0.25 mM, from about 0.25 mM to about 0.5 mM, from about 0.5 mM to about 0.75 mM, or from about 0.75 mM to about 1 mM. In some cases, the concentration of dopamine in the culture medium required to yield an amount of a BIA compound or a BIA precursor compound is 75% or less, 60% or less, 50% or less, 45% or less, 40% or less, 35% or less, 30% or less, 25% or less, 20% or less, 15% or less, 10% or less, 5% or less, or 1% or less, of the amount of dopamine in the culture medium required to yield the same amount of the BIA compound or BIA precursor compound in a control cell that is not genetically modified with the heterologous tyrosine hydroxylase comprising an amino acid sequence having at least 75%, at least 80%, at least 85%, at least 90%, at least 95%, or at least 98%, amino acid sequence identity to SEQ ID NO:1.

The present disclosure provides methods of making dopamine in a host cell. The methods generally involve culturing a host cell genetically modified to express a heterologous tyrosine hydroxylase, where the heterologous tyrosine hydroxylase comprises an amino acid sequence having at least 75%, at least 80%, at least 85%, at least 90%, at least 95%, or at least 98%, amino acid sequence identity to SEQ ID NO:1, where the variant tyrosine hydroxylase is produced in the cell, and catalyzes the conversion of tyrosine to L-DOPA; where the host cell is also genetically modified to express a heterologous DOPA decarboxylase (DODC), where the DODC is produced in the cell, and catalyzes the conversion of L-DOPA to dopamine. For example, the host cell is genetically modified with one or more nucleic acids comprising nucleotide sequences encoding the heterologous tyrosine hydroxylase and the heterologous DODC. In some cases, the cell is a prokaryotic cell. In some cases, the cell is a eukaryotic cell. In some cases, the cell is a yeast cell. In some cases, the cell is a yeast cell; and the cell is genetically modified with one or more nucleic acids comprising nucleotide sequences encoding the heterologous tyrosine hydroxylase and the heterologous DODC. In some cases, the cell is a yeast cell; and the cell is genetically modified with one or more nucleic acids comprising nucleotide sequences encoding the heterologous tyrosine hydroxylase and the heterologous DODC, where the nucleotide sequences encoding the heterologous tyrosine hydroxylase and the heterologous DODC are codon optimized for expression in yeast.

A suitable DODC can comprise an amino acid sequence having at least 75%, at least 80%, at least 85%, at least 90%, at least 95%, at least 98%, at least 99%, or 100%, amino acid sequence identity to a stretch of from 350 to 400 aa, or from 400 aa to 518, contiguous amino acids of the amino acid sequence set forth in any one of FIG. 14A-14C.

In some cases, a method of the present disclosure for producing dopamine provides for the production of dopamine in an amount of from about 5 mg/L to about 500 mg/L culture medium, e.g., from about 5 mg/L to about 10 mg/L, from about 10 mg/L to about 20 mg/L, from about 20 mg/L to about 30 mg/L, from about 30 mg/L to about 40 mg/L, from about 40 mg/L to about 50 mg/L, from about 50 mg/L to about 75 mg/L, from about 75 mg/L to about 100 mg/L, from about 100 mg/L to about 150 mg/L, from about 150 mg/L to about 200 mg/L, from about 200 mg/L to about 250 mg/L, from about 250 mg/L to about 300 mg/L, from about 300 mg/L to about 350 mg/L, from about 350 mg/L to about 400 mg/L, from about 400 mg/L to about 450 mg/L, or from about 450 mg/L to about 500 mg/L culture medium, or greater than 500 mg/L culture medium. In some cases, a method of the present disclosure for producing dopamine provides for the production of dopamine in an amount of at least 5 mg/L, at least 10 mg/L, at least 20 mg/L, at least 25 mg/L, at least 30 mg/L, at least 40 mg/L, at least 50 mg/L, at least 75 mg/L, at least 100 mg/L, at least 150 mg/L, at least 200 mg/L, at least 250 mg/L, at least 300 mg/L, at least 350 mg/L, at least 400 mg/L, at least 450 mg/L, or at least 500 mg/L. In some cases, the cells are grown in culture medium comprising from 2% glucose to 20% glucose. For example, in some cases, the cells are grown in culture medium comprising 2% glucose. In some cases, the cells are grown in culture medium comprising from 2% to 5% glucose, from 5% to 10% glucose, from 10% to 15% glucose, or from 15% to 20% glucose. In some cases, the cells are cultured in culture medium for 24 hours to 7 days; e.g., the cells are cultured from 24 hours to 36 hours, from 36 hours to 48 hours, from 48 hours to 3 days, from 3 days to 4 days, from 4 days to 5 days, from 5 days to 6 days, or from 6 days to 7 days. In some cases, the cells are cultured for longer than 7 days.

The present disclosure provides methods of making 3,4-DHPAA or 4-HPA in a host cell. The methods generally involve culturing a host cell genetically modified to express a heterologous tyrosine hydroxylase, where the heterologous tyrosine hydroxylase comprises an amino acid sequence having at least 75%, at least 80%, at least 85%, at least 90%, at least 95%, or at least 98%, amino acid sequence identity to SEQ ID NO:1, where the heterologous tyrosine hydroxylase is produced in the cell, and catalyzes the conversion of tyrosine to L-DOPA; where the host cell is also genetically modified to express a heterologous DODC, where the DODC is produced in the cell, and catalyzes the conversion of L-DOPA to dopamine; and where the host cell is also genetically modified to express a heterologous monamine oxidase (MAO) or a heterologous tyramine oxidase, where the MAO (or the tyramine oxidase) is produced in the cell, and catalyzes conversion of dopamine to 3,4-DHPAA or 4-HPA. For example, the host cell is genetically modified with one or more nucleic acids comprising nucleotide sequences encoding the heterologous tyrosine hydroxylase, the heterologous DODC, and the heterologous MAO (or the tyramine oxidase). In some cases, the cell is a prokaryotic cell. In some cases, the cell is a eukaryotic cell. In some cases, the cell is a yeast cell. In some cases, the cell is a yeast cell; and the cell is genetically modified with one or more nucleic acids comprising nucleotide sequences encoding the heterologous tyrosine hydroxylase, the heterologous DODC, and the heterologous MAO (or the tyramine oxidase). In some cases, the cell is a yeast cell; and the cell is genetically modified with one or more nucleic acids comprising nucleotide sequences encoding the heterologous tyrosine hydroxylase, the heterologous DODC, and the heterologous MAO (or the tyramine oxidase), where the nucleotide sequences encoding the heterologous tyrosine hydroxylase, the heterologous DODC, and the heterologous MAO (or the tyramine oxidase) are codon optimized for expression in yeast.

A suitable MAO (or tyramine oxidase) can comprise an amino acid sequence having at least 75%, at least 80%, at least 85%, at least 90%, at least 95%, at least 98%, at least 99%, or 100%, amino acid sequence identity to a stretch of from 350 to 400, or from 400-443, contiguous amino acids of the amino acid sequence set forth in FIG. 15A. A suitable MAO (or tyramine oxidase) can comprise an amino acid sequence having at least 75%, at least 80%, at least 85%, at least 90%, at least 95%, at least 98%, at least 99%, or 100%, amino acid sequence identity to a stretch of from 650 to 700, from 700 to 750, or from 750 to 792 contiguous amino acids of the amino acid sequence set forth in FIG. 15B. A suitable MAO (or tyramine oxidase) can comprise an amino acid sequence having at least 75%, at least 80%, at least 85%, at least 90%, at least 95%, at least 98%, at least 99%, or 100%, amino acid sequence identity to a stretch of from 450 to 500 contiguous amino acids, or from 500 to 527 contiguous amino acids, of the amino acid sequence set forth in FIG. 15C.

The present disclosure provides methods of making 3,4-DHPAA or 4-HPA in a host cell. The methods generally involve culturing a host cell genetically modified to express a heterologous tyrosine hydroxylase, where the heterologous tyrosine hydroxylase comprises an amino acid sequence having at least 75%, at least 80%, at least 85%, at least 90%, at least 95%, or at least 98%, amino acid sequence identity to SEQ ID NO:1, where the heterologous tyrosine hydroxylase is produced in the cell, and catalyzes the conversion of tyrosine to L-DOPA; where the host cell is also genetically modified to express a heterologous DODC, where the DODC is produced in the cell, and catalyzes the conversion of L-DOPA to dopamine; and where the host cell comprises endogenous enzyme(s) that catalyzes conversion of dopamine to 3,4-DHPAA or 4-HPA. For example, the host cell is genetically modified with one or more nucleic acids comprising nucleotide sequences encoding the heterologous tyrosine hydroxylase, and the heterologous DODC. In some cases, the cell is a prokaryotic cell. In some cases, the cell is a eukaryotic cell. In some cases, the cell is a yeast cell. In some cases, the cell is a yeast cell; and the cell is genetically modified with one or more nucleic acids comprising nucleotide sequences encoding the heterologous tyrosine hydroxylase, and the heterologous DODC. In some cases, the cell is a yeast cell; and the cell is genetically modified with one or more nucleic acids comprising nucleotide sequences encoding the heterologous tyrosine hydroxylase and the heterologous DODC, where the nucleotide sequences encoding the heterologous tyrosine hydroxylase and the heterologous DODC are codon optimized for expression in yeast.

Norcoclaurine, coclaurine, N-methylcoclaurine, 3'-hydroxy-N-methylcoclaurine, reticuline The present disclosure provides methods of making (S)-norcoclaurine in a host cell. The methods generally involve culturing a host cell genetically modified to express a heterologous tyrosine hydroxylase, where the heterologous tyrosine hydroxylase comprises an amino acid sequence having at least 75%, at least 80%, at least 85%, at least 90%, at least 95%, or at least 98%, amino acid sequence identity to SEQ ID NO:1, where the heterologous tyrosine hydroxylase is produced in the cell, and catalyzes the conversion of tyrosine to L-DOPA; where the host cell is also genetically modified to express a heterologous DODC, where the DODC is produced in the cell, and catalyzes the conversion of L-DOPA to dopamine; where the host cell is also genetically modified to express a heterologous MAO, where the MAO is produced in the cell, and catalyzes conversion of dopamine to 4-HPA; and where the host cell is also genetically modified to express a heterologous norcoclaurine synthase (NCS), where the NCS is produced in the cell, and catalyzes the condensation of 4-HPA and dopamine to (S)-norcoclaurine. For example, the host cell is genetically modified with one or more nucleic acids comprising nucleotide sequences encoding the heterologous tyrosine hydroxylase, the heterologous DODC, the heterologous MAO, and the heterologous NCS. In some cases, the cell is a prokaryotic cell. In some cases, the cell is a eukaryotic cell. In some cases, the cell is a yeast cell. In some cases, the cell is a yeast cell; and the cell is genetically modified with one or more nucleic acids comprising nucleotide sequences encoding the heterologous tyrosine hydroxylase and the heterologous DODC, the heterologous MAO, and the heterologous NCS. In some cases, the cell is a yeast cell; and the cell is genetically modified with one or more nucleic acids comprising nucleotide sequences encoding the heterologous tyrosine hydroxylase and the heterologous DODC, the heterologous MAO, and the heterologous NCS, where the nucleotide sequences encoding the heterologous tyrosine hydroxylase, the heterologous DODC, the heterologous MAO, and the heterologous NCS are codon optimized for expression in yeast.

The present disclosure provides methods of making (S)-norcoclaurine in a host cell. The methods generally involve culturing a host cell genetically modified to express a heterologous tyrosine hydroxylase, where the heterologous tyrosine hydroxylase comprises an amino acid sequence having at least 75%, at least 80%, at least 85%, at least 90%, at least 95%, or at least 98%, amino acid sequence identity to SEQ ID NO:1, where the heterologous tyrosine hydroxylase is produced in the cell, and catalyzes the conversion of tyrosine to L-DOPA; where the host cell is also genetically modified to express a heterologous DODC, where the DODC is produced in the cell, and catalyzes the conversion of L-DOPA to dopamine; and where the host cell is also genetically modified to express a heterologous norcoclaurine synthase (NCS), where the NCS is produced in the cell, and catalyzes the condensation of 4-HPA and dopamine to (S)-norcoclaurine. For example, the host cell is genetically modified with one or more nucleic acids comprising nucleotide sequences encoding the heterologous tyrosine hydroxylase, the heterologous DODC, and the heterologous NCS. In some cases, the cell is a prokaryotic cell. In some cases, the cell is a eukaryotic cell. In some cases, the cell is a yeast cell. In some cases, the cell is a yeast cell; and the cell is genetically modified with one or more nucleic acids comprising nucleotide sequences encoding the heterologous tyrosine hydroxylase and the heterologous DODC, and the heterologous NCS. In some cases, the cell is a yeast cell; and the cell is genetically modified with one or more nucleic acids comprising nucleotide sequences encoding the heterologous tyrosine hydroxylase and the heterologous DODC, and the heterologous NCS, where the nucleotide sequences encoding the heterologous tyrosine hydroxylase, the heterologous DODC, and the heterologous NCS are codon optimized for expression in yeast. In many of these embodiments, the host cell is not genetically modified to express a heterologous MAO; instead, enzymes endogenous to the host cell (e.g., where the host cell is a eukaryotic host cell such as a yeast cell) catalyze the conversion of L-tyrosine to 4-hydroxyphenylacetaldehyde.

A suitable NCS can comprise an amino acid sequence having at least 50%, at least 60%, at least 70%, at least 75%, at least 80%, at least 85%, at least 90%, at least 95%, at least 98%, at least 99%, or 100%, amino acid sequence identity to a stretch of from 150 to 200, or from 200 to 231, contiguous amino acids of the amino acid sequence set forth in FIG. 16A. A suitable NCS can comprise an amino acid sequence having at least 50%, at least 60%, at least 70%, at least 75%, at least 80%, at least 85%, at least 90%, at least 95%, at least 98%, at least 99%, or 100%, amino acid sequence identity to a stretch of from 150 to 200, or from 200 to 210, contiguous amino acids of the amino acid sequence set forth in FIG. 16B.

A suitable NCS can comprise an amino acid sequence having at least 50%, at least 60%, at least 70%, at least 75%, at least 80%, at least 85%, at least 90%, at least 95%, at least 98%, at least 99%, or 100%, amino acid sequence identity to a stretch of from 150 to 200 contiguous amino acids of the amino acid sequence set forth in FIG. 21A. A suitable NCS can comprise an amino acid sequence having at least 50%, at least 60%, at least 70%, at least 75%, at least 80%, at least 85%, at least 90%, at least 95%, at least 98%, at least 99%, or 100%, amino acid sequence identity to a stretch of from 150 to 192, contiguous amino acids of the amino acid sequence set forth in FIG. 21B.

The present disclosure provides methods of making (S)-coclaurine in a host cell. The methods generally involve culturing a host cell genetically modified to express a heterologous tyrosine hydroxylase, where the heterologous tyrosine hydroxylase comprises an amino acid sequence having at least 75%, at least 80%, at least 85%, at least 90%, at least 95%, or at least 98%, amino acid sequence identity to SEQ ID NO:1, where the heterologous tyrosine hydroxylase is produced in the cell, and catalyzes the conversion of tyrosine to L-DOPA; where the host cell is also genetically modified to express a heterologous DODC, where the DODC is produced in the cell, and catalyzes the conversion of L-DOPA to dopamine; where the host cell is also genetically modified to express a heterologous MAO, where the MAO is produced in the cell, and catalyzes conversion of dopamine to 4-HPA; where the host cell is also genetically modified to express a heterologous NCS, where the NCS is produced in the cell, and catalyzes the condensation of 4-HPA and dopamine to (S)-norcoclaurine; and where the host cell is also genetically modified to express a heterologous norcoclaurine 6-O-methyltransferase (6OMT), where the heterologous 6OMT is produced in the cell and catalyzes conversion of (S)-norcoclaurine to (S)-coclaurine. For example, the host cell is genetically modified with one or more nucleic acids comprising nucleotide sequences encoding the heterologous tyrosine hydroxylase, the heterologous DODC, the heterologous MAO, the heterologous NCS, and the heterologous 6OMT. In some cases, the cell is a prokaryotic cell. In some cases, the cell is a eukaryotic cell. In some cases, the cell is a yeast cell. In some cases, the cell is a yeast cell; and the cell is genetically modified with one or more nucleic acids comprising nucleotide sequences encoding the heterologous tyrosine hydroxylase and the heterologous DODC, the heterologous MAO, the heterologous NCS, and the heterologous 6OMT. In some cases, the cell is a yeast cell; and the cell is genetically modified with one or more nucleic acids comprising nucleotide sequences encoding the heterologous tyrosine hydroxylase and the heterologous DODC, the heterologous MAO, the heterologous NCS, and the heterologous 6OMT, where the nucleotide sequences encoding the heterologous tyrosine hydroxylase, the heterologous DODC, the heterologous MAO, the heterologous NCS, and the heterologous 6OMT are codon optimized for expression in yeast.

The present disclosure provides methods of making (S)-coclaurine in a host cell. The methods generally involve culturing a host cell genetically modified to express a heterologous tyrosine hydroxylase, where the heterologous tyrosine hydroxylase comprises an amino acid sequence having at least 75%, at least 80%, at least 85%, at least 90%, at least 95%, or at least 98%, amino acid sequence identity to SEQ ID NO:1, where the heterologous tyrosine hydroxylase is produced in the cell, and catalyzes the conversion of tyrosine to L-DOPA; where the host cell is also genetically modified to express a heterologous DODC, where the DODC is produced in the cell, and catalyzes the conversion of L-DOPA to dopamine; where the host cell is also genetically modified to express a heterologous NCS, where the NCS is produced in the cell, and catalyzes the condensation of 4-HPA and dopamine to (S)-norcoclaurine; and where the host cell is also genetically modified to express a heterologous norcoclaurine 6-O-methyltransferase (6OMT), where the heterologous 6OMT is produced in the cell and catalyzes conversion of (S)-norcoclaurine to (S)-coclaurine. For example, the host cell is genetically modified with one or more nucleic acids comprising nucleotide sequences encoding the heterologous tyrosine hydroxylase, the heterologous DODC, the heterologous NCS, and the heterologous 6OMT. In some cases, the cell is a prokaryotic cell. In some cases, the cell is a eukaryotic cell. In some cases, the cell is a yeast cell. In some cases, the cell is a yeast cell; and the cell is genetically modified with one or more nucleic acids comprising nucleotide sequences encoding the heterologous tyrosine hydroxylase and the heterologous DODC, the heterologous NCS, and the heterologous 6OMT. In some cases, the cell is a yeast cell; and the cell is genetically modified with one or more nucleic acids comprising nucleotide sequences encoding the heterologous tyrosine hydroxylase and the heterologous DODC, the heterologous NCS, and the heterologous 6OMT, where the nucleotide sequences encoding the heterologous tyrosine hydroxylase, the heterologous DODC, the heterologous NCS, and the heterologous 6OMT are codon optimized for expression in yeast.

A suitable 6OMT can comprise an amino acid sequence having at least 75%, at least 80%, at least 85%, at least 90%, at least 95%, at least 98%, at least 99%, or 100%, amino acid sequence identity to a stretch of from 250 to 300, or from 300 to 346 or 347, contiguous amino acids of the amino acid sequence set forth in FIG. 17A or FIG. 17B.

The present disclosure provides methods of making (S)—N-methylcoclaurine in a host cell. The methods generally involve culturing a host cell genetically modified to express a heterologous tyrosine hydroxylase, where the heterologous tyrosine hydroxylase comprises an amino acid sequence having at least 75%, at least 80%, at least 85%, at least 90%, at least 95%, or at least 98%, amino acid sequence identity to SEQ ID NO:1, where the heterologous tyrosine hydroxylase is produced in the cell, and catalyzes the conversion of tyrosine to L-DOPA; where the host cell is also genetically modified to express a heterologous DODC, where the DODC is produced in the cell, and catalyzes the conversion of L-DOPA to dopamine; where the host cell is also genetically modified to express a heterologous MAO, where the MAO is produced in the cell, and catalyzes conversion of dopamine to 4-HPA; where the host cell is also genetically modified to express a heterologous NCS, where the NCS is produced in the cell, and catalyzes the condensation of 4-HPA and dopamine to (S)-norcoclaurine; where the host cell is also genetically modified to express a heterologous 6OMT, where the heterologous 6OMT is produced in the cell and catalyzes conversion of (S)-norcoclaurine to (S)-coclaurine; and where the host cell is also genetically modified to express a heterologous coclaurine-N-methyltransferase (CNMT), where the heterologous CNMT is produced in the cell and catalyzes the conversion of (S)-coclaurine to (S)—N-methylcoclaurine. For example, the host cell is genetically modified with one or more nucleic acids comprising nucleotide sequences encoding the heterologous tyrosine hydroxylase, the heterologous DODC, the heterologous MAO, the heterologous NCS, the heterologous 6OMT, and the heterologous CNMT. In some cases, the cell is a prokaryotic cell. In some cases, the cell is a eukaryotic cell. In some cases, the cell is a yeast cell. In some cases, the cell is a yeast cell; and the cell is genetically modified with one or more nucleic acids comprising nucleotide sequences encoding the heterologous tyrosine hydroxylase and the heterologous DODC, the heterologous MAO, the heterologous NCS, the heterologous 6OMT, and the heterologous CNMT. In some cases, the cell is a yeast cell; and the cell is genetically modified with one or more nucleic acids comprising nucleotide sequences encoding the heterologous tyrosine hydroxylase and the heterologous DODC, the heterologous MAO, the heterologous NCS, the heterologous 6OMT, and the heterologous CNMT, where the nucleotide sequences encoding the heterologous tyrosine hydroxylase, the heterologous DODC, the heterologous MAO, the heterologous NCS, the heterologous 6OMT, and the heterologous CNMT are codon optimized for expression in yeast.

The present disclosure provides methods of making (S)—N-methylcoclaurine in a host cell. The methods generally involve culturing a host cell genetically modified to express a heterologous tyrosine hydroxylase, where the heterologous tyrosine hydroxylase comprises an amino acid sequence having at least 75%, at least 80%, at least 85%, at least 90%, at least 95%, or at least 98%, amino acid sequence identity to SEQ ID NO:1, where the heterologous tyrosine hydroxylase is produced in the cell, and catalyzes the conversion of tyrosine to L-DOPA; where the host cell is also genetically modified to express a heterologous DODC, where the DODC is produced in the cell, and catalyzes the conversion of L-DOPA to dopamine; where the host cell is also genetically modified to express a heterologous NCS, where the NCS is produced in the cell, and catalyzes the condensation of 4-HPA and dopamine to (S)-norcoclaurine; where the host cell is also genetically modified to express a heterologous 6OMT, where the heterologous 6OMT is produced in the cell and catalyzes conversion of (S)-norcoclaurine to (S)-coclaurine; and where the host cell is also genetically modified to express a heterologous coclaurine-N-methyltransferase (CNMT), where the heterologous CNMT is produced in the cell and catalyzes the conversion of (S)-coclaurine to (S)—N-methylcoclaurine. For example, the host cell is genetically modified with one or more nucleic acids comprising nucleotide sequences encoding the heterologous tyrosine hydroxylase, the heterologous DODC, the heterologous NCS, the heterologous 6OMT, and the heterologous CNMT. In some cases, the cell is a prokaryotic cell. In some cases, the cell is a eukaryotic cell. In some cases, the cell is a yeast cell. In some cases, the cell is a yeast cell; and the cell is genetically modified with one or more nucleic acids comprising nucleotide sequences encoding the heterologous tyrosine hydroxylase and the heterologous DODC, the heterologous NCS, the heterologous 6OMT, and the heterologous CNMT. In some cases, the cell is a yeast cell; and the cell is genetically modified with one or more nucleic acids comprising nucleotide sequences encoding the heterologous tyrosine hydroxylase and the heterologous DODC, the heterologous NCS, the heterologous 6OMT, and the heterologous CNMT, where the nucleotide sequences encoding the heterologous tyrosine hydroxylase, the heterologous DODC, the heterologous MAO, the heterologous NCS, the heterologous 6OMT, and the heterologous CNMT are codon optimized for expression in yeast.

A suitable CNMT can comprise an amino acid sequence having at least 75%, at least 80%, at least 85%, at least 90%, at least 95%, at least 98%, at least 99%, or 100%, amino acid sequence identity to a stretch of from 250 to 300, or from 300 to 351 or 361, contiguous amino acids of the amino acid sequence set forth in FIG. 18A or FIG. 18B.

The present disclosure provides methods of making (S)-3'-hydroxy-N-methylcoclaurine in a host cell. The methods generally involve culturing a host cell genetically modified to express a heterologous tyrosine hydroxylase, where the heterologous tyrosine hydroxylase comprises an amino acid sequence having at least 75%, at least 80%, at least 85%, at least 90%, at least 95%, or at least 98%, amino acid sequence identity to SEQ ID NO:1, where the heterologous tyrosine hydroxylase is produced in the cell, and catalyzes the conversion of tyrosine to L-DOPA; where the host cell is also genetically modified to express a heterologous DODC, where the DODC is produced in the cell, and catalyzes the conversion of L-DOPA to dopamine; where the host cell is also genetically modified to express a heterologous MAO, where the MAO is produced in the cell, and catalyzes conversion of dopamine to 4-HPA; where the host cell is also genetically modified to express a heterologous NCS, where the NCS is produced in the cell, and catalyzes the condensation of 4-HPA and dopamine to (S)-norcoclaurine; where the host cell is also genetically modified to express a heterologous 6OMT, where the heterologous 6OMT is produced in the cell and catalyzes conversion of (S)-norcoclaurine to (S)-coclaurine; where the host cell is also genetically modified to express a heterologous CNMT, where the heterologous CNMT is produced in the cell and catalyzes the conversion of (S)-coclaurine to (S)—N-methylcoclaurine; and where the host cell is also genetically modified to express a heterologous CYP80B1, where the heterologous CYP80B1 is produced in the cell, and catalyzes the conversion of (S)—N-methylcoclaurine to (S)-3'-hydroxy-N-methylcoclaurine. For example, the host cell is genetically modified with one or more nucleic acids comprising nucleotide sequences encoding the heterologous tyrosine hydroxylase, the heterologous DODC, the heterologous MAO, the heterologous NCS, the heterologous 6OMT, the heterologous CNMT, and the heterologous CYP80B1. In some cases, the cell is a prokaryotic cell. In some cases, the cell is a eukaryotic cell. In some cases, the cell is a yeast cell. In some cases, the cell is a yeast cell; and the cell is genetically modified with one or more nucleic acids comprising nucleotide sequences encoding the heterologous tyrosine hydroxylase and the heterologous DODC, the heterologous MAO, the heterologous NCS, the heterologous 6OMT, the heterologous CNMT, and the heterologous CYP80B1. In some cases, the cell is a yeast cell; and the cell is genetically modified with one or more nucleic acids comprising nucleotide sequences encoding the heterologous tyrosine hydroxylase and the heterologous DODC, the heterologous MAO, the heterologous NCS, the heterologous 6OMT, the heterologous CNMT, and the heterologous CYP80B1, where the nucleotide sequences encoding the heterologous tyrosine hydroxylase, the heterologous DODC, the heterologous MAO, the heterologous NCS, the heterologous 6OMT, the heterologous CNMT, and the heterologous CYP80B1 are codon optimized for expression in yeast.

The present disclosure provides methods of making (S)-3'-hydroxy-N-methylcoclaurine in a host cell. The methods generally involve culturing a host cell genetically modified to express a heterologous tyrosine hydroxylase, where the heterologous tyrosine hydroxylase comprises an amino acid sequence having at least 75%, at least 80%, at least 85%, at least 90%, at least 95%, or at least 98%, amino acid sequence identity to SEQ ID NO:1, where the heterologous tyrosine hydroxylase is produced in the cell, and catalyzes the conversion of tyrosine to L-DOPA; where the host cell is also genetically modified to express a heterologous DODC, where the DODC is produced in the cell, and catalyzes the conversion of L-DOPA to dopamine; where the host cell is also genetically modified to express a heterologous NCS, where the NCS is produced in the cell, and catalyzes the condensation of 4-HPA and dopamine to (S)-norcoclaurine; where the host cell is also genetically modified to express a heterologous 6OMT, where the heterologous 6OMT is produced in the cell and catalyzes conversion of (S)-norcoclaurine to (S)-coclaurine; where the host cell is also genetically modified to express a heterologous CNMT, where the heterologous CNMT is produced in the cell and catalyzes the conversion of (S)-coclaurine to (S)—N-methylcoclaurine; and where the host cell is also genetically modified to express a heterologous CYP80B1, where the heterologous CYP80B1 is produced in the cell, and catalyzes the conversion of (S)—N-methylcoclaurine to (S)-3'-hydroxy-N-methylcoclaurine. For example, the host cell is genetically modified with one or more nucleic acids comprising nucleotide sequences encoding the heterologous tyrosine hydroxylase, the heterologous DODC, the heterologous NCS, the heterologous 6OMT, the heterologous CNMT, and the heterologous CYP80B1. In some cases, the cell is a prokaryotic cell. In some cases, the cell is a eukaryotic cell. In some cases, the cell is a yeast cell. In some cases, the cell is a yeast cell; and the cell is genetically modified with one or more nucleic acids comprising nucleotide sequences encoding the heterologous tyrosine hydroxylase and the heterologous DODC, the heterologous NCS, the heterologous 6OMT, the heterologous CNMT, and the heterologous CYP80B1. In some cases, the cell is a yeast cell; and the cell is genetically modified with one or more nucleic acids comprising nucleotide sequences encoding the heterologous tyrosine hydroxylase and the heterologous DODC, the heterologous NCS, the heterologous 6OMT, the heterologous CNMT, and the heterologous CYP80B1, where the nucleotide sequences encoding the heterologous tyrosine hydroxylase, the heterologous DODC, the heterologous NCS, the heterologous 6OMT, the heterologous CNMT, and the heterologous CYP80B1 are codon optimized for expression in yeast.

A suitable CYP80B1 ((S)—N-methylcoclaurine 3'-hydroxylase; also referred to herein as N-methylcoclaurine hydroxylase or NMCH) can comprise an amino acid sequence having at least 75%, at least 80%, at least 85%, at least 90%, at least 95%, at least 98%, at least 99%, or 100%, amino acid sequence identity to a stretch of from 350 to 400, from 400 to 450, or from 450 to 481, contiguous amino acids of the amino acid sequence set forth in FIG. 19.

A suitable CYP80B1 can comprise an amino acid sequence having at least 75%, at least 80%, at least 85%, at least 90%, at least 95%, at least 98%, at least 99%, or 100%, amino acid sequence identity to a stretch of from 350 to 400, from 400 to 450, or from 450 to 487, contiguous amino acids of the amino acid sequence set forth in FIG. 29.

The present disclosure provides methods of making reticuline in a host cell. The methods generally involve culturing a host cell genetically modified to express a heterologous tyrosine hydroxylase, where the heterologous tyrosine hydroxylase comprises an amino acid sequence having at least 75%, at least 80%, at least 85%, at least 90%, at least 95%, or at least 98%, amino acid sequence identity to SEQ ID NO:1, where the heterologous tyrosine hydroxylase is produced in the cell, and catalyzes the conversion of tyrosine to L-DOPA; where the host cell is also genetically modified to express a heterologous DODC, where the DODC is produced in the cell, and catalyzes the conversion of L-DOPA to dopamine; where the host cell is also genetically modified to express a heterologous MAO, where the MAO is produced in the cell, and catalyzes conversion of dopamine to 4-HPA; where the host cell is also genetically modified to express a heterologous NCS, where the NCS is produced in the cell, and catalyzes the condensation of 4-HPA and dopamine to (S)-norcoclaurine; where the host cell is also genetically modified to express a heterologous 6OMT, where the heterologous 6OMT is produced in the cell and catalyzes conversion of (S)-norcoclaurine to (S)-coclaurine; where the host cell is also genetically modified to express a heterologous CNMT, where the heterologous CNMT is produced in the cell and catalyzes the conversion of (S)-coclaurine to (S)—N-methylcoclaurine; where the host cell is also genetically modified to express a heterologous CYP80B1, where the heterologous CYP80B1 is produced in the cell, and catalyzes the conversion of (S)—N-methylcoclaurine to (S)-3'-hydroxy-N-methylcoclaurine; and where the host cell is also genetically modified to express a heterologous 3'-hydroxy-N-methylcoclaurine-4'-O-methyltransferase (4'OMT), where the heterologous 4'OMT is produced in the cell, and catalyzes the conversion of (S)-3'-hydroxy-N-methylcoclaurine to reticuline. For example, the host cell is genetically modified with one or more nucleic acids comprising nucleotide sequences encoding the heterologous tyrosine hydroxylase, the heterologous DODC, the heterologous MAO, the heterologous NCS, the heterologous 6OMT, the heterologous CNMT, the heterologous CYP80B1, and the heterologous 4'OMT. In some cases, the cell is a prokaryotic cell. In some cases, the cell is a eukaryotic cell. In some cases, the cell is a yeast cell. In some cases, the cell is a yeast cell; and the cell is genetically modified with one or more nucleic acids comprising nucleotide sequences encoding the heterologous tyrosine hydroxylase and the heterologous DODC, the heterologous MAO, the heterologous NCS, the heterologous 6OMT, the heterologous CNMT, the heterologous CYP80B1, and the heterologous 4'OMT. In some cases, the cell is a yeast cell; and the cell is genetically modified with one or more nucleic acids comprising nucleotide sequences encoding the heterologous tyrosine hydroxylase and the heterologous DODC, the heterologous MAO, the heterologous NCS, the heterologous 6OMT, the heterologous CNMT, the heterologous CYP80B1, and the heterologous 4'OMT, where the nucleotide sequences encoding the heterologous tyrosine hydroxylase, the heterologous DODC, the heterologous MAO, the heterologous NCS, the heterologous 6OMT, the heterologous CNMT, the heterologous CYP80B1, and the heterologous 4'OMT are codon optimized for expression in yeast. In some cases, the reticuline is purified from the host cell.

The present disclosure provides methods of making reticuline in a host cell. The methods generally involve culturing a host cell genetically modified to express a heterologous tyrosine hydroxylase, where the heterologous tyrosine hydroxylase comprises an amino acid sequence having at least 75%, at least 80%, at least 85%, at least 90%, at least 95%, or at least 98%, amino acid sequence identity to SEQ ID NO:1, where the heterologous tyrosine hydroxylase is produced in the cell, and catalyzes the conversion of tyrosine to L-DOPA; where the host cell is also genetically modified to express a heterologous DODC, where the DODC is produced in the cell, and catalyzes the conversion of L-DOPA to dopamine; where the host cell is also genetically modified to express a heterologous NCS, where the NCS is produced in the cell, and catalyzes the condensation of 4-HPA and dopamine to (S)-norcoclaurine; where the host cell is also genetically modified to express a heterologous 6OMT, where the heterologous 6OMT is produced in the cell and catalyzes conversion of (S)-norcoclaurine to (S)-coclaurine; where the host cell is also genetically modified to express a heterologous CNMT, where the heterologous CNMT is produced in the cell and catalyzes the conversion of (S)-coclaurine to (S)—N-methylcoclaurine; where the host cell is also genetically modified to express a heterologous CYP80B1, where the heterologous CYP80B1 is produced in the cell, and catalyzes the conversion of (S)—N-methylcoclaurine to (S)-3'-hydroxy-N-methylcoclaurine; and where the host cell is also genetically modified to express a heterologous 3'-hydroxy-N-methylcoclaurine-4'-O-methyltransferase (4'OMT), where the heterologous 4'OMT is produced in the cell, and catalyzes the conversion of (S)-3'-hydroxy-N-methylcoclaurine to reticuline. For example, the host cell is genetically modified with one or more nucleic acids comprising nucleotide sequences encoding the heterologous tyrosine hydroxylase, the heterologous DODC, the heterologous NCS, the heterologous 6OMT, the heterologous CNMT, the heterologous CYP80B1, and the heterologous 4'OMT. In some cases, the cell is a prokaryotic cell. In some cases, the cell is a eukaryotic cell. In some cases, the cell is a yeast cell. In some cases, the cell is a yeast cell; and the cell is genetically modified with one or more nucleic acids comprising nucleotide sequences encoding the heterologous tyrosine hydroxylase and the heterologous DODC, the heterologous NCS, the heterologous 6OMT, the heterologous CNMT, the heterologous CYP80B1, and the heterologous 4'OMT. In some cases, the cell is a yeast cell; and the cell is genetically modified with one or more nucleic acids comprising nucleotide sequences encoding the heterologous tyrosine hydroxylase and the heterologous DODC, the heterologous NCS, the heterologous 6OMT, the heterologous CNMT, the heterologous CYP80B1, and the heterologous 4'OMT, where the nucleotide sequences encoding the heterologous tyrosine hydroxylase, the heterologous DODC, the heterologous NCS, the heterologous 6OMT, the heterologous CNMT, the heterologous CYP80B1, and the heterologous 4'OMT are codon optimized for expression in yeast. In some cases, the reticuline is purified from the host cell.

Norlaudanosoline, 3'-hydroxycoclaurine, 3'-hydroxy-N-methylcoclaurine, reticuline The present disclosure provides methods of making (S)-norlaudanosoline (NLDS) in a host cell. The methods generally involve culturing a host cell genetically modified to express a heterologous tyrosine hydroxylase, where the heterologous tyrosine hydroxylase comprises an amino acid sequence having at least 75%, at least 80%, at least 85%, at least 90%, at least 95%, or at least 98%, amino acid sequence identity to SEQ ID NO:1, where the heterologous tyrosine hydroxylase is produced in the cell, and catalyzes the conversion of tyrosine to L-DOPA; where the host cell is also genetically modified to express a heterologous DODC, where the DODC is produced in the cell, and catalyzes the conversion of L-DOPA to dopamine; where the host cell is also genetically modified to express a heterologous MAO, where the MAO is produced in the cell, and catalyzes conversion of dopamine to 3,4-DHPAA; and where the host cell is also genetically modified to express a heterologous norcoclaurine synthase (NCS), where the NCS is produced in the cell, and catalyzes the condensation of 3,4-DHPAA and dopamine to NLDS. For example, the host cell is genetically modified with one or more nucleic acids comprising nucleotide sequences encoding the heterologous tyrosine hydroxylase, the heterologous DODC, the heterologous MAO, and the heterologous NCS. In some cases, the cell is a prokaryotic cell. In some cases, the cell is a eukaryotic cell. In some cases, the cell is a yeast cell. In some cases, the cell is a yeast cell; and the cell is genetically modified with one or more nucleic acids comprising nucleotide sequences encoding the heterologous tyrosine hydroxylase and the heterologous DODC, the heterologous MAO, and the heterologous NCS. In some cases, the cell is a yeast cell; and the cell is genetically modified with one or more nucleic acids comprising nucleotide sequences encoding the heterologous tyrosine hydroxylase and the heterologous DODC, the heterologous MAO, and the heterologous NCS, where the nucleotide sequences encoding the heterologous tyrosine hydroxylase, the heterologous DODC, the heterologous MAO, and the heterologous NCS are codon optimized for expression in yeast.

The present disclosure provides methods of making (S)-norlaudanosoline (NLDS) in a host cell. The methods generally involve culturing a host cell genetically modified to express a heterologous tyrosine hydroxylase, where the heterologous tyrosine hydroxylase comprises an amino acid sequence having at least 75%, at least 80%, at least 85%, at least 90%, at least 95%, or at least 98%, amino acid sequence identity to SEQ ID NO:1, where the heterologous tyrosine hydroxylase is produced in the cell, and catalyzes the conversion of tyrosine to L-DOPA; where the host cell is also genetically modified to express a heterologous DODC, where the DODC is produced in the cell, and catalyzes the conversion of L-DOPA to dopamine; and where the host cell is also genetically modified to express a heterologous norcoclaurine synthase (NCS), where the NCS is produced in the cell, and catalyzes the condensation of 3,4-DHPAA and dopamine to NLDS. For example, the host cell is genetically modified with one or more nucleic acids comprising nucleotide sequences encoding the heterologous tyrosine hydroxylase, the heterologous DODC, and the heterologous NCS. In some cases, the cell is a prokaryotic cell. In some cases, the cell is a eukaryotic cell. In some cases, the cell is a yeast cell. In some cases, the cell is a yeast cell; and the cell is genetically modified with one or more nucleic acids comprising nucleotide sequences encoding the heterologous tyrosine hydroxylase and the heterologous DODC, and the heterologous NCS. In some cases, the cell is a yeast cell; and the cell is genetically modified with one or more nucleic acids comprising nucleotide sequences encoding the heterologous tyrosine hydroxylase and the heterologous DODC, and the heterologous NCS, where the nucleotide sequences encoding the heterologous tyrosine hydroxylase, the heterologous DODC, and the heterologous NCS are codon optimized for expression in yeast.

A suitable NCS can comprise an amino acid sequence having at least 50%, at least 60%, at least 70%, at least 75%, at least 80%, at least 85%, at least 90%, at least 95%, at least 98%, at least 99%, or 100%, amino acid sequence identity to a stretch of from 150 to 200, or from 200 to 231, contiguous amino acids of the amino acid sequence set forth in FIG. 16A. A suitable NCS can comprise an amino acid sequence having at least 50%, at least 60%, at least 70%, at least 75%, at least 80%, at least 85%, at least 90%, at least 95%, at least 98%, at least 99%, or 100%, amino acid sequence identity to a stretch of from 150 to 200, or from 200 to 210, contiguous amino acids of the amino acid sequence set forth in FIG. 16B.

A suitable NCS can comprise an amino acid sequence having at least 50%, at least 60%, at least 70%, at least 75%, at least 80%, at least 85%, at least 90%, at least 95%, at least 98%, at least 99%, or 100%, amino acid sequence identity to a stretch of from 150 to 200 contiguous amino acids of the amino acid sequence set forth in FIG. 21A. A suitable NCS can comprise an amino acid sequence having at least 50%, at least 60%, at least 70%, at least 75%, at least 80%, at least 85%, at least 90%, at least 95%, at least 98%, at least 99%, or 100%, amino acid sequence identity to a stretch of from 150 to 192, contiguous amino acids of the amino acid sequence set forth in FIG. 21B.

The present disclosure provides methods of making (S)-3'-hydroxycoclaurine in a host cell. The methods generally involve culturing a host cell genetically modified to express a heterologous tyrosine hydroxylase, where the heterologous tyrosine hydroxylase comprises an amino acid sequence having at least 75%, at least 80%, at least 85%, at least 90%, at least 95%, or at least 98%, amino acid sequence identity to SEQ ID NO:1, where the heterologous tyrosine hydroxylase is produced in the cell, and catalyzes the conversion of tyrosine to L-DOPA; where the host cell is also genetically modified to express a heterologous DODC, where the DODC is produced in the cell, and catalyzes the conversion of L-DOPA to dopamine; where the host cell is also genetically modified to express a heterologous MAO, where the MAO is produced in the cell, and catalyzes conversion of dopamine to 3,4-DHPAA; where the host cell is also genetically modified to express a heterologous norcoclaurine synthase (NCS), where the NCS is produced in the cell, and catalyzes the condensation of 3,4-DHPAA and dopamine to NLDS; and where the host cell is also genetically modified to express a heterologous 6OMT, where the heterologous 6OMT is produced in the cell, and catalyzes the conversion of NLDS to (S)-3'-hydroxycoclaurine. For example, the host cell is genetically modified with one or more nucleic acids comprising nucleotide sequences encoding the heterologous tyrosine hydroxylase, the heterologous DODC, the heterologous MAO, the heterologous NCS, and the heterologous 6OMT. In some cases, the cell is a prokaryotic cell. In some cases, the cell is a eukaryotic cell. In some cases, the cell is a yeast cell. In some cases, the cell is a yeast cell; and the cell is genetically modified with one or more nucleic acids comprising nucleotide sequences encoding the heterologous tyrosine hydroxylase and the heterologous DODC, the heterologous MAO, the heterologous NCS, and the heterologous 6OMT. In some cases, the cell is a yeast cell; and the cell is genetically modified with one or more nucleic acids comprising nucleotide sequences encoding the heterologous tyrosine hydroxylase and the heterologous DODC, the heterologous MAO, the heterologous NCS, and the heterologous 6OMT, where the nucleotide sequences encoding the heterologous tyrosine hydroxylase, the heterologous DODC, the heterologous MAO, the heterologous NCS, and the heterologous 6OMT are codon optimized for expression in yeast.

The present disclosure provides methods of making (S)-3'-hydroxycoclaurine in a host cell. The methods generally involve culturing a host cell genetically modified to express a heterologous tyrosine hydroxylase, where the heterologous tyrosine hydroxylase comprises an amino acid sequence having at least 75%, at least 80%, at least 85%, at least 90%, at least 95%, or at least 98%, amino acid sequence identity to SEQ ID NO:1, where the heterologous tyrosine hydroxylase is produced in the cell, and catalyzes the conversion of tyrosine to L-DOPA; where the host cell is also genetically modified to express a heterologous DODC, where the DODC is produced in the cell, and catalyzes the conversion of L-DOPA to dopamine; where the host cell is also genetically modified to express a heterologous norcoclaurine synthase (NCS), where the NCS is produced in the cell, and catalyzes the condensation of 3,4-DHPAA and dopamine to NLDS; and where the host cell is also genetically modified to express a heterologous 6OMT, where the heterologous 6OMT is produced in the cell, and catalyzes the conversion of NLDS to (S)-3'-hydroxycoclaurine. For example, the host cell is genetically modified with one or more nucleic acids comprising nucleotide sequences encoding the heterologous tyrosine hydroxylase, the heterologous DODC, the heterologous NCS, and the heterologous 6OMT. In some cases, the cell is a prokaryotic cell. In some cases, the cell is a eukaryotic cell. In some cases, the cell is a yeast cell. In some cases, the cell is a yeast cell; and the cell is genetically modified with one or more nucleic acids comprising nucleotide sequences encoding the heterologous tyrosine hydroxylase and the heterologous DODC, the heterologous NCS, and the heterologous 6OMT. In some cases, the cell is a yeast cell; and the cell is genetically modified with one or more nucleic acids comprising nucleotide sequences encoding the heterologous tyrosine hydroxylase and the heterologous DODC, the heterologous NCS, and the heterologous 6OMT, where the nucleotide sequences encoding the heterologous tyrosine hydroxylase, the heterologous DODC, the heterologous NCS, and the heterologous 6OMT are codon optimized for expression in yeast.

A suitable 6OMT can comprise an amino acid sequence having at least 75%, at least 80%, at least 85%, at least 90%, at least 95%, at least 98%, at least 99%, or 100%, amino acid sequence identity to a stretch of from 250 to 300, or from 300 to 346 or 347, contiguous amino acids of the amino acid sequence set forth in FIG. 17A or FIG. 17B.

The present disclosure provides methods of making (S)-3'-hydroxy-N-methylcoclaurine in a host cell. The methods generally involve culturing a host cell genetically modified to express a heterologous tyrosine hydroxylase, where the heterologous tyrosine hydroxylase comprises an amino acid sequence having at least 75%, at least 80%, at least 85%, at least 90%, at least 95%, or at least 98%, amino acid sequence identity to SEQ ID NO:1, where the heterologous tyrosine hydroxylase is produced in the cell, and catalyzes the conversion of tyrosine to L-DOPA; where the host cell is also genetically modified to express a heterologous DODC, where the DODC is produced in the cell, and catalyzes the conversion of L-DOPA to dopamine; where the host cell is also genetically modified to express a heterologous MAO, where the MAO is produced in the cell, and catalyzes conversion of dopamine to 3,4-DHPAA; where the host cell is also genetically modified to express a heterologous norcoclaurine synthase (NCS), where the NCS is produced in the cell, and catalyzes the condensation of 3,4-DHPAA and dopamine to NLDS; where the host cell is also genetically modified to express a heterologous 6OMT, where the heterologous 6OMT is produced in the cell, and catalyzes the conversion of NLDS to (S)-3'-hydroxycoclaurine; and where the host cell is also genetically modified to express a heterologous CNMT, where the heterologous CNMT catalyzes the conversion of to (S)-3'-hydroxycoclaurine to (S)-3'-hydroxy-N-methylcoclaurine. For example, the host cell is genetically modified with one or more nucleic acids comprising nucleotide sequences encoding the heterologous tyrosine hydroxylase, the heterologous DODC, the heterologous MAO, the heterologous NCS, the heterologous 6OMT, and the heterologous CNMT. In some cases, the cell is a prokaryotic cell. In some cases, the cell is a eukaryotic cell. In some cases, the cell is a yeast cell. In some cases, the cell is a yeast cell; and the cell is genetically modified with one or more nucleic acids comprising nucleotide sequences encoding the heterologous tyrosine hydroxylase and the heterologous DODC, the heterologous MAO, the heterologous NCS, the heterologous 6OMT, and the heterologous CNMT. In some cases, the cell is a yeast cell; and the cell is genetically modified with one or more nucleic acids comprising nucleotide sequences encoding the heterologous tyrosine hydroxylase and the heterologous DODC, the heterologous MAO, the heterologous NCS, the heterologous 6OMT, and the heterologous CNMT, where the nucleotide sequences encoding the heterologous tyrosine hydroxylase, the heterologous DODC, the heterologous MAO, the heterologous NCS, the heterologous 6OMT, and the heterologous CNMT are codon optimized for expression in yeast.

The present disclosure provides methods of making (S)-3'-hydroxy-N-methylcoclaurine in a host cell. The methods generally involve culturing a host cell genetically modified to express a heterologous tyrosine hydroxylase, where the heterologous tyrosine hydroxylase comprises an amino acid sequence having at least 75%, at least 80%, at least 85%, at least 90%, at least 95%, or at least 98%, amino acid sequence identity to SEQ ID NO:1, where the heterologous tyrosine hydroxylase is produced in the cell, and catalyzes the conversion of tyrosine to L-DOPA; where the host cell is also genetically modified to express a heterologous DODC, where the DODC is produced in the cell, and catalyzes the conversion of L-DOPA to dopamine; where the host cell is also genetically modified to express a heterologous norcoclaurine synthase (NCS), where the NCS is produced in the cell, and catalyzes the condensation of 3,4-DHPAA and dopamine to NLDS; where the host cell is also genetically modified to express a heterologous 6OMT, where the heterologous 6OMT is produced in the cell, and catalyzes the conversion of NLDS to (S)-3'-hydroxycoclaurine; and where the host cell is also genetically modified to express a heterologous CNMT, where the heterologous CNMT catalyzes the conversion of to (S)-3'-hydroxycoclaurine to (S)-3'-hydroxy-N-methylcoclaurine. For example, the host cell is genetically modified with one or more nucleic acids comprising nucleotide sequences encoding the heterologous tyrosine hydroxylase, the heterologous DODC, the heterologous NCS, the heterologous 6OMT, and the heterologous CNMT. In some cases, the cell is a prokaryotic cell. In some cases, the cell is a eukaryotic cell. In some cases, the cell is a yeast cell. In some cases, the cell is a yeast cell; and the cell is genetically modified with one or more nucleic acids comprising nucleotide sequences encoding the heterologous tyrosine hydroxylase and the heterologous DODC, the heterologous NCS, the heterologous 6OMT, and the heterologous CNMT. In some cases, the cell is a yeast cell; and the cell is genetically modified with one or more nucleic acids comprising nucleotide sequences encoding the heterologous tyrosine hydroxylase and the heterologous DODC, the heterologous NCS, the heterologous 6OMT, and the heterologous CNMT, where the nucleotide sequences encoding the heterologous tyrosine hydroxylase, the heterologous DODC, the heterologous NCS, the heterologous 6OMT, and the heterologous CNMT are codon optimized for expression in yeast.

A suitable CNMT can comprise an amino acid sequence having at least 75%, at least 80%, at least 85%, at least 90%, at least 95%, at least 98%, at least 99%, or 100%, amino acid sequence identity to a stretch of from 250 to 300, or from 300 to 351 or 361, contiguous amino acids of the amino acid sequence set forth in FIG. 18A or FIG. 18B.

The present disclosure provides methods of making reticuline in a host cell. The methods generally involve culturing a host cell genetically modified to express a heterologous tyrosine hydroxylase, where the heterologous tyrosine hydroxylase comprises an amino acid sequence having at least 75%, at least 80%, at least 85%, at least 90%, at least 95%, or at least 98%, amino acid sequence identity to SEQ ID NO:1, where the heterologous tyrosine hydroxylase is produced in the cell, and catalyzes the conversion of tyrosine to L-DOPA; where the host cell is also genetically modified to express a heterologous DODC, where the DODC is produced in the cell, and catalyzes the conversion of L-DOPA to dopamine; where the host cell is also genetically modified to express a heterologous MAO, where the MAO is produced in the cell, and catalyzes conversion of dopamine to 3,4-DHPAA; where the host cell is also genetically modified to express a heterologous norcoclaurine synthase (NCS), where the NCS is produced in the cell, and catalyzes the condensation of 3,4-DHPAA and dopamine to NLDS; where the host cell is also genetically modified to express a heterologous 6OMT, where the heterologous 6OMT is produced in the cell, and catalyzes the conversion of NLDS to (S)-3'-hydroxycoclaurine; where the host cell is also genetically modified to express a heterologous CNMT, where the heterologous CNMT catalyzes the conversion of to (S)-3'-hydroxycoclaurine to (S)-3'-hydroxy-N-methylcoclaurine; where the host cell is also genetically modified to express a heterologous 4'OMT, where the heterologous 4'OMT is produced in the cell and catalyzes the conversion of (S)-3'-hydroxy-N-methylcoclaurine to reticuline. For example, the host cell is genetically modified with one or more nucleic acids comprising nucleotide sequences encoding the heterologous tyrosine hydroxylase, the heterologous DODC, the heterologous MAO, the heterologous NCS, the heterologous 6OMT, the heterologous CNMT, and the heterologous 4'OMT. In some cases, the cell is a prokaryotic cell. In some cases, the cell is a eukaryotic cell. In some cases, the cell is a yeast cell. In some cases, the cell is a yeast cell; and the cell is genetically modified with one or more nucleic acids comprising nucleotide sequences encoding the heterologous tyrosine hydroxylase and the heterologous DODC, the heterologous MAO, the heterologous NCS, the heterologous 6OMT, the heterologous CNMT, and the heterologous 4'OMT. In some cases, the cell is a yeast cell; and the cell is genetically modified with one or more nucleic acids comprising nucleotide sequences encoding the heterologous tyrosine hydroxylase and the heterologous DODC, the heterologous MAO, the heterologous NCS, the heterologous 6OMT, the heterologous CNMT, and the heterologous 4'OMT, where the nucleotide sequences encoding the heterologous tyrosine hydroxylase, the heterologous DODC, the heterologous MAO, the heterologous NCS, the heterologous 6OMT, the heterologous CNMT, and the heterologous 4'OMT are codon optimized for expression in yeast.

The present disclosure provides methods of making reticuline in a host cell. The methods generally involve culturing a host cell genetically modified to express a heterologous tyrosine hydroxylase, where the heterologous tyrosine hydroxylase comprises an amino acid sequence having at least 75%, at least 80%, at least 85%, at least 90%, at least 95%, or at least 98%, amino acid sequence identity to SEQ ID NO:1, where the heterologous tyrosine hydroxylase is produced in the cell, and catalyzes the conversion of tyrosine to L-DOPA; where the host cell is also genetically modified to express a heterologous DODC, where the DODC is produced in the cell, and catalyzes the conversion of L-DOPA to dopamine; where the host cell is also genetically modified to express a heterologous norcoclaurine synthase (NCS), where the NCS is produced in the cell, and catalyzes the condensation of 3,4-DHPAA and dopamine to NLDS; where the host cell is also genetically modified to express a heterologous 6OMT, where the heterologous 6OMT is produced in the cell, and catalyzes the conversion of NLDS to (S)-3'-hydroxycoclaurine; where the host cell is also genetically modified to express a heterologous CNMT, where the heterologous CNMT catalyzes the conversion of to (S)-3'-hydroxycoclaurine to (S)-3'-hydroxy-N-methylcoclaurine; where the host cell is also genetically modified to express a heterologous 4'OMT, where the heterologous 4'OMT is produced in the cell and catalyzes the conversion of (S)-3'-hydroxy-N-methylcoclaurine to reticuline. For example, the host cell is genetically modified with one or more nucleic acids comprising nucleotide sequences encoding the heterologous tyrosine hydroxylase, the heterologous DODC, the heterologous NCS, the heterologous 6OMT, the heterologous CNMT, and the heterologous 4'OMT. In some cases, the cell is a prokaryotic cell. In some cases, the cell is a eukaryotic cell. In some cases, the cell is a yeast cell. In some cases, the cell is a yeast cell; and the cell is genetically modified with one or more nucleic acids comprising nucleotide sequences encoding the heterologous tyrosine hydroxylase and the heterologous DODC, the heterologous NCS, the heterologous 6OMT, the heterologous CNMT, and the heterologous 4'OMT. In some cases, the cell is a yeast cell; and the cell is genetically modified with one or more nucleic acids comprising nucleotide sequences encoding the heterologous tyrosine hydroxylase and the heterologous DODC, the heterologous NCS, the heterologous 6OMT, the heterologous CNMT, and the heterologous 4'OMT, where the nucleotide sequences encoding the heterologous tyrosine hydroxylase, the heterologous DODC, the heterologous NCS, the heterologous 6OMT, the heterologous CNMT, and the heterologous 4'OMT are codon optimized for expression in yeast.

The genetically modified host cells used in a method of producing the BIA or BIA precursor compounds described above can be grown in cell culture in vitro. The cell culture conditions for a particular cell type are well known in the art. For example, the host cells that comprise the various heterologous coding sequences can be cultured under standard or readily optimized conditions, with standard cell culture media and supplements. As one example, standard growth media when selective pressure for plasmid maintenance is not required may contain 20 g/L yeast extract, 10 g/L peptone, and 20 g/L dextrose (YPD). Host cells containing plasmids can be grown in synthetic complete (SC) media containing 1.7 g/L yeast nitrogen base, 5 g/L ammonium sulfate, and 20 g/L dextrose supplemented with the appropriate amino acids required for growth and selection. Alternative carbon sources which may be useful for inducible enzyme expression include sucrose, raffinose, and galactose. Cells can be grown at 30° C. with shaking at 200 rpm, e.g., in test tubes or flasks in volumes ranging from 1 mL to 1000 mL, or greater than 1 L, in the laboratory. Culture volumes can also be scaled up for growth in larger fermentation vessels, for example, as part of an industrial process.

A method of the present disclosure can be modified such that products downstream of reticuline are produced. Such products include, e.g., thebaine, berberine, and sanguinarine. The host cell can be further genetically modified to express enzymes that modify reticuline to generate products downstream of reticuline. As an example, as described in Fossatie et al. ((2014) *Nature Communications* 5:3283) dihydrosanguinarine, sanguinarine, N-methylscoulerine and N-methylcheilanthifoline can be synthesized by introducing into a host cell that produces reticuline, as described above, one or more nucleic acids comprising nucleotide sequences encoding berberine bridge enzyme (BBE), P450s cheilanthofoline synthase (CFS), stylopine synthase (SPS), S-Adenosyl-1-methionine:tetrahydroprotoberberine cis-N-methyltransferase (TNMT), (S)-cis-N-methylstylopine 14-hydroxylase (MSH), and protopine 6-hydroxylase (P6H).

Methods of Detecting L-DOPA

The present disclosure provides a method of detecting a level of L-DOPA, the method comprising detecting, in a host cell genetically modified to produce a heterologous L-3,4-dihydroxyphenylalanine (L-DOPA) 4,5-dioxygenase (DOD), betalamic acid or a colored or fluorescent product of betalamic acid, produced by action of the heterologous DOD on L-DOPA produced in the cell, wherein the level of L-DOPA produced in the cell is directly proportional to the level of betalamic acid or a colored or fluorescent product of betalamic acid produced in the cell. In some cases, a level of betalamic acid is detected. In some cases, the colored product of betalamic acid is betaxanthin. In some cases, the colored product of betalamic acid is betanidin. In some cases, the fluorescent product of betalamic acid is betaxanthin. The betalamic acid, or colored product of betalamic acid, can be detected colorimetrically; the detection can be visual, or can be detected by instrumentation. Betaxanthin can be detected colorimetrically or via any means of detecting a fluorescent product, including, e.g., using a fluorescence activated cell sorter, a fluorimeter, etc. In some cases, the host cell is a prokaryotic cell. In some cases, the host cell is a eukaryotic cell. In some cases, the host cell is a yeast cell. In some cases, the host cell is a *Saccharomyces cerevisiae* cell.

A method of the present disclosure for detecting L-DOPA is useful for identifying variant enzymes that modulate levels of tyrosine in a cell; for identifying gene products (mRNA; polypeptides) that modulate levels of tyrosine in a cell; for identifying a variant tyrosine hydroxylase that provides for increased production of dopamine in a cell; for identifying a variant BIA pathway enzyme that modulates the level of a BIA pathway intermediate (e.g., a BIA compound or a BIA precursor compound) in a cell; and the like.

In some cases, a method of the present disclosure for detecting a level of L-DOPA comprises: detecting, in a host cell genetically modified to produce a heterologous DOD, betalamic acid or a colored or fluorescent product of betalamic acid, produced by action of the heterologous DOD on L-DOPA produced in the cell; where the host cell is also genetically modified with a nucleic acid comprising a nucleotide sequence encoding a biosynthetic pathway enzyme other than tyrosine hydroxylase, where the biosynthetic pathway enzyme is downstream of L-DOPA; and where a level of betalamic acid or a colored or fluorescent product of betalamic acid that is lower than the level of the betalamic acid or the colored or fluorescent product of betalamic acid in a control cell not comprising the nucleotide sequence encoding the downstream pathway enzyme, indicates that the downstream pathway enzyme increases flux through the biosynthetic pathway.

In some cases, a method of the present disclosure for detecting a level of L-DOPA comprises: detecting, in a host cell genetically modified to produce a heterologous DOD, betalamic acid or a colored or fluorescent product of betalamic acid, produced by action of the heterologous DOD on L-DOPA produced in the cell; where the host cell is also genetically modified with a nucleic acid comprising a nucleotide sequence encoding a variant benzylisoquinoline alkaloid (BIA) biosynthetic pathway enzyme other than tyrosine hydroxylase; and where a level of betalamic acid or a colored or fluorescent product of betalamic acid that is lower than the level of the betalamic acid or the colored or fluorescent product of betalamic acid in a control cell not comprising the nucleotide sequence encoding the variant BIA pathway enzyme, indicates that the variant BIA pathway enzyme increases flux through the BIA biosynthetic pathway.

In some cases, a method of the present disclosure for detecting a level of L-DOPA comprises: detecting, in a host cell genetically modified to produce a heterologous DOD, betalamic acid or a colored or fluorescent product of betalamic acid, produced by action of the heterologous DOD on L-DOPA produced in the cell; where the host cell is also genetically modified with a nucleic acid comprising a nucleotide sequence encoding a variant BIA biosynthetic pathway enzyme other than tyrosine hydroxylase; where a level of betalamic acid or a colored or fluorescent product of betalamic acid that is higher than the level of the betalamic acid or the colored or fluorescent product of betalamic acid in a control cell not comprising the nucleotide sequence encoding the variant BIA pathway enzyme indicates that the variant BIA pathway enzyme decreases flux through the BIA biosynthetic pathway.

Variant BIA pathway enzymes can be produced by any known method, including, e.g., mutating a nucleic acid encoding a BIA pathway enzyme, e.g., by an error-prone polymerase chain reaction, and the like.

In some cases, a method of the present disclosure for detecting a level of L-DOPA comprises: detecting, in a host cell genetically modified to produce a heterologous DOD, betalamic acid or a colored or fluorescent product of betalamic acid, produced by action of the heterologous DOD on L-DOPA produced in the cell; where the host cell is treated to introduce one or more mutations into a nucleic acid (genomic DNA, etc.) in the host cell; and where a level of betalamic acid or a colored or fluorescent product of betalamic acid that is lower than the level of the betalamic acid or the colored or fluorescent product of betalamic acid in a control cell not comprising the mutation indicates that the mutation decreases L-DOPA levels in the cell.

In some cases, a method of the present disclosure for detecting a level of L-DOPA comprises: detecting, in a host cell genetically modified to produce a heterologous DOD, betalamic acid or a colored or fluorescent product of betalamic acid, produced by action of the heterologous DOD on L-DOPA produced in the cell; where the host cell is treated to introduce one or more mutations into a nucleic acid (genomic DNA, etc.) in the host cell; and where a level of betalamic acid or a colored or fluorescent product of betalamic acid that is higher than the level of the betalamic acid or the colored or fluorescent product of betalamic acid in a control cell not comprising the mutation indicates that the mutation increases L-DOPA levels in the cell.

Methods of introducing mutations into a nucleic acid in a host cell are well known in the art; any such method can be used. Mutations can be random or site-directed.

Methods of Identifying Variant Tyrosine Hydroxylase

The present disclosure provides methods of identifying a variant tyrosine hydroxylase that exhibits increased enzymatic activity. For example, the method provides for identifying a variant tyrosine hydroxylase that exhibits at least 10%, at least 15%, at least 20%, or at least 25% greater enzymatic activity than the enzymatic activity of the tyrosine hydroxylase of SEQ ID NO:1 or SEQ ID NO:8. The method generally involves detecting, in a host cell genetically modified with a nucleic acid encoding a test tyrosine hydroxylase and a nucleic acid comprising a nucleotide sequence encoding a heterologous L-3,4-dihydroxyphenylalanine (L-DOPA) 4,5-dioxygenase (DOD), betalamic acid or a colored or fluorescent product of betalamic acid, produced by action of the heterologous 4,5-dioxygenase on L-DOPA produced by action of the test tyrosine hydroxylase. A level of betalamic acid or a colored or fluorescent product of betalamic acid produced in the host cell genetically modified with nucleic acid encoding the test tyrosine hydroxylase and a nucleic acid encoding the heterologous DOD, that is higher than the level of betalamic acid or a colored or fluorescent product of betalamic acid produced in a control host cell genetically modified with the tyrosine hydroxylase of SEQ ID NO:1 and the heterologous DOD indicates that the test tyrosine hydroxylase is a variant tyrosine hydroxylase that exhibits at least 10%, at least 15%, at least 20%, or at least 25% greater enzymatic activity than the enzymatic activity of the tyrosine hydroxylase of SEQ ID NO:1 or SEQ ID NO:8. In some cases, a level of betalamic acid is detected. In some cases, the colored product of betalamic acid is betaxanthin. In some cases, the colored product of betalamic acid is betanidin. In some cases, the fluorescent product of betalamic acid is betaxanthin. The betalamic acid, or colored product of betalamic acid, can be detected colorimetrically; the detection can be visual, or can be detected by instrumentation. Betaxanthin can be detected colorimetrically or via any means of detecting a fluorescent product, including, e.g., using a fluorescence activated cell sorter, a fluorimeter, etc. In some cases, the host cell is a prokaryotic cell. In some cases, the host cell is a eukaryotic cell. In some cases, the host cell is a yeast cell. In some cases, the host cell is a *Saccharomyces cerevisiae* cell.

For convenience, the host cell genetically modified with nucleic acid encoding the test tyrosine hydroxylase and a nucleic acid encoding the heterologous DOD is referred to as the "test" host cell. A host cell genetically modified with the tyrosine hydroxylase of SEQ ID NO:1 and the heterologous DOD, and not genetically modified with the test tyrosine hydroxylase, is referred to as a "control" host cell.

In some cases, the level of betaxanthin in the test cell is at least 10%, at least 25%, at least 50%, at least 75%, at least 100% (or 2-fold), at least 2.5-fold, at least 5-fold, at least 10-fold, at least 25-fold, at least 50-fold, at least 100-fold, or more than 100-fold, higher that the level of betaxanthin produced in the control cell.

In some cases, the host cell (test cell and control cell) is a eukaryotic cell. In some cases, the eukaryotic cell is a yeast cell, e.g., *Saccharomyces cerevisiae*.

Detection of betaxanthin can be carried out visually, e.g., the betaxanthin is detected colorimetrically. Detection of betaxanthin can be carried out by detecting betaxanthin fluorescence.

In some cases, the method involves isolating a genetically modified host cell that comprises a variant tyrosine hydroxylase identified as exhibiting at least 10%, at least 15%, at least 20%, or at least 25% greater enzymatic activity than the enzymatic activity of the tyrosine hydroxylase of SEQ ID NO:1. In some cases, the cell is isolated using fluorescence activated cell sorting (FACS).

In some cases, the method involves isolating a nucleic acid encoding a variant tyrosine hydroxylase identified as exhibiting at least 10%, at least 15%, at least 20%, or at least 25% greater enzymatic activity than the enzymatic activity of the tyrosine hydroxylase of SEQ ID NO:1. The isolated nucleic acid can be cloned into a vector, which may be an expression vector.

In some cases, the method involves isolating a genetically modified host cell that comprises a variant tyrosine hydroxylase identified as exhibiting at least 10%, at least 15%, at least 20%, or at least 25% greater enzymatic activity than the enzymatic activity of the tyrosine hydroxylase of SEQ ID NO:8. In some cases, the cell is isolated using FACS.

In some cases, the method involves isolating a nucleic acid encoding a variant tyrosine hydroxylase identified as exhibiting at least 10%, at least 15%, at least 20%, or at least 25% greater enzymatic activity than the enzymatic activity of the tyrosine hydroxylase of SEQ ID NO:8. The isolated nucleic acid can be cloned into a vector, which may be an expression vector.

As noted above, the test host cell and control host cell is genetically modified with a nucleic acid comprising a nucleotide sequence encoding a heterologous DOD. A suitable DOD comprises an amino acid sequence having at least 75%, at least 80%, at least 85%, at least 90%, at least 95%, at least 96%, at least 97%, at least 98%, at least 99%, or 100%, amino acid sequence identity to the amino acid sequence set forth in SEQ ID NO:9.

Methods of Identifying Gene Products that Increase Tyrosine Production

The present disclosure provides a method of identifying a gene product that increases tyrosine production in a cell. The method generally involves: detecting, in a host cell genetically modified with: i) a test modified gene; ii) a heterologous tyrosine hydroxylase; and iii) a heterologous L-3,4-dihydroxyphenylalanine (L-DOPA) 4,5-dioxygenase (DOD), betalamic acid or a colored or fluorescent product of betalamic acid produced by action of the heterologous 4,5-dioxygenase on L-DOPA produced by action of the tyrosine hydroxylase on tyrosine produced by action of the gene product. A level of betalamic acid or a colored or fluorescent product of betalamic acid produced that is higher than the level of betalamic acid or a colored or fluorescent product of betalamic acid produced in a control host cell genetically modified with the heterologous tyrosine hydroxylase and the heterologous L-DOPA-4,5-dioxygenase indicates that the test gene product is a gene product that increases tyrosine production in the cell. In some cases, the cell is a yeast cell, e.g., *S. cerevisiae*. In some cases, the method comprises isolating the modified gene. In some cases, a level of betalamic acid is detected. In some cases, the colored product of betalamic acid is betaxanthin. In some cases, the colored product of betalamic acid is betanidin. In some cases, the fluorescent product of betalamic acid is betaxanthin. The betalamic acid, or colored product of betalamic acid, can be detected colorimetrically; the detection can be visual, or can be detected by instrumentation. Betaxanthin can be detected colorimetrically or via any means of detecting a fluorescent product, including, e.g., using a fluorescence activated cell sorter, a fluorimeter, etc. In some cases, the host cell is a prokaryotic cell. In some cases, the host cell is a eukaryotic cell. In some cases, the host cell is a yeast cell. In some cases, the host cell is a *Saccharomyces cerevisiae* cell.

Suitable tyrosine hydroxylases comprise an amino acid sequence having at least 75%, at least 80%, at least 85%, at least 90%, at least 95%, at least 96%, at least 97%, at least 98%, at least 99%, or 100%, amino acid sequence identity to the amino acid sequence set forth in SEQ ID NO:1. Suitable tyrosine hydroxylases comprise an amino acid sequence having at least 75%, at least 80%, at least 85%, at least 90%, at least 95%, at least 96%, at least 97%, at least 98%, at least 99%, or 100%, amino acid sequence identity to the amino acid sequence set forth in SEQ ID NO:8.

In some cases, the tyrosine hydroxylase exhibits tyrosine hydroxylase enzymatic activity that is no more than about 2-fold to 10-fold higher than the enzymatic activity of a tyrosine hydroxylase comprising the amino acid sequence set forth in SEQ ID NO:8. For example, the present disclosure provides a method of identifying a gene product that increases tyrosine production in a cell. The method generally involves: detecting, in a host cell genetically modified with: i) a test modified gene; ii) a heterologous tyrosine hydroxylase that exhibits tyrosine hydroxylase enzymatic activity that is no more than about 2-fold to 10-fold higher than the enzymatic activity of a tyrosine hydroxylase comprising the amino acid sequence set forth in SEQ ID NO:8; and iii) a heterologous L-3,4-dihydroxyphenylalanine (L-DOPA) 4,5-dioxygenase (DOD), betalamic acid or a colored or fluorescent product of betalamic acid produced by action of the heterologous 4,5-dioxygenase on L-DOPA produced by action of the tyrosine hydroxylase on tyrosine produced by action of the gene product. A level of betalamic acid or a colored or fluorescent product of betalamic acid produced that is higher than the level of betalamic acid or a colored or fluorescent product of betalamic acid produced in a control host cell genetically modified with the heterologous tyrosine hydroxylase and the heterologous L-DOPA-4,5-dioxygenase indicates that the test gene product is a gene product that increases tyrosine production in the cell. In some cases, the cell is a yeast cell, e.g., S. cerevisiae. In some cases, the method comprises isolating the modified gene. In some cases, a level of betalamic acid is detected. In some cases, the colored product of betalamic acid is betaxanthin. In some cases, the colored product of betalamic acid is betanidin. In some cases, the fluorescent product of betalamic acid is betaxanthin. The betalamic acid, or colored product of betalamic acid, can be detected colorimetrically; the detection can be visual, or can be detected by instrumentation. Betaxanthin can be detected colorimetrically or via any means of detecting a fluorescent product, including, e.g., using a fluorescence activated cell sorter, a fluorimeter, etc.

In some cases, the test modified gene comprises a modification that renders the gene non-functional. For example, in some cases, modification is a deletion of all or a portion of the gene, where the deletion renders the gene non-functional. For example, in some cases, a method of the present disclosure comprises detecting betaxanthin levels in a plurality of host yeast cells that are genetically modified with: i) a heterologous tyrosine hydroxylase; and ii) a heterologous DOD, where each of the plurality of host yeast cells comprises a different gene modification that renders a gene non-functional. For example, in some cases, the plurality of host yeast cells is a knockout library, in which one gene in each of the plurality of host yeast cells has a knockout deletion, and where the gene that comprises the knockout deletion is different in each of the plurality of host yeast cells. A level of betaxanthin produced in a genetically modified host cell within the plurality of genetically modified host cells that is higher than the level of betaxanthin produced in a control host cell genetically modified with the heterologous tyrosine hydroxylase and the heterologous L-DOPA-4,5-dioxygenase indicates that genetically modified host cell comprises a gene modification that leads to increased tyrosine production.

In some cases, the test modified gene comprises a modification that increases the level and or activity of a product of the gene. For example, in some cases, a modification that increases the activity of a product of a gene (e.g., a polypeptide encoded by a gene) comprises one or more nucleotide substitutions relative to a parent unmodified gene. In some cases, the one or more nucleotide substitutions result in a change in amino acid sequence of a polypeptide encoded by the gene, such that the activity of the polypeptide is increased, where increased activity of the polypeptide results in increased tyrosine production in the cell. In some cases, a method of the present disclosure comprises detecting betalamic acid or a colored or fluorescent product of betalamic acid levels in a plurality of host yeast cells that are genetically modified with: i) a heterologous tyrosine hydroxylase; and ii) a heterologous DOD, where each of the plurality of host yeast cells is also genetically modified with a different test modified gene that comprises one or more nucleotide sequence substitutions relative to a parent unmodified gene. A level of betalamic acid or a colored or fluorescent product of betalamic acid produced in a genetically modified host cell within the plurality of genetically modified host cells that is higher than the level of betalamic acid or a colored or fluorescent product of betalamic acid produced in a control host cell genetically modified with the heterologous tyrosine hydroxylase and the heterologous L-DOPA-4,5-dioxygenase indicates that genetically modified host cell comprises a gene modification that leads to increased tyrosine production.

EXAMPLES

The following examples are put forth so as to provide those of ordinary skill in the art with a complete disclosure and description of how to make and use the present invention, and are not intended to limit the scope of what the inventors regard as their invention nor are they intended to represent that the experiments below are all or the only experiments performed. Efforts have been made to ensure accuracy with respect to numbers used (e.g. amounts, temperature, etc.) but some experimental errors and deviations should be accounted for. Unless indicated otherwise, parts are parts by weight, molecular weight is weight average molecular weight, temperature is in degrees Celsius, and pressure is at or near atmospheric. Standard abbreviations may be used, e.g., bp, base pair(s); kb, kilobase(s); pl, picoliter(s); s or sec, second(s); min, minute(s); h or hr, hour(s); aa, amino acid(s); kb, kilobase(s); bp, base pair(s); nt, nucleotide(s); i.m., intramuscular(ly); i.p., intraperitoneal (ly); s.c., subcutaneous(ly); and the like.

Materials and Methods

The following materials and methods were used in the Examples, below.

Strains and Growth Media

The base S. cerevisiae strain for the experiments was BY4741 (MATa his3Δ1 leuΔ0 met15Δ0 ura3Δ0). Wildtype yeast cultures were grown in YPD (10 g/l Bacto Yeast Extract; 20 g/l Bacto Peptone; 20 g/l Dextrose). Selection of auxotrophic markers (URA3, LEU2, and/or HISS) was performed in synthetic complete media (6.7 g/l Difco Yeast Nitrogen Base without amino acids; 2 g/l Drop-out Mix Synthetic Minus appropriate amino acids, without Yeast Nitrogen Base (US Biological); 20 g/l Dextrose).

Golden gate assembly reactions were transformed in TG1 chemically competent E. coli. Error-prone PCR libraries were transformed in TransforMax EPI300 (Epicentre) electrocompetent E. coli. Transformed cells were selected on Lysogeny Broth (LB) containing the antibiotics ampicillin or kanamycin.

Yeast Expression Vectors

Yeast expression vectors were built using Golden Gate Assembly. Weber, E., Engler, C., Gruetzner, R., Werner, S. & Marillonnet, S. A Modular Cloning System for Standardized Assembly of Multigene Constructs. PLoS ONE 6, e16765 (2011). Vector sequences were derived form the pRS series of plasmids. Promoter and terminator sequences for heterologous enzyme expression were derived from the yeast genome. Unique restriction sites (BsaI and BsmBI) were removed to facilitate plasmid construction.

Error-prone PCR library plasmids included a CEN6/ARS4 low copy number origin of replication to enable high-efficiency library transformations. All other plasmids contained no yeast origin of replication and were designed for direct integration into the yeast genome via homologous recombination at the URA3 or LEU2 locus. All plasmids used in this work are listed in Tables 1 and 2 (FIG. 26A-26B and FIG. 27). Sequences are also provided as GenBank files.

Yeast Strain Construction

Aside from mutant libraries, all genetic modifications to yeast were made via genomic integration. Yeast integration plasmids (YIPs) were constructed that lacked a yeast origin of replication but included regions of homology to either the URA3 or LEU2 locus. Five hundred μg of plasmid was linearized by digestion with NotI and transformed directly into yeast using a standard LiOAc transformation. Cells were plated onto dropout plates corresponding to the YIP's auxotrophic marker. Replicate colonies were picked directly from this transformation plate for further analysis.

Error-Prone PCR Library Construction

Error-prone PCR was performed using the GeneMorph II Random Mutagenesis Kit (Agilent Technologies). Oligos 1 and 2 were used to amplify the CYP76AD1 coding sequence off of the template for PCR (Plasmid 1). Plasmid template was added to the PCR reaction at a concentration of 40 ng/μl to achieve the desired error rate. The PCR reaction was run as suggested in the GeneMorph II user manual, using an annealing temperature of 45° C.

The PCR was incubated with DpnI for 1 hour at 37° C. before being cleaned up using a Zymo DNA Clean and Concentrator kit. A BsaI Golden Gate Assembly reaction was run using 40 fmol of both the PCR product and Plasmid 2. This reaction was again cleaned up, eluted in 10 μl of water, and transformed in its entirety into TransforMax EPI300 (Epicentre) electrocompetent cells. After a 1-hour rescue, the cells were grown to saturation in 500 ml of LB+kanamycin overnight. 2 ml of saturated culture was miniprepped and all resulting DNA was transformed into Strain 2 for screening using a standard LiOAc transformation.

DNA Shuffling Library Construction

CYP76AD1 mutants were shuffled using Golden Gate Shuffling. Engler, C., Gruetzner, R., Kandzia, R. & Marillonnet, S. Golden gate shuffling: a one-pot DNA shuffling method based on type IIs restriction enzymes. PLoS One 4, e5553 (2009). The coding sequence was divided into four regions that equally distributed the set of mutations being shuffled. Oligos 5-14 were used to PCR amplify fragments using the mutant plasmids as templates. These PCR's were mixed in a Golden Gate Assembly reaction and prepped for library screening as described in the above section on error-prone PCR library construction.

Library Screening for Improved Betaxanthin Production

For screening of tyrosine hydroxylase mutants, yeast transformations were plated on multiple 500 cm² agar plates (with synthetic dropout media) at a density of approximately 50,000 colonies per plate. After 72 hours of growth at 30° C., the most intensely yellow colonies were isolated for further analysis.

Flow Cytometry

Strains 1 and 2 were grown overnight in synthetic complete media (minus uracil) with 2% glucose. Saturated cultures were back-diluted 100× into fresh media supplemented with L-DOPA (Sigma #D9628) and grown in 24-well blocks with shaking at 30° C. for 18 hours. Cells were spun down and washed in PBS (pH=7.4).

A Guava easyCyte flow cytometer was used to quantify betaxanthin fluorescence at an excitation of 488 nm and emission of 510 nm. The gain was set to 20. Histograms were prepared using the software package FlowJo (available on the world wide web at flowjo.com).

Fluorescence Microscopy

Strain 23 was grown with or without 1 mM L-DOPA in synthetic complete media (minus uracil) with 2% glucose overnight. Cultures were concentrated by centrifugation, washed in PBS, and spotted onto plain glass slides to be examined with a Zeiss Observer D1 microscope using a 100×DIC objective. Images were captured using a Hamamatsu Orca-flash 4.0 (C11440) camera using auto-exposure. Fluorescence images were taken using an X-Cite Series 120 lamp, Zeiss filter set 45 (excitation at 560/40 nm and emission at 630/75 nm) for mKate2, and Zeiss filter set 46 (excitation at 500/20 nm and emission at 535/30 nm) for betaxanthin. Images were analyzed and composites were created using Fiji (available on the world wide web at fiji.sc).

Betaxanthin Fluorescence Quantification

Colonies were picked into synthetic complete media with 2% glucose and grown overnight. Saturated cultures were back-diluted 50× into fresh media in 96-deep-well blocks. Cultures were grown for 48 hours in a Multitron ATR shaker at 30° C. Cells were pelleted, washed, and resuspended in PBS (pH=7.4). The cells were transferred to glass-bottomed microplates and measured for fluorescence in a TECAN Safire2 (excitation: 485/5 nm, emission: 505/5 nm, gain: 120). Fold over background fluorescence measurements were obtained by normalizing to the fluorescence observed in control Strain 3.

Dopamine Production Assay

Colonies were picked into 2.5 ml of synthetic complete media (minus uracil) with 2% glucose. After overnight growth, saturated cultures were back-diluted 50× into 24-deep-well blocks containing fresh synthetic complete media (minus uracil) with 2% glucose. The cultures were grown in a Multitron ATR shaker for 48 hours at 30° C. Cultures were pelleted and culture supernatants were measured for dopamine titer via LC/MS.

Betanidin Production Assay

Special media was required to observe the production of betanidin in culture supernatants. It was discovered that the standard media component para-aminobenzoic acid (PABA) was capable of spontaneous condensation with betalamic acid to produce PABA-betaxanthin. PABA-betaxanthin had similar absorbance properties to betanidin, making it difficult to visualize changes in betanidin formation.

Minimal media lacking PABA was prepared (7.6 g/l Difco Yeast Nitrogen Base without amino acids or vitamins; 76 mg/l Histidine; 76 mg/l Methionine; 76 mg/l Tryptophan; 380 mg/l Leucine; 2 mg/l Biotin; 400 mg/l Calcium Pantothenate; 2 g/l Inositol; 400 mg/l Pyridoxin HCL; 400 mg/l Thiamine HCL; 20 g/l Dextrose).

Cells were first grown to saturation in synthetic complete media (minus uracil) with 2% glucose. They were then back-diluted 50× into our custom minimal media which was supplemented with 10 mM ascorbic acid to prevent betanidin oxidation and 1 mM tyrosine. Cultures were grown in 24-deep-well blocks at 30° C. in a Multitron ATR shaker for 24 hours. Cells were pelleted and supernatants were analyzed. Absorbance spectra of culture supernatants were acquired using a TECAN Safire2 plate reader. LC/MS analysis was performed as described below.

Shake-Flask Fermentations for Norcoclaurine and Reticuline

Colonies were picked into 2.5 ml of selective synthetic media with 2% glucose. After overnight growth, saturated cultures were back-diluted 50× into 250 ml baffled shake flasks containing 50 ml of fresh 2× selective synthetic media with 4% glucose. The cultures were grown at 30° C. with shaking at 250 rpm for 96 hours. At designated time points, aliquots were taken from the cultures to measure OD600, and media was stored at −20° C. for later analysis by LC/MS.

LC/MS and LC/DAD/MS Analysis

Dopamine, Betaxanthin, and Betanidin Detection

Ten µl of each culture supernatant was separated on an Agilent 1260 Infinity Quaternary LC System with Zorbax Eclipse Plus C18 4.6×100 mm–3.5 µm reversed-phase column (Agilent) at ~20° C. using a 0.5 ml/min flow rate. Samples were eluted with a linear gradient from 100% water/0% acetonitrile+0.1% formic acid to 65% water/35% acetonitrile+0.1% formic acid over the course of 15 minutes. Absorbance was measured using a diode array detector at 430 nm (betalamic acid), 460 nm (betaxanthin) and 540 nm (betanidin) with 4 nm bandwidth. Mass spectrometry was carried out using an attached Agilent 6120 Quadrupole LC/MS, in atmospheric pressure ionization-positive electrospray (API-ES positive) mode at 100V fragmentor voltage, scanning masses between 100 and 700 Da. For quantification of betalamic acid (m/z 212.055 and $R_t$ 10.24 minutes), tyrosine-betaxanthin/portulacaxanthin II (m/z 375.119 and $R_t$ 10.35 minutes), and betanidin (m/z 389.098 and $R_t$ 9.87 minutes), extracted ion counts were integrated and reported. For quantification of dopamine, ion counts with m/z of 154.086 [M+H]+ and a retention time of 2.99 minutes were extracted, integrated, and quantified against an 8-point dopamine calibration curve ranging from 0.004 mM to 1 mM in twofold steps.

Norcoclaurine and Reticuline Detection

Time course and tandem mass spectrometry (MS/MS) data were collected with the same column, pump, and gradient as above, but using an Agilent 6520 Accurate-Mass Q-TOF LC/MS for fragmentation and mass detection. The system was run in atmospheric pressure ionization-positive electrospray (API-ES positive) mode, with a 100V fragmentor voltage and, for MS/MS, a 23V collision energy. The species targeted were (S)-norcoclaurine (m/z 272.1281 [M+H]+ and $R_t$ 10.7 minutes) and (R)-reticuline (m/z 330.17 [M+H]+ and $R_t$ 13.3 minutes). For quantification purposes, these extracted ion counts were integrated and compared against six-point calibration curves covering 0.078-2.50 µM and 0.039-1.25 µM in twofold steps for S-norcoclaurine and R-reticuline, respectively.

Example 1: Development of an Enzyme-Coupled L-DOPA Biosensor

A long-standing inability to achieve L-tyrosine hydroxylation to L-DOPA in yeast prompted the development of an enzyme-coupled biosensor for L-DOPA that could be used to quickly screen candidate tyrosine hydroxylases for activity. DOPA dioxygenase (DOD) is a plant enzyme that converts L-DOPA into a yellow, highly fluorescent family of pigments called betaxanthins in members of the order Caryophyllales (FIG. 1A) (Sasaki et al. 2009). These betaxanthins, all of which have similar optical properties, are the result of a spontaneous reaction between free amines and betalamic acid produced by DOD (FIG. 2)(Gandía-Herrero et al. 2005). For simplicity, this entire family of molecules is referred to simply as betaxanthin.

A DOD variant from the flowering plant *Mirabilis jalapa* was expressed in yeast. It was found that cells grown in media supplemented with L-DOPA produced enough betaxanthin to be easily detected by eye in both the supernatant and the cell pellet. Fluorescence microscopy indicated that betaxanthin, which is highly water soluble, accumulates in the yeast vacuole in addition to getting pumped out of the cell through unknown mechanisms (FIG. 1B). Because a substantial fraction of betaxanthin remains intracellular, L-DOPA production can be measured in single cells, allowing the screening methodology described herein to be easily paired with fluorescence-activated cell sorting (FACS). When measured by flow cytometry, changes in intracellular betaxanthin fluorescence were readily detectable across a range of 0.02 to 2 mM L-DOPA supplemented in the growth media (FIG. 1C). The sensor demonstrated a 35-fold dynamic range within this concentration regime. On a fluorescence microplate reader with optimal excitation and emission settings, the fluorescence of a DOD-expressing strain grown in 2 mM L-DOPA measured 94.8 fold over background. Such a broad dynamic range is atypical for intracellular metabolite biosensors and extremely enabling for high-throughput library screening.

Importantly, this enzyme-coupled biosensor is specific for L-DOPA and can differentiate between tyrosine hydroxylase and DOPA oxidase activities exhibited by tyrosinases. For the production of BIAs, the secondary DOPA oxidase activity is undesirable as it diverts L-DOPA to melanin (Santos & Stephanopoulos 2008). While a tyrosinase from the button mushroom *Agaricus bisporus* (polyphenol oxidase 2, AbPPO2) has been successfully expressed in yeast, this enzyme had over 10-fold higher activity on L-DOPA than it did on L-tyrosine (Lezzi et al. 2012). Given the existence of bacterial tyrosinases with relatively low DOPA oxidase activity (Hernandez-Romero et al. 2006), it was hypothesized that our betaxanthin production assay could be used alongside enzyme mutagenesis to alter the relative substrate specificity for L-DOPA and L-tyrosine in enzymes that preferentially act on L-DOPA and are active in yeast. In this manner, undesired DOPA oxidase activity (activity 2 in FIG. 1A and FIG. 2) could be minimized and tyrosine hydroxylase activity maximized (activity 1 in FIG. 1A and FIG. 2).

Identification of an Active Tyrosine Hydroxylase in *S. cerevisiae*

A tyrosine hydroxylase variant was sought that yielded measurable levels of betaxanthin when expressed with DOD to use as a starting point for enzyme mutagenesis. Two candidate enzymes were selected for initial screening—AbPPO2 from *A. bisporus* (discussed above) and CYP76AD1 from the sugar beet *Beta vulgaris*. The latter is a recently identified cytochrome P450 DOPA oxidase (Hatlestad et al. 2012). This enzyme is responsible for the production of the red pigment betanidin (a betaxanthin analog) in beets (FIG. 2). Functional expression of CYP76AD1 in yeast was demonstrated previously to characterize this enzyme's role in determining beet color, making it an attractive candidate for our purposes (Hatlestad et al. 2012). Notably, tyrosine hydroxylase activity was not previously reported for this enzyme; it was selected with the objective of altering its substrate specificity from L-DOPA to L-tyrosine.

Figure 3A:
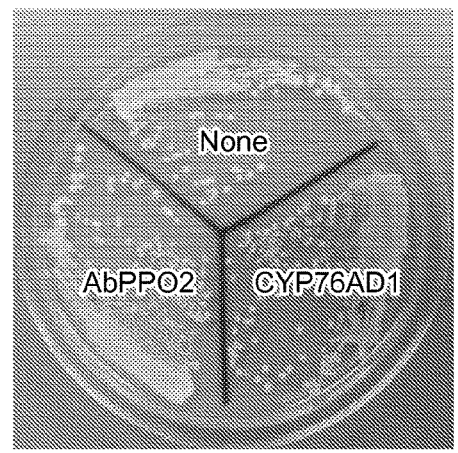
FIG. 3A-3C depict isolation and improvement of a tyrosine hydroxylase in yeast.

Both AbPPO2 and CYP76AD1 were codon optimized for yeast and expressed along with DOD. As expected based on previous work, AbPPO2 showed extremely low, but detectable, betaxanthin production. Surprisingly, however, CYP76AD1 exhibited considerable tyrosine hydroxylase activity, leading to levels of betaxanthin that were clearly visible in colonies growing on agar plates (FIG. 3a). This result was particularly unexpected given previous work in which CYP76AD1 and a DOD were co-expressed in yeast and yielded no observable betaxanthin (Hatlestad et al. 2012). One experimental difference that could account for these contradictory results is the identity of the DOD enzyme used. While the strains described in this example utilized a DOD from *M. jalapa*, previous experiments with CYP76AD1 were conducted using a *B. vulgaris* DOD, which has a $K_m$ of 7 mM (Gandía-Herrero & García-Carmona 2012)—well above the levels that are likely to accumulate in yeast given the competing DOPA oxidase activity of CYP76AD1.

Figure 3B:
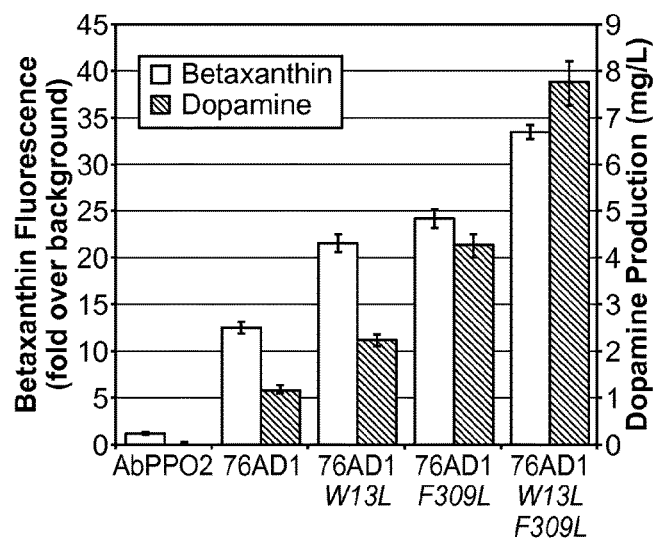

After achieving clearly detectable betaxanthin synthesis with CYP76AD1, its ability to catalyze the synthesis of the BIA intermediate dopamine was tested, together with a DOPA decarboxylase (DODC) from *Pseudomonas puinda* that is highly specific for L-DOPA (Koyanagi et al. 2012). The specificity of the DODC is important, as decarboxylation of L-tyrosine would introduce a side pathway to tyramine and reduce flux to dopamine. When combined into a single strain, both activities resulted in dopamine production, something that had not been achieved previously in *S. cerevisiae*. This result also validated the utility of the betaxanthin biosensor for optimizing L-DOPA production, as the betaxanthin levels from AbPPO2 and CYP76AD1 were predictive of dopamine titers (FIG. 3b). Using wildtype CYP76AD1, a dopamine titer of 1.2 mg/l was achieved. It was hypothesized that titers could be improved by abolishing CYP76AD1's DOPA oxidase. Mutagenesis and screening were performed with the L-DOPA biosensor.

Example 2: Generation and Characterization of Variant Tyrosine Hydroxylases

Error-prone polymerase chain reaction (PCR) was performed to generate a library of CYP76AD1 mutants that was transformed into a yeast strain expressing DOD. This mutant library contained approximately 200,000 members with an average mutation rate of approximately 4 mutations/gene. The difference in betaxanthin production between library clones was sufficiently large that obvious differences between colonies could be detected by eye. 17 of the highest betaxanthin producers were visually identified, and selected for sequence analysis. Six of the 17 mutants contained an F309L missense mutation; among those with this mutation, there were 2 distinct genotypes (FIG. 4B).

Figures 4A, 4B:
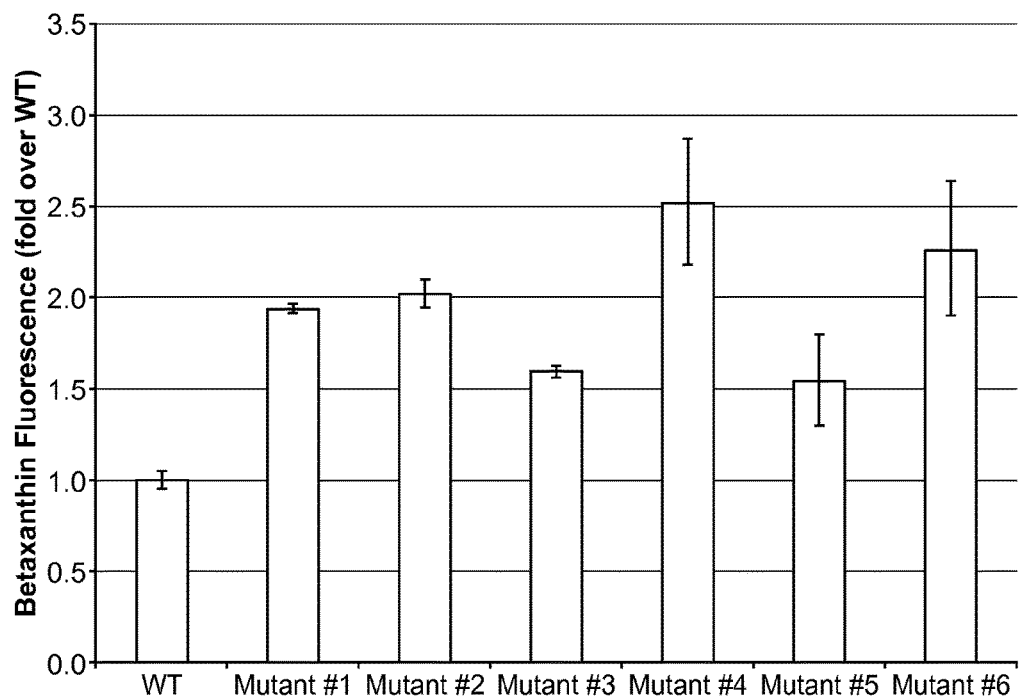
FIG. 4A-4B depict increased betaxanthin production by CYP76AD1 mutants.

The set of hits was narrowed to six by removing duplicate genotypes and any mutant that showed less than 1.5-fold improvement in betaxanthin production upon isolation and retransformation into the L-DOPA sensor base strain (FIG. 4A-4B). These six mutants were used to construct a DNA shuffling library in order to randomly associate potentially beneficial mutations. The resulting library was again transformed into yeast expressing DOD and screened for betaxanthin production. Out of the 22 highest producers that were analyzed from the DNA shuffling library, 20 had incorporated the same two mutations (W13L and F309L), suggesting that the effects of these mutations were additive. An additional silent mutation that was linked to W13L (9T>C) was also enriched for and included in future experiments involving the W13L mutation. (This linked double mutation is also referred to herein as W13L for convenience).

Because W13L and F309L appeared to be the two best mutations, their effects on betaxanthin and dopamine production were analyzed individually and in combination. Both of the single mutants yielded approximately 2-fold more betaxanthin, while the double mutant showed a net increase of almost 3-fold over wildtype production (FIG. 3B). When expressed with DODC to produce dopamine, CYP76AD1 with the W13L, F309L, and W13L/F309L mutations improved upon the dopamine titer of wildtype CYP76AD1 by 1.9-fold, 3.6-fold, and 6.6-fold, respectively (FIG. 3B).

Figure 3C:
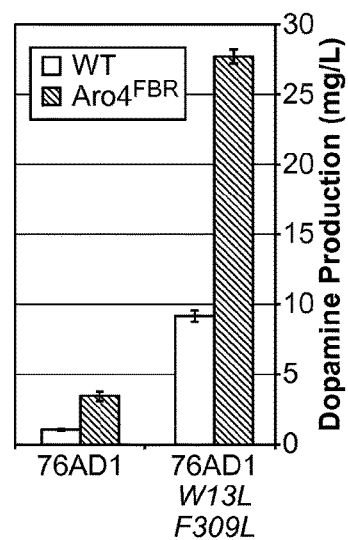

Given the high tyrosine hydroxylase activity of the CYP76AD1 W13L/F309L double mutant, it was hypothesized that L-tyrosine availability might be limiting dopamine production in our strain. Therefore, a feedback-insensitive mutant of the L-tyrosine pathway enzyme Aro4p that is known to markedly increase the intracellular L-tyrosine concentration in *S. cerevsiae* (Luttik et al. 2008), was overexpressed. Doing so resulted in an additional 3-fold increase in dopamine levels. In this strain background, a final dopamine titer of 27.8 mg/l (compared to 1.2 mg/l prior to optimization) was achieved when cells were grown for 48 hours in synthetic complete media with 2% glucose (FIG. 3C).

Characterization of Reduced DOPA Oxidase Activity in Mutant Enzymes

The mechanism by which our CYP76AD1 mutants increased tyrosine hydroxylase activity was characterized. While pelleting the dopamine-producing cultures with feedback-insensitive Aro4p overexpression, it was noticed that cells expressing AbPPO2 or the wildtype CYP76AD1 were brown in color compared to cells containing no tyrosine hydroxylase. This color is likely due to the accumulation of melanin generated by the DOPA oxidase activity of these enzymes. Notably, the CYP76AD1 W13L/F309L double mutant, which led to more dopamine production than either of these wildtype enzymes, showed no brown color, suggesting that DOPA oxidase activity (activity 2 from FIG. 1A) had been reduced in this mutant. F309L was suspected to be the more likely candidate mutation to be the cause of this apparent reduction in DOPA oxidase activity since W13L lies in a predicted signal peptide and is more likely to improve enzyme expression than to alter the catalytic properties of the enzyme.

Figure 5A:
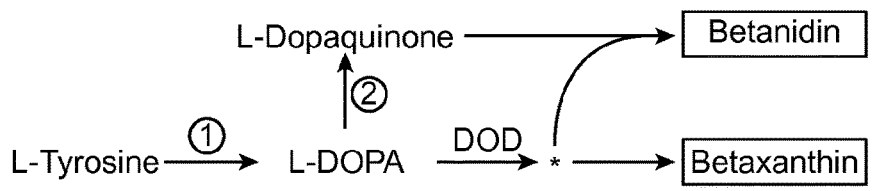
FIG. 5A-5C depict characterization of reduced DOPA oxidase activity in F309L mutants.

To directly compare the relative levels of tyrosine hydroxylase and DOPA oxidase activity between mutant and wildtype versions of CYP76AD1, the betaxanthin pathway was used. As stated previously, the pathway from L-DOPA to betaxanthin goes through the intermediate betalamic acid, which undergoes spontaneous condensation with amines (FIG. 2). If L-dopaquinone is generated via a DOPA oxidase, however, betalamic acid can react with the L-dopaquinone derivative cyclo-DOPA to form a red pigment called betanidin (FIG. 5A and FIG. 2). In fact, CYP76AD1 is the DOPA oxidase responsible for betanidin production in red beets; the yellow color of golden beets is the result of a missense mutation that renders CYP76AD1 nonfunctional (Hatlestad et al. 2012).

The ratio of betaxanthin/betanidin was used as an indicator of DOPA oxidase activity in yeast. Doing so required supplementing the growth media with ascorbic acid as a reducing agent to prevent spontaneous betanidin oxidation that causes the pigment to polymerize and lose its red color (Gandía-Herrero et al. 2007). When co-expressed with DOD, candidate enzymes with higher DOPA oxidase activity relative to their tyrosine hydroxylase activity will produce a red supernatant composed primarily of betanidin, while enzymes with the opposite ratio will generate a yellow supernatant that is composed mostly of betaxanthin. As expected, when wildtype CYP76AD1 was tested in this betaxanthin/betanidin assay, the supernatant was red, indicative of high DOPA oxidase activity. However, when the F309L point mutation was introduced into this enzyme, a dramatic shift in color from red to yellow was observed (FIG. 3b). This color change demonstrates that the F309L mutation reduces DOPA oxidase activity in CYP76AD1.

Figure 5B:
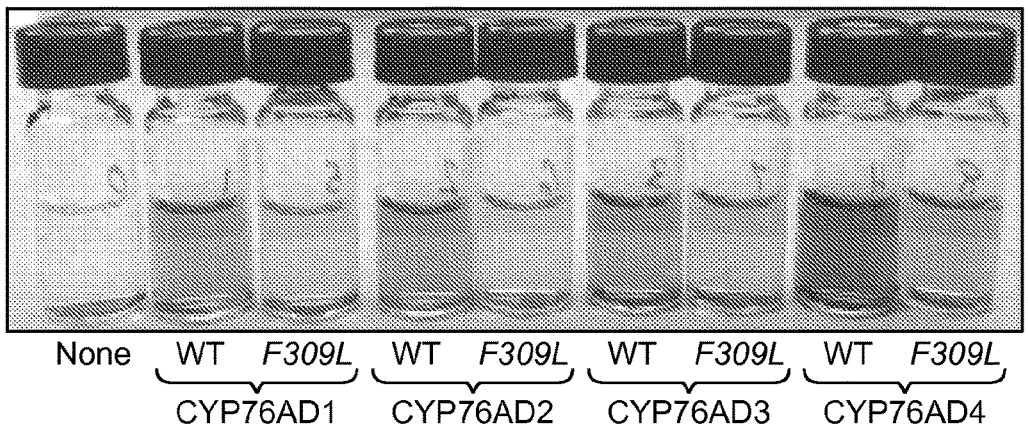
Figure 5C:
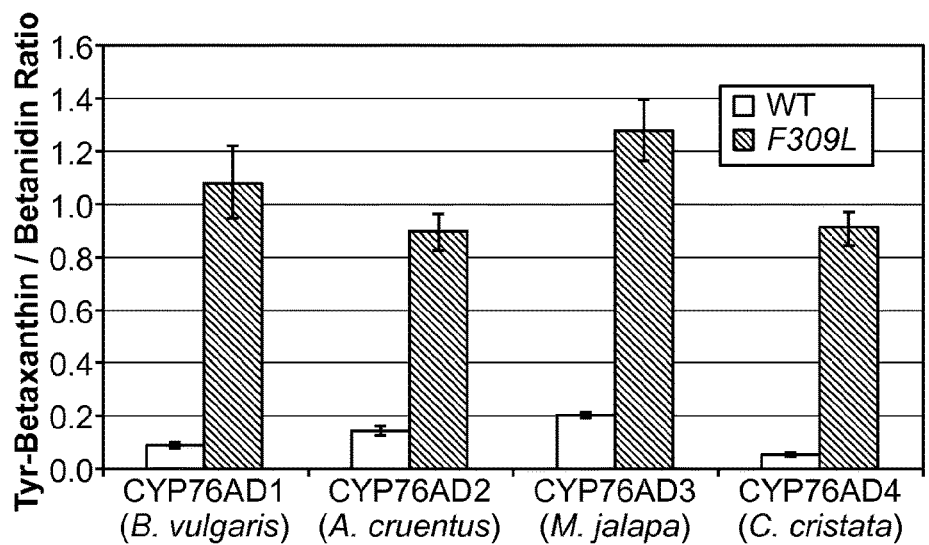
Figure 7:
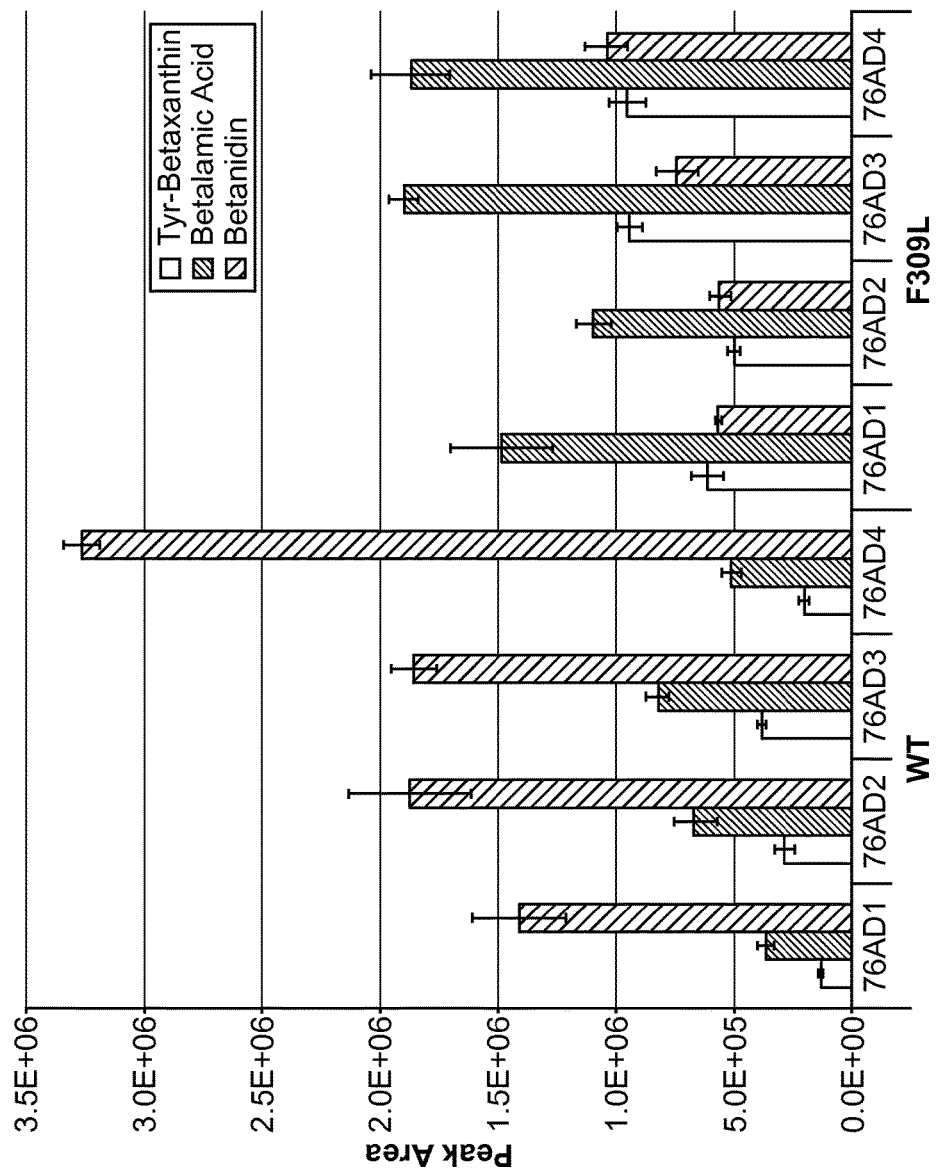
FIG. 7 depicts relative production of three pigments in the supernatants pictured in FIG. 5B.

A protein alignment of CYP76AD1 to its three known orthologs (CYP76AD2, CYP76AD3, and CYP76AD4) showed that the F309 residue is conserved in each (FIGS. 6A and 6B). To determine whether the F309L mutation would have similar effects in these orthologs, the genes for expression in yeast were codon optimized. Wildtype and F309L mutants were tested in the betaxanthin/betanidin assay. In all cases, introduction of the mutation produced a shift from red to yellow supernatants (FIG. 5B). To quantify these color changes, betanidin and betaxanthin were measured using liquid chromatography-mass spectrometry (LC/MS). Tyrosine-betaxanthin was selected as a representative member of the betaxanthin species since many different betaxanthins can form from the spontaneous conjugation of an amine with betalamic acid. For CYP76AD1, the F309L mutant yielded a 10-fold increase in the ratio of betaxanthin to betanidin, with all orthologs showing similar changes (FIG. 5C). This change was the result of both a decrease in betanidin and a corresponding increase in betaxanthin (FIG. 7). It should be noted that while the F309L single mutants of CYP76AD3 and CYP76AD4 both had higher tyrosine hydroxylase activity in yeast than CYP76AD1 F309L, neither was more active than the CYP76AD1 W13L/F309L double mutant.

Example 3: Production of NLDS and Norcoclaurine

Figure 8A:
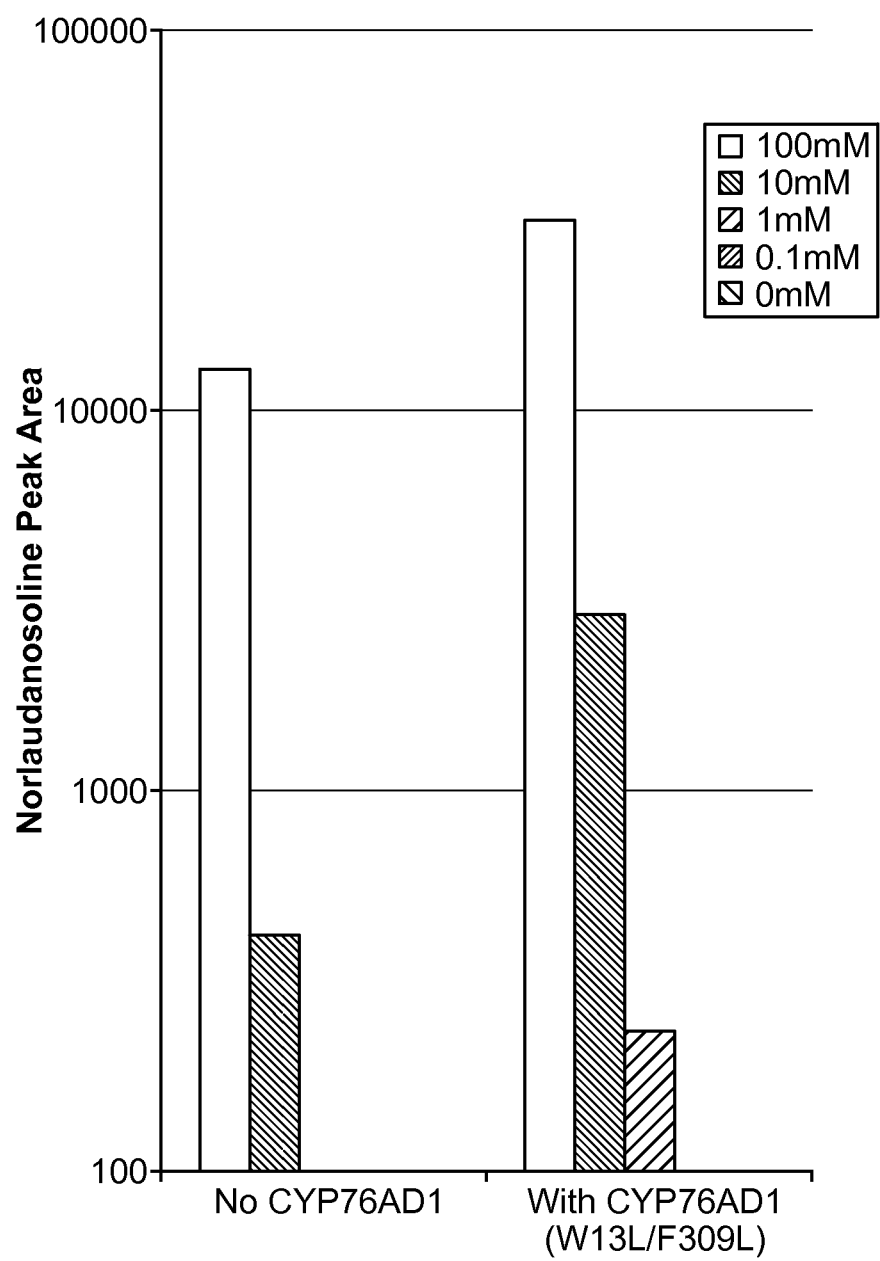
FIG. 8A-8B depict production of norlaudanosoline (FIG. 8A) and norcoclaurine (FIG. 8B) in yeast expressing no tyrosine hydroxylase (no CYP76AD1), or in yeast expressing CYP76AD1 (W13L/F309L) cultured in medium containing various concentrations of dopamine.
Figure 8B:
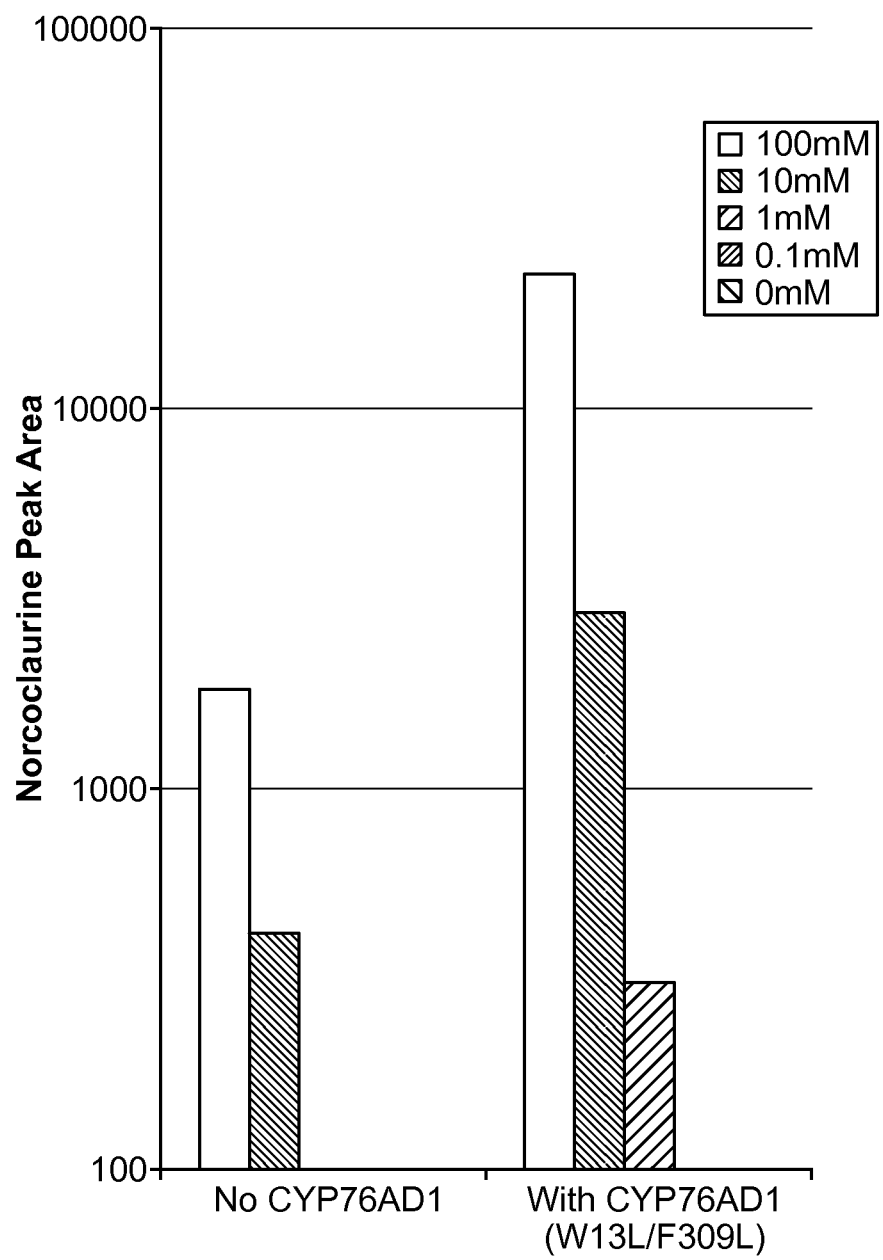

Norlaudanosoline (NLDS) and norcoclaurine production was detected in yeast genetically modified to express CYP76AD1 (W13L/F309L) and human monoamine oxidase (MAO). Cells were grown in culture medium containing 0 mM, 0.1 mM, 1 mM, 10 mM, or 100 mM dopamine. As shown in FIG. 8A, a yeast strain genetically modified to express CYP76AD1 (W13L/F309L) produced NLDS with only 1 mM dopamine in the culture medium; without expression of CYP76AD1, no NDLS was detected at 1 mM dopamine in the culture medium. As shown in FIG. 8B, a yeast strain genetically modified to express CYP76AD1 (W13L/F309L) produced norcoclaurine with only 1 mM dopamine in the culture medium; without expression of CYP76AD1, no norcoclaurine was detected at 1 mM dopamine in the culture medium.

Example 4: Identification of Variants that Provide for Increased Tyrosine Production The L-DOPA biosensor assay described in Example 1 can be used to identify variants in genes upstream of L-DOPA production, where the variants provide for increased tyrosine production.

Figure 9:
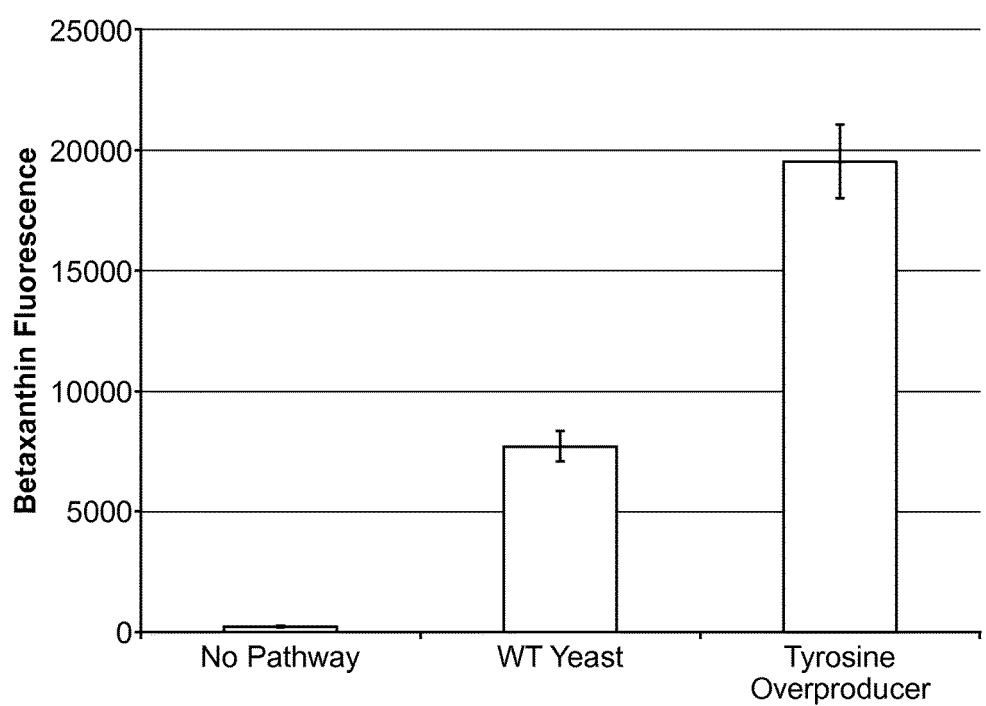
FIG. 9 depicts betaxanthin fluorescence produced by wild-type yeast, and a yeast strain variant that is a tyrosine overproducer.

To demonstrate that the L-DOPA biosensor can identify mutations that lead to increased tyrosine production, the K229L mutation in the ARO4 gene was tested. This mutation destroys feedback inhibition and results in tyrosine overproduction. As shown in FIG. 9, yeast harboring the K229L mutation in the ARO4 gene produced about 2.5 times more betaxanthin than wildtype yeast, and were readily detected in the L-DOPA biosensor assay.

Example 4: Production of (S)-reticuline from Glucose

Having achieved efficient dopamine production from L-tyrosine in *S. cerevisiae*, the pathway towards downstream BIA intermediates was extended. The first committed step in BIA biosynthesis is the formation of the backbone molecule (S)-norcoclaurine via condensation of dopamine and 4-hydroxyphenylacetaldehyde (4-HPA), a reaction that is catalyzed by NCS (FIG. 10A). 4-HPA is produced endogenously in *S. cerevisiae* as an intermediate of the Ehrlich pathway for amino acid catabolism (Sentheshanmuganathan & Elsden 1958). In this pathway, L-tyrosine is converted to 4-HPA through the sequential action of Aro8p/Aro9p and Aro10p prior to being broken down into tyrosol or 4-hydroxyphenylacetic acid (4-HPAA) by a host of redundant enzymes.

Figure 11:
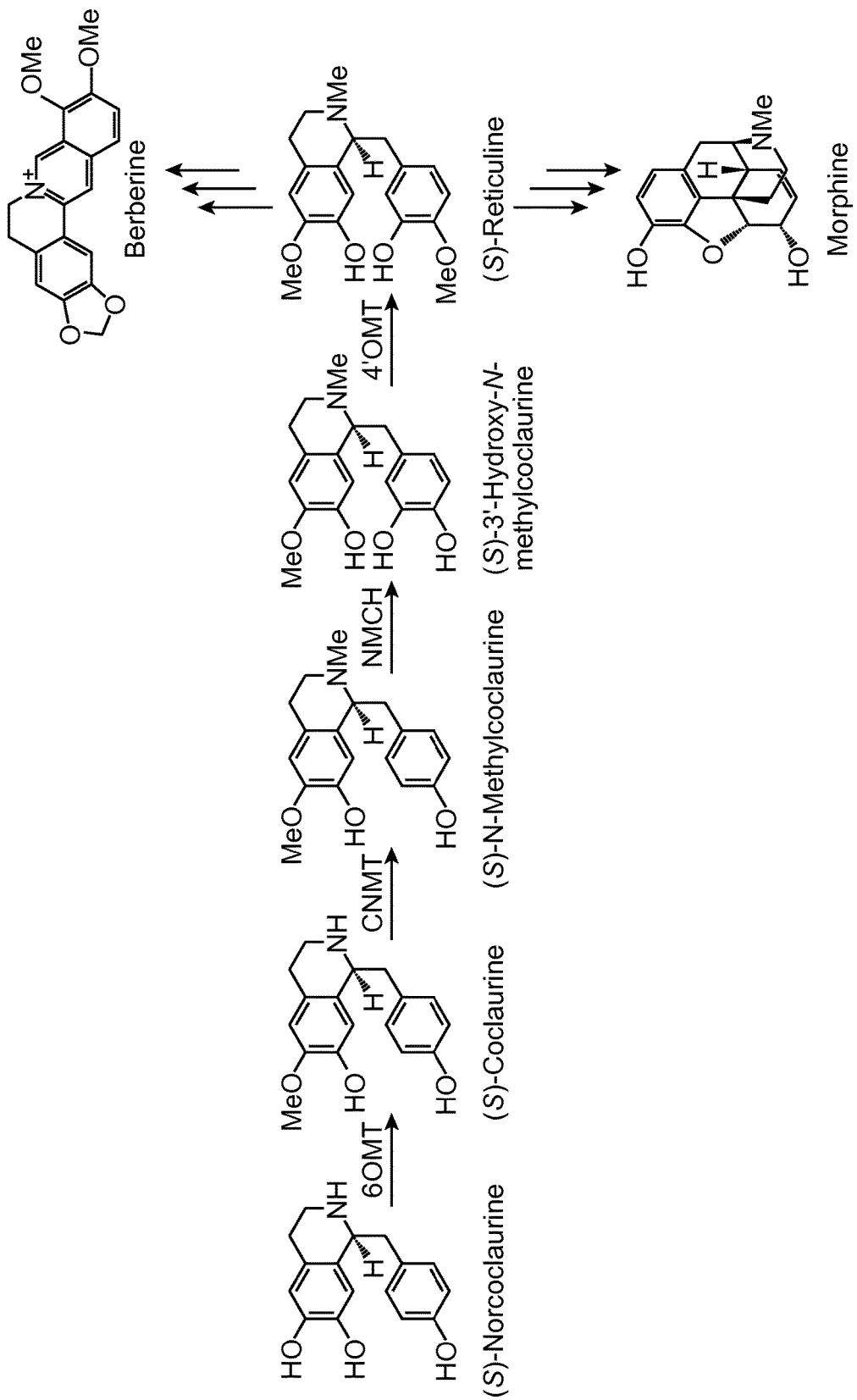
FIG. 11 depicts a pathway from (S)-norcoclaurine to (S)-reticuline.

From (S)-norcoclaurine, four additional enzymatic steps are needed to produce (S)-reticuline, the last shared intermediate of the major BIA pathway branches (FIG. 11). Three of these enzymes catalyze methylation reactions: 6-O-methyltransferase (6OMT), coclaurine N-methyltransferase (CNMT), and 4'-O-methyltransferase (4'OMT). Variants of each methyltransferase from *P. somniferum* have been demonstrated to function in *S. cerevisiae* (Hawkins & Smolke 2008). The remaining enzyme is the cytochrome P450 NMCH, N-methylcoclaurine hydroxylase (CYP80B1). Previous work to synthesize reticuline in *S. cerevisiae* circumvented this enzyme by feeding a hydroxylated derivative of norcoclaurine, norlaudanosoline, which is commercially available, albeit expensive. NMCH has, however, been isolated from the California poppy (*Eschscholzia californica*) and functionally expressed in yeast (Pauli & Kutchan 1998).

The (S)-reticuline pathway was divided into three modules (FIG. 10A). Module A combines the tyrosine hydroxylase mutant (CYP76AD1 W13L/F309L) and DODC to produce dopamine. The endogenous machinery of yeast was used for 4-HPA production. The strains also overexpress feedback-insensitive Aro4p, which increases flux through 4-HPA in addition to increasing L-tyrosine levels. Module B included an NCS from *P. somniferum*. Module C consists of the four enzymes required for the conversion of (S)-norcoclaurine to (S)-reticuline, including 6OMT, CNMT, and 4'OMT from *P. somniferum* and NMCH from *E. californica*. Three strains were constructed for testing, which are referred to here by the pathway modules that they express (A, AB, and ABC). All heterologous genes in these strains are expressed using high strength promoters and are either integrated into the chromosome (modules A and B) or maintained on a low-copy plasmid (module C).

Strain AB produced easily detectable levels of norcoclaurine when grown in synthetic complete media with glucose (FIG. 10B and FIG. 10D). Given that this product was not observed in the supernatant of strain A, norcoclaurine synthesis (which can occur spontaneously) appeared to be dependent on NCS expression. While spontaneously formed norcoclaurine is racemic, NCS is known to be stereoselective, producing only (S)-norococlaurine. Chiral analysis confirmed that all norcoclaurine produced by strain AB was the (S)-enantiomer. Reticuline was also clearly detected in the supernatant of strain ABC (FIG. 10C and FIG. 10E). The reticuline-producing strain had no detectable norcoclaurine in the supernatant, indicating that the conversion efficiency from norcoclaurine to reticuline was high. While the chirality of the reticuline produced by strain ABC was not confirmed, it is expected that only (S)-reticuline is present given that only (S)-norcoclaurine is produced by strain AB. To quantify titers, a 96-hour fermentation was performed in shake flasks for strains AB and ABC (FIG. 12). Maximum titers for norcoclaurine and reticuline were 104.6 µg/l and 80.6 µg/l respectively and did not show substantial increases after cell saturation. Cell pellets were analyzed for norcoclaurine and reticuline using extraction with methanol, however only trace amounts were observed, suggesting that these products readily escape into the media.

Figure 1B:
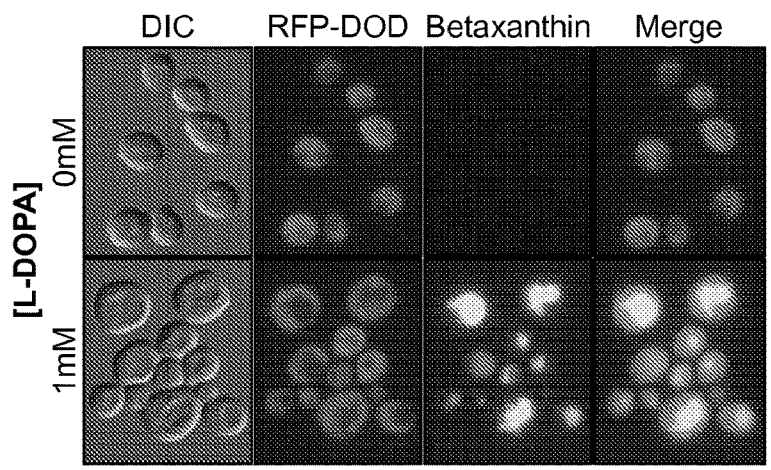
Figure 1C:
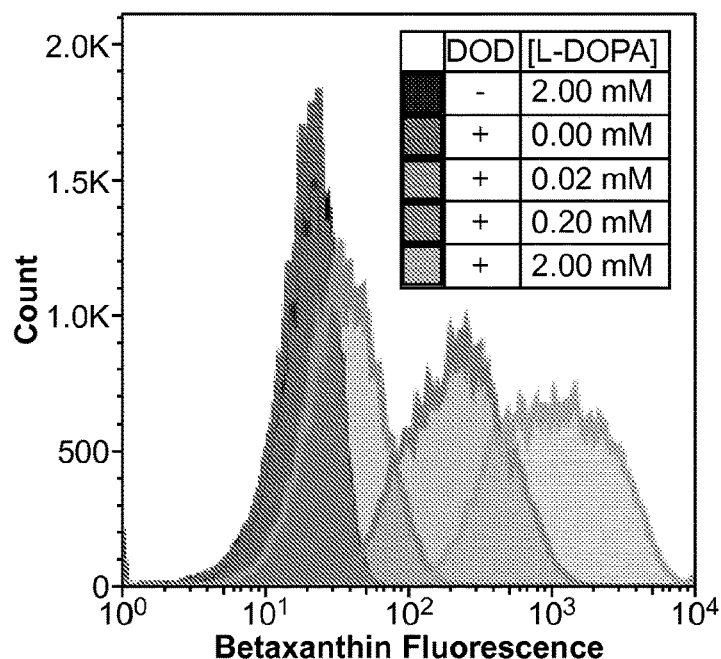

FIG. 1A-1C. Development of an enzyme-coupled L-DOPA biosensor. (FIG. 1A) L-DOPA can be acted on by three distinct enzymes. For the production of benzylisoquinoline alkaloids (BIAs), DOPA decarboxylase (DODC) is the desired activity. However, many enzymes that produce L-DOPA (tyrosine hydroxylases, activity 1) also have a second activity (DOPA oxidase, activity 2) that introduces a competing pathway towards melanin. DOPA dioxygenase (DOD) converts L-DOPA into the fluorescent, yellow pigment betaxanthin in plants and was used in yeast as an L-DOPA biosensor to find an active tyrosine hydroxylase variant with correspondingly low DOPA oxidase activity. Red arrows denote enzymatic reactions; black arrows denote spontaneous reactions. See FIG. 2 for a more detailed pathway diagram. (FIG. 1B) Fluorescence microscopy of cells expressing DOD with the red fluorescent protein mKate2 fused to the N-terminus, grown in media with and without L-DOPA. While DOD localizes to the cytosol, its fluorescent product, betaxanthin, is found primarily in the vacuole. (FIG. 1C) Flow cytometry histograms for DOD-expressing yeast cells grown in media supplemented with 0 mM (red), 0.02 mM (green), 0.2 mM (blue), or 2.0 mM (yellow) L-DOPA. Cells without DOD in 2 mM L-DOPA (black) were included as a control.

FIG. 2. Utilizing the betaxanthin pathway as a biosensor for L-DOPA in Yeast. To improve L-DOPA production in yeast cells, DOPA dioxygenase (DOD) was expressed in the cells, which expression enabled rapid monitoring of upstream enzymatic activity through the production of plant pigments (shaded in blue). Enzymes that produce L-DOPA via tyrosine hydroxylation (activity 1) often catalyze a second step to L-dopaquinone (DOPA oxidase, activity 2). This second activity is undesirable for the production of BIAs from tyrosine because it introduces a competing pathway to melanin. When co-expressed with a tyrosine hydroxylase, DOD will generate betalamic acid, a reactive aldehyde that undergoes spontaneous condensation with amino acids and other amines to form betaxanthins, which are yellow and fluorescent. Increases in tyrosine hydroxylase activity can be easily detected by increased betaxanthin production. Tyrosine hydroxylases with a high level of DOPA oxidase activity will produce L-dopaquinone. After a spontaneous conversion to cyclo-DOPA, L-dopaquinone can undergo condensation with betalamic acid to form betanidin, a red pigment. While betanidin is prone to oxidative polymerization in normal yeast media, the addition of ascorbic acid as a reducing agent stabilizes betanidin, allowing DOPA oxidase activity to be easily monitored. (S)-Reticuline is a key intermediate in the BIA pathway that represents a branch point from which the majority of BIAs can be produced. Red arrows denote enzymatic reactions; black arrows denote spontaneous reactions.

FIG. 3A-3C. Isolation and improvement of a tyrosine hydroxylase in yeast. (FIG. 3A) Yeast cells expressing DOD alone or with a candidate tyrosine hydroxylase (either AbPPO2 from *A. bisporus* or CYP76AD1 from *B. vulgaris*), streaked on an agar plate with synthetic complete media. Betaxanthin production in the strain expressing CYP76AD1 is indicative of tyrosine hydroxylase activity. (FIG. 3A) Mutagenesis and screening yielded additional improvements to CYP76AD1's tyrosine hydroxylase activity. Yellow bars represent betaxanthin production in cells co-expressing a tyrosine hydroxylase variant with DOD as measured by cellular fluorescence. Blue bars show dopamine titer when the variants were co-expressed with DOPA decarboxylase (DODC) as measured by LC/MS of culture supernatants and comparison to a standard curve. In both cases, cells were grown for 48 hours in synthetic complete media with 2% glucose. 76AD1=CYP76AD1 and amino acid substitutions are denoted in italics. (FIG. 3C) A feedback resistant mutant of Aro4p known to increase intracellular tyrosine levels (Aro4$^{FBR}$) was overexpressed (green bars), leading to additional improvements in dopamine titer in cells expressing CYP76AD1 and DODC. Blue bars represent yeast without Aro4$^{FBR}$ overexpression. All bars indicate the mean±1 s.d. of four biological replicates.

FIG. 4A-4B. CYP76AD1 mutants yield increased betaxanthin production. Six mutants from the first round of betaxanthin screening were selected to undergo DNA shuffling. (FIG. 4A) CYP76AD1 mutants 1-6 were genomically integrated into a strain expressing DOD. Betaxanthin fluorescence was measured on a microplate fluorometer and normalized to cells expressing wildtype CYP76AD1. Bars represent mean±1 s.d. of six biological replicates. (FIG. 4B) Sequence of CYP76AD1 mutants 1-6. Silent mutations (italicized) are indicated with their nucleotide substitution and indexed by their distance from the start codon.

FIG. 5A-5C. Characterization of reduced DOPA oxidase activity in F309L mutants. (FIG. 5A) DOD generates a transient intermediate (betalamic acid, denoted by an asterisk) that can either react with amines to produce betaxanthins (a yellow pigment) or with L-dopaquinone to produce betanidin (a red pigment). Betanidin is labile but can be stabilized with the addition of the reducing agent ascorbic acid. Doing so allows DOPA oxidase activity (activity 2) to be measured relative to tyrosine hydroxylase activity (activity 1) by comparing betaxanthin and betanidin levels. (FIG. 5B) Culture supernatant from strains co-expressing DOD and one of four CYP76AD orthologs grown in minimal media with ascorbic acid. All wildtype (WT) enzymes produced a red supernatant, while mutants with an F309L substitution produced yellow supernatants, indicative of reduced DOPA oxidase activity. (None=DOD expression alone). Note: F309L indicates mutation of the residue corresponding to F309 in CYP76AD1 based on sequence alignment, not necessarily the exact position of the mutated amino acid in each ortholog. (FIG. 5C) Ratio of LC/MS peak area for tyrosine-betaxanthin and betanidin in the samples from (FIG. 5B) (red bars=WT enzymes, yellow bars=F309L mutants). Tyrosine-betaxanthin was selected as a representative member of the betaxanthins since many different species exist in the culture supernatant. Bars represent the mean±1 s.d. of six biological replicates.

FIG. 6A-6B. Multiple sequence alignment of CYP76AD orthologs. W13 and F309 residues are highlighted in yellow. Amino acids are color-coded based on their properties (red=small; blue=acidic; magenta=basic; green=hydroxyl, sulfhydryl, amine; grey=other). Asterisks indicate fully conserved residues, colons and periods indicate strong and weak conservation respectively. CYP76AD1 (*Beta vulgaris*, UniProt: I3PFJ5); CYP76AD2 (*Amaranthus cruentus*, UniProt: I3PFJ7); CYP76AD3 (*Mirabilis jalapa*, UniProt: I3PFJ8); CYP76AD4 (*Celosia cristata*, Uniprot: M9RR47).

FIG. 7. Relative production of three pigments in the supernatants pictured in FIG. 5B. Samples were analyzed by LC-MS. Absolute quantification could not be performed due to lack of standards, so peak area is instead shown. F309L mutants show reduced betanidin production (red) and corresponding increases in tyrosine-betaxanthin (orange) and betalamic acid (yellow) levels compared to wildtype enzymes. Bars represent mean±1 s.d. of six biological replicates.

FIG. 10A-10E. Production of (S)-reticuline from glucose. (FIG. 10A) The (S)-reticuline pathway was divided into three modules to facilitate analysis. Because 4-hydroxyphenyl acetaldehyde (4-HPA) is produced endogenously in *S. cerevisiae* (unlabeled black arrows), enzymes catalyzing 4-HPA synthesis from L-tyrosine were not heterologously expressed. CYP76AD1, tyrosine hydroxylase (W13L/F309L double mutant); DODC, DOPA decarboxylase; NCS, norcoclaurine synthase; 6OMT, 6-O-methyltransferase; CNMT, coclaurine N-methyltransferase; NMCH, N-methylcoclaurine hydroxylase (CYP80B1); 4'OMT, 4'-O-methyltransferase. See FIG. 11 for a more detailed pathway diagram of module C. (FIG. 10B-10C) LC/MS analysis of norcoclaurine (FIG. 10B) and reticuline (c) in the supernatant of strains expressing modules A, AB, and ABC after 48 hours of growth in synthetic media with 4% glucose. Strain AB produces norcoclaurine, and strain ABC produces reticuline. Traces are normalized to the maximum peak height across all three samples. Std. denotes a 5 uM chemical standard, which was normalized separately. (FIG. 10D-10E) Tandem mass spectra of norcoclaurine from strain AB (FIG. 10D) and reticuline from stain ABC (FIG. 10E) confirm their identity in comparison to chemical standards. Parent ion: ♦

FIG. 11. Pathway from (S)-norcoclaurine to (S)-reticuline. (S)-reticuline is the last shared intermediate between the morphinan (down) and sanguinarine/berberine (up) branches in BIA biosynthesis. 6OMT, 6-O-methyltransferase; CNMT, coclaurine N-methyltransferase; NMCH, N-methylcoclaurine hydroxylase (CYP80B1); 4'OMT, 4'-O-methyltransferase.

Figure 12A:
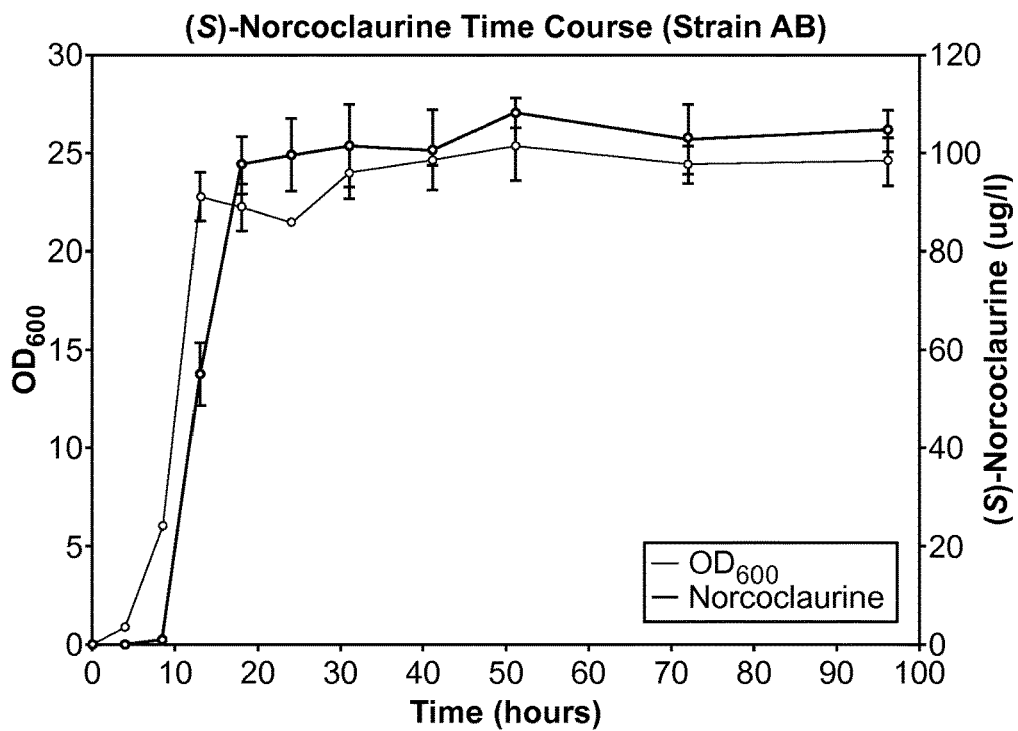
FIG. 12A-12B depict time courses for BIA intermediate production.
Figure 12B:
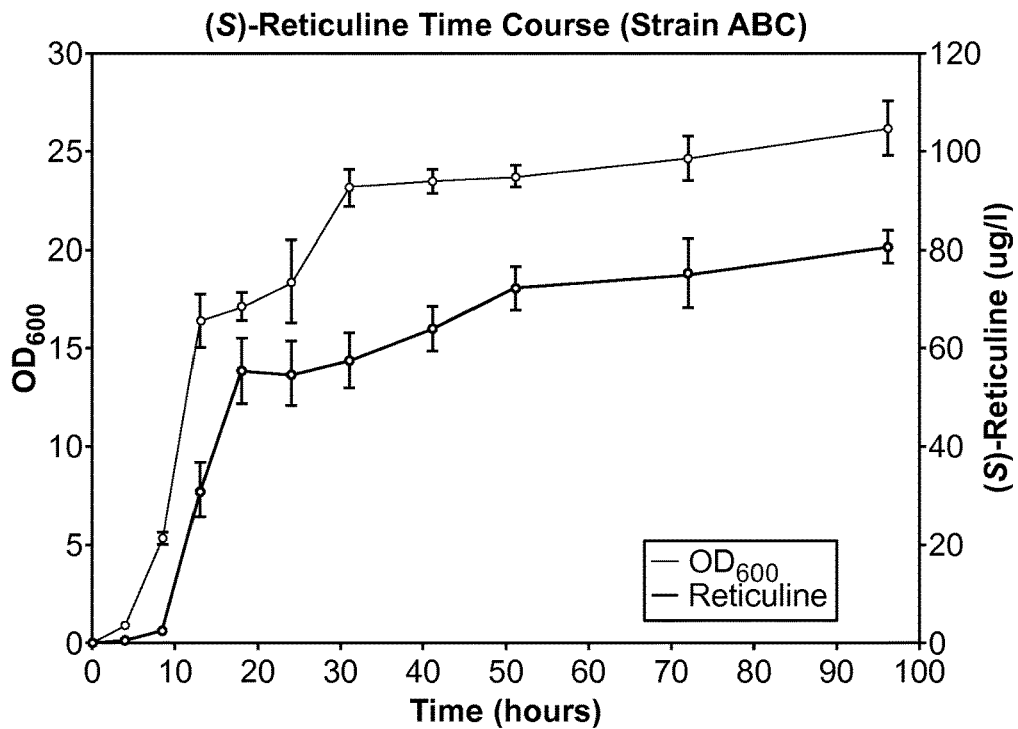

FIG. 12A-12B. Time courses for BIA intermediate production. Strains producing (S)-norcoclaurine (FIG. 12A) and (S)-reticuline (FIG. 12B) were grown for 96-hours in shake flasks with 2× synthetic dropout media and 4% glucose. Measurements of culture optical density (OD600, red lines) and product titer (blue lines) were taken periodically. Product titer was measured by LC/MS of culture supernatants and comparison to a standard curve. Final (S)-norcoclaurine and (S)-reticuline titers were 104.6 µg/l and 80.6 µg/l respectively. Data points represent the mean±1 s.d. of three biological replicates.

Figure 24:
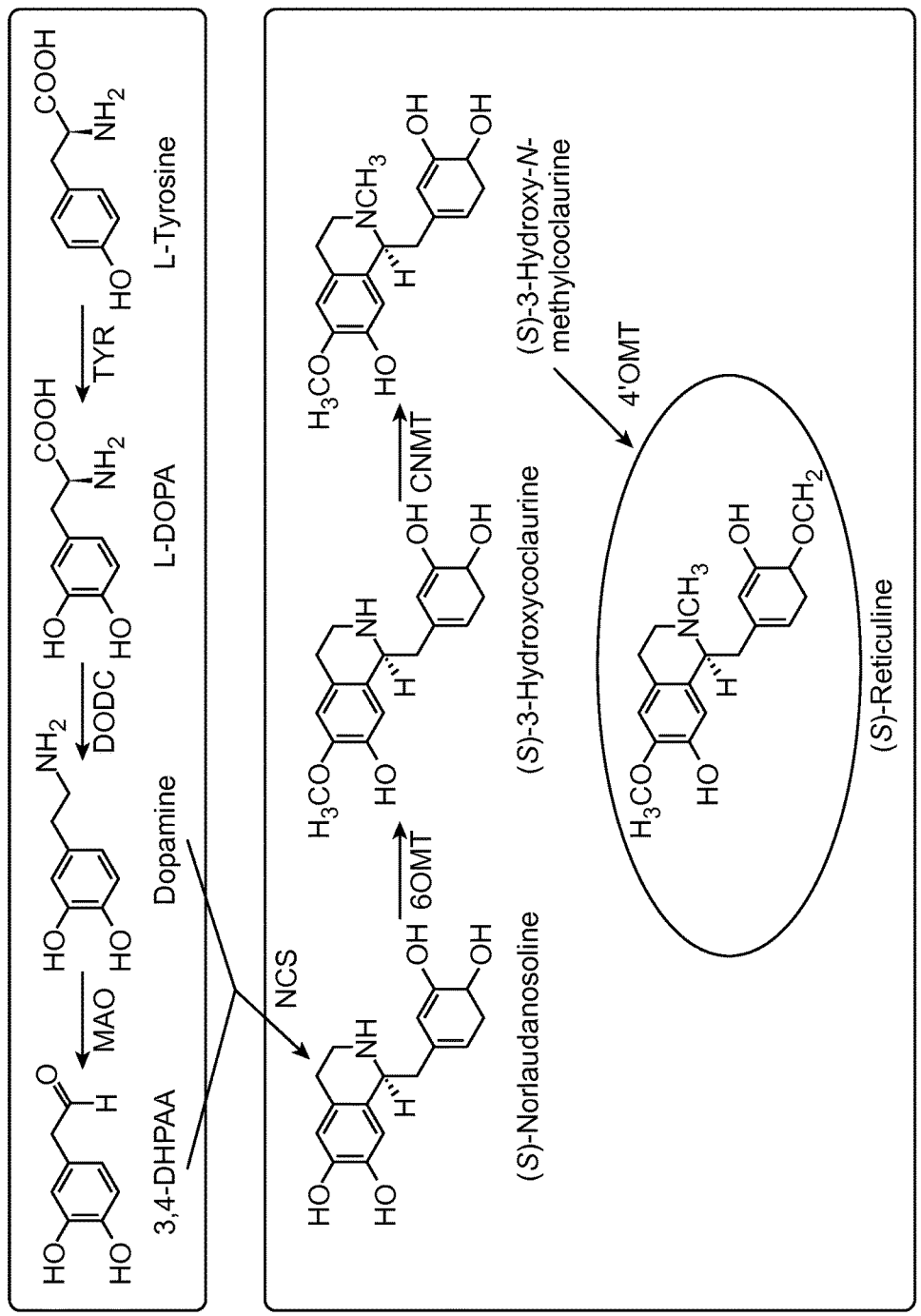
FIG. 24 depicts a synthetic pathway from L-DOPA to (S)-reticuline.

FIG. 24. FIG. 24 is a schematic diagram of a pathway from tyrosine to (S)-reticuline. TYR: tyrosine hydroxylase; DODC: DOPA decarboxylase; NCS: norcoclaurine synthase; MAO: monoamine oxidase; 6OMT: 6-O-methyltransferase; CNMT: coclaurine N-methyltransferase; 4'OMT: 4'-O-methyltransferase.

FIG. 25A-25F. Multiple sequence alignment, and percent amino acid identity, relating to CYP76AD1 and paralogs. (FIG. 25A-25F) Multiple sequence alignment of CYP76AD1 with its seven closest paralogs from *B. vulgaris*. The F309 residue is highlighted in yellow. Note that all paralogs contain the F309L substitution identified by PCR mutagenesis and screening. Expression of Bv9_228610_yqeq or Bv9_228860_ickx in *S. cerevisiae* did not lead to betaxanthin production. Amino acids are color-coded based on their properties (red=small; blue=acidic; magenta=basic; green=hydroxyl, sulfhydryl, amine; grey=other). Asterisks indicate fully conserved residues, colons and periods indicate strong and weak conservation respectively. (FIG. 25F) Percent identities between paralogs.

FIG. 26A-26B. Table 1. List of yeast strains used in this work. Strains were made by chromosomal integration of plasmids directly into the parent strain as indicated (except for yWCD782 which contains the CEN6/ARS4 plasmid pWCD2353). Strains 32, 33, and 34 are referred to as strains A, AB, and ABC in the main text respectively. Annotated plasmid sequences are included as GenBank files.

FIG. 27. Table 2. List of additional plasmids used in this work. Plasmids shown are those not included in Table 1. Annotated plasmid sequences are included as GenBank files.

FIG. 28. Table 3. List of oligonucleotides (oligos) used in this work. Oligos 13 and 14 were used in place of Oligo 5 for amplifying mutants 3 and 4 respectively since mutations were present in the primer binding region of these mutants.

REFERENCES

Arkin, A. P. & Fletcher, D. A., 2006. Fast, cheap and somewhat in control. Genome biology, 7(8), p. 114.

Beaudoin, G. A. W. & Facchini, P. J., 2014. Benzylisoquinoline alkaloid biosynthesis in opium poppy. *Planta*, 240(1), pp. 19-32.

Claus, H. & Decker, H., 2006. Bacterial tyrosinases. *Systematic and applied microbiology*, 29(1), pp. 3-14.

Dohm, J. C. et al., 2014. The genome of the recently domesticated crop plant sugar beet (*Beta vulgaris*). *Nature*, 505(7484), pp. 546-549.

Facchini, P. J. et al., 2012. Synthetic biosystems for the production of high-value plant metabolites. *Trends in biotechnology*, 30(3), pp. 127-131.

Fitzpatrick, P. F., 1999. Tetrahydropterin-dependent amino acid hydroxylases. *Annual review of biochemistry*, 68(1), pp. 355-381.

Fossati, E. et al., 2014. Reconstitution of a 10-gene pathway for synthesis of the plant alkaloid dihydrosanguinarine in *Saccharomyces cerevisiae*. *Nature communications*, 5, p. 3283.

Gandía-Herrero, F. & García-Carmona, F., 2012. Characterization of recombinant *Beta vulgaris* 4,5-DOPA-extradiol-dioxygenase active in the biosynthesis of betalains. *Planta*, 236(1), pp. 91-100.

Gandía-Herrero, F., Escribano, J. & García-Carmona, F., 2007. Characterization of the activity of tyrosinase on betanidin. Journal of agricultural and food chemistry, 55(4), pp. 1546-1551.

Gandía-Herrero, F., García-Carmona, F. & Escribano, J., 2005. A novel method using high-performance liquid chromatography with fluorescence detection for the determination of betaxanthins. *Journal of chromatography. A*, 1078 (1-2), pp. 83-89.

Hagel, J. M. & Facchini, P. J., 2013. Benzylisoquinoline alkaloid metabolism: a century of discovery and a brave new world. *Plant & cell physiology*, 54(5), pp. 647-672.

Halaouli, S. et al., 2006. Fungal tyrosinases: new prospects in molecular characteristics, bioengineering and biotechnological applications. *Journal of applied microbiology*, 100(2), pp. 219-232.

Hatlestad, G. J. et al., 2012. The beet R locus encodes a new cytochrome P450 required for red betalain production. *Nature genetics*, 44(7), pp. 816-820.

Hawkins, K. M. & Smolke, C. D., 2008. Production of benzylisoquinoline alkaloids in *Saccharomyces cerevisiae*. *Nature chemical biology*, 4(9), pp. 564-573.

Hazelwood, L. A. et al., 2008. The Ehrlich pathway for fusel alcohol production: a century of research on *Saccha-* romyces cerevisiae metabolism. *Applied and Environmental Microbiology*, 74(8), pp. 2259-2266.

Hernandez-Romero, D., Sanchez-Amat, A. & Solano, F., 2006. A tyrosinase with an abnormally high tyrosine hydroxylase/dopa oxidase ratio. *FEBS Journal*, 273(2), pp. 257-270.

Koyanagi, T. et al., 2012. Eukaryotic-type aromatic amino acid decarboxylase from the root colonizer *Pseudomonas putida* is highly specific for 3,4-dihydroxyphenyl-L-alanine, an allelochemical in the rhizosphere. *Microbiology (Reading, England)*, 158(Pt 12), pp. 2965-2974.

Lezzi, C. et al., 2012. Production of recombinant *Agaricus bisporus* tyrosinase in *Saccharomyces cerevisiae* cells. *Journal of Industrial Microbiology & Biotechnology*, 39(12), pp. 1875-1880.

Luttik, M. A. H. et al., 2008. Alleviation of feedback inhibition in *Saccharomyces cerevisiae* aromatic amino acid biosynthesis: quantification of metabolic impact. *Metabolic Engineering*, 10(3-4), pp. 141-153.

Minami, H. et al., 2008. Microbial production of plant benzylisoquinoline alkaloids. *Proceedings of the National Academy of Sciences of the United States of America*, 105(21), pp. 7393-7398.

Nakagawa, A. et al., 2014. (R,S)-Tetrahydropapaveroline production by stepwise fermentation using engineered *Escherichia coli*. *Scientific reports*, 4, p. 6695.

Nakagawa, A. et al., 2011. A bacterial platform for fermentative production of plant alkaloids. *Nature communications*, 2, p. 326.

Paddon, C. J. et al., 2013. High-level semi-synthetic production of the potent antimalarial artemisinin. *Nature*, pp. 1-9.

Pauli, H. H. & Kutchan, T. M., 1998. Molecular cloning and functional heterologous expression of two alleles encoding (S)—N-methylcoclaurine 3'-hydroxylase (CYP80B1), a new methyl jasmonate-inducible cytochrome P-450-dependent mono-oxygenase of benzylisoquinoline alkaloid biosynthesis. *The Plant journal: for cell and molecular biology*, 13(6), pp. 793-801.

Santos, C. N. S. & Stephanopoulos, G., 2008. Melanin-based high-throughput screen for L-tyrosine production in *Escherichia coli*. *Applied and Environmental Microbiology*, 74(4), pp. 1190-1197.

Sasaki, N. et al., 2009. Detection of DOPA 4,5-dioxygenase (DOD) activity using recombinant protein prepared from *Escherichia coli* cells harboring cDNA encoding DOD from *Mirabilis jalapa*. *Plant & cell physiology*, 50(5), pp. 1012-1016.

Sentheshanmuganathan, S. & Elsden, S. R., 1958. The mechanism of the formation of tyrosol by *Saccharomyces cerevisiae*. *The Biochemical journal*, 69(2), pp. 210-218.

Siddiqui, M. S. et al., 2012. Advancing secondary metabolite biosynthesis in yeast with synthetic biology tools. *FEMS yeast research*, 12(2), pp. 144-170.

Thodey, K., Galanie, S. & Smolke, C. D., 2014. A microbial biomanufacturing platform for natural and semi-synthetic opioids. *Nature chemical biology*, 10(10), pp. 837-844.

While the present invention has been described with reference to the specific embodiments thereof, it should be understood by those skilled in the art that various changes may be made and equivalents may be substituted without departing from the true spirit and scope of the invention. In addition, many modifications may be made to adapt a particular situation, material, composition of matter, process, process step or steps, to the objective, spirit and scope of the present invention. All such modifications are intended to be within the scope of the claims appended hereto.

---

SEQUENCE LISTING

```
<160> NUMBER OF SEQ ID NOS: 50

<210> SEQ ID NO 1
<211> LENGTH: 497
<212> TYPE: PRT
<213> ORGANISM: Beta vulgaris

<400> SEQUENCE: 1

Met Asp His Ala Thr Leu Ala Met Ile Leu Ala Ile Trp Phe Ile Ser
1               5                   10                  15

Phe His Phe Ile Lys Leu Leu Phe Ser Gln Gln Thr Thr Lys Leu Leu
            20                  25                  30

Pro Pro Gly Pro Lys Pro Leu Pro Ile Ile Gly Asn Ile Leu Glu Val
        35                  40                  45

Gly Lys Lys Pro His Arg Ser Phe Ala Asn Leu Ala Lys Ile His Gly
    50                  55                  60

Pro Leu Ile Ser Leu Arg Leu Gly Ser Val Thr Thr Ile Val Val Ser
65                  70                  75                  80

Ser Ala Asp Val Ala Lys Glu Met Phe Leu Lys Lys Asp His Pro Leu
                85                  90                  95

Ser Asn Arg Thr Ile Pro Asn Ser Val Thr Ala Gly Asp His His Lys
            100                 105                 110

Leu Thr Met Ser Trp Leu Pro Val Ser Pro Lys Trp Arg Asn Phe Arg
        115                 120                 125

Lys Ile Thr Ala Val His Leu Leu Ser Pro Gln Arg Leu Asp Ala Cys
    130                 135                 140
```

Gln Thr Phe Arg His Ala Lys Val Gln Gln Leu Tyr Glu Tyr Val Gln
145                 150                 155                 160

Glu Cys Ala Gln Lys Gly Gln Ala Val Asp Ile Gly Lys Ala Ala Phe
                165                 170                 175

Thr Thr Ser Leu Asn Leu Leu Ser Lys Leu Phe Phe Ser Val Glu Leu
            180                 185                 190

Ala His His Lys Ser His Thr Ser Gln Glu Phe Lys Glu Leu Ile Trp
        195                 200                 205

Asn Ile Met Glu Asp Ile Gly Lys Pro Asn Tyr Ala Asp Tyr Phe Pro
210                 215                 220

Ile Leu Gly Cys Val Asp Pro Ser Gly Ile Arg Arg Arg Leu Ala Cys
225                 230                 235                 240

Ser Phe Asp Lys Leu Ile Ala Val Phe Gln Gly Ile Ile Cys Glu Arg
                245                 250                 255

Leu Ala Pro Asp Ser Ser Thr Thr Thr Thr Thr Thr Asp Asp Val
            260                 265                 270

Leu Asp Val Leu Leu Gln Leu Phe Lys Gln Asn Glu Leu Thr Met Gly
        275                 280                 285

Glu Ile Asn His Leu Leu Val Asp Ile Phe Asp Ala Gly Thr Asp Thr
290                 295                 300

Thr Ser Ser Thr Phe Glu Trp Val Met Thr Glu Leu Ile Arg Asn Pro
305                 310                 315                 320

Glu Met Met Glu Lys Ala Gln Glu Glu Ile Lys Gln Val Leu Gly Lys
                325                 330                 335

Asp Lys Gln Ile Gln Glu Ser Asp Ile Ile Asn Leu Pro Tyr Leu Gln
            340                 345                 350

Ala Ile Ile Lys Glu Thr Leu Arg Leu His Pro Pro Thr Val Phe Leu
        355                 360                 365

Leu Pro Arg Lys Ala Asp Thr Asp Val Glu Leu Tyr Gly Tyr Ile Val
370                 375                 380

Pro Lys Asp Ala Gln Ile Leu Val Asn Leu Trp Ala Ile Gly Arg Asp
385                 390                 395                 400

Pro Asn Ala Trp Gln Asn Ala Asp Ile Phe Ser Pro Glu Arg Phe Ile
                405                 410                 415

Gly Cys Glu Ile Asp Val Lys Gly Arg Asp Phe Gly Leu Leu Pro Phe
            420                 425                 430

Gly Ala Gly Arg Arg Ile Cys Pro Gly Met Asn Leu Ala Ile Arg Met
        435                 440                 445

Leu Thr Leu Met Leu Ala Thr Leu Leu Gln Phe Phe Asn Trp Lys Leu
450                 455                 460

Glu Gly Asp Ile Ser Pro Lys Asp Leu Asp Met Asp Glu Lys Phe Gly
465                 470                 475                 480

Ile Ala Leu Gln Lys Thr Lys Pro Leu Lys Leu Ile Pro Ile Pro Arg
                485                 490                 495

Tyr

<210> SEQ ID NO 2
<211> LENGTH: 496
<212> TYPE: PRT
<213> ORGANISM: Amaranthus cruentus
<400> SEQUENCE: 2

Met Asp Asn Ala Thr Leu Ala Met Ile Leu Thr Ile Trp Phe Ile Ser
1               5                   10                  15

```
Ile Asn Phe Ile Lys Met Phe Phe Tyr His Gln Asn Thr Lys Leu Ser
            20                  25                  30

Leu Pro Pro Gly Pro Lys Pro Leu Pro Ile Ile Gly Asn Ile Leu Glu
        35                  40                  45

Val Gly Lys Lys Pro His Arg Ser Phe Ala Asn Leu Ala Lys Ile His
50                  55                  60

Gly Pro Leu Ile Ser Leu Arg Leu Gly Ser Val Thr Thr Ile Val Val
65                  70                  75                  80

Ser Ser Ala Glu Val Ala Lys Glu Met Phe Leu Lys Lys Asp Gln Pro
                85                  90                  95

Leu Ser Asn Arg Asn Val Pro Asn Ser Val Thr Ala Gly Asp His His
            100                 105                 110

Lys Leu Thr Met Ser Trp Leu Pro Val Ser Pro Lys Trp Arg Asn Phe
        115                 120                 125

Arg Lys Ile Thr Ala Val His Leu Leu Ser Pro Leu Arg Leu Asp Ala
130                 135                 140

Cys Gln Ser Leu Arg His Ala Lys Val Gln Gln Leu Tyr Gln Tyr Val
145                 150                 155                 160

Gln Glu Cys Ala Leu Lys Gly Gln Ser Val Asp Ile Gly Lys Ala Ala
                165                 170                 175

Phe Thr Thr Ser Leu Asn Leu Leu Ser Lys Leu Phe Phe Ser Lys Glu
            180                 185                 190

Leu Ala Cys His Lys Ser His Glu Ser Gln Glu Leu Lys Gln Leu Ile
        195                 200                 205

Trp Asn Ile Met Glu Asp Ile Gly Lys Pro Asn Tyr Ala Asp Tyr Phe
210                 215                 220

Pro Ile Leu Gly Cys Ile Asp Pro Leu Gly Ile Arg Arg Arg Leu Ala
225                 230                 235                 240

Ala Asn Phe Asp Lys Leu Ile Ser Val Phe Gln Thr Ile Ile Ser Glu
                245                 250                 255

Arg Leu Glu Asn Asp Ile Asn Ser Asn Ala Thr Thr Asn Asp Val Leu
            260                 265                 270

Asp Val Leu Leu Gln Leu Tyr Lys Gln Lys Glu Leu Ser Met Gly Glu
        275                 280                 285

Ile Asn His Leu Leu Val Asp Ile Phe Asp Ala Gly Thr Asp Thr Thr
290                 295                 300

Ser Ser Thr Phe Glu Trp Val Met Ala Glu Leu Ile Arg Asn Pro Lys
305                 310                 315                 320

Met Met Glu Lys Ala Gln Gln Glu Ile His Glu Val Leu Gly Lys Asp
                325                 330                 335

Arg Gln Ile Gln Glu Ser Asp Ile Ile Lys Leu Pro Tyr Leu Gln Ala
            340                 345                 350

Leu Ile Lys Glu Thr Leu Arg Leu His Pro Pro Thr Val Phe Leu Leu
        355                 360                 365

Pro Arg Lys Ala Asp Met Asp Val Glu Leu Tyr Gly Tyr Val Val Pro
370                 375                 380

Lys Asp Ala Gln Ile Leu Val Asn Leu Trp Ala Ile Gly Arg Asp Ser
385                 390                 395                 400

Gln Val Trp Glu Lys Pro Asn Val Phe Leu Pro Glu Arg Phe Leu Gly
                405                 410                 415

Ser Asp Val Asp Val Lys Gly Arg Asp Phe Gly Leu Leu Pro Phe Gly
            420                 425                 430
```

```
Ala Gly Lys Arg Ile Cys Pro Gly Met Asn Leu Ala Ile Arg Met Leu
            435                 440                 445

Thr Leu Met Leu Ala Thr Leu Leu Gln Phe Phe Asn Trp Lys Leu Glu
450                 455                 460

Asp Gly Met Asn Pro Gln Asp Leu Asp Met Asp Glu Lys Phe Gly Ile
465                 470                 475                 480

Ala Leu Gln Lys Asn Lys Pro Leu Glu Ile Ile Pro Ser Leu Arg His
                485                 490                 495

<210> SEQ ID NO 3
<211> LENGTH: 496
<212> TYPE: PRT
<213> ORGANISM: Mirabilis jalapa

<400> SEQUENCE: 3

Met Asp Phe Leu Thr Leu Val Met Ile Leu Ser Ile Ile Phe Phe Phe
1               5                   10                  15

Tyr Asn Leu Leu Lys Met Lys Phe Thr Thr His Ser Asp Ala Gln Leu
            20                  25                  30

Pro Pro Gly Pro Lys Pro Met Pro Ile Phe Gly Asn Ile Phe Glu Leu
        35                  40                  45

Gly Glu Lys Pro His Arg Ser Phe Ala Asn Leu Ala Lys Thr His Gly
    50                  55                  60

Pro Leu Met Ser Leu Arg Leu Gly Ser Val Thr Thr Ile Val Val Ser
65                  70                  75                  80

Ser Ala Glu Val Ala Lys Glu Met Phe Leu Lys Asn Asp Gln Ser Leu
                85                  90                  95

Ala Asp Arg Ser Val Pro Asn Ser Val Thr Ala Gly Asp His His Lys
            100                 105                 110

Leu Thr Met Ser Trp Leu Pro Val Ser Pro Lys Trp Lys Asn Phe Arg
        115                 120                 125

Lys Ile Thr Ala Val His Leu Leu Ser Pro Gln Arg Leu Asp Ala Cys
    130                 135                 140

His Ala Leu Arg His Ala Lys Val Lys Gln Leu Tyr Glu Tyr Val Gln
145                 150                 155                 160

Glu Cys Ala Leu Lys Gly Glu Ala Val Asp Ile Gly Lys Ala Ala Phe
                165                 170                 175

Thr Thr Ser Leu Asn Leu Leu Ser Asn Leu Phe Phe Ser Val Glu Leu
            180                 185                 190

Ala Asn His Thr Ser Asn Thr Ser Gln Glu Phe Lys Gln Leu Ile Trp
        195                 200                 205

Asp Ile Met Glu Asp Ile Gly Lys Pro Asn Tyr Ala Asp Tyr Phe Pro
    210                 215                 220

Leu Leu Lys Tyr Val Asp Pro Ser Gly Ile Arg Arg Arg Leu Ala Ala
225                 230                 235                 240

Asn Phe Asp Lys Leu Ile Asp Val Phe Gln Ser Phe Ile Ser Lys Arg
                245                 250                 255

Leu Ser Ser Ala Tyr Ser Ser Ala Thr Ser Leu Asp Asp Val Leu Asp
            260                 265                 270

Val Leu Leu Lys Leu Leu Lys Glu Lys Glu Leu Asn Met Gly Glu Ile
        275                 280                 285

Asn His Leu Leu Val Asp Ile Phe Asp Ala Gly Thr Asp Thr Thr Ser
    290                 295                 300

Asn Thr Phe Glu Trp Ala Met Ala Glu Leu Met Arg Asn Pro Ile Met
305                 310                 315                 320
```

Met Lys Arg Ala Gln Asn Glu Ile Ala Leu Val Leu Gly Lys Asp Asn
                325                 330                 335

Ala Thr Ile Gln Glu Ser Asp Ile Ala Asn Met Pro Tyr Leu Gln Ala
            340                 345                 350

Ile Ile Lys Glu Thr Leu Arg Leu His Pro Thr Val Phe Leu Leu
        355                 360                 365

Pro Arg Lys Ala Ile Thr Asn Val Lys Leu Tyr Gly Tyr Ile Val Pro
    370                 375                 380

Lys Asn Ala Gln Ile Leu Val Asn Leu Trp Ala Ile Gly Arg Asp Pro
385                 390                 395                 400

Lys Val Trp Lys Asn Pro Asn Glu Phe Leu Pro Asp Arg Phe Leu Asn
                405                 410                 415

Ser Asp Ile Asp Val Lys Gly Arg Asp Phe Gly Leu Leu Pro Phe Gly
            420                 425                 430

Ala Gly Arg Arg Ile Cys Pro Gly Met Asn Leu Ala Tyr Arg Met Leu
        435                 440                 445

Thr Leu Met Leu Ala Thr Leu Leu Gln Ser Phe Asp Trp Lys Leu Pro
    450                 455                 460

His Arg Asn Ser Pro Leu Asp Leu Asp Met Asp Glu Lys Phe Gly Ile
465                 470                 475                 480

Ala Leu Gln Lys Thr Lys Pro Leu Glu Ile Ile Pro Leu Ile Lys Tyr
                485                 490                 495

<210> SEQ ID NO 4
<211> LENGTH: 494
<212> TYPE: PRT
<213> ORGANISM: Celosis cristata

<400> SEQUENCE: 4

Met Asp Asn Ala Thr Leu Ala Met Leu Leu Ala Ile Trp Phe Ile Ser
1               5                   10                  15

Phe His Phe Ile Lys Met Leu Phe Thr Asn Gln Ser Thr Lys Leu Leu
                20                  25                  30

Pro Pro Gly Pro Lys Pro Leu Pro Ile Ile Gly Asn Ile Leu Glu Val
            35                  40                  45

Gly Lys Lys Pro His Arg Ser Phe Ala Asn Leu Ala Lys Ile His Gly
        50                  55                  60

Pro Leu Ile Ser Leu Lys Leu Gly Ser Val Thr Thr Ile Val Val Ser
65                  70                  75                  80

Ser Ala Glu Val Ala Lys Glu Met Phe Leu Lys Lys Asp Gln Pro Leu
                85                  90                  95

Ser Asn Arg Thr Val Pro Asn Ser Val Thr Ala Gly Asp His His Lys
            100                 105                 110

Leu Thr Met Ser Trp Leu Pro Val Ser Pro Lys Trp Arg Asn Phe Arg
        115                 120                 125

Lys Ile Thr Ala Val His Leu Leu Ser Pro Leu Arg Leu Asp Ala Cys
    130                 135                 140

Gln Ser Leu Arg His Ala Lys Val Gln Gln Leu Phe Gln Tyr Val Gln
145                 150                 155                 160

Glu Cys Ala Gln Lys Gly Gln Ala Val Asp Ile Gly Lys Ala Ala Phe
                165                 170                 175

Thr Thr Ser Leu Asn Leu Leu Ser Lys Leu Phe Phe Ser Lys Glu Leu
            180                 185                 190

Ala Ser His Lys Ser Arg Glu Ser Gln Glu Phe Lys Gln Leu Ile Trp

```
                  195                 200                 205
Asn Ile Met Glu Asp Ile Gly Lys Pro Asn Tyr Ala Asp Tyr Phe Pro
        210                 215                 220

Ile Leu Gly Cys Val Asp Pro Ser Gly Ile Arg Arg Leu Ala Ser
225                 230                 235                 240

Asn Phe Asp Lys Leu Ile Glu Val Phe Gln Cys Ile Ile Arg Gln Arg
                245                 250                 255

Leu Glu Arg Asn Pro Ser Thr Pro Pro Thr Asn Asp Val Leu Asp Val
            260                 265                 270

Leu Leu Glu Leu Tyr Lys Gln Asn Glu Leu Ser Met Gly Glu Ile Asn
            275                 280                 285

His Leu Leu Val Asp Ile Phe Asp Ala Gly Thr Asp Thr Thr Ser Ser
        290                 295                 300

Thr Phe Glu Trp Val Met Ala Glu Leu Ile Arg Asn Pro Glu Met Met
305                 310                 315                 320

Ala Lys Ala Gln Asp Glu Ile Glu Gln Val Leu Gly Lys Asp Arg Gln
                325                 330                 335

Ile Gln Glu Ser Asp Ile Ile Lys Leu Pro Tyr Leu Gln Ala Ile Ile
            340                 345                 350

Lys Glu Thr Leu Arg Leu His Pro Pro Thr Val Phe Leu Leu Pro Arg
            355                 360                 365

Lys Ala Asp Thr Asp Val Glu Leu Tyr Gly Tyr Ile Val Pro Lys Asp
370                 375                 380

Ala Gln Ile Leu Val Asn Leu Trp Ala Ile Gly Arg Asp Ser Gln Ala
385                 390                 395                 400

Trp Glu Asn Pro Lys Val Phe Ser Pro Asp Arg Phe Leu Gly Cys Glu
                405                 410                 415

Ile Asp Val Lys Gly Arg Asp Phe Gly Leu Leu Pro Phe Gly Ala Gly
            420                 425                 430

Lys Arg Ile Cys Pro Gly Met Asn Leu Ala Ile Arg Met Leu Thr Leu
            435                 440                 445

Met Leu Ala Thr Leu Leu Gln Phe Phe Asn Trp Lys Leu Gln Asp Gly
450                 455                 460

Met Ser Leu Glu Asp Leu Asp Met Glu Glu Lys Phe Gly Ile Ala Leu
465                 470                 475                 480

Gln Lys Thr Lys Pro Leu Arg Ile Ile Pro Val Ser Arg Tyr
                485                 490

<210> SEQ ID NO 5
<211> LENGTH: 497
<212> TYPE: PRT
<213> ORGANISM: Artificial sequence
<220> FEATURE:
<223> OTHER INFORMATION: Synthetic polypeptide sequence

<400> SEQUENCE: 5

Met Asp His Ala Thr Leu Ala Met Ile Leu Ala Ile Leu Phe Ile Ser
1               5                   10                  15

Phe His Phe Ile Lys Leu Leu Phe Ser Gln Gln Thr Thr Lys Leu Leu
                20                  25                  30

Pro Pro Gly Pro Lys Pro Leu Pro Ile Ile Gly Asn Ile Leu Glu Val
            35                  40                  45

Gly Lys Lys Pro His Arg Ser Phe Ala Asn Leu Ala Lys Ile His Gly
        50                  55                  60

Pro Leu Ile Ser Leu Arg Leu Gly Ser Val Thr Thr Ile Val Val Ser
```

-continued

```
                65                  70                  75                  80
Ser Ala Asp Val Ala Lys Glu Met Phe Leu Lys Lys Asp His Pro Leu
                    85                  90                  95

Ser Asn Arg Thr Ile Pro Asn Ser Val Thr Ala Gly Asp His His Lys
                    100                 105                 110

Leu Thr Met Ser Trp Leu Pro Val Ser Pro Lys Trp Arg Asn Phe Arg
                    115                 120                 125

Lys Ile Thr Ala Val His Leu Leu Ser Pro Gln Arg Leu Asp Ala Cys
130                 135                 140

Gln Thr Phe Arg His Ala Lys Val Gln Gln Leu Tyr Glu Tyr Val Gln
145                 150                 155                 160

Glu Cys Ala Gln Lys Gly Gln Ala Val Asp Ile Gly Lys Ala Ala Phe
                    165                 170                 175

Thr Thr Ser Leu Asn Leu Leu Ser Lys Leu Phe Phe Ser Val Glu Leu
                    180                 185                 190

Ala His His Lys Ser His Thr Ser Gln Glu Phe Lys Glu Leu Ile Trp
                    195                 200                 205

Asn Ile Met Glu Asp Ile Gly Lys Pro Asn Tyr Ala Asp Tyr Phe Pro
210                 215                 220

Ile Leu Gly Cys Val Asp Pro Ser Gly Ile Arg Arg Leu Ala Cys
225                 230                 235                 240

Ser Phe Asp Lys Leu Ile Ala Val Phe Gln Gly Ile Ile Cys Glu Arg
                    245                 250                 255

Leu Ala Pro Asp Ser Ser Thr Thr Thr Thr Thr Thr Asp Asp Val
                    260                 265                 270

Leu Asp Val Leu Leu Gln Leu Phe Lys Gln Asn Glu Leu Thr Met Gly
                    275                 280                 285

Glu Ile Asn His Leu Leu Val Asp Ile Phe Asp Ala Gly Thr Asp Thr
                    290                 295                 300

Thr Ser Ser Thr Phe Glu Trp Val Met Thr Glu Leu Ile Arg Asn Pro
305                 310                 315                 320

Glu Met Met Glu Lys Ala Gln Glu Glu Ile Lys Gln Val Leu Gly Lys
                    325                 330                 335

Asp Lys Gln Ile Gln Glu Ser Asp Ile Ile Asn Leu Pro Tyr Leu Gln
                    340                 345                 350

Ala Ile Ile Lys Glu Thr Leu Arg Leu His Pro Pro Thr Val Phe Leu
                    355                 360                 365

Leu Pro Arg Lys Ala Asp Thr Asp Val Glu Leu Tyr Gly Tyr Ile Val
                    370                 375                 380

Pro Lys Asp Ala Gln Ile Leu Val Asn Leu Trp Ala Ile Gly Arg Asp
385                 390                 395                 400

Pro Asn Ala Trp Gln Asn Ala Asp Ile Phe Ser Pro Glu Arg Phe Ile
                    405                 410                 415

Gly Cys Glu Ile Asp Val Lys Gly Arg Asp Phe Gly Leu Leu Pro Phe
                    420                 425                 430

Gly Ala Gly Arg Arg Ile Cys Pro Gly Met Asn Leu Ala Ile Arg Met
                    435                 440                 445

Leu Thr Leu Met Leu Ala Thr Leu Leu Gln Phe Asn Trp Lys Leu
                    450                 455                 460

Glu Gly Asp Ile Ser Pro Lys Asp Leu Asp Met Asp Glu Lys Phe Gly
465                 470                 475                 480

Ile Ala Leu Gln Lys Thr Lys Pro Leu Lys Leu Ile Pro Ile Pro Arg
                    485                 490                 495
```

Tyr

<210> SEQ ID NO 6
<211> LENGTH: 497
<212> TYPE: PRT
<213> ORGANISM: Artificial sequence
<220> FEATURE:
<223> OTHER INFORMATION: Synthetic polypeptide sequence

<400> SEQUENCE: 6

```
Met Asp His Ala Thr Leu Ala Met Ile Leu Ala Ile Trp Phe Ile Ser
1               5                   10                  15

Phe His Phe Ile Lys Leu Leu Phe Ser Gln Gln Thr Thr Lys Leu Leu
            20                  25                  30

Pro Pro Gly Pro Lys Pro Leu Pro Ile Ile Gly Asn Ile Leu Glu Val
        35                  40                  45

Gly Lys Lys Pro His Arg Ser Phe Ala Asn Leu Ala Lys Ile His Gly
    50                  55                  60

Pro Leu Ile Ser Leu Arg Leu Gly Ser Val Thr Thr Ile Val Val Ser
65                  70                  75                  80

Ser Ala Asp Val Ala Lys Glu Met Phe Leu Lys Lys Asp His Pro Leu
                85                  90                  95

Ser Asn Arg Thr Ile Pro Asn Ser Val Thr Ala Gly Asp His His Lys
            100                 105                 110

Leu Thr Met Ser Trp Leu Pro Val Ser Pro Lys Trp Arg Asn Phe Arg
        115                 120                 125

Lys Ile Thr Ala Val His Leu Leu Ser Pro Gln Arg Leu Asp Ala Cys
    130                 135                 140

Gln Thr Phe Arg His Ala Lys Val Gln Gln Leu Tyr Glu Tyr Val Gln
145                 150                 155                 160

Glu Cys Ala Gln Lys Gly Gln Ala Val Asp Ile Gly Lys Ala Ala Phe
                165                 170                 175

Thr Thr Ser Leu Asn Leu Leu Ser Lys Leu Phe Phe Ser Val Glu Leu
            180                 185                 190

Ala His His Lys Ser His Thr Ser Gln Glu Phe Lys Glu Leu Ile Trp
        195                 200                 205

Asn Ile Met Glu Asp Ile Gly Lys Pro Asn Tyr Ala Asp Tyr Phe Pro
    210                 215                 220

Ile Leu Gly Cys Val Asp Pro Ser Gly Ile Arg Arg Arg Leu Ala Cys
225                 230                 235                 240

Ser Phe Asp Lys Leu Ile Ala Val Phe Gln Gly Ile Ile Cys Glu Arg
                245                 250                 255

Leu Ala Pro Asp Ser Ser Thr Thr Thr Thr Thr Thr Asp Asp Val
            260                 265                 270

Leu Asp Val Leu Leu Gln Leu Phe Lys Gln Asn Glu Leu Thr Met Gly
        275                 280                 285

Glu Ile Asn His Leu Leu Val Asp Ile Phe Asp Ala Gly Thr Asp Thr
    290                 295                 300

Thr Ser Ser Thr Leu Glu Trp Val Met Thr Glu Leu Ile Arg Asn Pro
305                 310                 315                 320

Glu Met Met Glu Lys Ala Gln Glu Glu Ile Lys Gln Val Leu Gly Lys
                325                 330                 335

Asp Lys Gln Ile Gln Glu Ser Asp Ile Ile Asn Leu Pro Tyr Leu Gln
            340                 345                 350
```

```
Ala Ile Ile Lys Glu Thr Leu Arg Leu His Pro Pro Thr Val Phe Leu
            355                 360                 365

Leu Pro Arg Lys Ala Asp Thr Asp Val Glu Leu Tyr Gly Tyr Ile Val
370                 375                 380

Pro Lys Asp Ala Gln Ile Leu Val Asn Leu Trp Ala Ile Gly Arg Asp
385                 390                 395                 400

Pro Asn Ala Trp Gln Asn Ala Asp Ile Phe Ser Pro Glu Arg Phe Ile
            405                 410                 415

Gly Cys Glu Ile Asp Val Lys Gly Arg Asp Phe Gly Leu Leu Pro Phe
            420                 425                 430

Gly Ala Gly Arg Arg Ile Cys Pro Gly Met Asn Leu Ala Ile Arg Met
            435                 440                 445

Leu Thr Leu Met Leu Ala Thr Leu Leu Gln Phe Phe Asn Trp Lys Leu
            450                 455                 460

Glu Gly Asp Ile Ser Pro Lys Asp Leu Asp Met Asp Glu Lys Phe Gly
465                 470                 475                 480

Ile Ala Leu Gln Lys Thr Lys Pro Leu Lys Leu Ile Pro Ile Pro Arg
                485                 490                 495

Tyr

<210> SEQ ID NO 7
<211> LENGTH: 497
<212> TYPE: PRT
<213> ORGANISM: Artificial sequence
<220> FEATURE:
<223> OTHER INFORMATION: Synthetic polypeptide sequence

<400> SEQUENCE: 7

Met Asp His Ala Thr Leu Ala Met Ile Leu Ala Ile Leu Phe Ile Ser
1               5                   10                  15

Phe His Phe Ile Lys Leu Leu Phe Ser Gln Gln Thr Thr Lys Leu Leu
                20                  25                  30

Pro Pro Gly Pro Lys Pro Leu Pro Ile Ile Gly Asn Ile Leu Glu Val
            35                  40                  45

Gly Lys Lys Pro His Arg Ser Phe Ala Asn Leu Ala Lys Ile His Gly
50                  55                  60

Pro Leu Ile Ser Leu Arg Leu Gly Ser Val Thr Thr Ile Val Val Ser
65                  70                  75                  80

Ser Ala Asp Val Ala Lys Glu Met Phe Leu Lys Lys Asp His Pro Leu
                85                  90                  95

Ser Asn Arg Thr Ile Pro Asn Ser Val Thr Ala Gly Asp His His Lys
            100                 105                 110

Leu Thr Met Ser Trp Leu Pro Val Ser Pro Lys Trp Arg Asn Phe Arg
            115                 120                 125

Lys Ile Thr Ala Val His Leu Leu Ser Pro Gln Arg Leu Asp Ala Cys
130                 135                 140

Gln Thr Phe Arg His Ala Lys Val Gln Gln Leu Tyr Glu Tyr Val Gln
145                 150                 155                 160

Glu Cys Ala Gln Lys Gly Gln Ala Val Asp Ile Gly Lys Ala Ala Phe
                165                 170                 175

Thr Thr Ser Leu Asn Leu Leu Ser Lys Leu Phe Ser Val Glu Leu
            180                 185                 190

Ala His His Lys Ser His Thr Ser Gln Glu Phe Lys Glu Leu Ile Trp
            195                 200                 205

Asn Ile Met Glu Asp Ile Gly Lys Pro Asn Tyr Ala Asp Tyr Phe Pro
```

-continued

```
                210                 215                 220
Ile Leu Gly Cys Val Asp Pro Ser Gly Ile Arg Arg Leu Ala Cys
225                 230                 235                 240

Ser Phe Asp Lys Leu Ile Ala Val Phe Gln Gly Ile Ile Cys Glu Arg
                245                 250                 255

Leu Ala Pro Asp Ser Ser Thr Thr Thr Thr Thr Thr Asp Asp Val
                260                 265                 270

Leu Asp Val Leu Leu Gln Leu Phe Lys Gln Asn Glu Leu Thr Met Gly
                275                 280                 285

Glu Ile Asn His Leu Leu Val Asp Ile Phe Asp Ala Gly Thr Asp Thr
290                 295                 300

Thr Ser Ser Thr Leu Glu Trp Val Met Thr Glu Leu Ile Arg Asn Pro
305                 310                 315                 320

Glu Met Met Glu Lys Ala Gln Glu Ile Lys Gln Val Leu Gly Lys
                325                 330                 335

Asp Lys Gln Ile Gln Glu Ser Asp Ile Ile Asn Leu Pro Tyr Leu Gln
                340                 345                 350

Ala Ile Ile Lys Glu Thr Leu Arg Leu His Pro Pro Thr Val Phe Leu
                355                 360                 365

Leu Pro Arg Lys Ala Asp Thr Asp Val Glu Leu Tyr Gly Tyr Ile Val
370                 375                 380

Pro Lys Asp Ala Gln Ile Leu Val Asn Leu Trp Ala Ile Gly Arg Asp
385                 390                 395                 400

Pro Asn Ala Trp Gln Asn Ala Asp Ile Phe Ser Pro Glu Arg Phe Ile
                405                 410                 415

Gly Cys Glu Ile Asp Val Lys Gly Arg Asp Phe Gly Leu Leu Pro Phe
                420                 425                 430

Gly Ala Gly Arg Arg Ile Cys Pro Gly Met Asn Leu Ala Ile Arg Met
                435                 440                 445

Leu Thr Leu Met Leu Ala Thr Leu Leu Gln Phe Phe Asn Trp Lys Leu
                450                 455                 460

Glu Gly Asp Ile Ser Pro Lys Asp Leu Asp Met Asp Glu Lys Phe Gly
465                 470                 475                 480

Ile Ala Leu Gln Lys Thr Lys Pro Leu Lys Leu Ile Pro Ile Pro Arg
                485                 490                 495

Tyr

<210> SEQ ID NO 8
<211> LENGTH: 351
<212> TYPE: PRT
<213> ORGANISM: Agaricus bisporus

<400> SEQUENCE: 8

Gly Thr Arg Ala Ala Gln Asp Leu Arg Gln Pro Tyr Trp Asp Trp Gly
1               5                   10                  15

Phe Glu Leu Met Pro Pro Asp Glu Val Ile Lys Asn Glu Glu Val Asn
                20                  25                  30

Ile Thr Asn Tyr Asp Gly Lys Lys Ile Ser Val Lys Asn Pro Ile Leu
                35                  40                  45

Arg Tyr His Phe His Pro Ile Asp Pro Ser Phe Lys Pro Tyr Gly Asp
                50                  55                  60

Phe Ala Thr Trp Arg Thr Thr Val Arg Asn Pro Asp Arg Asn Arg Arg
65                  70                  75                  80

Glu Asp Ile Pro Gly Leu Ile Lys Lys Met Arg Leu Glu Glu Gly Gln
```

```
            85                  90                  95
Ile Arg Glu Lys Thr Tyr Asn Met Leu Lys Phe Asn Asp Ala Trp Glu
            100                 105                 110

Arg Phe Ser Asn His Gly Ile Ser Asp Gln His Ala Asn Ser Leu
            115                 120                 125

Glu Ser Val His Asp Asp Ile His Val Met Val Gly Tyr Gly Lys Ile
            130                 135                 140

Glu Gly His Met Asp His Pro Phe Phe Ala Ala Phe Asp Pro Ile Phe
145                 150                 155                 160

Trp Leu His His Thr Asn Val Asp Arg Leu Leu Ser Leu Trp Lys Ala
                    165                 170                 175

Ile Asn Pro Asp Val Trp Val Thr Ser Gly Arg Asn Arg Asp Gly Thr
                    180                 185                 190

Met Gly Ile Ala Pro Asn Ala Gln Ile Asn Ser Glu Thr Pro Leu Glu
                    195                 200                 205

Pro Phe Tyr Gln Ser Gly Asp Lys Val Trp Thr Ser Ala Ser Leu Ala
            210                 215                 220

Asp Thr Ala Arg Leu Gly Tyr Ser Tyr Pro Asp Phe Asp Lys Leu Val
225                 230                 235                 240

Gly Gly Thr Lys Glu Leu Ile Arg Asp Ala Ile Asp Leu Ile Asp
                    245                 250                 255

Glu Arg Tyr Gly Ser Lys Pro Ser Ser Gly Ala Arg Asn Thr Ala Phe
                    260                 265                 270

Asp Leu Leu Ala Asp Phe Lys Gly Ile Thr Lys Glu His Lys Glu Asp
            275                 280                 285

Leu Lys Met Tyr Asp Trp Thr Ile His Val Ala Phe Lys Lys Phe Glu
            290                 295                 300

Leu Lys Glu Ser Phe Ser Leu Leu Phe Tyr Phe Ala Ser Asp Gly Gly
305                 310                 315                 320

Asp Tyr Asp Gln Glu Asn Ala Leu Leu Asp Gln Leu Thr Pro Ser Val
                    325                 330                 335

Gly Leu Leu Pro Lys Leu Ala Arg Thr Ala Lys Ile Thr Arg Thr
                    340                 345                 350

<210> SEQ ID NO 9
<211> LENGTH: 267
<212> TYPE: PRT
<213> ORGANISM: Mirabilis jalapa

<400> SEQUENCE: 9

Met Lys Gly Thr Tyr Tyr Ile Asn His Gly Asp Pro Leu Met Tyr Leu
1               5                   10                  15

Lys Lys His Ile Lys Leu Arg Gln Phe Leu Glu Gly Trp Gln Glu Asn
            20                  25                  30

Val Val Ile Glu Lys Pro Lys Ser Ile Leu Ile Ser Ala His Trp
            35                  40                  45

Asp Thr Asn Val Pro Thr Val Asn Phe Val Glu His Cys Asp Thr Ile
50                  55                  60

His Asp Phe Asp Asp Tyr Pro Asp Pro Leu Tyr Gln Ile Gln Tyr Arg
65                  70                  75                  80

Ala Pro Gly Ala Pro Asn Leu Ala Lys Lys Val Glu Leu Leu Lys
                85                  90                  95

Glu Ser Gly Met Glu Cys Glu Ile Asp Thr Lys Arg Gly Leu Asp His
            100                 105                 110
```

```
Ala Ala Trp Phe Pro Leu Met Phe Met Tyr Pro Glu Ala Asn Ile Pro
        115                 120                 125

Ile Cys Glu Leu Ser Val Gln Pro Ser Lys Asp Gly Ile His His Tyr
130                 135                 140

Asn Val Gly Lys Ala Leu Ser Pro Leu Leu Gln Gln Gly Val Leu Ile
145                 150                 155                 160

Ile Gly Ser Gly Gly Thr Val His Pro Ser Asp Asp Thr Pro His Cys
                165                 170                 175

Pro Asn Gly Val Ala Pro Trp Ala Ile Glu Phe Asp Asn Trp Leu Glu
            180                 185                 190

Asp Ala Leu Leu Ser Gly Arg Tyr Glu Asp Val Asn Asn Phe Lys Lys
        195                 200                 205

Leu Ala Pro Asn Trp Glu Ile Ser His Pro Gly Gln Glu His Leu Tyr
210                 215                 220

Pro Leu His Val Ala Leu Gly Ala Ala Gly Lys Asn Pro Lys Thr Gln
225                 230                 235                 240

Leu Ile His Arg Ser Trp Ala Ala Asn Gly Val Phe Gly Tyr Ser Thr
                245                 250                 255

Tyr Asn Phe Thr Pro Thr Thr Gln Lys Thr Asp
            260                 265

<210> SEQ ID NO 10
<211> LENGTH: 228
<212> TYPE: PRT
<213> ORGANISM: Amanita muscaria

<400> SEQUENCE: 10

Met Val Pro Ser Phe Val Val Tyr Ser Ser Trp Val Asn Gly Arg Gln
1               5                   10                  15

Arg Tyr Ile Arg Gln Ala Phe Ala Ser Ile Leu Phe Tyr Ile Ile Arg
            20                  25                  30

Asp Thr Thr Leu Ser Phe Pro Ser His Thr Thr Met Ser Thr Lys Pro
        35                  40                  45

Glu Thr Asp Leu Gln Thr Val Leu Asp Ser Glu Ile Lys Glu Trp His
50                  55                  60

Phe His Ile Tyr Phe His Gln Asn Asn Ala Ala Glu His Gln Ala Ala
65                  70                  75                  80

Leu Glu Leu Arg Asp Ala Val Leu Arg Leu Arg Gln Asp Gly Ala Phe
                85                  90                  95

Val Ala Val Pro Leu Phe Arg Val Asn Met Asp Pro Met Gly Pro His
            100                 105                 110

Pro Val Gly Ser Tyr Glu Ile Trp Val Pro Ser Glu Thr Phe Ala Ser
        115                 120                 125

Val Phe Ser Tyr Leu Cys Met Asn Arg Gly Arg Leu Ser Ile Leu Val
130                 135                 140

His Pro Leu Thr Arg Glu Glu Leu Arg Asp His Glu Ile Arg Asn Ala
145                 150                 155                 160

Trp Ile Gly Pro Ser Phe Pro Leu Asn Leu Ala Asn Leu Pro Ile Lys
                165                 170                 175

Ser Asp Glu Ile Pro Leu Gln Tyr Pro Ser Leu Lys Leu Gly Tyr Ser
            180                 185                 190

Ser Thr Ala His Lys Met Ser Leu Glu Glu Arg Arg Lys Leu Gly Asp
        195                 200                 205

Asp Ile Glu Ala Val Leu Arg Gly Glu Lys Glu Ala Ala Arg Ala Pro
210                 215                 220
```

His Arg Asp Ala
225

<210> SEQ ID NO 11
<211> LENGTH: 518
<212> TYPE: PRT
<213> ORGANISM: Thalictrum flavum

<400> SEQUENCE: 11

Met Gly Ser Leu His Val Glu Asp Leu Asp Asn Ile Ser Lys Cys Thr
1               5                   10                  15

Val Glu Asn Pro Leu Asp Pro Glu Glu Phe Arg Arg Gln Gly His Met
            20                  25                  30

Met Ile Asp Phe Leu Ala Asp Tyr Tyr Arg Asp Ile Glu Lys Tyr Pro
        35                  40                  45

Val Arg Ser Gln Val Glu Pro Gly Tyr Leu Arg Lys Glu Ile Pro Asp
    50                  55                  60

Ser Ala Pro Tyr Asn Pro Glu Ser Ile Glu Thr Ile Leu Glu Asp Val
65                  70                  75                  80

His Lys Gln Ile Ile Pro Gly Ile Thr His Trp Gln Ser Pro Asn Tyr
                85                  90                  95

Phe Ala Tyr Phe Pro Ser Ser Gly Ser Val Ala Gly Phe Leu Gly Glu
            100                 105                 110

Met Leu Ser Thr Gly Phe Asn Val Val Gly Phe Asn Trp Met Ser Ser
        115                 120                 125

Pro Ala Ala Thr Glu Leu Glu Ser Ile Val Met Asp Trp Leu Gly Lys
    130                 135                 140

Met Leu Lys Leu Pro Lys Ser Phe Leu Phe Ser Gly Asn Gly Gly Gly
145                 150                 155                 160

Val Leu Gln Gly Thr Thr Cys Glu Ala Ile Leu Cys Thr Leu Thr Ala
                165                 170                 175

Ala Arg Asp Arg Met Leu Asn Lys Ile Gly Arg Glu Asn Ile Cys Lys
            180                 185                 190

Leu Val Val Tyr Gly Ser Asp Gln Thr His Cys Ala Leu Gln Lys Ala
        195                 200                 205

Ala Gln Ile Ala Gly Ile His Pro Asn Asn Phe Arg Ala Val Pro Thr
    210                 215                 220

Thr Lys Ala Asn Asp Tyr Gly Leu Ser Ala Ser Ala Leu Arg Ser Thr
225                 230                 235                 240

Ile Leu Glu Asp Ile Glu Ala Gly Leu Val Pro Leu Phe Leu Cys Ala
                245                 250                 255

Thr Val Gly Thr Thr Ser Ser Thr Ala Val Asp Pro Ile Gly Pro Leu
            260                 265                 270

Cys Lys Val Ala Ser Asp Tyr Ser Ile Trp Val His Val Asp Ala Ala
        275                 280                 285

Tyr Ala Gly Ser Ala Cys Ile Cys Pro Glu Phe Arg His Phe Ile Asp
    290                 295                 300

Gly Val Glu Asn Ala Asp Ser Phe Ser Leu Asn Ala His Lys Trp Phe
305                 310                 315                 320

Phe Thr Thr Leu Asp Cys Cys Cys Leu Trp Val Lys Glu Pro Ser Ala
                325                 330                 335

Leu Ile Lys Ala Leu Ser Thr Asn Pro Glu Tyr Leu Arg Asn Lys Ala
            340                 345                 350

Thr Glu Ser His Gln Val Val Asp Tyr Lys Asp Trp Gln Ile Ala Leu

```
                355                 360                 365
Ser Arg Arg Phe Arg Ala Met Lys Leu Trp Leu Val Leu Arg Ser Tyr
370                 375                 380

Gly Val Ala Asn Leu Arg Asn Phe Leu Arg Ser His Val Lys Met Ala
385                 390                 395                 400

Lys Asn Phe Glu Gly Phe Ile Ala Leu Asp Lys Arg Phe Glu Ile Val
                    405                 410                 415

Val Pro Arg Thr Phe Ala Met Val Cys Phe Arg Leu Leu Pro Pro Arg
                420                 425                 430

Ser Pro Leu Ile Ile Lys Thr Asn Gly Tyr Gln Asn Gly Asn Gly Val
                435                 440                 445

Tyr His Lys Asp Glu Ser Arg Ala Asn Glu Leu Asn Arg Arg Leu Leu
                450                 455                 460

Glu Ser Ile Asn Ala Ser Gly Ser Ala Tyr Met Thr His Ser Met Val
465                 470                 475                 480

Gly Gly Val Tyr Met Ile Arg Phe Ala Val Gly Ala Ser Leu Thr Glu
                    485                 490                 495

Glu Arg His Val Ile Leu Ala Trp Lys Val Val Gln Glu His Ala Asp
                500                 505                 510

Ala Val Leu Ala Thr Phe
                515

<210> SEQ ID NO 12
<211> LENGTH: 518
<212> TYPE: PRT
<213> ORGANISM: Papaver somniferum

<400> SEQUENCE: 12

Met Gly Ser Leu Pro Ala Asn Asn Phe Glu Ser Met Ser Leu Cys Ser
1               5                   10                  15

Gln Asn Pro Leu Asp Pro Asp Glu Phe Arg Arg Gln Gly His Met Ile
                20                  25                  30

Ile Asp Phe Leu Ala Asp Tyr Tyr Lys Asn Val Glu Lys Tyr Pro Val
                35                  40                  45

Arg Thr Gln Val Asp Pro Gly Tyr Leu Lys Lys Arg Leu Pro Glu Ser
            50                  55                  60

Ala Pro Tyr Asn Pro Glu Ser Ile Glu Thr Ile Leu Glu Asp Val Thr
65                  70                  75                  80

Asn Asp Ile Ile Pro Gly Leu Thr His Trp Gln Ser Pro Asn Tyr Phe
                    85                  90                  95

Ala Tyr Phe Pro Ser Ser Gly Ser Ile Ala Gly Phe Leu Gly Glu Met
                    100                 105                 110

Leu Ser Thr Gly Phe Asn Val Val Gly Phe Asn Trp Met Ser Ser Pro
                115                 120                 125

Ala Ala Thr Glu Leu Glu Ser Ile Val Met Asn Trp Leu Gly Gln Met
                130                 135                 140

Leu Thr Leu Pro Lys Ser Phe Leu Phe Ser Ser Asp Gly Ser Ser Gly
145                 150                 155                 160

Gly Gly Gly Val Leu Gln Gly Thr Thr Cys Glu Ala Ile Leu Cys Thr
                    165                 170                 175

Leu Thr Ala Ala Arg Asp Lys Met Leu Asn Lys Ile Gly Arg Glu Asn
                180                 185                 190

Ile Asn Lys Leu Val Val Tyr Ala Ser Asp Gln Thr Leu Ser Ala Leu
                195                 200                 205
```

```
Gln Lys Ala Ala Gln Ile Ala Gly Ile Asn Pro Lys Asn Phe Leu Ala
    210                 215                 220
Ile Ala Thr Ser Lys Ala Thr Asn Phe Gly Leu Ser Pro Asn Ser Leu
225                 230                 235                 240
Gln Ser Thr Ile Leu Ala Asp Ile Glu Ser Gly Leu Val Pro Leu Phe
            245                 250                 255
Leu Cys Ala Thr Val Gly Thr Ser Ser Thr Ala Val Asp Pro Ile
            260                 265                 270
Gly Pro Leu Cys Ala Val Ala Lys Leu His Gly Ile Trp Val His Ile
            275                 280                 285
Asp Ala Ala Tyr Ala Gly Ser Ala Cys Ile Cys Pro Glu Phe Arg His
    290                 295                 300
Phe Ile Asp Gly Val Glu Asp Ala Asp Ser Phe Ser Leu Asn Ala His
305                 310                 315                 320
Lys Trp Phe Phe Thr Thr Leu Asp Cys Cys Cys Leu Trp Val Lys Asp
                325                 330                 335
Ser Asp Ser Leu Val Lys Ala Leu Ser Thr Ser Pro Glu Tyr Leu Lys
            340                 345                 350
Asn Lys Ala Thr Asp Ser Lys Gln Val Ile Asp Tyr Lys Asp Trp Gln
    355                 360                 365
Ile Ala Leu Ser Arg Arg Phe Arg Ser Met Lys Leu Trp Leu Val Leu
370                 375                 380
Arg Ser Tyr Gly Ile Ala Asn Leu Arg Thr Phe Leu Arg Ser His Val
385                 390                 395                 400
Lys Met Ala Lys His Phe Gln Gly Leu Ile Gly Met Asp Asn Arg Phe
                405                 410                 415
Glu Ile Val Val Pro Arg Thr Phe Ala Met Val Cys Phe Arg Leu Lys
            420                 425                 430
Pro Ala Ala Ile Phe Arg Lys Lys Ile Val Glu Asp Asp His Ile Glu
    435                 440                 445
Ala Gln Thr Asn Glu Val Asn Ala Lys Leu Leu Glu Ser Val Asn Ala
450                 455                 460
Ser Gly Lys Ile Tyr Met Thr His Ala Val Val Gly Val Tyr Met
465                 470                 475                 480
Ile Arg Phe Ala Val Gly Ala Thr Leu Thr Glu Glu Arg His Val Thr
                485                 490                 495
Gly Ala Trp Lys Val Val Gln Glu His Thr Asp Ala Ile Leu Gly Ala
            500                 505                 510
Leu Gly Glu Asp Val Cys
            515

<210> SEQ ID NO 13
<211> LENGTH: 470
<212> TYPE: PRT
<213> ORGANISM: Pseudomonas putida

<400> SEQUENCE: 13

Met Thr Pro Glu Gln Phe Arg Gln Tyr Gly His Gln Leu Ile Asp Leu
1               5                   10                  15
Ile Ala Asp Tyr Arg Gln Thr Val Gly Glu Arg Pro Val Met Ala Gln
            20                  25                  30
Val Glu Pro Gly Tyr Leu Lys Ala Ala Leu Pro Ala Thr Ala Pro Gln
        35                  40                  45
Gln Gly Glu Pro Phe Ala Ala Ile Leu Asp Asp Val Asn Asn Leu Val
    50                  55                  60
```

```
Met Pro Gly Leu Ser His Trp Gln His Pro Asp Phe Tyr Gly Tyr Phe
 65                  70                  75                  80
Pro Ser Asn Gly Thr Leu Ser Ser Val Leu Gly Asp Phe Leu Ser Thr
                 85                  90                  95
Gly Leu Gly Val Leu Gly Leu Ser Trp Gln Ser Ser Pro Ala Leu Ser
            100                 105                 110
Glu Leu Glu Glu Thr Thr Leu Asp Trp Leu Arg Gln Leu Leu Gly Leu
        115                 120                 125
Ser Gly Gln Trp Ser Gly Val Ile Gln Asp Thr Ala Ser Thr Ser Thr
    130                 135                 140
Leu Val Ala Leu Ile Ser Ala Arg Glu Arg Ala Thr Asp Tyr Ala Leu
145                 150                 155                 160
Val Arg Gly Gly Leu Gln Ala Glu Pro Lys Pro Leu Ile Val Tyr Val
                165                 170                 175
Ser Ala His Ala His Ser Ser Val Asp Lys Ala Ala Leu Leu Ala Gly
            180                 185                 190
Phe Gly Arg Asp Asn Ile Arg Leu Ile Pro Thr Asp Glu Arg Tyr Ala
        195                 200                 205
Leu Arg Pro Glu Ala Leu Gln Ala Ala Ile Glu Gln Asp Leu Ala Ala
    210                 215                 220
Gly Asn Gln Pro Cys Ala Val Val Ala Thr Thr Gly Thr Thr Thr Thr
225                 230                 235                 240
Thr Ala Leu Asp Pro Leu Arg Pro Val Gly Glu Ile Ala Gln Ala Asn
                245                 250                 255
Gly Leu Trp Leu His Val Asp Ser Ala Met Ala Gly Ser Ala Met Ile
            260                 265                 270
Leu Pro Glu Cys Arg Trp Met Trp Asp Gly Ile Glu Leu Ala Asp Ser
        275                 280                 285
Val Val Val Asn Ala His Lys Trp Leu Gly Val Ala Phe Asp Cys Ser
    290                 295                 300
Ile Tyr Tyr Val Arg Asp Pro Gln His Leu Ile Arg Val Met Ser Thr
305                 310                 315                 320
Asn Pro Ser Tyr Leu Gln Ser Ala Val Asp Gly Glu Val Lys Asn Leu
                325                 330                 335
Arg Asp Trp Gly Ile Pro Leu Gly Arg Arg Phe Arg Ala Leu Lys Leu
            340                 345                 350
Trp Phe Met Leu Arg Ser Glu Gly Val Asp Ala Leu Gln Ala Arg Leu
        355                 360                 365
Arg Arg Asp Leu Asp Asn Ala Gln Trp Leu Ala Gly Gln Val Glu Ala
    370                 375                 380
Ala Ala Glu Trp Glu Val Leu Ala Pro Val Gln Leu Gln Thr Leu Cys
385                 390                 395                 400
Ile Arg His Arg Pro Ala Gly Leu Glu Gly Glu Ala Leu Asp Ala His
                405                 410                 415
Thr Lys Gly Trp Ala Glu Arg Leu Asn Ala Ser Gly Ala Ala Tyr Val
            420                 425                 430
Thr Pro Ala Thr Leu Asp Gly Arg Trp Met Val Arg Val Ser Ile Gly
        435                 440                 445
Ala Leu Pro Thr Glu Arg Gly Asp Val Gln Arg Leu Trp Ala Arg Leu
    450                 455                 460
Gln Asp Val Ile Lys Gly
465                 470
```

<210> SEQ ID NO 14
<211> LENGTH: 443
<212> TYPE: PRT
<213> ORGANISM: Micrococcus luteus

<400> SEQUENCE: 14

```
Met Ser Asn Pro His Val Ile Val Gly Ala Gly Phe Ala Gly Leu
 1               5                  10                  15

Val Ala Ala Arg Glu Leu Gln Met Ala Gly Val Asp Val Glu Ile Val
             20                  25                  30

Glu Ala Arg Asp Arg Val Gly Gly Arg Ala Trp Thr Glu Glu Arg Met
             35                  40                  45

Gly Arg Pro Leu Glu Leu Gly Ala Thr Trp Val His Trp Met Gln Pro
 50                  55                  60

His Val Trp Ser Glu Ile Thr Arg Tyr Asp Gln Ser Ile Tyr Pro Ser
 65                  70                  75                  80

Pro Phe Cys Asp Asp Ala Tyr Trp Ile Thr Gly Gly Arg Val Glu His
                 85                  90                  95

Gly Thr Glu Ala Asp Leu Asp Ala Ala Leu Ala Arg Pro Met Ala Lys
                100                 105                 110

Ile Phe Glu Asp Ser Arg Glu Phe Phe Pro Tyr Pro Tyr Glu Pro Leu
            115                 120                 125

His Val Leu Asp Glu Ser Ser Gly Ser Thr Pro Glu Leu Arg Glu Arg
            130                 135                 140

Phe Arg Ala Ala Asp Gln Gly Ser Val Leu Asp Cys Leu Lys Gly Gly
145                 150                 155                 160

Asp Phe Thr Gln Glu Glu Arg Asp Leu Cys Asp Ala Tyr Trp Ser Ala
                165                 170                 175

Ala Tyr Ile Gly Asp Pro His Gln Gly Ser Pro Leu Met Ala Lys Gln
            180                 185                 190

Trp Ala Ala Leu Ser Asp His Arg Leu Ser Leu Val Asp Glu Gln Thr
            195                 200                 205

Leu Arg Phe Lys Leu Thr His Gly Met Arg Gly Leu Tyr Glu Asn Ile
            210                 215                 220

Ala Ala Asp Leu Arg Cys Pro Ile Arg Leu Asn Thr Pro Val Thr Ala
225                 230                 235                 240

Val Asp His Arg Ser Asp Gly Ala Thr Val Thr Leu Gly Thr Gly Glu
                245                 250                 255

Lys Ile Ser Cys Asp Ser Val Ile Val Thr Val Pro Val Gly Ala Leu
            260                 265                 270

Pro Thr Ile Glu Phe Thr Pro Gly Leu Pro Ser Gly Met Arg Thr Val
            275                 280                 285

Ile Asp Gln Arg Trp Asn Ser Thr Gly Cys Lys Ile Trp Val Lys Val
            290                 295                 300

Lys Gly His His Ser Ile Leu Gly Tyr Ala Pro Thr Pro His Lys Ala
305                 310                 315                 320

Ala Val Phe Arg Ser Glu Phe Phe Met Asp Asp Thr Thr Ile Cys
                325                 330                 335

Val Gly Phe Gly Ser His His Asp Ala Val Asp Leu Thr Asp Pro Arg
            340                 345                 350

Asp Ala Gln Ala Ile Val Asp Gln Trp Arg Pro Asp Leu Glu Val Val
            355                 360                 365

Asp Cys Thr Gly His Asp Trp Val Ala Asp Arg Trp Ser Gly Gln Ala
            370                 375                 380
```

-continued

```
Trp Ala Thr Leu Arg Ser Gly Gln Phe Thr Asn Gly Trp His His Phe
385                 390                 395                 400

Arg Ser Thr Asp Ser Arg Leu Arg Phe Ala Gly Ala Asp Trp Ala Arg
            405                 410                 415

Gly Trp Arg Gly Val Val Val Asp Gly Ala Ile Glu Thr Gly Leu Ser
            420                 425                 430

Thr Ala Arg Asp Val Leu Arg Asp Ile Arg Ala
        435                 440

<210> SEQ ID NO 15
<211> LENGTH: 792
<212> TYPE: PRT
<213> ORGANISM: Oryza sativa

<400> SEQUENCE: 15

Met Leu Cys His Val Gly Val Ala Ser Gly Gly Gly Gly Asp Glu Tyr
1               5                   10                  15

Thr Gln Thr Gln Ile Cys Ile Gln Arg Leu Lys Ala Arg His Ala Ala
            20                  25                  30

Thr Val Leu Ala Ala Leu Arg Ser Ala Phe Gly Gly Gly Ala Glu Phe
        35                  40                  45

Ser Leu Arg His Gly Arg Arg Arg Arg Trp Glu Ser Ala Ala
50                  55                  60

Arg Trp Ser Ala Ser Gly Glu Lys Ser Gly Gly Ser Ala Phe Ile Leu
65                  70                  75                  80

Thr Arg Asp Glu Ala Ile Arg Thr Tyr Arg Glu Arg Gly Glu Thr Ile
                85                  90                  95

Ser Gly Val Glu Ile Ile Ala Arg Thr Gln Arg Ser His Pro Leu Asp
            100                 105                 110

Pro Leu Ser Ala Ala Glu Ile Ala Val Ala Val Thr Thr Val Lys Ala
        115                 120                 125

Ala Ala Ser Thr Pro Glu Val Arg Asp Gly Met Arg Phe Val Glu Val
    130                 135                 140

Ala Leu Leu Glu Pro Glu Lys Asn Val Val Ala Leu Ala Asp Ala Tyr
145                 150                 155                 160

Phe Phe Pro Pro Phe Gln Pro Ser Leu Leu Pro Gly Asn Arg Asn Ala
                165                 170                 175

Pro Ile Ile Pro Thr Lys Leu Pro Pro Ser Arg Ala Lys Leu Val Val
            180                 185                 190

Tyr Asn Arg Gln Thr Asn Glu Thr Ser Ile Trp Ile Val Glu Phe Ser
        195                 200                 205

Glu Val His Ala Asp Ser Asp Thr Arg Gly Gly Tyr Glu Arg Gly Gly
    210                 215                 220

Lys Leu Val Ser Ser Glu Val Val Pro Asp Val Gln Pro Ala Met Asp
225                 230                 235                 240

Ala Met Glu Phe Val Glu Cys Glu Ala Thr Val Lys Ser His Pro Pro
                245                 250                 255

Phe Ile Glu Ala Met Arg Lys Arg Gly Ile Asp Asp Met Asp Leu Val
            260                 265                 270

Thr Val Asp Pro Trp Cys Ala Gly Tyr Tyr Ser Asp Ala Asp Ala Pro
        275                 280                 285

Ser Arg Arg Ile Ala Lys Pro Leu Val Phe Cys Arg Thr Glu Ser Asp
    290                 295                 300

Asn Pro Ile Glu Asn Gly Tyr Ala Arg Pro Val Glu Gly Val His Ile
```

-continued

```
               305                 310                 315                 320
           Ile Val Asp Met Gln Asn Asn Thr Val Ile Glu Phe Glu Asp Arg Lys
                           325                 330                 335
           Leu Val Pro Leu Pro Pro Ser Asp His Leu Arg Asn Tyr Thr Ser Gly
                           340                 345                 350
           Glu Thr Arg Gly Gly Val Asp Arg Thr Asp Val Lys Pro Leu Val Ile
                           355                 360                 365
           Asn Gln Pro Gln Gly Pro Ser Phe His Val Asn Gly Tyr Leu Val Glu
                           370                 375                 380
           Trp Gln Lys Trp Asn Phe Arg Ile Gly Phe Thr Pro Lys Glu Gly Leu
           385                 390                 395                 400
           Val Leu His Ser Val Ala Tyr Val Asp Gly Asn Arg Gly Arg Arg Pro
                           405                 410                 415
           Ile Ala His Arg Leu Ser Phe Val Glu Met Val Val Pro Tyr Gly Asp
                           420                 425                 430
           Pro Asn Glu Pro His Tyr Arg Lys Asn Ala Phe Asp Ala Gly Glu Asp
                           435                 440                 445
           Gly Leu Gly Lys Asn Ala Asn Ser Leu Lys Lys Gly Cys Asp Cys Leu
                           450                 455                 460
           Gly Val Ile Lys Tyr Phe Asp Ala His Phe Thr Asn Phe Thr Gly Gly
           465                 470                 475                 480
           Val Glu Thr Ile Glu Asn Ala Val Cys Leu His Glu Glu Asp His Gly
                           485                 490                 495
           Ile Leu Trp Lys His Arg Asp Trp Arg Thr Gly Leu Ala Glu Val Arg
                           500                 505                 510
           Arg Ser Arg Arg Leu Thr Val Ser Phe Ile Cys Thr Ile Ala Asn Tyr
                           515                 520                 525
           Glu Tyr Gly Phe Tyr Trp His Phe Tyr Gln Asp Gly Lys Ile Glu Ala
                           530                 535                 540
           Glu Val Lys Leu Thr Gly Ile Leu Ser Val Gly Ala Leu Met Pro Gly
           545                 550                 555                 560
           Glu Gln Arg Lys Tyr Gly Thr Thr Ile Ala Pro Ser Leu Tyr Ala Pro
                           565                 570                 575
           Val His Gln His Phe Phe Val Thr Arg Met Asp Met Ala Val Asp Cys
                           580                 585                 590
           Lys Pro Asn Glu Ala Tyr Asn Gln Val Val Glu Val Asn Val Asn Thr
                           595                 600                 605
           Glu Cys Ala Gly Pro Asn Asn Met His Asn Asn Ala Phe Tyr Ala Glu
                           610                 615                 620
           Glu Lys Leu Leu Lys Ser Glu Leu Gln Ala Met Arg Asp Cys His Pro
           625                 630                 635                 640
           Ser Ser Ala Arg Tyr Trp Ile Val Arg Asn Thr Arg Thr Val Asn Arg
                           645                 650                 655
           Thr Gly Gln Pro Thr Gly Tyr Lys Leu Ile Pro Gly Ser Asn Cys Leu
                           660                 665                 670
           Pro Leu Ala Leu Pro Glu Ala Lys Phe Leu Arg Arg Ala Gly Phe Leu
                           675                 680                 685
           Lys His Asn Leu Trp Val Thr Ser Tyr Lys Asn Asp Glu Met Tyr Pro
                           690                 695                 700
           Gly Gly Glu Phe Pro Asn Gln Asn Pro Arg Ile Asn Glu Gly Leu Ala
           705                 710                 715                 720
           Thr Trp Val Lys Gln Asp Arg Ser Leu Glu Glu Thr Asn Ile Val Leu
                           725                 730                 735
```

```
Trp Tyr Val Phe Gly Val Thr His Val Pro Arg Leu Glu Asp Trp Pro
            740                 745                 750

Val Met Pro Val Glu His Ile Gly Phe Met Leu Lys Pro Asp Gly Phe
        755                 760                 765

Phe Asp Cys Ser Pro Ala Ile Asp Val Pro Leu Gly Ser Glu Val His
    770                 775                 780

Thr Lys Asn Gly Trp Ile Asn Tyr
785                 790

<210> SEQ ID NO 16
<211> LENGTH: 527
<212> TYPE: PRT
<213> ORGANISM: Homo sapiens

<400> SEQUENCE: 16

Met Glu Asn Gln Glu Lys Ala Ser Ile Ala Gly His Met Phe Asp Val
1               5                   10                  15

Val Val Ile Gly Gly Gly Ile Ser Gly Leu Ser Ala Ala Lys Leu Leu
            20                  25                  30

Thr Glu Tyr Gly Val Ser Val Leu Val Leu Glu Ala Arg Asp Arg Val
        35                  40                  45

Gly Gly Arg Thr Tyr Thr Ile Arg Asn Glu His Val Asp Tyr Val Asp
    50                  55                  60

Val Gly Gly Ala Tyr Val Gly Pro Thr Gln Asn Arg Ile Leu Arg Leu
65                  70                  75                  80

Ser Lys Glu Leu Gly Ile Glu Thr Tyr Lys Val Asn Val Ser Glu Arg
                85                  90                  95

Leu Val Gln Tyr Val Lys Gly Lys Thr Tyr Pro Phe Arg Gly Ala Phe
            100                 105                 110

Pro Pro Val Trp Asn Pro Ile Ala Tyr Leu Asp Tyr Asn Asn Leu Trp
        115                 120                 125

Arg Thr Ile Asp Asn Met Gly Lys Glu Ile Pro Thr Asp Ala Pro Trp
    130                 135                 140

Glu Ala Gln His Ala Asp Lys Trp Asp Lys Met Thr Met Lys Glu Leu
145                 150                 155                 160

Ile Asp Lys Ile Cys Trp Thr Lys Thr Ala Arg Arg Phe Ala Tyr Leu
                165                 170                 175

Phe Val Asn Ile Asn Val Thr Ser Glu Pro His Glu Val Ser Ala Leu
            180                 185                 190

Trp Phe Leu Trp Tyr Val Lys Gln Cys Gly Gly Thr Thr Arg Ile Phe
        195                 200                 205

Ser Val Thr Asn Gly Gly Gln Glu Arg Lys Phe Val Gly Gly Ser Gly
    210                 215                 220

Gln Val Ser Glu Arg Ile Met Asp Leu Leu Gly Asp Gln Val Lys Leu
225                 230                 235                 240

Asn His Pro Val Thr His Val Asp Gln Ser Ser Asp Asn Ile Ile Ile
                245                 250                 255

Glu Thr Leu Asn His Glu His Tyr Glu Cys Lys Tyr Val Ile Asn Ala
            260                 265                 270

Ile Pro Pro Thr Leu Thr Ala Lys Ile His Phe Arg Pro Glu Leu Pro
        275                 280                 285

Ala Glu Arg Asn Gln Leu Ile Gln Arg Leu Pro Met Gly Ala Val Ile
    290                 295                 300

Lys Cys Met Met Tyr Tyr Lys Glu Ala Phe Trp Lys Lys Lys Asp Tyr
```

```
                        305                 310                 315                 320
Cys Gly Cys Met Ile Ile Glu Asp Glu Asp Ala Pro Ile Ser Ile Thr
                325                 330                 335

Leu Asp Asp Thr Lys Pro Asp Gly Ser Leu Pro Ala Ile Met Gly Phe
                340                 345                 350

Ile Leu Ala Arg Lys Ala Asp Arg Leu Ala Lys Leu His Lys Glu Ile
                355                 360                 365

Arg Lys Lys Lys Ile Cys Glu Leu Tyr Ala Lys Val Leu Gly Ser Gln
370                 375                 380

Glu Ala Leu His Pro Val His Tyr Glu Glu Lys Asn Trp Cys Glu Glu
385                 390                 395                 400

Gln Tyr Ser Gly Gly Cys Tyr Thr Ala Tyr Phe Pro Pro Gly Ile Met
                405                 410                 415

Thr Gln Tyr Gly Arg Val Ile Arg Gln Pro Val Gly Arg Ile Phe Phe
                420                 425                 430

Ala Gly Thr Glu Thr Ala Thr Lys Trp Ser Gly Tyr Met Glu Gly Ala
                435                 440                 445

Val Glu Ala Gly Glu Arg Ala Ala Arg Glu Val Leu Asn Gly Leu Gly
                450                 455                 460

Lys Val Thr Glu Lys Asp Ile Trp Val Gln Glu Pro Glu Ser Lys Asp
465                 470                 475                 480

Val Pro Ala Val Glu Ile Thr His Thr Phe Trp Glu Arg Asn Leu Pro
                485                 490                 495

Ser Val Ser Gly Leu Leu Lys Ile Ile Gly Phe Ser Thr Ser Val Thr
                500                 505                 510

Ala Leu Gly Phe Val Leu Tyr Lys Tyr Lys Leu Leu Pro Arg Ser
                515                 520                 525

<210> SEQ ID NO 17
<211> LENGTH: 231
<212> TYPE: PRT
<213> ORGANISM: Papaver somniferum

<400> SEQUENCE: 17

Met Ser Lys Leu Ile Thr Thr Glu Pro Leu Lys Ser Met Ala Glu Val
1               5                   10                  15

Ile Ser Asn Tyr Ala Met Lys Gln Gln Ser Val Ser Glu Arg Asn Ile
                20                  25                  30

Pro Lys Lys Gln Ser Leu Leu Arg Lys Glu Ile Thr Tyr Glu Thr Glu
                35                  40                  45

Val Gln Thr Ser Ala Asp Ser Ile Trp Asn Val Tyr Ser Ser Pro Asp
                50                  55                  60

Ile Pro Arg Leu Leu Arg Asp Val Leu Leu Pro Gly Val Phe Glu Lys
65                  70                  75                  80

Leu Asp Val Ile Ala Gly Asn Gly Gly Val Gly Thr Val Leu Asp Ile
                85                  90                  95

Ala Phe Pro Leu Gly Ala Val Pro Arg Arg Tyr Lys Glu Lys Phe Val
                100                 105                 110

Lys Ile Asn His Glu Lys Arg Leu Lys Glu Val Val Met Ile Glu Gly
                115                 120                 125

Gly Tyr Leu Asp Met Gly Cys Thr Phe Tyr Met Asp Arg Ile His Ile
                130                 135                 140

Phe Glu Lys Thr Pro Asn Ser Cys Val Ile Glu Ser Ser Ile Ile Tyr
145                 150                 155                 160
```

```
Glu Val Lys Glu Glu Tyr Ala Gly Lys Met Ala Lys Leu Ile Thr Thr
                165                 170                 175

Glu Pro Leu Glu Ser Met Ala Glu Val Ile Ser Gly Tyr Val Leu Lys
            180                 185                 190

Lys Arg Leu Gln Val Phe Gly Phe Glu Ile Lys Pro Lys Leu Arg Phe
        195                 200                 205

Asn Leu Leu Leu Cys Leu Ile Ile Cys Leu Val Ile Ala Gly Gly Met
    210                 215                 220

Phe Val Ala Gly Val Pro Leu
225                 230

<210> SEQ ID NO 18
<211> LENGTH: 210
<212> TYPE: PRT
<213> ORGANISM: Thalictrum flavum

<400> SEQUENCE: 18

Met Met Lys Met Glu Val Val Phe Val Phe Leu Met Leu Leu Gly Thr
1               5                   10                  15

Ile Asn Cys Gln Lys Leu Ile Leu Thr Gly Arg Pro Phe Leu His His
            20                  25                  30

Gln Gly Ile Ile Asn Gln Val Ser Thr Val Thr Lys Val Ile His His
        35                  40                  45

Glu Leu Glu Val Ala Ala Ser Ala Asp Asp Ile Trp Thr Val Tyr Ser
    50                  55                  60

Trp Pro Gly Leu Ala Lys His Leu Pro Asp Leu Leu Pro Gly Ala Phe
65                  70                  75                  80

Glu Lys Leu Glu Ile Ile Gly Asp Gly Gly Val Gly Thr Ile Leu Asp
                85                  90                  95

Met Thr Phe Val Pro Gly Glu Phe Pro His Glu Tyr Lys Glu Lys Phe
            100                 105                 110

Ile Leu Val Asp Asn Glu His Arg Leu Lys Lys Val Gln Met Ile Glu
        115                 120                 125

Gly Gly Tyr Leu Asp Leu Gly Val Thr Tyr Tyr Met Asp Thr Ile His
    130                 135                 140

Val Val Pro Thr Gly Lys Asp Ser Cys Val Ile Lys Ser Ser Thr Glu
145                 150                 155                 160

Tyr His Val Lys Pro Glu Phe Val Lys Ile Val Glu Pro Leu Ile Thr
                165                 170                 175

Thr Gly Pro Leu Ala Ala Met Ala Asp Ala Ile Ser Lys Leu Val Leu
            180                 185                 190

Glu His Lys Ser Lys Ser Asn Ser Asp Glu Ile Glu Ala Ala Ile Ile
        195                 200                 205

Thr Val
    210

<210> SEQ ID NO 19
<211> LENGTH: 347
<212> TYPE: PRT
<213> ORGANISM: Coptis japonica

<400> SEQUENCE: 19

Met Glu Val Lys Lys Asp Asn Leu Ser Ser Gln Ala Lys Leu Trp Asn
1               5                   10                  15

Phe Ile Tyr Gly Phe Ala Glu Ser Leu Val Leu Lys Cys Ala Val Gln
            20                  25                  30
```

```
Leu Asp Leu Ala Asn Ile Ile His Asn Ser Gly Thr Ser Met Thr Leu
         35                  40                  45

Ser Glu Leu Ser Ser Arg Leu Pro Ser Gln Pro Val Asn Glu Asp Ala
 50                  55                  60

Leu Tyr Arg Val Met Arg Tyr Leu Val His Met Lys Leu Phe Thr Lys
 65                  70                  75                  80

Ala Ser Ile Asp Gly Glu Leu Arg Tyr Gly Leu Ala Pro Pro Ala Lys
                 85                  90                  95

Tyr Leu Val Lys Gly Trp Asp Lys Cys Met Val Gly Ser Ile Leu Ala
                100                 105                 110

Ile Thr Asp Lys Asp Phe Met Ala Pro Trp His Tyr Leu Lys Asp Gly
            115                 120                 125

Leu Ser Gly Glu Ser Gly Thr Ala Phe Glu Lys Ala Leu Gly Thr Asn
130                 135                 140

Ile Trp Gly Tyr Met Ala Glu His Pro Glu Lys Asn Gln Leu Phe Asn
145                 150                 155                 160

Glu Ala Met Ala Asn Asp Ser Arg Leu Ile Met Ser Ala Leu Val Lys
                165                 170                 175

Glu Cys Gly Asn Ile Phe Asn Gly Ile Thr Thr Leu Val Asp Val Gly
                180                 185                 190

Gly Gly Thr Gly Thr Ala Val Arg Asn Ile Ala Asn Ala Phe Pro His
            195                 200                 205

Ile Lys Cys Thr Val Tyr Asp Leu Pro His Val Ile Ala Asp Ser Pro
            210                 215                 220

Gly Tyr Ser Glu Val His Cys Val Ala Gly Asp Met Phe Lys Phe Ile
225                 230                 235                 240

Pro Lys Ala Asp Ala Ile Met Met Lys Cys Ile Leu His Asp Trp Asp
                245                 250                 255

Asp Lys Glu Cys Ile Glu Ile Leu Lys Arg Cys Lys Glu Ala Val Pro
                260                 265                 270

Val Lys Gly Gly Lys Val Ile Ile Val Asp Ile Val Leu Asn Val Gln
            275                 280                 285

Ser Glu His Pro Tyr Thr Lys Met Arg Leu Thr Leu Asp Leu Asp Met
290                 295                 300

Met Leu Asn Thr Gly Gly Lys Glu Arg Thr Glu Glu Glu Trp Lys Lys
305                 310                 315                 320

Leu Ile His Asp Ala Gly Tyr Lys Gly His Lys Ile Thr Gln Ile Thr
                325                 330                 335

Ala Val Gln Ser Val Ile Glu Ala Tyr Pro Tyr
            340                 345

<210> SEQ ID NO 20
<211> LENGTH: 346
<212> TYPE: PRT
<213> ORGANISM: Papaver somniferum

<400> SEQUENCE: 20

Met Glu Thr Val Ser Lys Ile Asp Gln Gln Asn Gln Ala Lys Ile Trp
 1               5                  10                  15

Lys Gln Ile Tyr Gly Phe Ala Glu Ser Leu Val Leu Lys Cys Ala Val
             20                  25                  30

Gln Leu Glu Ile Ala Glu Thr Leu His Asn Asn Val Lys Pro Met Ser
         35                  40                  45

Leu Ser Glu Leu Ala Ser Lys Leu Pro Val Ala Gln Pro Val Asn Glu
 50                  55                  60
```

```
Asp Arg Leu Phe Arg Ile Met Arg Tyr Leu Val His Met Glu Leu Phe
 65                  70                  75                  80

Lys Ile Asp Ala Thr Thr Gln Lys Tyr Ser Leu Ala Pro Pro Ala Lys
                 85                  90                  95

Tyr Leu Leu Arg Gly Trp Glu Lys Ser Met Val Asp Ser Ile Leu Cys
            100                 105                 110

Ile Asn Asp Lys Asp Phe Leu Ala Pro Trp His His Leu Gly Asp Gly
        115                 120                 125

Leu Thr Gly Asn Cys Asp Ala Phe Glu Lys Ala Leu Gly Lys Ser Ile
130                 135                 140

Trp Val Tyr Met Ser Val Asn Pro Glu Lys Asn Gln Leu Phe Asn Ala
145                 150                 155                 160

Ala Met Ala Cys Asp Thr Arg Leu Val Thr Ser Ala Leu Ala Asn Glu
                165                 170                 175

Cys Lys Ser Ile Phe Ser Asp Gly Ile Ser Thr Leu Val Asp Val Gly
            180                 185                 190

Gly Gly Thr Gly Thr Ala Val Lys Ala Ile Ser Lys Ala Phe Pro Asp
        195                 200                 205

Ile Lys Cys Thr Ile Tyr Asp Leu Pro His Val Ile Ala Asp Ser Pro
210                 215                 220

Glu Ile Pro Asn Ile Thr Lys Ile Ser Gly Asp Met Phe Lys Ser Ile
225                 230                 235                 240

Pro Ser Ala Asp Ala Ile Phe Met Lys Cys Ile Leu His Asp Trp Asn
                245                 250                 255

Asp Asp Glu Cys Ile Gln Ile Leu Lys Arg Cys Lys Glu Ala Leu Pro
            260                 265                 270

Lys Gly Gly Lys Val Ile Ile Val Asp Val Val Ile Asp Met Asp Ser
        275                 280                 285

Thr His Pro Tyr Ala Lys Ile Arg Leu Thr Leu Asp Leu Asp Met Met
290                 295                 300

Leu Asn Thr Gly Gly Lys Glu Arg Thr Lys Glu Trp Lys Thr Leu
305                 310                 315                 320

Phe Asp Ala Ala Gly Phe Ala Ser His Lys Val Thr Gln Ile Ser Ala
                325                 330                 335

Val Gln Ser Val Ile Glu Ala Tyr Pro Tyr
            340                 345

<210> SEQ ID NO 21
<211> LENGTH: 361
<212> TYPE: PRT
<213> ORGANISM: Thalictrum flavum

<400> SEQUENCE: 21

Met Ala Val Glu Gly Lys Gln Val Ala Pro Lys Lys Ala Ile Ile Val
 1               5                  10                  15

Glu Leu Leu Lys Lys Leu Glu Leu Gly Leu Val Pro Asp Asp Glu Ile
             20                  25                  30

Lys Lys Leu Ile Arg Ile Gln Leu Gly Arg Arg Leu Gln Trp Gly Cys
         35                  40                  45

Lys Ser Thr Tyr Glu Glu Ile Ala Gln Leu Val Asn Leu Thr His
     50                  55                  60

Ser Leu Arg Gln Met Lys Ile Ala Thr Glu Val Glu Thr Leu Asp Asp
 65                  70                  75                  80

Gln Met Tyr Glu Val Pro Ile Asp Phe Leu Lys Ile Met Asn Gly Ser
```

85                  90                  95
Asn Leu Lys Gly Ser Cys Cys Tyr Phe Lys Asn Asp Ser Thr Thr Leu
            100                 105                 110

Asp Glu Ala Glu Ile Ala Met Leu Glu Leu Tyr Cys Glu Arg Ala Gln
            115                 120                 125

Ile Lys Asp Gly His Ser Val Leu Asp Leu Gly Cys Gly Gln Gly Ala
            130                 135                 140

Leu Thr Leu Tyr Val Ala Gln Lys Tyr Lys Asn Ser Arg Val Thr Ala
145                 150                 155                 160

Val Thr Asn Ser Val Ser Gln Lys Glu Phe Ile Glu Glu Ser Arg
            165                 170                 175

Lys Arg Asn Leu Ser Asn Val Glu Val Leu Ala Asp Ile Thr Thr
            180                 185                 190

His Lys Met Pro Asp Thr Tyr Asp Arg Ile Leu Val Val Glu Leu Phe
            195                 200                 205

Glu His Met Lys Asn Tyr Glu Leu Leu Leu Arg Lys Ile Lys Glu Trp
            210                 215                 220

Met Ala Lys Asp Gly Leu Leu Phe Val Glu His Ile Cys His Lys Thr
225                 230                 235                 240

Phe Ala Tyr His Tyr Glu Pro Ile Asp Glu Asp Trp Phe Thr Glu
            245                 250                 255

Tyr Val Phe Pro Ala Gly Thr Met Ile Ile Pro Ser Ala Ser Phe Phe
            260                 265                 270

Leu Tyr Phe Gln Asp Asp Val Ser Val Asn His Trp Thr Leu Ser
            275                 280                 285

Gly Lys His Phe Ser Arg Thr Asn Glu Glu Trp Leu Lys Arg Leu Asp
            290                 295                 300

Ala Asn Val Glu Leu Ile Lys Pro Met Phe Val Thr Ile Thr Gly Gln
305                 310                 315                 320

Cys Arg Gln Glu Ala Met Lys Leu Ile Asn Tyr Trp Arg Gly Phe Cys
            325                 330                 335

Leu Ser Gly Met Glu Met Phe Gly Tyr Asn Asn Gly Glu Glu Trp Met
            340                 345                 350

Ala Ser His Val Leu Phe Lys Lys Lys
            355                 360

<210> SEQ ID NO 22
<211> LENGTH: 351
<212> TYPE: PRT
<213> ORGANISM: Papaver somniferum

<400> SEQUENCE: 22

Met Gln Leu Lys Ala Lys Glu Glu Leu Arg Asn Met Glu Leu Gly
1               5                   10                  15

Leu Ile Pro Asp Gln Glu Ile Arg Gln Leu Ile Arg Val Glu Leu Glu
            20                  25                  30

Lys Arg Leu Gln Trp Gly Tyr Lys Glu Thr His Glu Glu Gln Leu Ser
            35                  40                  45

Gln Leu Leu Asp Leu Val His Ser Leu Lys Gly Met Lys Met Ala Thr
            50                  55                  60

Glu Met Glu Asn Leu Asp Leu Lys Leu Tyr Glu Ala Pro Met Glu Phe
65                  70                  75                  80

Leu Lys Ile Gln His Gly Ser Asn Met Lys Gln Ser Ala Gly Tyr Tyr
            85                  90                  95

```
Thr Asp Glu Ser Thr Thr Leu Asp Glu Ala Glu Ile Ala Met Leu Asp
                100                 105                 110

Leu Tyr Met Glu Arg Ala Gln Ile Lys Asp Gly Gln Ser Val Leu Asp
            115                 120                 125

Leu Gly Cys Gly Leu Gly Ala Val Ala Leu Phe Gly Ala Asn Lys Phe
        130                 135                 140

Lys Lys Cys Gln Phe Thr Gly Val Thr Ser Ser Val Glu Gln Lys Asp
145                 150                 155                 160

Tyr Ile Glu Gly Lys Cys Lys Glu Leu Lys Leu Thr Asn Val Lys Val
                165                 170                 175

Leu Leu Ala Asp Ile Thr Thr Tyr Glu Thr Glu Glu Arg Phe Asp Arg
            180                 185                 190

Ile Phe Ala Val Glu Leu Ile Glu His Met Lys Asn Tyr Gln Leu Leu
        195                 200                 205

Leu Lys Lys Ile Ser Glu Trp Met Lys Asp Asp Gly Leu Leu Phe Val
210                 215                 220

Glu His Val Cys His Lys Thr Leu Ala Tyr His Tyr Glu Pro Val Asp
225                 230                 235                 240

Ala Glu Asp Trp Tyr Thr Asn Tyr Ile Phe Pro Ala Gly Thr Leu Thr
                245                 250                 255

Leu Ser Ser Ala Ser Met Leu Leu Tyr Phe Gln Asp Asp Val Ser Val
            260                 265                 270

Val Asn Gln Trp Thr Leu Ser Gly Lys His Tyr Ser Arg Ser His Glu
        275                 280                 285

Glu Trp Leu Lys Asn Met Asp Lys Asn Ile Val Glu Phe Lys Glu Ile
290                 295                 300

Met Arg Ser Ile Thr Lys Thr Glu Lys Glu Ala Ile Lys Leu Leu Asn
305                 310                 315                 320

Phe Trp Arg Ile Phe Cys Met Cys Gly Ala Glu Leu Phe Gly Tyr Lys
                325                 330                 335

Asn Gly Glu Glu Trp Met Leu Thr His Leu Leu Phe Lys Lys Lys
            340                 345                 350

<210> SEQ ID NO 23
<211> LENGTH: 481
<212> TYPE: PRT
<213> ORGANISM: Papaver somniferum

<400> SEQUENCE: 23

Ser Leu Val Ala Val Ile Thr Thr Phe Leu Tyr Leu Ile Phe Arg
1               5                   10                  15

Asp Ser Ser Pro Lys Gly Leu Pro Pro Gly Pro Lys Pro Trp Pro Ile
                20                  25                  30

Val Gly Asn Leu Leu Gln Leu Gly Glu Lys Pro His Ser Gln Phe Ala
            35                  40                  45

Gln Leu Ala Glu Thr Tyr Gly Asp Leu Phe Ser Leu Lys Leu Gly Ser
        50                  55                  60

Glu Thr Val Val Ala Ser Thr Pro Leu Ala Ala Ser Glu Ile Leu
65                  70                  75                  80

Lys Thr His Asp Arg Val Leu Ser Gly Arg Tyr Val Phe Gln Ser Phe
                85                  90                  95

Arg Val Lys Glu His Val Glu Asn Ser Ile Val Trp Ser Glu Cys Asn
            100                 105                 110

Glu Thr Trp Lys Lys Leu Arg Lys Val Cys Arg Thr Asp Leu Phe Thr
        115                 120                 125
```

Gln Lys Met Ile Glu Ser Gln Ala Glu Val Arg Ser Lys Ala Met
            130                 135                 140

Glu Met Val Glu Tyr Leu Lys Lys Asn Val Gly Asn Glu Val Lys Ile
145                 150                 155                 160

Ala Glu Val Val Phe Gly Thr Leu Val Asn Ile Phe Gly Asn Leu Ile
                165                 170                 175

Phe Ser Gln Asn Ile Phe Lys Leu Gly Asp Glu Ser Ser Gly Ser Val
            180                 185                 190

Glu Met Lys Glu His Leu Trp Arg Met Leu Glu Leu Gly Asn Ser Thr
        195                 200                 205

Asn Pro Ala Asp Tyr Phe Pro Phe Leu Gly Lys Phe Asp Leu Phe Gly
210                 215                 220

Gln Ser Lys Asp Val Ala Asp Cys Leu Gln Gly Ile Tyr Ser Val Trp
225                 230                 235                 240

Gly Ala Met Leu Lys Glu Ser Lys Ile Ala Lys Gln His Asn Asn Ser
                245                 250                 255

Lys Lys Asn Asp Phe Val Glu Ile Leu Leu Asp Ser Gly Leu Asp Asp
            260                 265                 270

Gln Gln Ile Asn Ala Leu Leu Met Glu Ile Phe Gly Ala Gly Thr Glu
        275                 280                 285

Thr Ser Ala Ser Thr Ile Glu Trp Ala Leu Ser Glu Leu Thr Lys Asn
290                 295                 300

Pro Gln Val Thr Ala Asn Met Arg Leu Glu Leu Leu Ser Val Val Gly
305                 310                 315                 320

Lys Arg Pro Val Lys Glu Ser Asp Ile Pro Asn Met Pro Tyr Leu Gln
                325                 330                 335

Ala Phe Val Lys Glu Thr Leu Arg Leu His Pro Ala Thr Pro Leu Leu
            340                 345                 350

Leu Pro Arg Arg Ala Leu Glu Thr Cys Lys Val Leu Asn Tyr Thr Ile
        355                 360                 365

Pro Lys Glu Cys Gln Ile Met Val Asn Ala Trp Gly Ile Gly Arg Asp
370                 375                 380

Pro Lys Arg Trp Thr Asp Pro Leu Lys Phe Ser Pro Glu Arg Phe Leu
385                 390                 395                 400

Asn Ser Ser Ile Asp Phe Lys Gly Asn Asp Phe Glu Leu Ile Pro Phe
                405                 410                 415

Gly Ala Gly Arg Arg Ile Cys Pro Gly Val Pro Leu Ala Thr Gln Phe
            420                 425                 430

Ile Ser Leu Ile Val Ser Ser Leu Val Gln Asn Phe Asp Trp Gly Leu
        435                 440                 445

Pro Lys Gly Met Asp Pro Ser Gln Leu Ile Met Glu Glu Lys Phe Gly
450                 455                 460

Leu Thr Leu Gln Lys Glu Pro Pro Leu Tyr Ile Val Pro Lys Thr Arg
465                 470                 475                 480

Asp

<210> SEQ ID NO 24
<211> LENGTH: 370
<212> TYPE: PRT
<213> ORGANISM: Artificial sequence
<220> FEATURE:
<223> OTHER INFORMATION: Synthetic polypeptide sequence

<400> SEQUENCE: 24

```
Met Ser Glu Ser Pro Met Phe Ala Ala Asn Gly Met Pro Lys Val Asn
1               5                   10                  15

Gln Gly Ala Glu Glu Asp Val Arg Ile Leu Gly Tyr Asp Pro Leu Ala
            20                  25                  30

Ser Pro Ala Leu Leu Gln Val Gln Ile Pro Ala Thr Pro Thr Ser Leu
        35                  40                  45

Glu Thr Ala Lys Arg Gly Arg Arg Glu Ala Ile Asp Ile Ile Thr Gly
50                  55                  60

Lys Asp Asp Arg Val Leu Val Ile Val Gly Pro Cys Ser Ile His Asp
65                  70                  75                  80

Leu Glu Ala Ala Gln Glu Tyr Ala Leu Arg Leu Lys Lys Leu Ser Asp
                85                  90                  95

Glu Leu Lys Gly Asp Leu Ser Ile Ile Met Arg Ala Tyr Leu Glu Lys
            100                 105                 110

Pro Arg Thr Thr Val Gly Trp Lys Gly Leu Ile Asn Asp Pro Asp Val
        115                 120                 125

Asn Asn Thr Phe Asn Ile Asn Lys Gly Leu Gln Ser Ala Arg Gln Leu
        130                 135                 140

Phe Val Asn Leu Thr Asn Ile Gly Leu Pro Ile Gly Ser Glu Met Leu
145                 150                 155                 160

Asp Thr Ile Ser Pro Gln Tyr Leu Ala Asp Leu Val Ser Phe Gly Ala
            165                 170                 175

Ile Gly Ala Arg Thr Thr Glu Ser Gln Leu His Arg Glu Leu Ala Ser
            180                 185                 190

Gly Leu Ser Phe Pro Val Gly Phe Lys Asn Gly Thr Asp Gly Thr Leu
        195                 200                 205

Asn Val Ala Val Asp Ala Cys Gln Ala Ala His Ser His His Phe
        210                 215                 220

Met Gly Val Thr Leu His Gly Val Ala Ala Ile Thr Thr Lys Gly
225                 230                 235                 240

Asn Glu His Cys Phe Val Ile Leu Arg Gly Gly Lys Lys Gly Thr Asn
            245                 250                 255

Tyr Asp Ala Lys Ser Val Ala Glu Ala Lys Ala Gln Leu Pro Ala Gly
        260                 265                 270

Ser Asn Gly Leu Met Ile Asp Tyr Ser His Gly Asn Ser Asn Lys Asp
        275                 280                 285

Phe Arg Asn Gln Pro Lys Val Asn Asp Val Val Cys Glu Gln Ile Ala
        290                 295                 300

Asn Gly Glu Asn Ala Ile Thr Gly Val Met Ile Glu Ser Asn Ile Asn
305                 310                 315                 320

Glu Gly Asn Gln Gly Ile Pro Ala Glu Gly Lys Ala Gly Leu Lys Tyr
            325                 330                 335

Gly Val Ser Ile Thr Asp Ala Cys Ile Gly Trp Glu Thr Thr Glu Asp
            340                 345                 350

Val Leu Arg Lys Leu Ala Ala Val Arg Gln Arg Glu Val Asn
        355                 360                 365

Lys Lys
    370

<210> SEQ ID NO 25
<211> LENGTH: 200
<212> TYPE: PRT
<213> ORGANISM: Papaver somniferum

<400> SEQUENCE: 25
```

```
Met Arg Lys Val Ile Lys Tyr Asp Met Glu Val Ala Val Ser Ala Asp
1               5                   10                  15

Ser Val Trp Ala Val Tyr Ser Ser Pro Asp Ile Pro Arg Leu Leu Arg
            20                  25                  30

Asp Val Leu Leu Pro Gly Val Phe Glu Lys Leu Asp Val Ile Glu Gly
        35                  40                  45

Asn Gly Gly Val Gly Thr Val Leu Asp Ile Val Phe Pro Pro Gly Ala
50                  55                  60

Val Pro Arg Ser Tyr Lys Glu Lys Phe Val Asn Ile Asp Arg Glu Lys
65                  70                  75                  80

Arg Leu Lys Glu Val Ile Met Ile Glu Gly Gly Tyr Leu Asp Met Gly
                85                  90                  95

Cys Thr Phe Tyr Leu Asp Arg Ile His Val Val Glu Lys Thr Lys Ser
                100                 105                 110

Ser Cys Val Ile Glu Ser Ser Ile Val Tyr Asp Val Lys Glu Glu Cys
            115                 120                 125

Ala Asp Ala Met Ser Lys Leu Ile Thr Thr Glu Pro Leu Lys Ser Met
130                 135                 140

Ala Glu Val Ile Ser Asn Tyr Val Ile Gln Lys Glu Leu Phe Ser Ala
145                 150                 155                 160

Arg Asn Ile Leu Ser Lys Gln Ser Val Val Lys Lys Glu Ile Arg Tyr
                165                 170                 175

Asp Leu Glu Val Pro Ile Ser Val Asp Ser Ile Trp Ser Val Tyr Ser
            180                 185                 190

Cys Pro Asp Ile Pro Arg Leu Leu
            195                 200

<210> SEQ ID NO 26
<211> LENGTH: 192
<212> TYPE: PRT
<213> ORGANISM: Thalictrum flavum

<400> SEQUENCE: 26

Met Gln Lys Leu Ile Leu Thr Gly Arg Pro Phe Leu His His Gln Gly
1               5                   10                  15

Ile Ile Asn Gln Val Ser Thr Val Thr Lys Val Ile His His Glu Leu
            20                  25                  30

Glu Val Ala Ala Ser Ala Asp Asp Ile Trp Thr Val Tyr Ser Trp Pro
        35                  40                  45

Gly Leu Ala Lys His Leu Pro Asp Leu Leu Pro Gly Ala Phe Glu Lys
50                  55                  60

Leu Glu Ile Ile Gly Asp Gly Val Gly Thr Ile Leu Asp Met Thr
65                  70                  75                  80

Phe Val Pro Gly Glu Phe Pro His Glu Tyr Lys Glu Lys Phe Ile Leu
                85                  90                  95

Val Asp Asn Glu His Arg Leu Lys Lys Val Gln Met Ile Glu Gly Gly
                100                 105                 110

Tyr Leu Asp Leu Gly Val Thr Tyr Tyr Met Asp Thr Ile His Val Val
            115                 120                 125

Pro Thr Gly Lys Asp Ser Cys Val Ile Lys Ser Ser Thr Glu Tyr His
130                 135                 140

Val Lys Pro Glu Phe Val Lys Ile Val Glu Pro Leu Ile Thr Thr Gly
145                 150                 155                 160

Pro Leu Ala Ala Met Ala Asp Ala Ile Ser Lys Leu Val Leu Glu His
```

```
                165                 170                 175
Lys Ser Lys Ser Asn Ser Asp Glu Ile Glu Ala Ala Ile Ile Thr Val
            180                 185                 190

<210> SEQ ID NO 27
<211> LENGTH: 488
<212> TYPE: PRT
<213> ORGANISM: Beta vulgaris

<400> SEQUENCE: 27

Met Glu Tyr Phe Thr Thr Leu Leu Leu Leu Ser Ile Ile Ile Leu
1               5                   10                  15

Thr Ile Leu Leu Ser Thr Lys Leu Phe Thr Lys Ser Asn Leu Pro Pro
            20                  25                  30

Gly Pro Lys Pro Trp Pro Ile Ile Gly Asn Ile Leu Glu Leu Gly Lys
            35                  40                  45

Leu Pro His Gln Ala Val Asp Lys Leu Ser Lys Thr Tyr Gly Pro Ile
        50                  55                  60

Leu Ser Leu Lys Leu Gly Ser Ile Thr Thr Ile Val Ile Ser Ser Pro
65                  70                  75                  80

Glu Ile Val Lys Glu Met Phe Leu Glu His Asp Leu Ala Leu Ser Ser
                85                  90                  95

Arg Pro Ser Pro Asp Ala Ser Arg Val Gly Asn His Asn Lys Phe Ser
            100                 105                 110

Ile Val Trp Leu Pro Val Ser Pro Lys Trp Arg Asp Leu Arg Lys Ile
        115                 120                 125

Ala Thr Ile Gln Leu Phe Thr Thr Gln Arg Leu Asp Ser Ser Gln Glu
    130                 135                 140

Leu Arg Gln Ile Lys Val Asn Glu Leu Val Asp Tyr Val Arg Gln Cys
145                 150                 155                 160

Cys Glu Lys Gly Leu Pro Val Asp Val Gly Lys Ala Gly Phe Thr Thr
                165                 170                 175

Thr Leu Asn Met Leu Ser Asn Thr Phe Phe Ser Met Asp Leu Ala Ser
            180                 185                 190

His Ala Ser Ser Asn Ser Gln Glu Phe Lys Asp Leu Val Trp Ser Leu
        195                 200                 205

Leu Glu Glu Gly Ala Lys Pro Asn Val Ser Asp Phe Phe Pro Ile Val
    210                 215                 220

Arg Glu Leu Asp Leu Gln Gly Val Ser Lys Asn Arg Arg Val His Met
225                 230                 235                 240

Lys Lys Leu Met Gly Ile Phe Glu Glu Ile Ile Asp Gly Arg Leu Thr
                245                 250                 255

Lys Leu Lys Asp Val Lys Asp Val Leu Ser Thr Leu Leu Lys Leu
            260                 265                 270

Val Lys Asp Glu Glu Leu Asn Leu Asp Asp Val Lys His Met Leu Met
        275                 280                 285

Asp Leu Phe Leu Ala Gly Thr Asp Thr Thr Ser Ile Thr Leu Glu Trp
    290                 295                 300

Ala Met Thr Glu Leu Leu Arg Asn Pro Glu Lys Met Glu Lys Val Gln
305                 310                 315                 320

Ile Glu Leu Asp Lys Val Leu Gly Lys Asp Ser Ser Leu Gln Glu Ser
                325                 330                 335

Met Ile Ser Lys Leu Pro Tyr Ile Gln Ala Ile Val Lys Glu Thr Leu
            340                 345                 350
```

```
Arg Leu His Pro Pro Thr Pro Phe Leu Ile Pro His Lys Ala Glu Lys
            355                 360                 365

Asp Val Leu Leu Cys Asn Tyr Leu Val Pro Lys Asn Ser Ile Ile Trp
370                 375                 380

Val Asn Leu Trp Ser Ile Ala Arg Ser Pro Ser Val Trp Pro Asn Pro
385                 390                 395                 400

Glu Ser Phe Ser Pro Glu Arg Phe Leu Glu Met Glu Ile Asp Ile Lys
                405                 410                 415

Gly Arg Asp Phe Lys Leu Ile Pro Phe Gly Ser Gly Arg Arg Met Cys
            420                 425                 430

Pro Gly Met Pro Leu Ala Tyr Arg Met Thr His Met Leu Leu Ala Thr
            435                 440                 445

Leu Leu His Ser Phe Asn Trp Lys Tyr Gly Glu Ala Ser Pro Lys Asp
        450                 455                 460

Ile Asp Met Lys Glu Lys Phe Gly Leu Thr Leu Gln Lys Ala Gln Pro
465                 470                 475                 480

Leu Gln Ala Ile Pro Ile Pro Arg
                485

<210> SEQ ID NO 28
<211> LENGTH: 488
<212> TYPE: PRT
<213> ORGANISM: Beta vulgaris

<400> SEQUENCE: 28

Met Glu Tyr Tyr Thr Leu Ser Leu Ile Phe Val Pro Ile Ile Phe Thr
1               5                   10                  15

Thr Leu Phe Phe Leu Gln Thr Leu Ser Lys Ser Lys Leu Pro Pro Gly
            20                  25                  30

Pro Lys Pro Trp Pro Ile Ile Gly Ser Leu His Lys Leu Gly Asp Arg
        35                  40                  45

Pro His Arg Ala Val Ala Glu Leu Ser Lys Ile Tyr Gly Pro Ile Met
    50                  55                  60

Ser Leu Lys Leu Gly Thr Ile Thr Thr Ile Val Ile Ser Ser Pro Glu
65                  70                  75                  80

Ile Val Lys Glu Leu Phe Leu Lys His Asp Leu Ala Val Ser Ser Arg
                85                  90                  95

Thr Val Pro Asn Ala Ala Arg Ala Val Asp His Asp Lys Phe Ser Met
            100                 105                 110

Val Trp Leu Pro Val Cys Pro Lys Trp Arg Asp Leu Arg Lys Ile Ala
        115                 120                 125

Thr Ile Gln Leu Phe Thr Thr Gln Arg Leu Asp Thr Ser Gln Phe Leu
    130                 135                 140

Arg Gln Lys Lys Val Lys Glu Leu Val Glu Tyr Ala Arg Gln Cys Cys
145                 150                 155                 160

Glu Lys Gly Val Ala Leu Asp Ile Gly Lys Ala Gly Phe Thr Thr Thr
                165                 170                 175

Leu Asn Leu Leu Ser Asn Thr Phe Phe Ser Met Asp Leu Ala Ser Tyr
            180                 185                 190

Asp Ser Leu Asp Ser Gln Glu Phe Lys Asp Leu Val Trp His Leu Leu
        195                 200                 205

Glu Glu Gly Ala Arg Pro Asn Val Ser Asp Phe Phe Pro Leu Val Lys
    210                 215                 220

His Phe Asp Leu Gln Gly Val Leu Lys Thr Thr Thr Ser Tyr Leu Lys
225                 230                 235                 240
```

Lys Leu Ile Gly Ile Phe Glu Glu Ile Ile Asp Lys Arg Leu Lys Asp
                245                 250                 255

Pro Thr Asp Val Lys Asp Asp Val Leu Ser Thr Leu Leu Lys Leu Val
                260                 265                 270

Glu Asp Asp Glu Leu Ser Leu Asp Asp Val Lys His Leu Leu Ala Asp
                275                 280                 285

Leu Phe Ile Ala Gly Thr Asp Thr Thr Ser Asn Thr Leu Glu Trp Ala
                290                 295                 300

Met Ala Glu Leu Leu Arg Asn Pro Glu Lys Met Glu Lys Ala Gln Ala
305                 310                 315                 320

Glu Ile Asn Lys Val Leu Gly Lys Asp Ser Ser Met Gln Glu Asn Asp
                325                 330                 335

Ile Ser Lys Leu Pro Tyr Val Gln Ala Ile Val Lys Glu Thr Phe Arg
                340                 345                 350

Leu His Pro Val Thr Pro Phe Leu Val Pro His Lys Ala Glu Lys Asp
                355                 360                 365

Ile Leu Leu Gly Asn Tyr Leu Val Pro Lys Asn Ser Thr Ile Trp Val
                370                 375                 380

Asn Val Trp Ser Ile Gly Arg Asn Pro Ser Val Trp Ser Lys Pro Glu
385                 390                 395                 400

Leu Phe Ser Pro Glu Arg His Leu Glu Leu Glu Ile Asp Val Lys Gly
                405                 410                 415

Gln Ala Phe Glu Leu Met Pro Phe Gly Ser Gly Arg Arg Thr Cys Pro
                420                 425                 430

Gly Met Pro Leu Ala Tyr Arg Met Thr His Leu Met Leu Ala Thr Leu
                435                 440                 445

Leu His Ser Phe His Trp Lys Tyr Gly His Gly Lys Ser Pro Glu Asp
                450                 455                 460

Ile Asp Met Glu Glu Lys Phe Gly Ile Thr Leu Gln Lys Val Glu Pro
465                 470                 475                 480

Leu Gln Ala Ile Pro Ile Ser Arg
                485

<210> SEQ ID NO 29
<211> LENGTH: 444
<212> TYPE: PRT
<213> ORGANISM: Beta vulgaris

<400> SEQUENCE: 29

Ser Ile His Lys Leu Gly Asp Lys Pro His Val Val Ala Lys Leu
1               5                   10                  15

Ser Lys Ile Tyr Gly Pro Ile Met Ser Leu Lys Leu Gly Ser Ile Thr
                20                  25                  30

Thr Ile Val Ile Ser Ser Pro Glu Ile Ala Lys Glu Met Phe Leu Glu
                35                  40                  45

His Asp Leu Ala Leu Ser Ser Arg Pro Met Gln Thr Lys Ser Leu Lys
                50                  55                  60

Lys Phe Ser Met Val Trp Leu Pro Val Cys Pro Lys Trp Arg His Leu
65                  70                  75                  80

Arg Lys Ile Ala Thr Leu Gln Leu Phe Thr Thr Gln Arg Leu Asp Ile
                85                  90                  95

Ser Gln Val Leu Arg His Thr Lys Val Lys Glu Leu Met Glu Tyr Ala
                100                 105                 110

Gln Gln Cys Cys Glu Asn Asn Leu Pro Val Asp Ile Gly Lys Ala Ala

```
                115                 120                 125
Phe Thr Thr Ser Leu Asn Leu Leu Ser Asn Thr Ile Phe Ser Met Asp
            130                 135                 140

Leu Ala Ser His Val Ser Ser Asn Ser Gln Glu Phe Lys Asp Ile Val
145                 150                 155                 160

Trp Asn Ile Met Glu Ser Arg Pro Asn Val Leu Asp Tyr Ile Pro Leu
                165                 170                 175

Val Arg Lys Leu Asp Leu Gln Gly Val Leu Lys Arg Lys Arg Ser Tyr
            180                 185                 190

Phe Lys Lys Ile Met Gly Val Phe Glu Glu Ile Ile Asp Val Arg Leu
        195                 200                 205

Lys Asp Pro Thr Asp Val Lys Asp Val Leu Gly Thr Leu Leu Lys
        210                 215                 220

Leu Val Lys Asp Glu Glu Leu Ser Leu His Asp Val Lys His Met Leu
225                 230                 235                 240

Phe Asp Leu Phe Leu Ala Gly Thr Asp Thr Thr Ser Ser Thr Leu Glu
                245                 250                 255

Trp Ala Met Thr Glu Leu Leu Arg Asn Pro Lys Val Met Glu Lys Ala
            260                 265                 270

Gln Ile Glu Ile Asp Gln Val Leu Gly Lys Asp Gly Ser Met Gln Glu
        275                 280                 285

Leu Asp Ile Ala Lys Leu Pro Tyr Ile Gln Ala Leu Val Lys Glu Ile
290                 295                 300

Leu Arg Leu His Pro Ala Pro Phe Leu Ile Pro His Met Ala Ile
305                 310                 315                 320

Glu Asp Val Gln Leu Cys Gly Tyr Leu Val Pro Lys Gln Ser Thr Ile
                325                 330                 335

Trp Val Asn Val Trp Ser Ile Gly Arg Asp Pro Ser Val Trp Thr Lys
            340                 345                 350

Ser Lys Met Phe Ser Pro Glu Arg Phe Leu Glu Lys Glu Ile Asp Val
        355                 360                 365

Lys Gly Arg Asn Phe Glu Leu Ile Pro Phe Gly Ser Gly Arg Arg Ile
370                 375                 380

Cys Pro Gly Met Pro Leu Ala Tyr Arg Met Val His Leu Thr Leu Ala
385                 390                 395                 400

Thr Leu Leu His Ser Phe Asn Trp Lys Tyr Val Asn Glu Ala Ser Ile
                405                 410                 415

Ala Thr Cys Thr Ile Asp Val Glu Glu Lys Phe Gly Ile Thr Leu Gln
            420                 425                 430

Lys Ala Glu Pro Leu Gln Ala Ile Pro Leu Pro Arg
        435                 440

<210> SEQ ID NO 30
<211> LENGTH: 501
<212> TYPE: PRT
<213> ORGANISM: Beta vulgaris

<400> SEQUENCE: 30

Met Asp Tyr Tyr Thr Thr Leu Leu Ile Leu Cys Ser Ile Phe Phe Ala
1               5                   10                  15

Phe Phe His Ile Tyr Lys Leu Ile Ser Pro Ser Ser Lys Leu Thr Ser
                20                  25                  30

Asn Asp Ser Arg Leu Pro Pro Gly Pro Lys Pro Ile Pro Ile Leu Gly
            35                  40                  45
```

```
Asn Leu Ser His Leu Gly Asp Ser Pro His Leu Ser Leu Ala Asn Leu
 50                  55                  60

Ala Lys Thr Tyr Gly Pro Leu Met Ser Leu Lys Phe Gly Ser Ile Thr
 65                  70                  75                  80

Thr Ile Val Val Ser Ser Ile Val Ala Lys Glu Met Phe Gln Lys
                 85                  90                  95

His Asp Leu Thr Leu Ser Ser Arg His Ala Ser Ala Ala Val Arg Ala
                100                 105                 110

Asn Gly His Asp Lys Cys Ser Ile Ala Trp Leu Pro Val Cys Ala Lys
                115                 120                 125

Trp Arg Ser Leu Arg Lys Ile Ser Ala Ile His Leu Phe Ser Ser Gln
130                 135                 140

Lys Leu Asp Ser Ser Gln Ala Leu Arg Gln Glu Lys Val Ser Lys Leu
145                 150                 155                 160

Ile Asp Tyr Val Lys Glu Cys Cys Asn Val Gly Glu Glu Ile Asp Val
                165                 170                 175

Gly Gly Val Ala Phe Thr Thr Ser Leu Asn Leu Leu Ser Asn Thr Phe
                180                 185                 190

Phe Ser Phe Asp Leu Ala Ser Tyr Asn Ser Ser Asp Ser Gly Glu Phe
                195                 200                 205

Lys Glu Leu Val Trp Lys Ile Met Glu Glu Ile Gly Lys Pro Asn Leu
                210                 215                 220

Val Asp Cys Phe Pro Met Leu Arg Phe Leu Ser Val Phe Ser Val Lys
225                 230                 235                 240

Gly Lys Leu Leu Gly Tyr Asp Asn Lys Leu Asn Glu Val Phe Glu Asn
                245                 250                 255

Ile Ile Gln Lys Arg Leu Gln Asn Tyr Cys Gly Asp Ser Ser Ser Gly
                260                 265                 270

Gly Asp Val Leu Asp Thr Leu Arg Leu Met Lys Glu Asn Glu Leu
                275                 280                 285

Asp Leu Asp Leu Gly Asp Ile Lys His Leu Leu Met Asp Phe Phe Thr
                290                 295                 300

Ala Gly Thr Asp Thr Thr Ser Ser Thr Leu Glu Trp Ala Met Thr Glu
305                 310                 315                 320

Leu Leu Arg Asn Pro Glu Lys Met Ala Lys Ala Gln Val Glu Leu Glu
                325                 330                 335

Gln Val Leu Gly Lys Asn Lys Val Val Gly Glu Phe Asp Ile Ser Lys
                340                 345                 350

Leu Pro Tyr Leu Gln Ala Ile Val Lys Glu Thr Leu Arg Met His Pro
                355                 360                 365

Pro Thr Val Phe Leu Leu Pro Arg Lys Ala Asn Asn Asp Val Glu Leu
                370                 375                 380

Tyr Gly Tyr Val Val Pro Lys Asn Ala Gln Val Phe Val Asn Val Trp
385                 390                 395                 400

Ala Ile Ser Arg Asp Pro Asn His Trp Glu Asn Pro Asn Ser Phe Ser
                405                 410                 415

Pro Glu Arg Phe Ile Glu His Glu Ile Asp Met Lys Gly Gln Asp Phe
                420                 425                 430

Gly Leu Ile Pro Phe Gly Ala Gly Arg Arg Ile Cys Pro Gly Asp Met
                435                 440                 445

Leu Ala Phe Arg Met Leu Asn Leu Met Leu Gly Ser Leu Leu His Gly
450                 455                 460

Phe Asn Trp Lys Val Gly Asp Gly Ile Ser Pro Gln Asp Leu Asp Met
```

Thr Asp Lys Phe Gly Ile Thr Ile Gln Lys Ala Ile Pro Leu Arg Ala
465                 470                 475                 480

Leu Pro Ile Pro Lys
            500

<210> SEQ ID NO 31
<211> LENGTH: 499
<212> TYPE: PRT
<213> ORGANISM: Beta vulgaris

<400> SEQUENCE: 31

Met Asp Tyr Tyr Thr Thr Leu Phe Phe Ile Leu Leu Pro Ile Phe Phe
1               5                   10                  15

Ala Leu Leu Tyr Leu Tyr Val Phe Lys Arg Asn Pro Thr Phe Thr Thr
                20                  25                  30

Asn Asn Asn Ala Arg Leu Pro Pro Gly Pro Lys Pro Ile Pro Ile Leu
            35                  40                  45

Gly Asn Leu Pro His Leu Gly Asp Lys Pro His His Ser Leu Ala Asn
        50                  55                  60

Leu Ala Lys Thr Tyr Gly Pro Leu Met Ser Leu Lys Phe Gly Ser Ile
65                  70                  75                  80

Thr Thr Ile Val Val Ser Ser Ile Val Ala Lys Glu Met Phe Gln
                85                  90                  95

Lys His Asp Leu Thr Leu Ser Ser Arg His Val Ser Ala Ala Val Arg
                100                 105                 110

Ala Asn Gly His Asp Lys Phe Ser Met Ala Trp Leu Pro Val Gly Pro
            115                 120                 125

Lys Trp Arg Ala Leu Arg Lys Ile Ala Thr Ile His Leu Phe Ser Ser
        130                 135                 140

Gln Arg Leu Asp Ser Ser Gln Ala Leu Arg Arg Glu Lys Val Ser Lys
145                 150                 155                 160

Leu Ile Asp Tyr Val Lys Glu Cys Cys Asn Val Gly Glu Ala Ile Asp
                165                 170                 175

Val Gly Gly Val Ala Phe Thr Thr Ser Leu Asn Leu Leu Ser Asn Thr
            180                 185                 190

Phe Phe Ser Phe Asp Leu Ala Ser Tyr Asn Ser Ser Asp Ser Gly Glu
        195                 200                 205

Phe Lys Glu Leu Val Trp Lys Ile Met Glu Glu Ile Gly Lys Pro Asn
210                 215                 220

Leu Ala Asp Cys Phe Pro Met Leu Arg Phe Leu Ser Val Phe Ser Val
225                 230                 235                 240

Asn Tyr Lys Val Met Val Tyr Gly Asn Arg Leu Asn Asp Val Phe Glu
                245                 250                 255

Asp Ile Ile Gln Asn Arg Leu Ile Ser Ser Ala Asp Lys Ile Gly
            260                 265                 270

Gly Asp Val Leu Asp Thr Leu Arg Leu Met Lys Glu Asn Glu Ser
        275                 280                 285

Glu Leu Ser Leu Asp Asp Ile Lys His Leu Leu Met Asp Phe Phe Thr
        290                 295                 300

Ala Gly Thr Asp Thr Thr Ser Ser Thr Leu Glu Trp Ala Met Thr Glu
305                 310                 315                 320

Leu Leu Arg Asn Pro Glu Lys Leu Ala Lys Ala Gln Ala Glu Leu Glu
                325                 330                 335

-continued

```
Gln Val Val Gly Lys Asn Lys Val Val Lys Glu Ala Asp Ile Ser Lys
            340                 345                 350

Leu Pro Tyr Leu Gln Ala Ile Ile Lys Glu Thr Leu Arg Met His Pro
        355                 360                 365

Pro Thr Val Phe Leu Leu Pro Arg Lys Ala Asn Asn Asp Val Lys Leu
    370                 375                 380

Tyr Gly Tyr Ile Val Pro Lys Asn Ala Gln Ile Phe Val Asn Leu Leu
385                 390                 395                 400

Ala Ile Ser Arg Asp Pro Thr His Trp Lys Asn Pro Asp Leu Phe Ser
                405                 410                 415

Pro Glu Arg Phe Phe Glu Leu Glu Ile Asp Leu Lys Gly His Asp Phe
            420                 425                 430

Gly Phe Ile Pro Phe Gly Ala Gly Arg Arg Thr Cys Pro Gly Asp Thr
        435                 440                 445

Leu Ala Phe Arg Met Leu Asn Leu Met Leu Gly Ser Leu Leu His Cys
    450                 455                 460

Phe Asn Trp Thr Phe Arg Asp Asp Glu Asp Leu Asp Met Asn Asp Lys
465                 470                 475                 480

Phe Gly Ile Thr Ile Gln Lys Ala Lys Pro Leu His Val Ile Pro Ile
                485                 490                 495

Ser Lys Leu

<210> SEQ ID NO 32
<211> LENGTH: 499
<212> TYPE: PRT
<213> ORGANISM: Beta vulgaris

<400> SEQUENCE: 32

Met Asp Asn Ala Thr Leu Ala Val Ile Leu Ser Ile Leu Phe Val Phe
1               5                   10                  15

Tyr His Ile Phe Lys Ser Phe Phe Thr Asn Ser Ser Ser Arg Arg Leu
            20                  25                  30

Pro Pro Gly Pro Lys Pro Val Pro Ile Phe Gly Asn Ile Phe Asp Leu
        35                  40                  45

Gly Glu Lys Pro His Arg Ser Phe Ala Asn Leu Ser Lys Ile His Gly
    50                  55                  60

Pro Leu Ile Ser Leu Lys Leu Gly Ser Val Thr Thr Ile Val Val Ser
65                  70                  75                  80

Ser Ala Ser Val Ala Glu Glu Met Phe Leu Lys Asn Asp Gln Ala Leu
                85                  90                  95

Ala Asn Arg Thr Ile Pro Asp Ser Val Arg Ala Gly Asp His Asp Lys
            100                 105                 110

Leu Ser Met Ser Trp Leu Pro Val Ser Gln Lys Trp Arg Asn Met Arg
        115                 120                 125

Lys Ile Ser Ala Val Gln Leu Leu Ser Asn Gln Lys Leu Asp Ala Ser
    130                 135                 140

Gln Pro Leu Arg Gln Thr Lys Val Lys Gln Leu Leu Ser Tyr Val Gln
145                 150                 155                 160

Asp Cys Ser Lys Lys Met Gln Pro Val Asp Ile Gly Arg Ala Ala Phe
                165                 170                 175

Thr Thr Ser Leu Asn Leu Leu Ser Asn Thr Phe Phe Ser Ile Glu Leu
            180                 185                 190

Ala Ser His Glu Ser Ser Ala Ser Gln Glu Phe Lys Gln Leu Met Trp
        195                 200                 205
```

-continued

Asn Ile Met Glu Glu Ile Gly Arg Pro Asn Tyr Ala Asp Phe Phe Pro
            210                 215                 220

Ile Leu Gly Tyr Ile Asp Pro Phe Gly Ile Arg Arg Leu Ala Gly
225                 230                 235                 240

Tyr Phe Asp Lys Leu Ile Asp Val Phe Gln Asp Ile Ile Arg Glu Arg
                245                 250                 255

Gln Lys Leu Arg Ser Ser Asn Ser Ser Gly Ala Lys Gln Thr Asn Asp
            260                 265                 270

Ile Leu Asp Thr Leu Leu Lys Leu His Glu Asp Asn Glu Leu Ser Met
            275                 280                 285

Pro Glu Ile Asn His Leu Leu Val Asp Ile Phe Asp Ala Gly Thr Asp
            290                 295                 300

Thr Thr Ala Ser Thr Leu Glu Trp Ala Met Ala Glu Leu Val Lys Asn
305                 310                 315                 320

Pro Glu Met Met Thr Lys Val Gln Ile Glu Ile Gln Ala Leu Gly
                325                 330                 335

Lys Asp Cys Leu Asp Ile Gln Glu Ser Asp Ile Ser Lys Leu Pro Tyr
                340                 345                 350

Leu Gln Gly Ile Ile Lys Glu Thr Leu Arg Leu His Pro Pro Thr Val
            355                 360                 365

Phe Leu Leu Pro Arg Lys Ala Asp Asn Asp Val Glu Leu Tyr Gly Tyr
370                 375                 380

Val Val Pro Lys Asn Ala Gln Val Leu Val Asn Leu Trp Ala Ile Gly
385                 390                 395                 400

Arg Asp Pro Lys Val Trp Lys Asn Pro Glu Val Phe Ser Pro Glu Arg
                405                 410                 415

Phe Leu Asp Cys Asn Ile Asp Tyr Lys Gly Arg Asp Phe Glu Leu Leu
                420                 425                 430

Pro Phe Gly Ala Gly Arg Arg Ile Cys Pro Gly Leu Thr Leu Ala Tyr
            435                 440                 445

Arg Met Leu Asn Leu Met Leu Ala Thr Leu Leu Gln Asn Tyr Asn Trp
            450                 455                 460

Lys Leu Glu Asp Gly Ile Asn Pro Lys Asp Leu Asp Met Asp Glu Lys
465                 470                 475                 480

Phe Gly Ile Thr Leu Gln Lys Val Lys Pro Leu Gln Val Ile Pro Val
                485                 490                 495

Pro Arg Asn

<210> SEQ ID NO 33
<211> LENGTH: 461
<212> TYPE: PRT
<213> ORGANISM: Beta vulgaris

<400> SEQUENCE: 33

Met Pro Ile Phe Gly Asn Ile Phe Asp Leu Gly Glu Lys Pro His Arg
1               5                   10                  15

Ser Phe Ala Asn Leu Ala Lys Ile His Gly Pro Leu Val Ser Leu Gln
            20                  25                  30

Leu Gly Ser Val Thr Thr Val Val Val Ser Ser Ala Asp Val Ala Lys
        35                  40                  45

Glu Met Phe Leu Lys Asn Asp Gln Ala Leu Ala Asn Arg Thr Ile Pro
    50                  55                  60

Asp Ser Val Arg Ala Gly Asp His Asp Lys Leu Ser Met Ser Trp Leu
65                  70                  75                  80

```
Pro Val Ser Ala Lys Trp Arg Asn Leu Arg Lys Ile Ser Ala Val Gln
             85                  90                  95

Leu Leu Ser Thr Gln Arg Leu Asp Ala Ser Gln Ala His Arg Gln Ser
        100                 105                 110

Lys Val Gln Gln Leu Leu Glu Tyr Val His Asp Cys Ser Lys Lys Gly
    115                 120                 125

Gln Pro Val Asp Ile Gly Arg Ala Phe Thr Thr Ser Leu Asn Leu
130                 135                 140

Leu Ser Asn Thr Phe Phe Ser Val Glu Leu Ala Ser His Glu Ser Ser
145                 150                 155                 160

Ala Ser Gln Glu Phe Lys Gln Leu Met Trp Asn Ile Met Glu Glu Ile
            165                 170                 175

Gly Arg Pro Asn Tyr Ala Asp Phe Phe Pro Ile Leu Gly Tyr Leu Asp
        180                 185                 190

Pro Phe Gly Ile Arg Arg Arg Leu Ala Gly Tyr Phe Asp Gln Leu Ile
    195                 200                 205

Ala Val Phe Gln Asp Ile Ile Gly Glu Arg Gln Lys Ile Arg Ser Ala
210                 215                 220

Asn Leu Ser Gly Gly Lys Gln Thr Asn Asp Ile Leu Asp Thr Leu Leu
225                 230                 235                 240

Asn Leu Tyr Asp Glu Lys Glu Leu Ser Met Gly Glu Ile Asn His Leu
            245                 250                 255

Leu Val Asp Ile Phe Asp Ala Gly Thr Asp Thr Thr Ala Ser Thr Leu
        260                 265                 270

Glu Trp Ala Met Ala Glu Leu Val Lys Asn Pro Tyr Met Met Val Lys
    275                 280                 285

Val Gln Asp Glu Ile Glu Lys Ala Ile Gly Lys Gly Cys Ser Met Val
290                 295                 300

Gln Glu Ser Asp Ile Ser Lys Leu Pro Tyr Leu Gln Ala Ile Ile Lys
305                 310                 315                 320

Glu Thr Leu Arg Leu His Pro Pro Thr Val Phe Leu Leu Pro Arg Lys
            325                 330                 335

Ala Asp Ala Asp Val Glu Leu Tyr Gly Tyr Ile Val Pro Lys Asn Ala
        340                 345                 350

Gln Val Leu Val Asn Leu Trp Ala Ile Gly Arg Asp Pro Lys Val Trp
    355                 360                 365

Lys Asn Pro Glu Val Phe Ser Pro Glu Arg Phe Leu Glu Ser Asn Ile
370                 375                 380

Asp Tyr Lys Gly Arg Asp Phe Glu Leu Leu Pro Phe Gly Ala Gly Arg
385                 390                 395                 400

Arg Ile Cys Pro Gly Leu Thr Leu Ala Tyr Arg Met Leu Asn Leu Met
            405                 410                 415

Met Ala Asn Phe Leu His Ser Tyr Asp Trp Lys Leu Glu Asp Gly Met
        420                 425                 430

His Pro Lys Asp Leu Asp Met Asp Glu Lys Phe Gly Ile Thr Leu Gln
    435                 440                 445

Lys Val Lys Pro Leu Gln Val Ile Pro Val Pro Arg Lys
450                 455                 460

<210> SEQ ID NO 34
<211> LENGTH: 497
<212> TYPE: PRT
<213> ORGANISM: Beta vulgaris

<400> SEQUENCE: 34
```

-continued

```
Met Asp His Ala Thr Leu Ala Met Ile Leu Ala Ile Trp Phe Ile Ser
1               5                   10                  15

Phe His Phe Ile Lys Leu Leu Phe Ser Gln Gln Thr Thr Lys Leu Leu
            20                  25                  30

Pro Pro Gly Pro Lys Pro Leu Pro Ile Ile Gly Asn Ile Leu Glu Val
        35                  40                  45

Gly Lys Lys Pro His Arg Ser Phe Ala Asn Leu Ala Lys Ile His Gly
50                  55                  60

Pro Leu Ile Ser Leu Arg Leu Gly Ser Val Thr Thr Ile Val Val Ser
65                  70                  75                  80

Ser Ala Asp Val Ala Lys Glu Met Phe Leu Lys Lys Asp His Pro Leu
                85                  90                  95

Ser Asn Arg Thr Ile Pro Asn Ser Val Thr Ala Gly Asp His His Lys
            100                 105                 110

Leu Thr Met Ser Trp Leu Pro Val Ser Pro Lys Trp Arg Asn Phe Arg
        115                 120                 125

Lys Ile Thr Ala Val His Leu Leu Ser Pro Gln Arg Leu Asp Ala Cys
130                 135                 140

Gln Thr Phe Arg His Ala Lys Val Gln Gln Leu Tyr Glu Tyr Val Gln
145                 150                 155                 160

Glu Cys Ala Gln Lys Gly Gln Ala Val Asp Ile Gly Lys Ala Ala Phe
                165                 170                 175

Thr Thr Ser Leu Asn Leu Leu Ser Lys Leu Phe Phe Ser Val Glu Leu
            180                 185                 190

Ala His His Lys Ser His Thr Ser Gln Glu Phe Lys Glu Leu Ile Trp
        195                 200                 205

Asn Ile Met Glu Asp Ile Gly Lys Pro Asn Tyr Ala Asp Tyr Phe Pro
210                 215                 220

Ile Leu Gly Cys Val Asp Pro Ser Gly Ile Arg Arg Arg Leu Ala Cys
225                 230                 235                 240

Ser Phe Asp Lys Leu Ile Ala Val Phe Gln Gly Ile Ile Cys Glu Arg
                245                 250                 255

Leu Ala Pro Asp Ser Ser Thr Thr Thr Thr Thr Thr Asp Asp Val
            260                 265                 270

Leu Asp Val Leu Leu Gln Leu Phe Lys Gln Asn Glu Leu Thr Met Gly
        275                 280                 285

Glu Ile Asn His Leu Leu Val Asp Ile Phe Ala Gly Thr Asp Thr
290                 295                 300

Thr Ser Ser Thr Phe Glu Trp Val Met Thr Glu Leu Ile Arg Asn Pro
305                 310                 315                 320

Glu Met Met Glu Lys Ala Gln Glu Ile Lys Gln Val Leu Gly Lys
                325                 330                 335

Asp Lys Gln Ile Gln Glu Ser Asp Ile Ile Asn Leu Pro Tyr Leu Gln
            340                 345                 350

Ala Ile Ile Lys Glu Thr Leu Arg Leu His Pro Pro Thr Val Phe Leu
        355                 360                 365

Leu Pro Arg Lys Ala Asp Thr Asp Val Glu Leu Tyr Gly Tyr Ile Val
370                 375                 380

Pro Lys Asp Ala Gln Ile Leu Val Asn Leu Trp Ala Ile Gly Arg Asp
385                 390                 395                 400

Pro Asn Ala Trp Gln Asn Ala Asp Ile Phe Ser Pro Glu Arg Phe Ile
                405                 410                 415
```

```
Gly Cys Glu Ile Asp Val Lys Gly Arg Asp Phe Gly Leu Leu Pro Phe
            420                 425                 430

Gly Ala Gly Arg Arg Ile Cys Pro Gly Met Asn Leu Ala Ile Arg Met
        435                 440                 445

Leu Thr Leu Met Leu Ala Thr Leu Leu Gln Phe Phe Asn Trp Lys Leu
    450                 455                 460

Glu Gly Asp Ile Ser Pro Lys Asp Leu Asp Met Asp Glu Lys Phe Gly
465                 470                 475                 480

Ile Ala Leu Gln Lys Thr Lys Pro Leu Lys Leu Ile Pro Ile Pro Arg
                485                 490                 495

Tyr

<210> SEQ ID NO 35
<211> LENGTH: 20
<212> TYPE: DNA
<213> ORGANISM: Artificial sequence
<220> FEATURE:
<223> OTHER INFORMATION: Synthetic nucleic acid sequence

<400> SEQUENCE: 35
ttggtagtcg gtctcctatg                                              20

<210> SEQ ID NO 36
<211> LENGTH: 24
<212> TYPE: DNA
<213> ORGANISM: Artificial sequence
<220> FEATURE:
<223> OTHER INFORMATION: Synthetic nucleic acid sequence

<400> SEQUENCE: 36
tttttattgg tctggtctca ggat                                         24

<210> SEQ ID NO 37
<211> LENGTH: 24
<212> TYPE: DNA
<213> ORGANISM: Artificial sequence
<220> FEATURE:
<223> OTHER INFORMATION: Synthetic nucleic acid sequence

<400> SEQUENCE: 37
caaaactacc tgtttcacca aagg                                         24

<210> SEQ ID NO 38
<211> LENGTH: 20
<212> TYPE: DNA
<213> ORGANISM: Artificial sequence
<220> FEATURE:
<223> OTHER INFORMATION: Synthetic nucleic acid sequence

<400> SEQUENCE: 38
acttgaagtg gtggttgttc                                              20

<210> SEQ ID NO 39
<211> LENGTH: 32
<212> TYPE: DNA
<213> ORGANISM: Artificial sequence
<220> FEATURE:
<223> OTHER INFORMATION: Synthetic nucleic acid sequence

<400> SEQUENCE: 39
gcatggtctc atatggatca tgcaacatta gc                                32

<210> SEQ ID NO 40
```

<211> LENGTH: 30
<212> TYPE: DNA
<213> ORGANISM: Artificial sequence
<220> FEATURE:
<223> OTHER INFORMATION: Synthetic nucleic acid sequence

<400> SEQUENCE: 40
atgcggtctc aacagcagtt atctttctga                              30

<210> SEQ ID NO 41
<211> LENGTH: 33
<212> TYPE: DNA
<213> ORGANISM: Artificial sequence
<220> FEATURE:
<223> OTHER INFORMATION: Synthetic nucleic acid sequence

<400> SEQUENCE: 41
gcatggtctc actgttcatt tattgtctcc aca                          33

<210> SEQ ID NO 42
<211> LENGTH: 33
<212> TYPE: DNA
<213> ORGANISM: Artificial sequence
<220> FEATURE:
<223> OTHER INFORMATION: Synthetic nucleic acid sequence

<400> SEQUENCE: 42
atgcggtctc aagttgtagt agttgtagtt gat                          33

<210> SEQ ID NO 43
<211> LENGTH: 32
<212> TYPE: DNA
<213> ORGANISM: Artificial sequence
<220> FEATURE:
<223> OTHER INFORMATION: Synthetic nucleic acid sequence

<400> SEQUENCE: 43
gcatggtctc aaactacaga tgatgtcttg ga                           32

<210> SEQ ID NO 44
<211> LENGTH: 31
<212> TYPE: DNA
<213> ORGANISM: Artificial sequence
<220> FEATURE:
<223> OTHER INFORMATION: Synthetic nucleic acid sequence

<400> SEQUENCE: 44
atgcggtctc aggcaacaag aaaactgtag g                            31

<210> SEQ ID NO 45
<211> LENGTH: 28
<212> TYPE: DNA
<213> ORGANISM: Artificial sequence
<220> FEATURE:
<223> OTHER INFORMATION: Synthetic nucleic acid sequence

<400> SEQUENCE: 45
gcatggtctc atgcctagaa aagccgac                                28

<210> SEQ ID NO 46
<211> LENGTH: 31
<212> TYPE: DNA
<213> ORGANISM: Artificial sequence
<220> FEATURE:
<223> OTHER INFORMATION: Synthetic nucleic acid sequence

<400> SEQUENCE: 46

```
atgcggtctc aggatccgta tcttggaatt g                                        31
```

<210> SEQ ID NO 47
<211> LENGTH: 47
<212> TYPE: DNA
<213> ORGANISM: Artificial sequence
<220> FEATURE:
<223> OTHER INFORMATION: Synthetic nucleic acid sequence

<400> SEQUENCE: 47

```
gcatcgtctc atcggtctcc tatggaacat gcaacattag ctatgat                       47
```

<210> SEQ ID NO 48
<211> LENGTH: 45
<212> TYPE: DNA
<213> ORGANISM: Artificial sequence
<220> FEATURE:
<223> OTHER INFORMATION: Synthetic nucleic acid sequence

<400> SEQUENCE: 48

```
gcatcgtctc atcggtctcc tatggatcac gcaacattag ctatg                         45
```

<210> SEQ ID NO 49
<211> LENGTH: 487
<212> TYPE: PRT
<213> ORGANISM: Eschscholzia californica

<400> SEQUENCE: 49

```
Gly Thr Ser Thr Val Ala Leu Ile Ala Val Ile Ile Ser Ser Ile Leu
1               5                   10                  15

Tyr Leu Leu Phe Gly Gly Ser Gly His Lys Asn Leu Pro Pro Gly Pro
            20                  25                  30

Lys Pro Trp Pro Ile Val Gly Asn Leu Leu Gln Leu Gly Glu Lys Pro
        35                  40                  45

His Ala Gln Phe Ala Glu Leu Ala Gln Thr Tyr Gly Asp Ile Phe Thr
    50                  55                  60

Leu Lys Met Gly Thr Glu Thr Val Val Ala Ser Thr Ser Ser Ala
65                  70                  75                  80

Ala Ser Glu Ile Leu Lys Thr His Asp Arg Ile Leu Ser Ala Arg Tyr
                85                  90                  95

Val Phe Gln Ser Phe Arg Val Lys Gly His Val Glu Asn Ser Ile Val
            100                 105                 110

Trp Ser Asp Cys Thr Glu Thr Trp Lys Asn Leu Arg Lys Val Cys Arg
        115                 120                 125

Thr Glu Leu Phe Thr Gln Lys Met Ile Glu Ser Gln Ala His Val Arg
    130                 135                 140

Glu Lys Lys Cys Glu Glu Met Val Glu Tyr Leu Met Lys Lys Gln Gly
145                 150                 155                 160

Glu Glu Val Lys Ile Val Glu Val Ile Phe Gly Thr Leu Val Asn Ile
                165                 170                 175

Phe Gly Asn Leu Ile Phe Ser Gln Asn Ile Phe Glu Leu Gly Asp Pro
            180                 185                 190

Asn Ser Gly Ser Ser Glu Phe Lys Glu Tyr Leu Trp Arg Met Leu Glu
        195                 200                 205

Leu Gly Asn Ser Thr Asn Pro Ala Asp Tyr Phe Pro Met Leu Gly Lys
    210                 215                 220

Phe Asp Leu Phe Gly Gln Arg Lys Glu Val Ala Glu Cys Leu Lys Gly
225                 230                 235                 240
```

```
Ile Tyr Ala Ile Trp Gly Ala Met Leu Gln Glu Arg Lys Leu Ala Lys
                245                 250                 255

Lys Val Asp Gly Tyr Lys Ser Lys Asn Asp Phe Val Asp Val Cys Leu
                260                 265                 270

Asp Ser Gly Leu Asn Asp Tyr Gln Ile Asn Ala Leu Leu Met Glu Leu
                275                 280                 285

Phe Gly Ala Gly Thr Glu Thr Ser Ala Ser Thr Ile Glu Trp Ala Met
                290                 295                 300

Thr Glu Leu Thr Lys Asn Pro Lys Ile Thr Ala Lys Ile Arg Ser Glu
305                 310                 315                 320

Ile Gln Thr Val Val Gly Glu Arg Ser Val Lys Glu Ser Asp Phe Pro
                325                 330                 335

Asn Leu Pro Tyr Leu Glu Ala Thr Val Lys Glu Thr Leu Arg Leu His
                340                 345                 350

Pro Pro Thr Pro Leu Leu Pro Arg Arg Ala Leu Glu Thr Cys Thr
                355                 360                 365

Ile Leu Asn Tyr Thr Ile Pro Lys Asp Cys Gln Ile Met Val Asn Ala
                370                 375                 380

Trp Gly Ile Gly Arg Asp Pro Lys Thr Trp Thr Asp Pro Leu Thr Phe
385                 390                 395                 400

Ser Pro Glu Arg Phe Leu Asn Ser Ser Val Asp Phe Arg Gly Asn Asp
                405                 410                 415

Phe Ser Leu Ile Pro Phe Gly Ala Gly Arg Arg Ile Cys Pro Gly Leu
                420                 425                 430

Pro Ile Ala Asn Gln Phe Ile Ala Leu Leu Val Ala Thr Phe Val Gln
                435                 440                 445

Asn Leu Asp Trp Cys Leu Pro Asn Gly Met Ser Val Asp His Leu Ile
                450                 455                 460

Val Glu Glu Lys Phe Gly Leu Thr Leu Gln Lys Glu Pro Pro Leu Phe
465                 470                 475                 480

Ile Val Pro Lys Ser Arg Val
                485

<210> SEQ ID NO 50
<211> LENGTH: 27
<212> TYPE: PRT
<213> ORGANISM: Artificial sequence
<220> FEATURE:
<223> OTHER INFORMATION: Synthetic polypeptide sequence

<400> SEQUENCE: 50

Ile Leu Glu Gln Pro Leu Lys Phe Val Leu Thr Ala Ala Val Val Leu
1               5                   10                  15

Leu Thr Thr Ser Val Cys Cys Val Val Phe Thr
                20                  25
```

What is claimed is:

1. A method of producing L-3,4-dihydroxyphenylalanine (L-DOPA), the method comprising:
   culturing a host cell to thereby produce L-DOPA,
   wherein the host cell is genetically modified to express a heterologous tyrosine hydroxylase, wherein the heterologous tyrosine hydroxylase comprises an amino acid sequence having at least 90% amino acid sequence identity to the amino acid sequence of SEQ ID NO: 1,
   wherein the tryptophan corresponding to amino acid 13 of SEQ ID NO: 1 is replaced with a different amino acid in the heterologous tyrosine hydroxylase, and/or
   the phenylalanine corresponding to amino acid 309 of SEQ ID NO: 1 is replaced with a different amino acid in the heterologous tyrosine hydroxylase, and
   wherein the heterologous tyrosine hydroxylase is produced in the host cell, and catalyzes the conversion of tyrosine to L-DOPA.

2. The method of claim 1, wherein L-DOPA is produced in an amount of at least 5 µg per milliliter of culture.

3. A method of producing (S)-reticuline, the method comprising:
   culturing a host cell to thereby produce (S)-reticuline,
   wherein the host cell is genetically modified to express a heterologous tyrosine hydroxylase, wherein the heterologous tyrosine hydroxylase comprises an amino acid sequence having at least 90% amino acid sequence identity to the amino acid sequence of SEQ ID NO: 1,
   wherein the heterologous tyrosine hydroxylase is produced in the host cell, and catalyzes the conversion of tyrosine to L-DOPA;
   wherein the host cell is genetically modified to express a heterologous DOPA decarboxylase (DODC), wherein the heterologous DODC catalyzes the conversion of L-DOPA to dopamine,
   wherein the host cell comprises endogenous enzymes that convert tyrosine to 4-hydroxyphenylacetaldehyde and the host cell converts tyrosine to 4-hydroxyphenylacetaldehyde,
   wherein the host cell is genetically modified to express a heterologous norcoclaurine synthase (NCS), and wherein the heterologous NCS condenses the 4-hydroxyphenylacetaldehyde with the dopamine to produce (S)-norcoclaurine, and
   wherein the host cell is genetically modified to express heterologous norcoclaurine 6-O-methyltransferase (6OMT), coclaurine-N-methyltransferase (CNMT), N-methylcoclaurine hydroxylase (NMCH), and 3'-hydroxy-N-methylcoclaurine-4'-O-methyltransferase (4'OMT), and wherein the heterologous 6OMT, CNMT, NMCH, and 4' OMT convert (S)-norcoclaurine to (S)-reticuline.

4. The method of claim 3, further comprising purifying the (S)-reticuline.

5. The method of claim 3, wherein the NCS comprises an amino acid sequence selected from the group consisting of SEQ ID NO: 17, SEQ ID NO: 18, SEQ ID NO: 25 and SEQ ID NO: 26.

6. A method of producing (S)-norcoclaurine, the method comprising:
   culturing a host cell to thereby produce (S)-nococlaurine,
   wherein the host cell is genetically modified to express a heterologous tyrosine hydroxylase, wherein the heterologous tyrosine hydroxylase comprises an amino acid sequence having at least 90% amino acid sequence identity to the amino acid sequence of SEQ ID NO: 1,
   wherein the heterologous tyrosine hydroxylase is produced in the host cell, and catalyzes the conversion of tyrosine to L-DOPA;
   wherein the host cell is genetically modified to express a heterologous DOPA decarboxylase (DODC), wherein the heterologous DODC catalyzes the conversion of L-DOPA to dopamine,
   wherein the host cell comprises endogenous enzymes that convert tyrosine to 4-hydroxyphenylacetaldehyde and the host cell converts tyrosine to 4-hydroxyphenylacetaldehyde, and
   wherein the host cell is genetically modified to express a heterologous norcoclaurine synthase (NCS), and wherein the heterologous NCS condenses the 4-hydroxyphenylacetaldehyde with the dopamine to produce (S)-norcoclaurine.

7. The method of claim 1, wherein the tryptophan corresponding to amino acid 13 of SEQ ID NO: 1 is replaced with leucine, isoleucine, or valine.

8. The method of claim 1, wherein the phenylalanine corresponding to amino acid 309 of SEQ ID NO: 1 is replaced with leucine, isoleucine, or valine.

* * * * *